US012162836B2

(12) United States Patent
Patel et al.

(10) Patent No.: US 12,162,836 B2
(45) Date of Patent: Dec. 10, 2024

(54) N-ACYL-{4-[(4-ARYL-PHENYL)SULFONYLMETHYL]PIPERIDINE} COMPOUNDS AND THEIR THERAPEUTIC USE

(71) Applicant: Modern Biosciences Limited, London (GB)

(72) Inventors: Lisa Patel, London (GB); Stephen Allan Smith, Wymondham (GB); Stephen Paul Collingwood, Sussex (GB)

(73) Assignee: Modern Biosciences Limited, London (GB)

( * ) Notice: Subject to any disclaimer, the term of this patent is extended or adjusted under 35 U.S.C. 154(b) by 649 days.

(21) Appl. No.: 17/602,408

(22) PCT Filed: Apr. 17, 2020

(86) PCT No.: PCT/EP2020/060879
§ 371 (c)(1),
(2) Date: Oct. 8, 2021

(87) PCT Pub. No.: WO2020/212581
PCT Pub. Date: Oct. 22, 2020

(65) Prior Publication Data
US 2023/0022917 A1    Jan. 26, 2023

(30) Foreign Application Priority Data
Apr. 18, 2019    (GB) .................................... 1905520

(51) Int. Cl.
*C07D 211/54*    (2006.01)
*A61P 19/02*    (2006.01)
*C07D 401/12*    (2006.01)

(52) U.S. Cl.
CPC ............ *C07D 211/54* (2013.01); *A61P 19/02* (2018.01); *C07D 401/12* (2013.01)

(58) Field of Classification Search
None
See application file for complete search history.

(56) References Cited

U.S. PATENT DOCUMENTS 9,624,167 B2 *   4/2017   Patel .................. A61P 25/00
9,796,670 B2 *  10/2017   Patel ................... C07C 311/20
(Continued)

FOREIGN PATENT DOCUMENTS

EP         1997804 A1       12/2008
WO    WO 96/35666 A1       11/1996
(Continued)

OTHER PUBLICATIONS

Astry et al., 2011, "A cytokine-centric view of the pathogenesis and treatment of autoimmune arthritis", J Interferon Cytokine Res., vol. 31, pp. 927-940.
(Continued)

*Primary Examiner* — Jeffrey S Lundgren
*Assistant Examiner* — Anthony Seitz
(74) *Attorney, Agent, or Firm* — McNeill PLLC

(57) ABSTRACT

The present invention pertains generally to the field of therapeutic compounds. More specifically the present invention pertains to certain N-acyl-{4-[(4-aryl-phenyl)sulfonylmethyl]piperidine} compounds of the following formula (collectively referred to herein as NASMP compounds) that are useful, for example, in the treatment of disorders (e.g., diseases) including, e.g., multiple myeloma, diffuse large B-cell lymphoma, acute myeloid leukemia, eosinophilic leukemia, glioblastoma, melanoma, ovarian cancer, chemotherapy resistant cancer, radiation resistant cancer, inflammatory arthritis, rheumatoid arthritis, psoriatic arthritis, psoriasis, ulcerative colitis, Crohn's disease, systemic lupus erythematosus (SLE), lupus nephritis, asthma, chronic
(Continued)

obstructive pulmonary disease (COPD), Hidradenitis suppurativa, autoimmune hepatitis, etc. The present invention also pertains to pharmaceutical compositions comprising such compounds, and the use of such compounds and compositions, for example, in therapy.

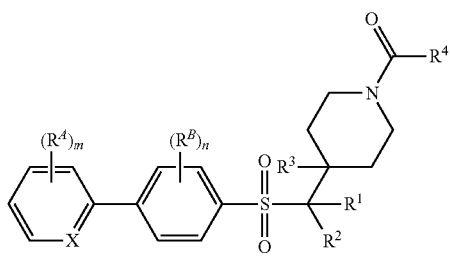

25 Claims, 3 Drawing Sheets

(56) References Cited

U.S. PATENT DOCUMENTS

| | | | | |
|---|---|---|---|---|
| 10,005,733 | B2 * | 6/2018 | Smith | A61P 19/10 |
| 10,029,979 | B2 * | 7/2018 | Patel | A61P 11/06 |
| 10,233,147 | B2 * | 3/2019 | Patel | A61P 9/00 |
| 11,834,414 | B2 * | 12/2023 | Patel | C07C 317/18 |
| 2018/0297955 | A1 * | 10/2018 | Smith | A61P 1/04 |
| 2024/0182418 | A1 * | 6/2024 | Patel | C07C 317/44 |

FOREIGN PATENT DOCUMENTS

| | | |
|---|---|---|
| WO | WO 01/70690 A1 | 9/2001 |
| WO | WO 03/053941 A2 | 7/2003 |
| WO | WO 2006/113261 A2 | 10/2006 |
| WO | WO 2007/003962 A2 | 1/2007 |
| WO | WO 2007/102392 A1 | 9/2007 |
| WO | WO 2008/061016 A1 | 5/2008 |
| WO | WO 2008/070692 A2 | 6/2008 |
| WO | WO 2009/020140 A1 | 2/2009 |
| WO | WO 2009/045382 A1 | 4/2009 |
| WO | WO 2010/032009 A1 | 3/2010 |
| WO | WO 2010/032010 A1 | 3/2010 |
| WO | WO 2013/187646 A1 | 12/2013 |
| WO | WO 2014/135495 A1 | 9/2014 |
| WO | WO 2014/207445 A1 | 12/2014 |
| WO | WO 2016/097001 A1 | 6/2016 |
| WO | WO 2016/118774 A1 | 7/2016 |

OTHER PUBLICATIONS

Auld et al., 2009, "A basis for reduced chemical library inhibition of firefly luciferase obtained from directed evolution", J. Med. Chem., vol. 52, No. 5, pp. 1450-1458.
Baud et al., 2009, "Is NFκB a good target for cancer therapy? Hopes and pitfalls", Nat. Rev. Drug Disc., vol. 8, pp. 33 40.
Billiau, 2010, "Etanercept improves linear growth and bone mass acquisition in MTX resistant polyarticular-course juvenile idiopathic arthritis", Rheumatology (Oxford), vol. 49, pp. 1550 1558.
Bridges et al., 2014, "Effects of metformin and other biguanides on oxidative phosphorylation in mitochondria", Biochem. J., vol. 462, No. 3, pp. 475-487.
Chimenti et al., 2015, "The interplay between inflammation and metabolism in rheumatoid arthritis", Cell Death and Disease, vol. 17, No. 6, e1887.
Dallas et al., 2011, "Osteoimmunology at the nexus of arthritis, osteoporosis, cancer, and infection", J. Clin. Invest., vol. 121, pp. 2534 2542.
Ellinghaus et al., 2013, "BAY 87-2243, a highly potent and selective inhibitor of hypoxia-induced gene activation has antitumor activities by inhibition of mitochondrial complex I", Cancer Med., vol. 2, No. 5, pp. 611-624.
Evans et al., 2005, "Metformin and reduced risk of cancer in diabetic patients", BMJ, vol. 330, pp. 1304-1305.
Fearon et al., 2016 "Hypoxia, mitochondrial dysfunction and synovial invasiveness in rheumatoid arthritis", Nat. Rev. Rheumatol., vol. 12, pp. 385 397.
Fiorillo et al., 2016, "Repurposing atovaquone: targeting mitochondrial complex III and OXPHOS to eradicate cancer stem cells", Oncotarget, vol. 7, pp. 34084-34099.
Firestein, 2005 "Immunologic mechanisms in the pathogenesis of rheumatoid arthritis", J. Clin. Rheumatol., vol. 11. pp. S39-S44.
Ganeshan et al., 2014, "Metabolic Regulation of Immune Responses", Ann. Rev. Immunol., vol. 32, pp. 609-634.
Garcia-Carbonnel et al., 2016, "Critical Role of Glucose Metabolism in Rheumatoid Arthritis Fibroblast-like Synoviocytes", Arthritis Rheumatol., vol. 68, No. 7, pp. 1614-1626.
Great Britain Search Report for GB1905520.1 issued Sep. 18, 2019, 5 pages (unpublished).
International Search Report and Written Opinion for PCT/EP2020/060879, dated Jun. 4, 2020, 12 pages.
International Preliminary Report on Patentability for PCT/EP2020/060879, dated Sep. 28, 2021, 6 pages.
Jiang et al., 2013, "Letm1, the mitochondrial Ca2+/H+ antiporter, is essential for normal glucose metabolism and alters brain function in Wolf-Hirschhorn syndrome", PNAS, E2249E2254.
Jung et al., 2014, "Cytokine-mediated bone destruction in rheumatoid arthritis", J. Immunol. Res., vol. 2014, p. 263625.
Kang et al., 2015, "Combinations of kinase inhibitors protecting myoblasts against hypoxia", PLOS, PLoS One 10(6): e0126718.
Karsenty et al., 2002, "Reaching a genetic and molecular understanding of skeletal development", Dev. Cell., vol. 2, pp. 389 406.
Klareskog et al., 2006, "Mechanisms of disease: Genetic susceptibility and environmental triggers in the development of rheumatoid arthritis," Nat. Clin. Pract. Rheumatol., vol. 2, pp. 425-433.
Kleyer et al., 2014, "Arthritis and bone loss: a hen and egg story", Curr. Opin. Rheumatol., vol. 26, No. 1, pp. 80-84.
Koppenol et al., 2011, "Otto Warburg's contributions to current concepts of cancer metabolism", Nat. Rev. Cancer, vol. 11, No. 5, pp. 325-337.
Lack et al., 2011, "Targeting the binding function 3 (BF3) site of the human androgen receptor through virtual screening", Journal of Medicinal Chemistry, vol. 54, No. 24, pp. 8563-8573.
Lebleu et al., 2014, "PGC-1α mediates mitochondrial biogenesis and oxidative phosphorylation in cancer cells to promote metastasis", Nat. Cell Biol., vol. 16, pp. 992-1003.
Long, 2012, "Osteoimmunology: the expanding role of immunoreceptors in osteoclasts and bone remodeling", Bone Key Rep., vol. 1, p. 59.
Malemud et al., 2011, "Myeloid-related protein activity in Rheumatoid Arthritis", International Journal of Interferon, Cytokine and Mediator Research, vol. 2, pp. 97 111.
Mantovani, 2009, "Inflaming metastasis", Nature, vol. 457, pp. 36 37.
McInnes et al., 2011, "The pathogenesis of rheumatoid arthritis", N. Engl. J. Med., vol. 365, No. 23, 2205-2219.
Nutsch et al. 2011, "When T cells run out of breath: the HIF-1α story", Cell, vol. 146, No. 5 pp. 673-674.
Ogata et al., 2012, "Safety and Efficacy of Tocilizumab for the Treatment of Rheumatoid Arthritis", Clin Med Insights Arthritis Musculoskelet Disord., vol. 5, pp. 27 42.
Perl, 2017, "Metabolic Control of Immune System Activation in Rheumatic Diseases", Arthritis & Rheumatology, vol. 69, No. 12, pp. 2259-2270.
Philchenkov et al., 2004, "Caspases and cancer: mechanisms of inactivation and new treatment modalities", Exp. Oncol., vol. 26, pp. 82-97.
Pollak, 2014, "Overcoming drug development bottlenecks with repurposing: repurposing biguanides to target energy metabolism for cancer treatment", Nat. Med., vol. 20, No. 6, pp. 591-593.

(56) References Cited

OTHER PUBLICATIONS

Procaccini et al., 2012, "Intracellular metabolic pathways control immune tolerance", Trends Immunol., vol. 33, No. 1, pp. 1-7.

Roodman, 2006, "Regulation of osteoclast differentiation", Ann. N. Y. Acad. Sci., vol. 1068, pp. 100-109.

Scott et al., 2010, "Rheumatoid Arthritis", Lancet, vol. 376, pp. 1094-1108.

Smolen et al., 2015, "Rheumatoid arthritis therapy reappraisal: strategies, opportunities and challenges", Nat. Rev. Rheumatol., vol. 11, pp. 276-289.

Spies et al., 2012, "Energy metabolism and rheumatic diseases: from cell to organism", Arthritis Research & Therapy, vol. 14, p. 216.

Steger et al., 2011, "Denosumab for the treatment of bone metastases in breast cancer: evidence and opinion", Ther. Adv. Med. Oncol., vol. 3, pp. 233 243.

Straub et al., 2010, "Energy regulation and neuroendocrine-immune control in chronic inflammatory diseases", J. Intern. Med., vol. 267, No. 6, pp. 543-560.

Sun, 2010, "Mechanical loading, cartilage degradation and arthritis", Annals of the New York Academy of Sciences, vol. 1211, pp. 37-50.

Takayanagi, 2009, "Osteoimmunology and the effects of the immune system on bone", Nature Reviews Rheumatology, vol. 5, pp. 667-676.

Tanaka et al., 2003, "Signal transduction pathways regulating osteoclast differentiation and function", J. Bone Miner. Metab., vol. 21, pp. 123-133.

Weaver, et al., 2003, "Cytochrome p450 inhibition using recombinant proteins and mass spectrometry/multiple reaction monitoring technology in a cassette incubation", Drug Metabolism and Disposition, vol. 31, No. 7, pp. 955-966.

Weinberg et al., 2010, "Mitochondrial metabolism and ROS generation are essential for Kras-mediated tumorigenicity", Proc. Natl. Acad. Sci. U S A, vol. 107, No. 19, pp. 8788-8793.

Weyand et al., 2017, "Immunometabolism in early and late stages of rheumatoid arthritis", Nature Reviews Rheumatology, vol. 13, pp. 291-301.

Weyand et al., 2017, "Metabolic Signatures of T-cells and Macrophages in Rheumatoid Arthritis", Curr. Opin. Immunol., vol. 46, pp. 112-120.

Wheaton et al., 2014, "Metformin inhibits mitochondrial complex I of cancer cells to reduce tumorigenesis", eLife, vol. 3, e02242.

Yang et al., 2013, "Phosphofructokinase deficiency impairs ATP generation, autophagy, and redox balance in rheumatoid arthritis T cells", J. Exp. Med., vol. 210, pp. 2119 2134.

* cited by examiner

N-ACYL-{4-[(4-ARYL-PHENYL)SULFONYLMETHYL]PIPERIDINE} COMPOUNDS AND THEIR THERAPEUTIC USE

This application claims priority to and is a 35 U.S.C. § 371 national phase application of PCT/EP2020/060879 (WO2020/212581), filed on Apr. 17, 2020. PCT/EP2020/060879 is related to, and claims priority to, Great Britain patent application number 1905520.1, filed Apr. 18, 2019, the contents of which are incorporated herein by reference in their entirety.

RELATED APPLICATION

This application is related to United Kingdom (GB) patent application number 1905520.1 filed 18 Apr. 2019, the contents of which are incorporated herein by reference in their entirety.

TECHNICAL FIELD

The present invention pertains generally to the field of therapeutic compounds. More specifically the present invention pertains to certain N-acyl-{4-[(4-aryl-phenyl)sulfonyl-methyl]piperidine} compounds (collectively referred to herein as NASMP compounds) that are useful, for example, in the treatment of disorders (e.g., diseases) including, e.g., multiple myeloma, diffuse large B-cell lymphoma, acute myeloid leukemia, eosinophilic leukemia, glioblastoma, melanoma, ovarian cancer, chemotherapy resistant cancer, radiation resistant cancer, inflammatory arthritis, rheumatoid arthritis, psoriatic arthritis, psoriasis, ulcerative colitis, Crohn's disease, systemic lupus erythematosus (SLE), lupus nephritis, asthma, chronic obstructive pulmonary disease (COPD), Hidradenitis suppurativa, autoimmune hepatitis, etc. The present invention also pertains to pharmaceutical compositions comprising such compounds, and the use of such compounds and compositions, for example, in therapy.

BACKGROUND

A number of publications are cited herein in order to more fully describe and disclose the invention and the state of the art to which the invention pertains. Each of these publications is incorporated herein by reference in its entirety into the present disclosure, to the same extent as if each individual publication was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

Cellular Metabolism

Cellular metabolism is a set of complex sequences of biochemical reactions which occur in the cells of living organisms to maintain life. Each sequence of reactions is known as a metabolic pathway, and these pathways act in concert to provide energy, the synthesis of new molecules and the breakdown and removal of other molecules within the cell. One key metabolic pathway is known as oxidative phosphorylation, the process by which energy, in the form of adenosine triphosphate (ATP), is formed by the transfer of electrons through carriers known as electron transport complexes. Other examples of metabolic pathways include glycolysis, the process by which glucose is broken down to release ATP, and beta oxidation, the process by which fatty acids are broken down.

Glycolysis occurs in the cytoplasm. Glucose, the substrate for glycolysis, is converted to pyruvate through a series of ten-enzyme-catalysed reactions. This pyruvate is, in turn, converted to lactic acid, the end product of glycolysis. ATP is directly formed through phosphate transfer from substrate to ATP, or substrate phosphorylation. Some of the pyruvate enters the tricarboxylic (TCA) cycle, whereas most of the end product, lactic acid, is flushed out of the cell. Oxidative phosphorylation occurs in the mitochondria of cells. Glutamine, glucose, or fatty acids are the suppliers for the electron transport chain and ATP is formed through a series of redox reactions involving oxygen as the final electron acceptor. The series of oxidative reduction reactions occur through the four complexes of the electron transport chain, which then generates an electrochemical gradient in the inner mitochondrial membrane. Protons return to the mitochondrial matrix through ATP synthase, and this process is coupled to ATP synthesis. A total of 36 mol of ATP are produced per 1 mol of glucose.

The metabolic properties of certain types of cells can vary greatly. For example, energy production in cancer cells is abnormally skewed towards aerobic glycolysis (a process known as the Warburg Effect), as well as showing increased fatty acid synthesis and increased rates of metabolism of the amino acid glutamine. In addition, changes in the metabolism of cancer cells may render them resistant to therapy and several studies have shown that chemoresistance, at least in part, is driven by mitochondrial metabolism and oxidative phosphorylation, whilst high levels of ATP in cancer cells can lead to increased efflux of chemotherapeutic agents and promote hypoxia-associated drug resistance.

Similar to cancer cells, immune cells show changes in metabolism depending on their activation status and the stimulatory signals they receive. The field of immunometabolism is the investigation of the interface between immunology and metabolism as it relates to both the governance of the function of immune cells, and their role in chronic inflammatory disease and cancer, among others.

Chronic Inflammatory Disease

Inflammation is the immune response of tissues due to bodily injury. Acute inflammation is a normal, protective response that protects and heals the body following physical injury or infection, characterised by heat, swelling, and redness at the site of the injury. However, if inflammation persists for a prolonged period, it becomes chronic. Chronic inflammation is a hallmark of, and a contributing factor to, a range of disease conditions including rheumatoid arthritis, inflammatory bowel disease, systemic lupus erythematosus, multiple sclerosis and psoriasis.

The inflammatory process is complex and involves a biological cascade of molecular and cellular signals that alter physiological responses. At the site of the injury, cells release molecular signals such as cytokines and interleukins that cause a number of changes in the affected area including dilation of blood vessels, increased blood flow, increased vascular permeability, invasion by leukocytes (white blood cells), and exudation of fluids containing proteins like immunoglobulins (antibodies). Several different types of leukocytes, including granulocytes, monocytes, and lymphocytes, are involved in the inflammatory cascade. However, chronic inflammation is primarily mediated by monocytes and long-lived macrophages; monocytes mature into macrophages once they leave the bloodstream and enter tissues. Macrophages engulf and digest microorganisms, foreign invaders, and senescent cells and macrophages release several different chemical mediators, including Tumour Necrosis Factor-alpha (TNFα), interleukins (e.g., IL-1, IL-6, IL-12 and IL-23) and prostaglandins that perpetuate the inflammatory response. At later stages, other cells, including lymphocytes, invade the affected tissues. Recent evidence has shown that many aberrant immune responses occur as a result of disruption to metabolic processes and that altering cellular metabolism may either enhance or reduce immune responses. Alterations in metabolism in monocytes, macrophages and lymphocytes (immunometabolism) are hence crucial in driving disease.

There is thus a common pathology underlying a wide variety of chronic inflammatory conditions. In addition, features of chronic inflammation are also observed in other diseases including cancer and metabolic diseases such as obesity, atherosclerosis, and diabetes.

One of the most common chronic inflammatory conditions is rheumatoid arthritis (RA), a condition which affects up to 2% of the population worldwide. Although it is a complex disease, there are a number of physiological, cellular, and biochemical factors associated with the progression of RA that are common to a range of other diseases, including those with a component of autoimmunity (e.g., multiple sclerosis), inflammation (e.g., atherosclerosis and cancer), bone loss (e.g., osteoporosis) and proliferation (e.g., haematological malignancies). This makes the understanding of RA important not only for the study of a much broader range of diseases, but also suggests that pharmaceutical agents that work via modification of these common processes may have utility beyond RA. The latter is borne out by clinical practice where RA drugs have been shown to have broad utility across a variety of other conditions.

Rheumatoid Arthritis and Related Autoimmune/Inflammatory Diseases

Rheumatoid arthritis (RA) is an autoimmune disorder characterized by chronic inflammation of the synovial lining of multiple joints coupled to progressive joint degradation. RA commonly affects the joints of the wrist and hands and may also affect the elbows, shoulders, hips, neck and knees leading to severe pain and disability (see, e.g., Scott et al., 2010). The World Health Organisation (WHO) Global Burden of Disease 2010 update estimated that 23.7 million people suffer from RA, with incidence rising due to the association between the condition and increasing age.

The exact cause of RA, as for all the autoimmune disorders, remains unclear, although possible triggers include reduced self-tolerance, an abnormal response to environmental factors, infectious agents, and hormonal stimulus (see, e.g., Klareskog et al., 2006; Firestein et al., 2005). A central feature of the condition is the dysregulation of innate and adaptive immunity, with an imbalance in pro-inflammatory and anti-inflammatory cytokines and a change in the balance between osteoclast-mediated degradation and osteoblast-mediated deposition in the bone marrow compartment (see, e.g., Kleyer et al., 2014; Jung et al., 2014).

At the cellular level, development of RA usually commences with T-cells infiltrating the synovial membrane lining the affected joint; this then leads to the activation of monocytes, macrophages and synovial fibroblasts by way of cell-cell contact and the subsequent release of various cytokines, including tumour necrosis factor-alpha (TNFα) and pro-inflammatory interleukins such as IL-1, IL-6, IL-12 and IL-23 (see, e.g., Astry et al., 2011). These pro-inflammatory cytokines are then instrumental in orchestrating several complex signal transduction cascades, including the NFκB, Interferon Regulatory Factor (IRF), Toll-like receptor (TLR), and Jak/STAT pathways (see, e.g., Malemud et al., 2010) which lead to the induction of genes coding for various products that propagate the inflammatory response and also promote tissue destruction. These products include tissue-degrading enzymes such as collagenases, matrix metalloproteinases (MMPs), cathepsins, and other pro-inflammatory factors such as selectins, integrins, leukotrienes, prostaglandins, chemokines, and other cytokines (see, e.g., McInnes et al., 2011; Chimenti et al., 2015). In addition, these cells also increase the production of MMPs, leading to the degradation of the extra cellular matrix and loss of cartilage within the joint (see, e.g., Sun, 2010), a process that also involves a specialised class of cells known as osteoclasts and a factor known as Receptor Activator of Nuclear Factor Kappa-B Ligand (RANKL) (see, e.g., Takayanagi, 2009).

RANKL is an essential factor for the generation of osteoclasts, and upregulated RANKL-production leads to increased osteoclast differentiation and ultimately bone destruction (see, e.g., Long et al., 2012). The inflammatory response in RA leads to the accumulation of lymphocytes, dendritic cells, and macrophages, all operating locally to produce cytokines and other pro-inflammatory mediators such as TNFα and IL-6 which further potentiate the effects of RANKL on bone destruction. In addition, the inflammatory cascade leads to the hyperplasia of synoviocytes (see, e.g., Takayanagi, 2009), which in turn leads to the thickening and vascularisation of the synovium into a destructive and aggressive tissue known as a pannus. The pannus contains both osteoclasts, which destroy bone, and metalloproteinases, which are involved in the destruction of cartilage.

As such, the RANKL axis is critical to the progression and pathology of RA as well as to the osteoimmune system (the interplay between the immune and bone systems), which is central to the pathology of a number of different disease conditions.

The Role of Immune Metabolism in RA

All cells produce adenosine triphosphate (ATP), a high-energy molecule which acts as fuel, and synthesize macromolecules to maintain their basic cellular functions, whether they are active, replicating, or quiescent (see, e.g., Spies et al., 2012). These bioenergetic needs are met by interconnected metabolic pathways within the cell:

glycolysis (the first step in the breakdown of glucose), the tricarboxylic acid cycle (a series of reactions releasing stored energy from carbohydrates, fats, and proteins), and oxidative phosphorylation (the process of forming ATP by the transfer of electrons). Changes in these pathways drive the effector functions of immune cells from lymphocytes to monocytes and macrophages and dendritic cells, and are also able to modulate cell fate.

In chronic inflammatory diseases including RA, very large amounts of energy (up to 2,000 kJ/day) are consumed by the activation of the immune system (see, e.g., Straub et al., 2010). This energy is used, at least in part, by the immune system to maintain the chronic inflammatory state in response to environmental signals (see, e.g., Procaccini et al., 2012; Nutsch et al., 2011) and the interplay between immunology and metabolism hence plays a central role in the pathophysiology of chronic inflammatory diseases (see, e.g., Perl, 2017; Ganeshan et al., 2014).

Several metabolic changes in cells that participate in inflammation are seen in immune cells in RA (see, e.g., Weyand et al., 2017a). Chronic stimulation and the synovial microenvironment alters T cell and macrophage metabolism in RA. For example, T cells from patients with RA show reduced expression of 6-phosphofructo 2-kinase/fructose-2, 6-bisphosphatase 3 (PFKFB3), an enzyme involved in ATP generation, and autophagy (see, e.g., Yang et al., 2013), whilst macrophages from patients with RA produce higher levels of ATP than cells from healthy individuals (see, e.g., Weyand et al., 2017b). In addition to direct changes in cells, the hypoxic environment in the RA synovium (see, e.g., Fearon et al., 2016) creates a chronic mitochondrial hyperpolarization, which is also seen in systemic lupus erythematosus (SLE) and in fibroblast-like synoviocytes from RA patients; there is a shift to glycolysis compared with cells from non-inflammatory settings (see, e.g., Garcia-Carbonnel et al., 2016). Thus, there is great potential for agents that modulate ATP or alter immune cell metabolism to be useful in the treatment of chronic inflammatory diseases such as RA, SLE, inflammatory bowel disease (IBD), psoriasis, and atherosclerosis.

Cellular Metabolism and Cancer

Cellular energy in the form of ATP is generated through two major pathways: mitochondrial oxidative phosphorylation and cytoplasmic glycolysis. In normal cells, glycolysis is followed by oxidation of pyruvate using the oxidative phosphorylation machinery of the mitochondria and this is the predominant pathway to generate ATP. However, in cancer cells glycolysis is upregulated and lactic acid is fermented in the cytosol of the cell in a process known as the Warburg effect. Thus, reprogrammed metabolism is a hallmark of cancer, and facilitates the growth and proliferation of cells under stressed conditions.

Mitochondrial metabolism is also important for the generation of building blocks required for cancer cell proliferation and cancer cells also require mitochondrial oxidative metabolism to maintain their redox balance. The majority of cancer cells display functional mitochondria and are able to generate ATP through mitochondrial metabolism (see, e.g., Koppenol, 2011). Depending on the cellular context, mitochondria substantially contribute to the generation of cellular reactive oxygen species (ROS) as a natural by-product of mitochondrial ATP generation. ROS formation occurs due to the incomplete reduction of molecular oxygen and in cancer cells, ROS have been shown to promote tumour development and progression by inducing oncogenic signalling, genetic instability and DNA mutations (see, e.g., Weinberg et al., 2010). However, when ROS production exceeds the capacity of intracellular ROS-detoxifying systems, cellular toxicity results. As such, cancer cells have to tightly control their metabolic machinery in order to maintain the balance between ROS generation and scavenging.

Changes in cellular and mitochondrial metabolism are thus critical for the growth and proliferation of tumours. Indeed, mitochondrial biogenesis and the associated increases in oxidative phosphorylation have been shown to promote tumour metastasis (see, e.g., LeBleu et al., 2014), whilst reducing oxidative phosphorylation has also been proposed as a means to target cancer stem cells (see, e.g., Fiorillo et al., 2016). Data also shows that targeting components of the mitochondrial electron transport chain may have anti-cancer effects. For example, complex I inhibition by the anti-diabetic metformin inhibits tumorigenesis (see, e.g., Evans et al., 2005; Pollak et al., 2014; Wheaton et al., 2014; Bridges et al., 2014) whilst novel small molecule inhibitors of electron transport also show anti-tumour activity in xenograft models of cancer (see, e.g., Ellinghaus et al., 2013). Altering cellular metabolism is thus emerging as a means by which to prevent cancer growth and progression, as well as to overcome resistance to chemotherapy and prevent metastasis.

The Osteoimmune System and Bone Disorders

The osteoimmune system is a term for the combined and related interplay between the immune system and the skeletal system.

Under normal physiological conditions, the skeletal system provides support, mobility, protection for vital organs, and a mineral reservoir for calcium and phosphate. In order to achieve and adapt to these functions, the skeleton exists in a dynamic equilibrium characterized by continuous osteoclast-mediated bone resorption and osteoblast-mediated bone deposition (see, e.g., Karsenty et al., 2002). This biological process has been termed bone "remodelling" and occurs in coupled fashion with osteoblasts producing the key osteoclast differentiation factors, including RANKL, described above, and osteoclasts promoting bone formation by producing osteoblastic mediators as they degrade bone.

Both innate and adaptive immune cells exert effects on osteoclasts and osteoblasts through a variety of cell-surface and secreted mediators (see, e.g., Takayanagi, 2009). Activation of the RANKL receptor (RANK) on osteoclast precursors starts a cascade of transcriptional changes which results in the formation of osteoclasts and the expression of the machinery needed for bone resorption including molecules needed for attachment to bone, acid secretion, and proteolysis. Many of the transcription factors important for osteoclast differentiation are key regulators of immune responses, such as NFκB and nuclear factor of activated T cells c1 (NFATc1) and this process is also potentiated by factors involved in inflammation such as TNFα and IL-6.

In addition to its critical role in the progression and pathogenesis of RA, the osteoimmune system plays a critical role in a number of other diseases including osteoporosis and other bone disorders and cancer (see, e.g., Dallas et al., 2011).

Osteoporosis is a common disease characterised by reduced bone density, deterioration of bone tissue, and an increased risk of fracture. Many factors contribute to the pathogenesis of osteoporosis including poor diet, lack of exercise, smoking, and excessive alcohol intake. Osteoporosis also arises in association with inflammatory diseases such as rheumatoid arthritis, endocrine diseases such as thyrotoxicosis, and with certain drug treatments such as treatment with glucocorticoids. Indeed, osteoporosis-related fragility fractures represent one of the most important complications that may occur in patients with rheumatic diseases such as RA, systemic lupus erythematosus, and ankylosing spondylitis.

Paget's disease of bone is a common condition of unknown cause, characterised by increased bone turnover and disorganised bone remodelling, with areas of increased osteoclastic and osteoblast activity. Although Pagetic bone is often denser than normal, the abnormal architecture causes the bone to be mechanically weak, resulting in bone deformity and increased susceptibility to pathological fracture.

IL-6, TNFα, and RANKL signalling have been shown to play a major role in osteoclast over-activity and a consequent increase in bone loss (see, e.g., Tanaka et al., 2003; Roodman, 2006). The use of drugs which affect these pathways have been validated by the completion of clinical trials of the monoclonal antibody against RANKL, AMG-162 (Denosumab®, Amgen), for the treatment of osteoporosis/multiple myeloma, as well as by an increasing body of evidence that shows that the anti-TNFα and anti-IL-6 therapies also prevent bone loss in arthritic diseases (see, e.g., Ogata et al., 2012; Billiau, 2010).

The Osteoimmune System and Cancer

Many types of cancer affect bone. Cancer-associated bone disease can be manifest by the occurrence of hypercalcaemia or the development of osteolytic and/or osteosclerotic metastases. Increased osteoclastic bone resorption plays a key role in the pathogenesis of both conditions. Whilst almost any cancer can be complicated by bone metastases, the most common sources are multiple myeloma, breast carcinoma, and prostate carcinoma. The most common tumours associated with hypercalcaemia are multiple myeloma, breast carcinoma, and lung carcinoma.

As described above, RANK/RANKL signalling is essential for osteoclast formation and bone resorption that occurs during skeletal remodelling. While physiological levels of RANK/RANKL signalling stimulate the proliferation and cell survival of mammary epithelial cells, aberrant RANK/RANKL signalling in these tissues has recently been shown to influence the onset and progression of breast tumorigenesis and blocking RANKL signalling using denosumab (Xgeva®, Amgen) has been shown to be an effective in preventing the secondary complications of bone metastases, such as pathologic fracture, and hypercalcaemia in patients with breast cancer (see, e.g., Steger et al., 2011).

Therapies that block RANK/RANKL signalling may also decrease the ability of osteotropic cancers to metastasize to bone. Signalling through RANK on the surface of human epithelial tumour cells as well as melanoma cells has been shown to induce a chemotactic response in these tumour cells whilst in a murine model of melanoma metastasis, therapeutic treatment of mice with osteoprotegrin, which neutralizes the RANKL receptor, RANK, significantly reduced tumour burden within the bones but not other organs.

In addition to a role for RANKL in cancer, there is growing evidence that activation of NFκB via molecules such as TNFα can play a major role in the promotion and progression of both haematological malignancies, such as myeloma and lymphomas, and solid tumours, such as breast, prostate, and lung cancer (see, e.g., Baud et al., 2009). There is also rising awareness of the role and importance of inflammation and the osteoimmune system in cancer and in the development of resistance to radiotherapy and to chemotherapeutic agents. Furthermore, it has been suggested that inflammation is in fact one of the basic hallmarks of cancer (see, e.g., Mantovani, 2009). Improving the efficacy of anti-cancer treatments by prevention of NFκB activation is therefore a promising strategy to augment existing therapeutic regimes and is currently under investigation, most notably for the treatment of multiple myeloma.

Defects in the normal apoptotic pathways are also implicated in the development and progression of tumour cell growth as well as in inflammation. Apoptosis (programmed cell death) plays a key role in the removal of abnormal cells; defects in the signalling cascades, which would normally lead to its induction, play a key role in oncogenesis. Radiotherapy and many chemotherapeutic agents act by causing cellular damage, which would normally induce apoptosis; defects in the pathway will therefore also reduce the effectiveness of such agents. The most important effector molecules in the signalling pathway leading to apoptosis are known as the caspases, which may be triggered by a number of stimuli, including TNFα binding to its receptor. Mutations in the genes which encode for the caspases have been found in a number of tumour types, including gastric, breast, renal cell, and cervical cancers as well as commonly in T-cell lymphoblastic lymphoma and basal cell ameloblastomas (see, e.g., Philchenkov et al., 2004). Compounds which activate caspases, and thus sensitise cells to apoptosis, would be highly effective as cancer therapies either as single agents or in enhancing the effectiveness of existing cancer chemotherapy and radiotherapy.

Agents that Modulate Cellular and Immune Metabolism, Prevent Inflammation, and Modify the Osteoimmune System The inventors have identified new compounds which, for example, modulate cellular and immune metabolism, prevent inflammation, and modify the osteoimmune system, and accordingly are useful in treatment of corresponding disorders, as described herein.

Without wishing to be bound by any particular theory, the inventors believe that this action may be via a mechanism that involves modulating cellular, and immune cell metabolism by reducing cellular ATP, with consequent effects on inflammatory signalling.

Known Compounds

Greig et al., 2010a, describes certain biphenyl-4-sulfonic acid amides for the treatment of inflammation and/or joint destruction and/or bone loss; disorders mediated by excessive and/or inappropriate and/or prolonged activation of the immune system; inflammatory and autoimmune disorders, for example, rheumatoid arthritis, psoriasis, psoriatic arthritis, chronic obstructive pulmonary disease (COPD), atherosclerosis, inflammatory bowel disease, and ankylosing spondylitis; disorders associated with bone loss, such as bone loss associated with excessive osteoclast activity in rheumatoid arthritis, osteoporosis, cancer-associated bone disease, and Paget's disease; and cancer, such as a haematological malignancy and a solid tumour. Examples of compounds shown therein include the following:

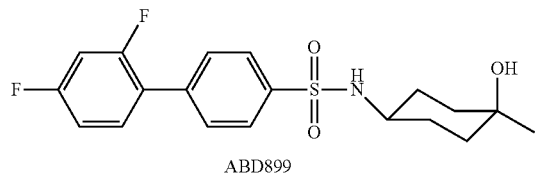

ABD899

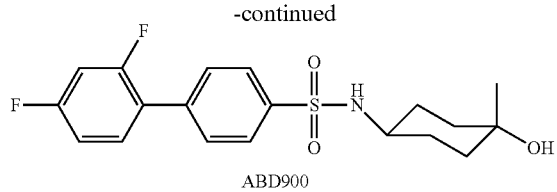

ABD900

Patel et al., 2014 and Patel et al., 2016 describe certain substituted N-(4-hydroxy-4-methyl-cyclohexyl)-4-phenyl-benzenesulfonamide and N-(4-hydroxy-4-methyl-cyclohexyl)-4-(2-pyridyl)benzenesulfonamide compounds (e.g., HMC-C-01, shown below) for the treatment of inflammation and/or joint destruction and/or bone loss; disorders mediated by excessive and/or inappropriate and/or prolonged activation of the immune system; inflammatory and autoimmune disorders, for example, rheumatoid arthritis; psoriasis; psoriatic arthritis; chronic obstructive pulmonary disease (COPD); asthma; atherosclerosis; inflammatory bowel disease; ankylosing spondylitis; multiple sclerosis; systemic lupus erythematosus; Sjogren's syndrome; a disorder associated with bone loss, such as bone loss associated with excessive osteoclast activity in rheumatoid arthritis, osteoporosis, cancer-associated bone disease, or Paget's disease; cancer, such as a haematological malignancy, such as multiple myeloma, leukemia, or lymphoma, or a solid tumour cancer, such as bladder cancer, breast cancer (female and/or male), colon cancer, renal cell carcinoma, kidney cancer, lung cancer, pancreatic cancer, gastric cancer, prostate cancer, brain cancer, skin cancer, thyroid cancer, basal cell ameloblastoma, or melanoma; a disorder associated with fibrosis, such as systemic sclerosis or scleroderma; or a rare vasculitide, such as Behçet's disease.

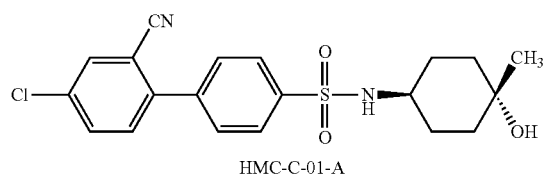 [SMILES: C[C@]1(O)CC[C@H](NS(=O)(=O)c2ccc(-c3ccc(Cl)cc3C#N)cc2)CC1]

HMC-C-01-A

Riemer et al., 1996, describes certain benzyl piperidine derivatives of the following formula which are allegedly useful in the treatment of psychotic disorders which are caused by damage to the dopamine system.

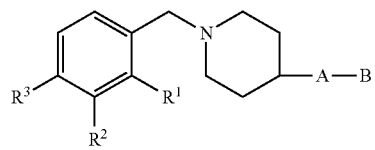

Duan et al., 2003, describes certain barbituric acid derivatives of the following formula which are allegedly useful as TACE inhibitors.

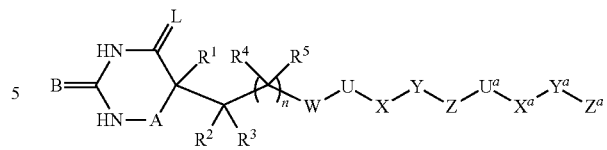

Li et al., 2006, describes certain compounds of the following formula which are allegedly inhibitors of 11-beta hydroxysteroid dehydrogenase type I (11β-HSD1).

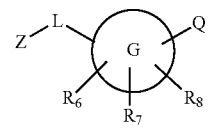

Hayashi et al., 2007, describes certain compounds of the following formula which are allegedly useful as MMP-13 selective inhibitors.

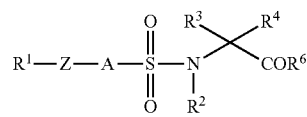

Moore et al., 2008, describes certain compounds of the following formula which are allegedly useful as modulators of the secreted frizzled related protein-1 for the treatment of osteoporosis, arthritis, COPD, etc.

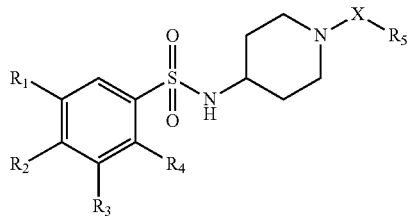

Fang et al., 2008, describes certain compounds of the following formula which are allegedly useful in the treatment of metabolic disorders such as diabetes mellitus (type I and type II), obesity, and related disorders.

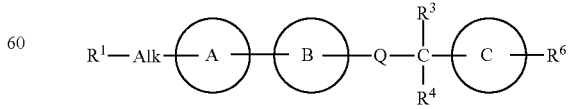

Horiuchi et al., 2009, describes certain compounds of the following formula which are allegedly useful in the treatment of diabetes.

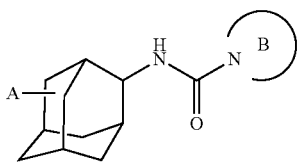

Lack et al., 2011, describe certain compounds (see Table 1 on page 8566 therein) which are allegedly useful as androgen receptor inhibitors for the treatment of prostate cancer.

Lee et al., 2003, describes certain piperidine derivatives of the following formula which are allegedly useful as GPR119 agonists.

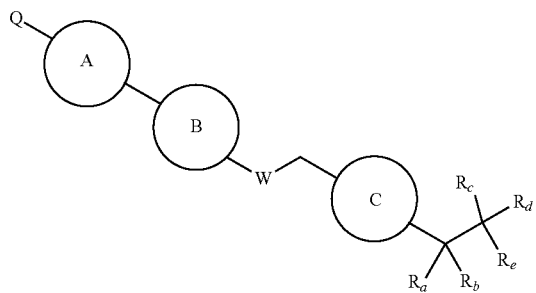

Bilotta et al., 2014, describes certain compounds of the following formula which are allegedly useful in the treatment of HCV infection.

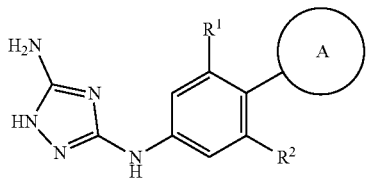

New Compounds with Improved Properties

In addition to having excellent biological properties, e.g., similar to or better than the related sulfonamide compounds (for example, as described in Greig et al., 2010a, Patel et al., 2014, and Patel et al., 2016), the NASMP compounds described herein have the additional advantage of forming little or none of an undesirable sulphonamide metabolite.

For example, as demonstrated by the data presented herein, the related sulfonamide compounds (for example, reference compound HMC-C-01-A) give rise to a biaryl sulphonamide metabolite (for example, MET-001) which has a long half-life and therefore persists in the circulation. This biaryl sulphonamide metabolite may induce metabolism in rats, thus complicating the assessment of toxicity in rodents, and potentially, in turn, impacting the developability of the compounds for human use. Therefore, compounds with a lower propensity to form a biaryl sulphonamide metabolite have a greater potential developability for human use.

As demonstrated by the data presented herein, the NASMP compounds show greatly reduced propensity to form a biaryl sulphonamide metabolite, and so have greatly increased suitability for development for human use, as compared to the known sulfonamide compounds.

In addition, the NASMP compounds described herein have other advantageous properties, equal to and often better than the properties of the related sulfonamide compounds, including, for example, improved metabolism and solubility.

If a drug is to be used in the clinic, it must have a suitable pharmacokinetic profile. It must show adequate absorption to allow dosing to humans at levels suitable to act at the therapeutic target. Solubility is a key factor in driving absorption of compounds into the circulation from the gastrointestinal tract. In addition, the drug must have an adequate distribution and metabolism profile to ensure dosing can occur at regular intervals, for example, once or twice daily.

The NASMP compounds described herein show good solubility and thus have good propensity to be absorbed from the gastrointestinal tract.

The NASMP compounds described herein also show significant advantages in their in vitro metabolic stability and their reduced propensity to form a metabolism inducing biaryl sulphonamide metabolite, e.g., similar to MET-001.

The optimisation of the metabolic and pharmacokinetic properties (Absorption, Distribution, Metabolism, Excretion—ADME) of a drug is a developmental barrier of equal challenge and importance as compared to the optimization of pharmacodynamics (action of the drug on the body) and safety (adverse effects) properties. The NASMP compounds described herein provide substantial advantages as oral therapeutic agents (as compared to the known compounds) by improving their metabolic and pharmacokinetic properties with little or no change loss of potency against the biological target.

The NASMP compounds described herein combine the required characteristics of agents for the treatment of, for example, autoimmune/inflammatory conditions and cancer, as described herein.

SUMMARY OF THE INVENTION

One aspect of the invention pertains to certain substituted N-acyl-{4-[(4-aryl-phenyl) sulfonylmethyl]piperidine} compounds (collectively referred to herein as NASMP compounds), as described herein.

Another aspect of the invention pertains to a composition (e.g., a pharmaceutical composition) comprising a NASMP compound, as described herein, and a carrier, diluent, or excipient (e.g., a pharmaceutically acceptable carrier, diluent, or excipient).

Another aspect of the invention pertains to a method of preparing a composition (e.g., a pharmaceutical composition) comprising the step of mixing a NASMP compound, as described herein, and a carrier, diluent, or excipient (e.g., a pharmaceutically acceptable carrier, diluent, or excipient).

Another aspect of the present invention pertains to a NASMP compound, as described herein, for use in a method of treatment of the human or animal body by therapy, for example, for use a method of treatment of a disorder (e.g., a disease) as described herein.

Another aspect of the present invention pertains to use of a NASMP compound, as described herein, in the manufacture of a medicament for treatment, for example, treatment of a disorder (e.g., a disease) as described herein.

Another aspect of the present invention pertains to a method of treatment, for example, of a disorder (e.g., a disease) as described herein, comprising administering to a patient in need of treatment a therapeutically effective amount of a NASMP compound, as described herein, preferably in the form of a pharmaceutical composition.

Another aspect of the present invention pertains to a kit comprising (a) a NASMP compound, as described herein, preferably provided as a pharmaceutical composition and in a suitable container and/or with suitable packaging; and (b) instructions for use, for example, written instructions on how to administer the compound.

Another aspect of the present invention pertains to a NASMP compound obtainable by a method of synthesis as described herein, or a method comprising a method of synthesis as described herein.

Another aspect of the present invention pertains to a NASMP compound obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspects of the invention.

DETAILED DESCRIPTION OF THE INVENTION

Compounds

Figure 1:
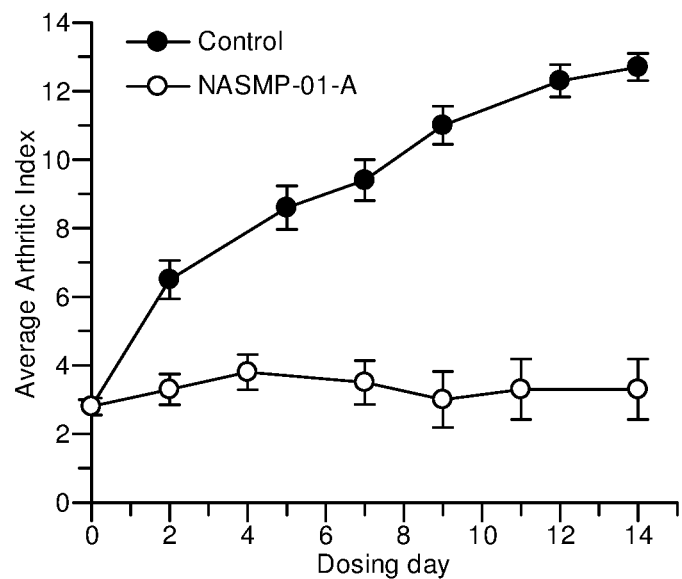
FIG. 1 is a graph of average arthritic index as a function of time (dosing day) for invention compound NASMP-01-A dosed at 10 mg/kg/day by oral gavage (open circles) and control (solid circles).
Figure 2:
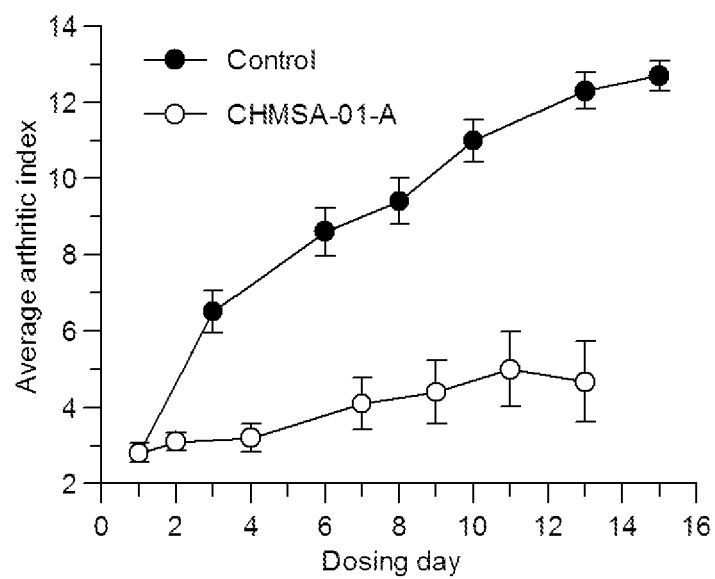
FIG. 2 is a graph of average arthritic index as a function of time (dosing day) for reference compound CHMSA-01-A dosed at 10 mg/kg/day by oral gavage (open circles) and control (solid circles).
Figure 3:
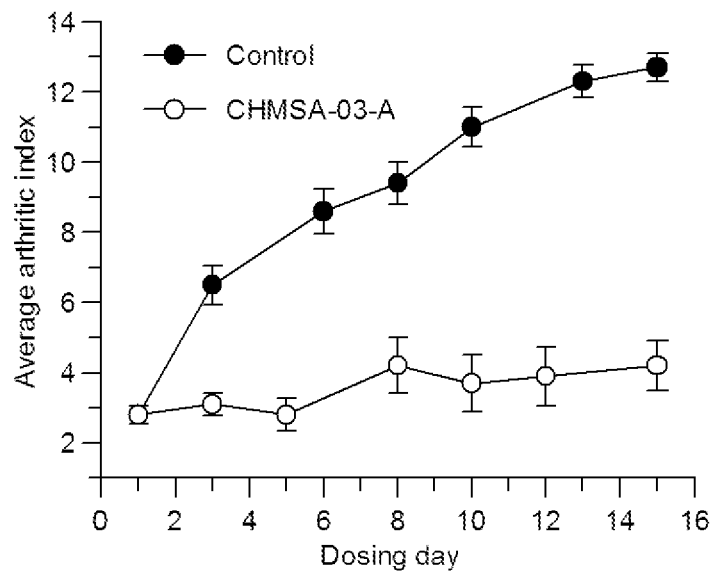
FIG. 3 is a graph of average arthritic index as a function of time (dosing day) for test reference CHMSA-03-A dosed at 10 mg/kg/day by oral gavage (open circles) and control (solid circles).
Figure 4:
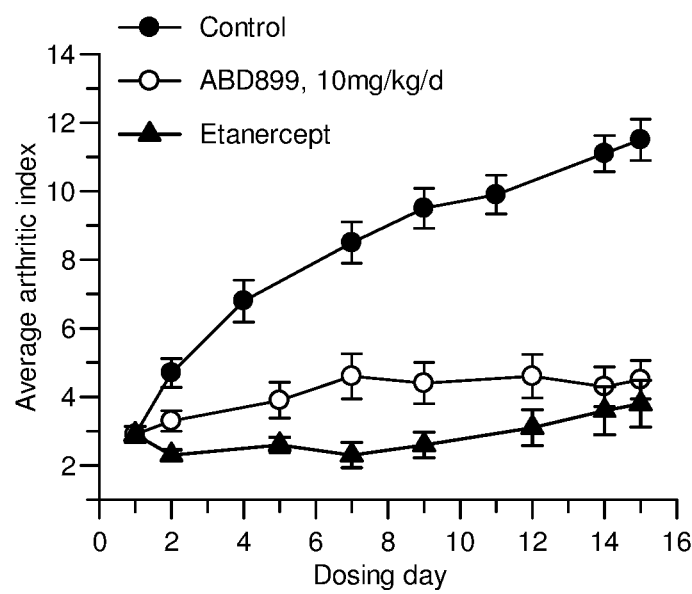
FIG. 4 is a graph of arthritic index as a function of time (dosing day) for reference compound ABD899 dosed at 10 mg/kg/day (open circles), control (solid circles), and positive control, the marketed drug etanercept (triangles).
Figure 5:
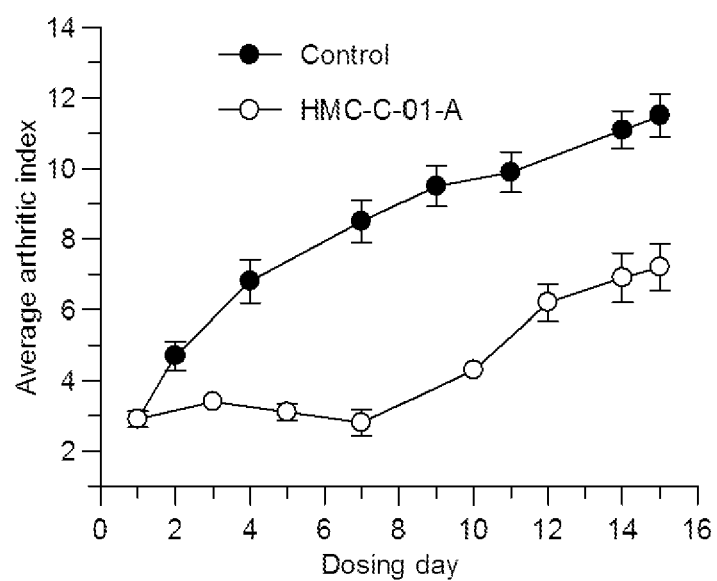
FIG. 5 is a graph of arthritic index as a function of time (dosing day) for reference compound HMC-C-01-A dosed at 10 mg/kg/day (open circles), and control (solid circles).

One aspect of the present invention relates to certain substituted N-acyl-{4-[(4-aryl-phenyl) sulfonylmethyl]piperidine} compounds which are related to the following biphenyl and pyridyl-phenyl compounds:

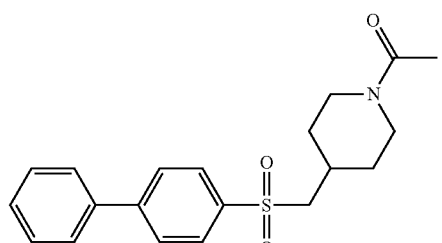

1-[4-[(4-phenylphenyl)
sulfonylmethyl]-
1-piperidyl]ethanone

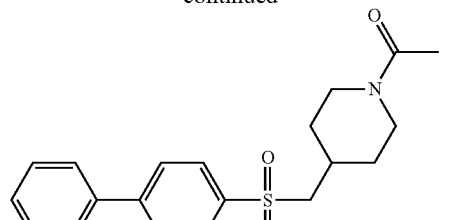

1-[4-[[4-(2-pyridyl)phenyl]
sulfonylmethyl]-
1-piperidyl]ethanone

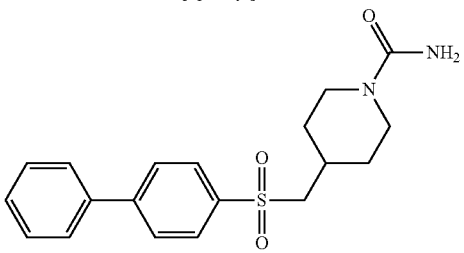

4-[(4-phenylphenyl)
sulfonylmethyl]piperidine-
1-carboxamide

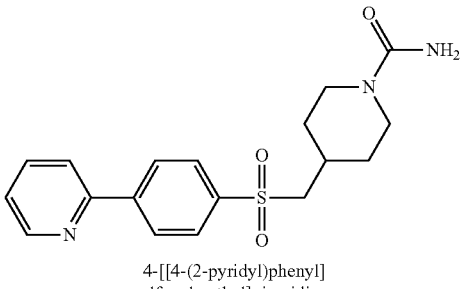

4-[[4-(2-pyridyl)phenyl]
sulfonylmethyl]piperidine-
1-carboxamide

Thus, one aspect of the present invention is a compound of the following formula, or a pharmaceutically acceptable salt or solvate thereof, wherein =X—, —$R^1$, —$R^2$, —$R^3$, —$R^4$, —$R^A$, —$R^B$, m, and n are as defined herein (for convenience, collectively referred to herein as "N-acyl-{4-[(4-aryl-phenyl)sulfonylmethyl]piperidine} compounds" and "NASMP compounds"):

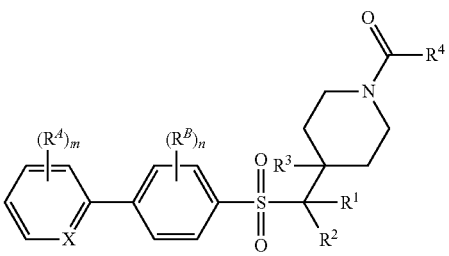

The Piperidine Ring

Unless otherwise indicated, it is intended that all relative orientations of substituents on the piperidine ring, and all conformations of the piperidine ring ("chair", "boat", "twist", etc.) are encompassed by a reference to a compound that does not specify a particular orientation and/or conformation.

The bond joining the nitrogen atom of the piperidine ring to the C(=O)R⁴ group may be subject to restricted rotation and may give rise to rotamers. Unless otherwise indicated, it is intended that all such rotamers are encompassed by a reference to a compound that does not specify a particular rotamer.

Configuration of Carbon to which —R¹ and —R² are Attached

Note that, depending upon the identity of the groups —R¹ and —R², the carbon atom to which they are attached may be chiral, and so may be in the (R) or (S) configuration.

Unless otherwise indicated, it is intended that all such configurations are encompassed by a reference to a compound that does not specify a particular configuration.

Compounds in one configuration may be indicated as follows:

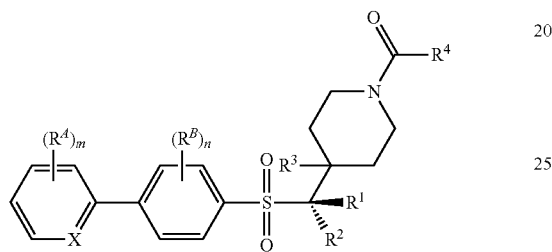

Compounds in the other configuration may be indicated as follows:

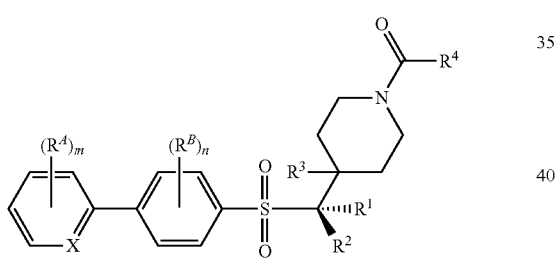

Other Substituents on the Piperidine Ring

For the avoidance of doubt, it is intended that, other than —R³ (which may be —H) and —C(=O)R⁴, the piperidine ring has no other non-hydrogen substituents.

Conformation of the Biaryl Group

Note that, depending upon the identity of the "m" groups —R$^A$, "n" groups —R$^B$, and X, there may be free rotation about the single bond joining the two aryl groups.

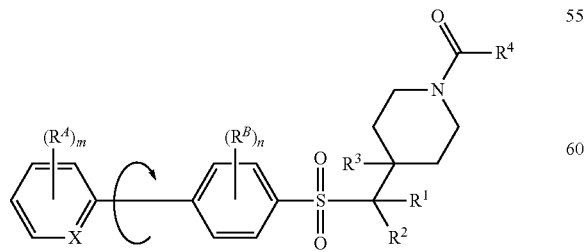

For the avoidance of doubt, it is intended that all such rotational conformations (i.e., different rotations about the single bond joining the two aryl groups) are encompassed. For example, the following formulae are intended to be equivalent and represent the same group:

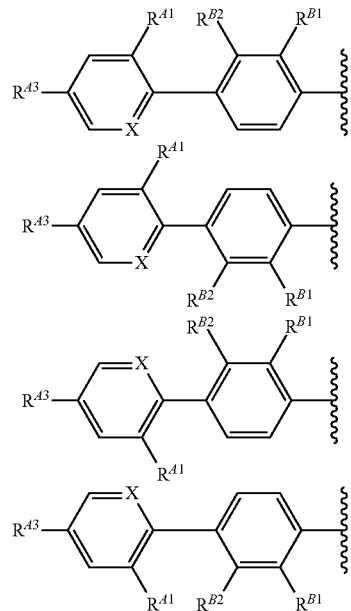

EMBODIMENTS

Some embodiments of the invention include the following:

(1) A compound of the following formula:

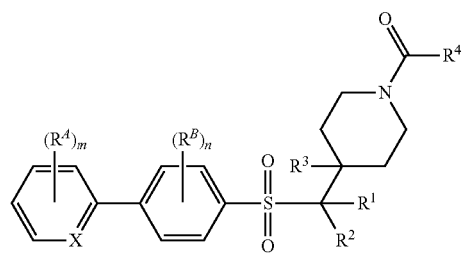

or a pharmaceutically acceptable salt or solvate thereof; wherein:

—X= is independently —CH= or —N=;

"m" is independently 0, 1, 2, or 3;

each —R$^{AC}$ is independently —F, —Cl, —R$^{AC}$, —R$^{AF}$, or —CN;

—R$^{AC}$ is independently saturated linear or branched $C_{1-3}$alkyl;

—R$^{AF}$ is independently saturated linear or branched $C_{1-3}$fluoroalkyl;

"n" is independently 0, 1, or 2;

each —R$^B$ is independently —F, —Cl, —R$^{BC}$, —R$^{BF}$, or —CN;

—R$^{BC}$ is independently saturated linear or branched $C_{1-3}$alkyl;

—R$^{BF}$ is independently saturated linear or branched $C_{1-3}$fluoroalkyl;

—R¹ is independently —H or —R$^{1X}$;

—$R^{1X}$ is independently —F, —$R^{1C}$, or —$R^{1F}$;
—$R^{1C}$ is independently saturated linear or branched $C_{1-3}$alkyl;
—$R^{1F}$ is independently saturated linear or branched $C_{1-3}$fluoroalkyl;
—$R^2$ is independently —H or —$R^{2X}$;
—$R^{2X}$ is independently —F, —$R^{2C}$, or —$R^{2F}$;
—$R^{2C}$ is independently saturated linear or branched $C_{1-3}$alkyl;
—$R^{2F}$ is independently saturated linear or branched $C_{1-3}$fluoroalkyl;
or —$R^1$ and —$R^2$, taken together with the carbon atom to which they are attached, form saturated $C_{3-6}$cycloalkyl;
—$R^3$ is independently —H or —$R^{3X}$;
—$R^{3X}$ is independently —$R^{3C}$ or —$R^{3F}$;
—$R^{3C}$ is independently saturated linear or branched $C_{1-3}$alkyl;
—$R^{3F}$ is independently saturated linear or branched $C_{1-3}$fluoroalkyl;
—$R^4$ is independently —$R^{4C}$, —$R^{4CC}$, or —N($R^{4N1}$)($R^{4N2}$);
—$R^{4C}$ is independently saturated linear or branched $C_{1-6}$ alkyl;
—$R^{4CC}$ is independently saturated $C_{3-6}$cycloalkyl;
—$R^{4N1}$ is independently —H or —$R^{4N1C}$;
—$R^{4N1C}$ is independently saturated linear or branched $C_{1-4}$alkyl;
—$R^{4N2}$ is independently —H or —$R^{4N2C}$; and
—$R^{4N2C}$ is independently saturated linear or branched $C_{1-4}$alkyl.
or —N($R^{4N1}$)($R^{4N2}$) is independently azetidinyl, pyrrolidinyl, piperidinyl, piperazinyl, or morpholinyl, and is optionally substituted with one or more saturated linear or branched $C_{1-4}$ alkyl groups.

Unless otherwise indicated, where a compound is shown or described which has one or more chiral centres, and two or more stereoisomers are possible, all such stereoisomers are disclosed and encompassed, both individually (e.g., as isolated from the other stereoisomer(s)) and as mixtures (e.g., as equimolar or non-equimolar mixtures of two or more stereoisomers). For example, unless otherwise indicated, where a compound has one chiral centre, each of the (R) and (S) enantiomers are disclosed and encompassed, both individually (e.g., as isolated from the other enantiomer) and as a mixture (e.g., as equimolar or non-equimolar mixtures of the two enantiomers).

For the avoidance of doubt, when —X═ is —CH═, and "m" is non-zero, then —X═ may be —C($R^4$)═.

The term "saturated linear or branched $C_{1-3}$alkyl" means —$CH_3$ (methyl), —$CH_2CH_3$ (ethyl), —$CH_2CH_2CH_3$ (n-propyl), and —$CH(CH_3)_2$ (iso-propyl).

The term "saturated linear or branched $C_{1-4}$ alkyl" additionally includes —$CH_2CH_2CH_2CH_3$ (n-butyl), —$CH_2CH(CH_3)_2$ (iso-butyl), —$CH(CH_3)CH_2CH_3$ (sec-butyl), and —$C(CH_3)_3$ (tert-butyl).

The term "saturated linear or branched $C_{1-6}$alkyl" additionally includes, e.g., —$CH_2CH_2CH_2CH_2CH_3$ (n-pentyl), —$CH_2CH_2CH(CH_3)_2$ (iso-pentyl), —$CH_2CH_2CH_2CH_2CH_2CH_3$ (n-hexyl), —$CH_2CH_2CH_2CH(CH_3)_2$ (iso-hexyl), etc.

The term "saturated linear or branched $C_{1-3}$fluoroalkyl" means a saturated linear or branched $C_{1-3}$alkyl group substituted with one or more fluoro groups. Accordingly, $C_{1-3}$fluoroalkyl includes, e.g., —$CF_3$, —$CH_2F$, —$CHF_2$, —$CH_2CF_3$, —$CH_2CH_2F$, etc.

The term "saturated $C_{3-6}$ cycloalkyl" means cyclopropyl, cyclobutyl, cyclopentyl, and cyclohexyl.

The Group=X—

(2) A compound according to (1), wherein —X═ is —CH═.

(3) A compound according to (1), wherein —X═ is —N═.

The Index "m"

(4) A compound according to any one of (1) to (3), wherein "m" is independently 0, 1, or 2.

(5) A compound according to any one of (1) to (3), wherein "m" is 1 or 2 or 3.

(6) A compound according to any one of (1) to (3), wherein "m" is 1 or 2.

(7) A compound according to any one of (1) to (3), wherein "m" is 1.

(8) A compound according to any one of (1) to (3), wherein "m" is 2.

(9) A compound according to any one of (1) to (3), wherein "m" is 3.

The Group —$R^A$

(10) A compound according to any one of (1) to (9), wherein each —$R^A$, if present, is independently —F, —Cl, or —CN.

(11) A compound according to any one of (1) to (9), wherein each —$R^A$, if present, is —F.

(12) A compound according to any one of (1) to (9), wherein each —$R^A$, if present, is —Cl.

The Group —$R^{AC}$

(13) A compound according to any one of (1) to (12), wherein each —$R^{AC}$, if present, is —$CH_3$.

The Group —$R^{AF}$

(14) A compound according to any one of (1) to (13), wherein each —$R^{AF}$, if present, is —$CF_3$.

The Index "n"

(15) A compound according to any one of (1) to (14), wherein "n" is independently 1 or 2.

(16) A compound according to any one of (1) to (14), wherein "n" is 0.

(17) A compound according to any one of (1) to (14), wherein "n" is 1.

(18) A compound according to any one of (1) to (14), wherein "n" is 2.

The Group —$R^B$

(19) A compound according to any one of (1) to (18), wherein each —$R^B$, if present, is independently —F, —Cl, or —CN.

(20) A compound according to any one of (1) to (18), wherein each —$R^B$, if present, is —F.

(21) A compound according to any one of (1) to (18), wherein each —$R^B$, if present, is —Cl.

The Group —$R^{BC}$

(22) A compound according to any one of (1) to (21), wherein each —$R^{BC}$, if present, is —$CH_3$.

The Group —$R^{BF}$

(23) A compound according to any one of (1) to (22), wherein each —$R^{BF}$, if present, is —$CF_3$.

The Terminal Aryl Group

(24) A compound according to (1), wherein the group:

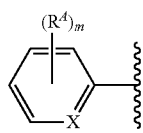

is independently selected from:

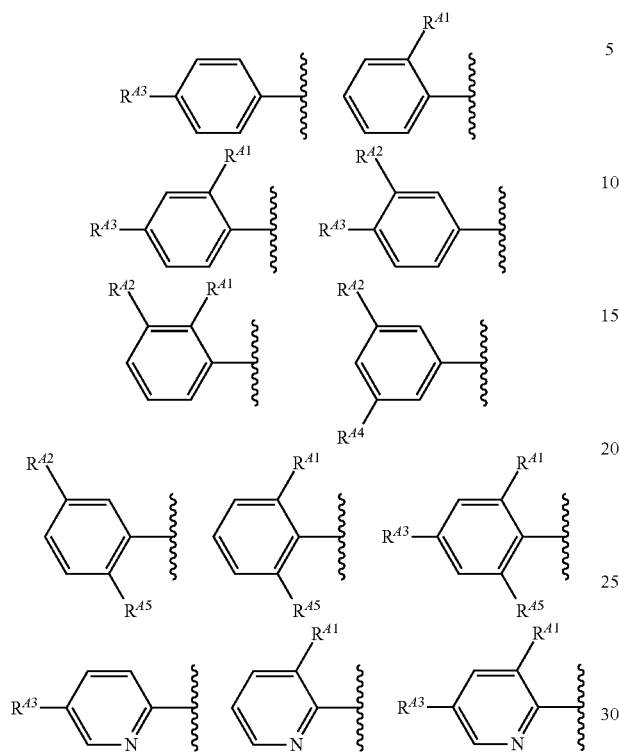

wherein each of —$R^{A1}$, —$R^{A2}$, —$R^{A3}$, —$R^{A4}$, and —$R^{A5}$ is independently as defined for —$R^A$.

(25) A compound according to (1), wherein the group:

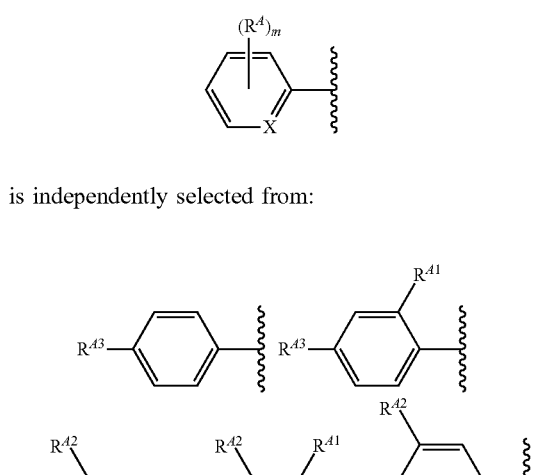

is independently selected from:

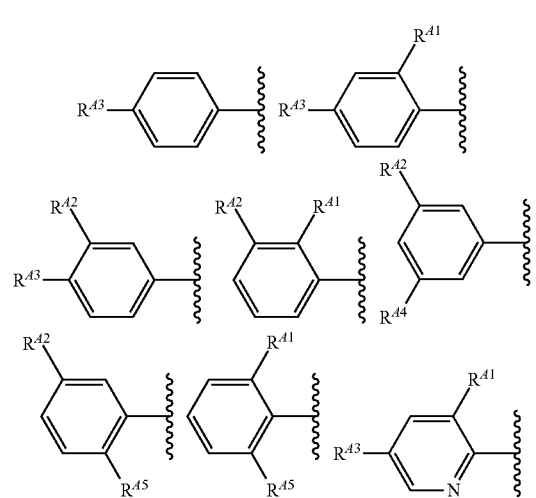

wherein each of —$R^{A1}$, —$R^{A2}$, —$R^{A3}$, —$R^{A4}$, and —$R^{A5}$ is independently as defined for —$R^A$.

(26) A compound according to (1), wherein the group:

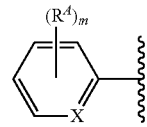

is independently selected from:

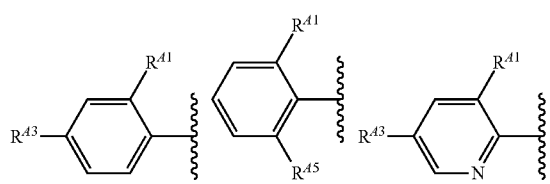

wherein each of —$R^{A1}$, —$R^{A3}$, and —$R^{A5}$ is independently as defined for —$R^A$.

(27) A compound according to (1), wherein the group:

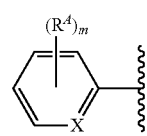

is:

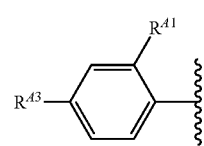

wherein each of —$R^{A1}$ and —$R^{A3}$ is independently as defined for —$R^A$.

The Linking Phenylene Group

(28) A compound according to any one of (1) and (24) to (27), wherein the group:

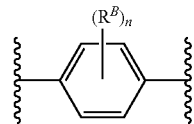

is independently selected from:

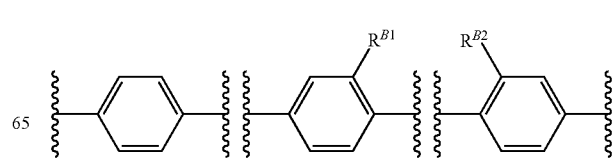

-continued

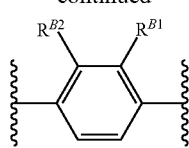

wherein each of —$R^{B1}$ and —$R^{B2}$ is independently as defined for —$R^B$.

(29) A compound according to any one of (1) and (24) to (27), wherein the group:

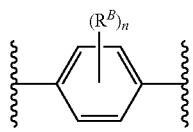

is independently selected from:

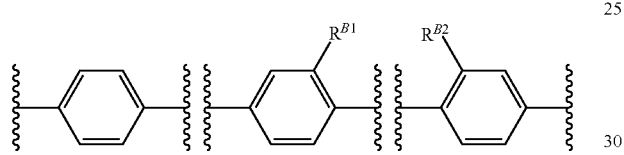

wherein each of —$R^{B1}$ and —$R^{B2}$ is independently as defined for —$R^B$.

(30) A compound according to any one of (1) and (24) to (27), wherein the group:

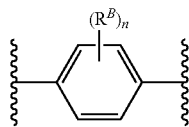

is:

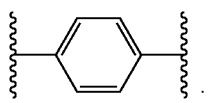

(31) A compound according to any one of (1) and (24) to (27), wherein the group:

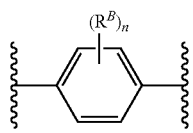

is independently selected from:

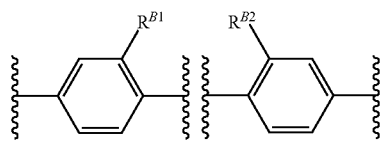

wherein each of —$R^{B1}$ and —$R^{B2}$ is independently as defined for —$R^B$.

The Biaryl Group

(32) A compound according to (1), wherein the group:

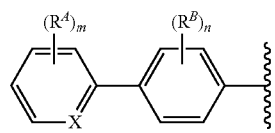

is independently selected from:

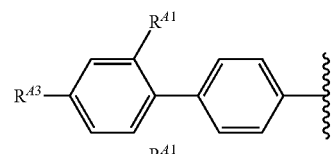

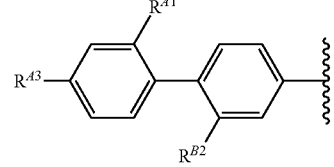

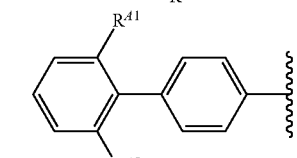

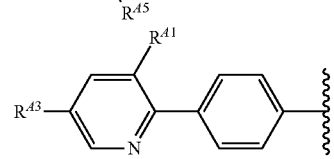

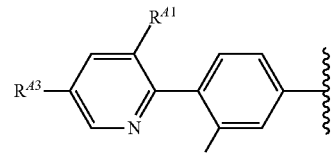

wherein:
each of —$R^{A1}$, —$R^{A3}$, and —$R^{A5}$ is independently as defined for —$R^A$; and
—$R^{B2}$ is independently as defined for —$R^B$.

(33) A compound according to (1), wherein the group:

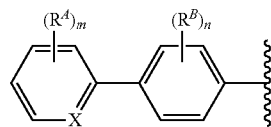

is independently selected from:

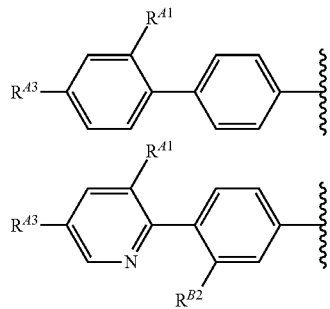

wherein:
each of —$R^{A1}$ and —$R^{A3}$ is independently as defined for —$R^A$; and
—$R^{B2}$ is independently as defined for —$R^B$.

(34) A compound according to (1), wherein the group:

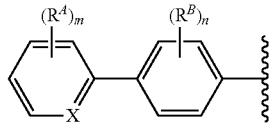

is:

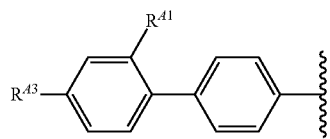

wherein each of —$R^{A1}$ and —$R^{A3}$ is independently as defined for —$R^A$.

The Group —$R^{A1}$

(35) A compound according to any one of (24) to (34), wherein —$R^{A1}$, if present, is independently —F, —Cl, —$R^{A1C}$, —$R^{A1F}$ or —CN.

(36) A compound according to any one of (24) to (34), wherein —$R^{A1}$, if present, is independently —F, —Cl, or —CN.

(37) A compound according to any one of (24) to (34), wherein —$R^{A1}$, if present, is —F.

(38) A compound according to any one of (24) to (34), wherein —$R^{A1}$, if present, is —Cl.

(39) A compound according to any one of (24) to (34), wherein —$R^{A1}$, if present, is —CN.

(40) A compound according to any one of (24) to (34), wherein —$R^{A1}$, if present, is —$R^{A1C}$.

(41) A compound according to any one of (24) to (34), wherein —$R^{A1}$, if present, is —$R^{A1F}$.

The Group —$R^{A1C}$

(42) A compound according to any one of (24) to (41), wherein —$R^{A1C}$, if present, is —$CH_3$.

The Group —$R^{A1F}$

(43) A compound according to any one of (24) to (42), wherein —$R^{A1F}$, if present, is —$CF_3$.

The Group —$R^{A2}$

(44) A compound according to any one of (24) to (43), wherein —$R^{A2}$, if present, is independently —F, —Cl, —$R^{A2C}$, —$R^{A2F}$ or —CN.

(45) A compound according to any one of (24) to (43), wherein —$R^{A2}$, if present, is independently —F, —Cl, or —CN.

(46) A compound according to any one of (24) to (43), wherein —$R^{A2}$, if present, is —F.

(47) A compound according to any one of (24) to (43), wherein —$R^{A2}$, if present, is —Cl.

(48) A compound according to any one of (24) to (43), wherein —$R^{A2}$, if present, is —CN.

(49) A compound according to any one of (24) to (43), wherein —$R^{A2}$, if present, is —$R^{A2C}$.

(50) A compound according to any one of (24) to (43), wherein —$R^{A2}$, if present, is —$R^{A2F}$.

The Group —$R^{A2C}$

(51) A compound according to any one of (24) to (50), wherein —$R^{2C}$, if present, is —$CH_3$.

The Group —$R^{A2F}$

(52) A compound according to any one of (24) to (51), wherein —$R^{A2F}$, if present, is —$CF_3$.

The Group —$R^{A3}$

(53) A compound according to any one of (24) to (52), wherein —$R^{A3}$, if present, is independently —F, —Cl, —$R^{A3C}$, —$R^{A3F}$, or —CN.

(54) A compound according to any one of (24) to (52), wherein —$R^{A3}$, if present, is independently —F, —Cl, or —CN.

(55) A compound according to any one of (24) to (52), wherein —$R^{A3}$, if present, is —F.

(56) A compound according to any one of (24) to (52), wherein —$R^{A3}$, if present, is —Cl.

(57) A compound according to any one of (24) to (52), wherein —$R^{A3}$, if present, is —CN.

(58) A compound according to any one of (24) to (52), wherein —$R^{A3}$, if present, is —$R^{A3C}$.

(59) A compound according to any one of (24) to (52), wherein —$R^{A3}$, if present, is —$R^{A3F}$.

The Group —$R^{A3C}$

(60) A compound according to any one of (24) to (59), wherein —$R^{3C}$, if present, is —$CH_3$.

The Group —$R^{A3F}$

(61) A compound according to any one of (24) to (60), wherein —$R^{A3F}$, if present, is —$CF_3$.

The Group —$R^{A4}$

(62) A compound according to any one of (24) to (61), wherein —$R^{A4}$, if present, is independently —F, —Cl, —$R^{A4C}$, —$R^{A4F}$, or —CN.

(63) A compound according to any one of (24) to (61), wherein —$R^{A4}$, if present, is independently —F, —Cl, or —CN.

(64) A compound according to any one of (24) to (61), wherein —$R^{A4}$, if present, is —F.

(65) A compound according to any one of (24) to (61), wherein —$R^{A4}$, if present, is —Cl.

(66) A compound according to any one of (24) to (61), wherein —$R^{A4}$, if present, is —CN.

(67) A compound according to any one of (24) to (61), wherein —$R^{A4}$, if present, is —$R^{A4C}$.

(68) A compound according to any one of (24) to (61), wherein —$R^{A4}$, if present, is —$R^{A4F}$.

The Group —$R^{A4C}$

(69) A compound according to any one of (24) to (68), wherein —$R^{A4C}$, if present, is —$CH_3$.

The Group —$R^{A4F}$

(70) A compound according to any one of (24) to (69), wherein —$R^{A4F}$, if present, is —$CF_3$.

The Group —$R^{A5}$

(71) A compound according to any one of (24) to (70), wherein —$R^{A5}$, if present, is independently —F, —Cl, —$R^{A5C}$, —$R^{A5F}$, or —CN.

(72) A compound according to any one of (24) to (70), wherein —$R^{A5}$, if present, is independently —F, —Cl, or —CN.

(73) A compound according to any one of (24) to (70), wherein —$R^{A5}$, if present, is —F.

(74) A compound according to any one of (24) to (70), wherein —$R^{A5}$, if present, is —Cl.

(75) A compound according to any one of (24) to (70), wherein —$R^{A5}$, if present, is —CN.

(76) A compound according to any one of (24) to (70), wherein —$R^{A5}$, if present, is —$R^{A5C}$.

(77) A compound according to any one of (24) to (70), wherein —$R^{A5}$, if present, is —$R^{A5F}$.

The Group —$R^{A5C}$

(78) A compound according to any one of (24) to (77), wherein —$R^{5C}$, if present, is —$CH_3$.

The Group —$R^{A5F}$

(79) A compound according to any one of (24) to (78), wherein —$R^{A5F}$, if present, is —$CF_3$.

The Group —$R^{B1}$

(80) A compound according to any one of (28) to (79), wherein —$R^{B1}$, if present, is independently —F, —Cl, —$R^{B1C}$, —$R^{B1F}$, or —CN.

(81) A compound according to any one of (28) to (79), wherein —$R^{B1}$, if present, is independently —F, —Cl, or —CN.

(82) A compound according to any one of (28) to (79), wherein —$R^{B1}$, if present, is —F.

(83) A compound according to any one of (28) to (79), wherein —$R^{B1}$, if present, is —Cl.

(84) A compound according to any one of (28) to (79), wherein —$R^{B1}$, if present, is —CN.

(85) A compound according to any one of (28) to (79), wherein —$R^{B1}$, if present, is —$R^{B1C}$.

(86) A compound according to any one of (28) to (79), wherein —$R^{B1}$, if present, is —$R^{B1F}$.

The Group —$R^{B1C}$

(87) A compound according to any one of (28) to (86), wherein —$R^{B1C}$, if present, is —$CH_3$.

The Group —$R^{B1F}$

(88) A compound according to any one of (28) to (87), wherein —$R^{B1F}$, if present, is —$CF_3$.

The Group —$R^{B2}$

(89) A compound according to any one of (28) to (88), wherein —$R^{B2}$, if present, is independently —F, —Cl, —$R^{B2c}$, —$R^{B2F}$ or —CN.

(90) A compound according to any one of (28) to (88), wherein —$R^{B2}$, if present, is independently —F, —Cl, or —CN.

(91) A compound according to any one of (28) to (88), wherein —$R^{B2}$, if present, is —F.

(92) A compound according to any one of (28) to (88), wherein —$R^{B2}$, if present, is —Cl.

(93) A compound according to any one of (28) to (88), wherein —$R^{B1}$, if present, is —CN.

(94) A compound according to any one of (28) to (88), wherein —$R^{B2}$, if present, is —$R^{B2C}$.

(95) A compound according to any one of (28) to (88), wherein —$R^{B2}$, if present, is —$R^{B2F}$.

The Group —$R^{B2C}$

(96) A compound according to any one of (28) to (95), wherein —$R^{2C}$, if present, is —$CH_3$.

The Group —$R^{B2F}$

(97) A compound according to any one of (28) to (96), wherein —$R^{2F}$, if present, is —$CF_3$.

The Group —$R^1$

(98) A compound according to any one of (1) to (97), wherein —$R^1$ is —Rix.

(99) A compound according to any one of (1) to (97), wherein —$R^1$ is —H.

The Group —$R^{1X}$ (100) A compound according to any one of (1) to (99), wherein —$R^{1X}$, if present, is independently —F, —$R^{1C}$, or —$R^{1F}$.

(101) A compound according to any one of (1) to (99), wherein —$R^{1X}$, if present, is —F.

(102) A compound according to any one of (1) to (99), wherein —$R^{1X}$, if present, is —$R^{1C}$.

(103) A compound according to any one of (1) to (99), wherein —$R^{1X}$, if present, is —$R^{1F}$.

The Group —$R^{1C}$ (104) A compound according to any one of (1) to (103), wherein —$R^{1C}$, if present, is —$CH_3$.

The Group —$R^{1F}$ (105) A compound according to any one of (1) to (104), wherein —$R^{1F}$, if present, is —$CF_3$.

The Group —$R^2$ (106) A compound according to any one of (1) to (105), wherein —$R^2$ is —$R^{2X}$.

(107) A compound according to any one of (1) to (105), wherein —$R^2$ is —H.

The Group —$R^{2X}$ (108) A compound according to any one of (1) to (107), wherein —$R^{2X}$, if present, is independently —F, —$R^{2C}$, or —$R^{2F}$.

(109) A compound according to any one of (1) to (107), wherein —$R^{2X}$, if present, is —F.

(110) A compound according to any one of (1) to (107), wherein —$R^{2X}$, if present, is —$R^{2C}$.

(111) A compound according to any one of (1) to (107), wherein —$R^{2X}$, if present, is —$R^{2F}$.

The Group —$R^{2C}$ (112) A compound according to any one of (1) to (111), wherein —$R^{2C}$, if present, is —$CH_3$.

The Group —$R^{2F}$ (113) A compound according to any one of (1) to (112), wherein —$R^{2F}$, if present, is —$CF_3$.

The Groups —$R^1$ and —$R^2$ Taken Together (114) A compound according to any one of (1) to (97), wherein —$R^1$ and —$R^2$, taken together with the carbon atom to which they are attached, form saturated $C_{3-6}$cycloalkyl.

(115) A compound according to any one of (1) to (97), wherein —$R^1$ and —$R^2$, taken together with the carbon atom to which they are attached, form cyclopropyl.

(116) A compound according to any one of (1) to (97), wherein —$R^1$ and —$R^2$, taken together with the carbon atom to which they are attached, form cyclobutyl.

(117) A compound according to any one of (1) to (97), wherein —$R^1$ and —$R^{62}$, taken together with the carbon atom to which they are attached, form cyclopentyl.

(118) A compound according to any one of (1) to (97), wherein —$R^1$ and —$R^2$, taken together with the carbon atom to which they are attached, form cyclohexyl.

The Group —$R^3$ (119) A compound according to any one of (1) to (118), wherein —$R^3$ is —$R^{3X}$.

(120) A compound according to any one of (1) to (118), wherein —$R^3$ is —H.

The Group —R³ˣ

(121) A compound according to any one of (1) to (120), wherein —R³ˣ, if present, is —R³ᶜ.

(122) A compound according to any one of (1) to (120), wherein —R³ˣ, if present, is —R³ᶠ.

The Group —R³ᶜ

(123) A compound according to any one of (1) to (122), wherein —R³ᶜ, if present, is —CH₃.

The Group —R³ᶠ

(124) A compound according to any one of (1) to (123), wherein —R³ᶠ, if present, is —CF₃.

The Group —R⁴

(125) A compound according to any one of (1) to (124), wherein —R⁴ is —R⁴ᶜ.

(126) A compound according to any one of (1) to (124), wherein —R⁴ is —R⁴ᶜᶜ.

(127) A compound according to any one of (1) to (124), wherein —R⁴ is —N(R⁴ᴺ¹)(R⁴ᴺ²).

The Group —R⁴ᶜ

(128) A compound according to any one of (1) to (127), wherein —R⁴ᶜ, if present, is saturated linear or branched C₁₋₄ alkyl.

(129) A compound according to any one of (1) to (127), wherein —R⁴ᶜ, if present, is saturated linear or branched C₁₋₃ alkyl.

(130) A compound according to any one of (1) to (127), wherein —R⁴ᶜ, if present, is —CH₃ or —CH₂CH₃.

(131) A compound according to any one of (1) to (127), wherein —R⁴ᶜ, if present, is —CH₃.

The Group —R⁴ᶜᶜ

(132) A compound according to any one of (1) to (131), wherein —R⁴ᶜᶜ, if present, is cyclopropyl.

(133) A compound according to any one of (1) to (131), wherein —R⁴ᶜᶜ, if present, is cyclobutyl.

(134) A compound according to any one of (1) to (131), wherein —R⁴ᶜᶜ, if present, is cyclopentyl.

(135) A compound according to any one of (1) to (131), wherein —R⁴ᶜᶜ, if present, is cyclohexyl.

The Group —R⁴ᴺ

(136) A compound according to any one of (1) to (135), wherein —R⁴ᴺ¹, if present, is —R⁴ᴺ¹ᶜ.

(137) A compound according to any one of (1) to (135), wherein —R⁴ᴺ¹, if present, is —H.

The Group —R⁴ᴺ¹ᶜ

(138) A compound according to any one of (1) to (137), wherein —R⁴ᴺ¹ᶜ, if present, is saturated linear or branched C₁₋₃ alkyl.

(139) A compound according to any one of (1) to (137), wherein —R⁴ᴺ¹ᶜ, if present, is —CH₃ or —CH₂CH₃.

(140) A compound according to any one of (1) to (137), wherein —R⁴ᴺ¹ᶜ, if present, is —CH₃.

The Group —R⁴ᴺ²

(141) A compound according to any one of (1) to (140), wherein —R⁴ᴺ², if present, is —R⁴ᴺ²ᶜ.

(142) A compound according to any one of (1) to (140), wherein —R⁴ᴺ², if present, is —H.

The Group —R⁴ᴺ²ᶜ

(143) A compound according to any one of (1) to (142), wherein —R⁴ᴺ²ᶜ, if present, is saturated linear or branched C₁₋₃ alkyl.

(144) A compound according to any one of (1) to (142), wherein —R⁴ᴺ²ᶜ, if present, is —CH₃ or —CH₂CH₃.

(145) A compound according to any one of (1) to (142), wherein —R⁴ᴺ²ᶜ, if present, is —CH₃.

The Group —N(R⁴ᴺ¹)(R⁴ᴺ²) (when Cyclic)

(146) A compound according to any one of (1) to (127), wherein —N(R⁴ᴺ¹)(R⁴ᴺ²), if present, is independently pyrrolidinyl, piperidinyl, piperazinyl, or morpholinyl; and is optionally substituted with one or more saturated linear or branched C₁₋₄ alkyl groups.

(147) A compound according to any one of (1) to (127), wherein —N(R⁴ᴺ¹)(R⁴ᴺ²), if present, is independently pyrrolidinyl, piperidinyl, piperazinyl, or morpholinyl.

Configuration of Carbon to which —R¹ and —R² are Attached (148) A compound according to any one of (1) to (147), wherein —R¹ and —R² are different, and the compound is a compound of the following formula, or a pharmaceutically acceptable salt or solvate thereof:

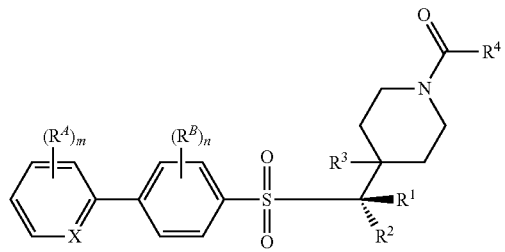

(149) A compound according to any one of (1) to (147), wherein —R¹ and —R² are different, and the compound is a compound of the following formula, or a pharmaceutically acceptable salt or solvate thereof:

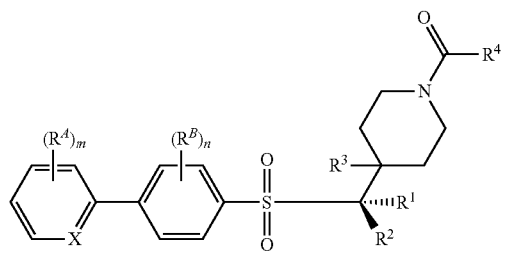

Some Preferred Compounds (150) A compound according to (1), which is a compound of one of following formulae, or a pharmaceutically acceptable salt or solvate thereof:

| Compound | Structure |
|---|---|
| NASMP-01 | 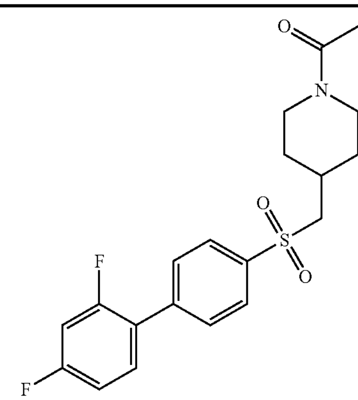 |

-continued
| Compound | Structure |
|---|---|
| NASMP-02 | 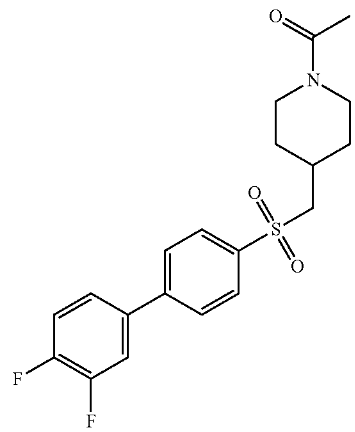 [SMILES: CC(=O)N1CCC(CS(=O)(=O)c2ccc(-c3ccc(F)c(F)c3)cc2)CC1] |
| NASMP-03 | 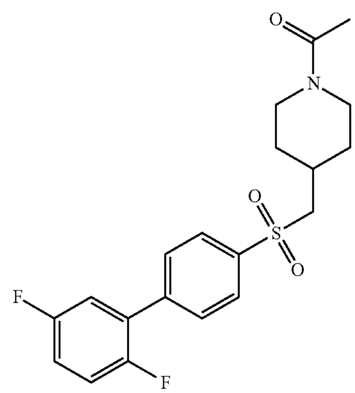 [SMILES: CC(=O)N1CCC(CS(=O)(=O)c2ccc(-c3cc(F)ccc3F)cc2)CC1] |
| NASMP-04 | 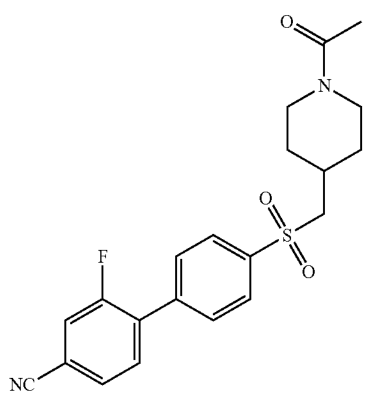 [SMILES: CC(=O)N1CCC(CS(=O)(=O)c2ccc(-c3ccc(C#N)cc3F)cc2)CC1] |
| NASMP-05 | 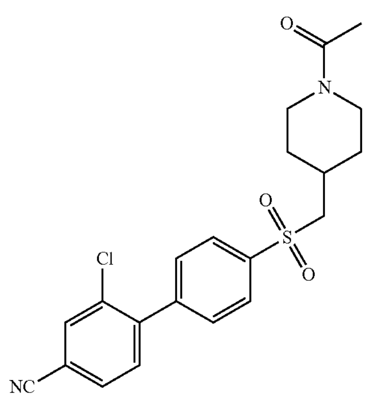 [SMILES: CC(=O)N1CCC(CS(=O)(=O)c2ccc(-c3ccc(C#N)cc3Cl)cc2)CC1] |
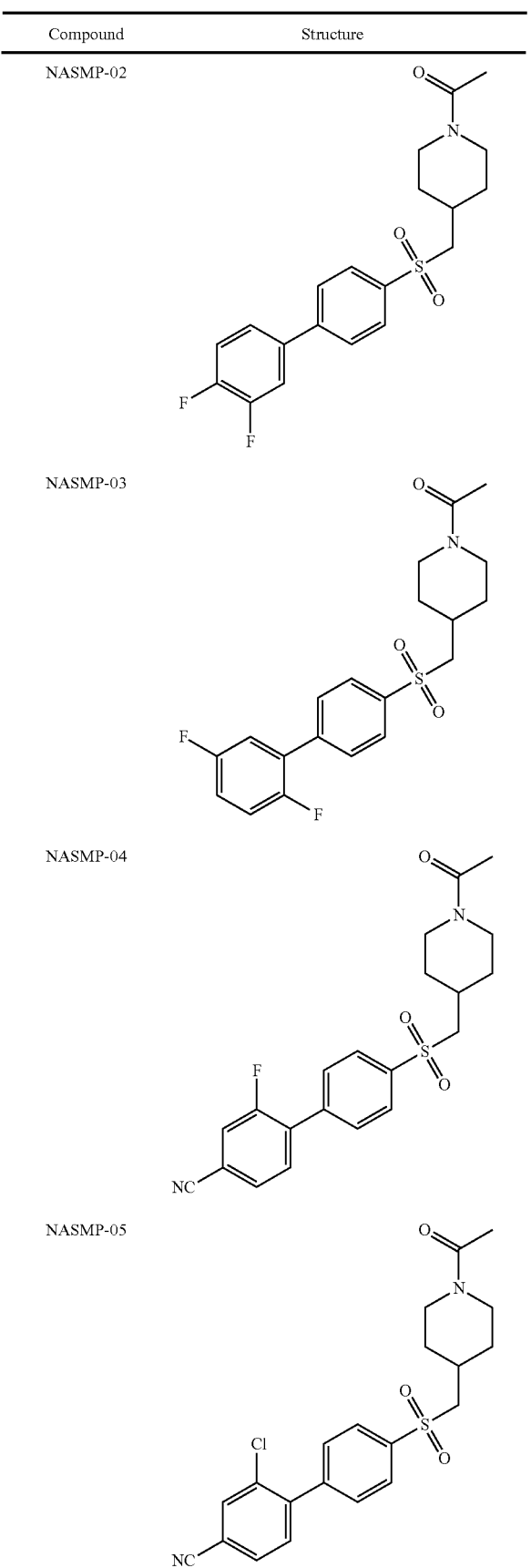
-continued
| Compound | Structure |
|---|---|
| NASMP-06 | 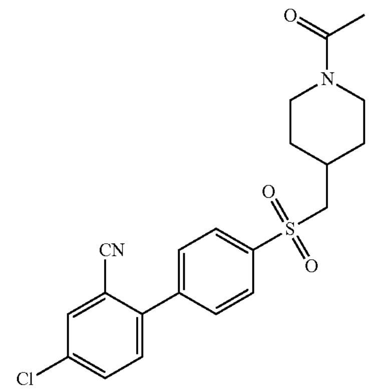 [SMILES: CC(=O)N1CCC(CS(=O)(=O)c2ccc(-c3ccc(Cl)cc3C#N)cc2)CC1] |
| NASMP-07 | 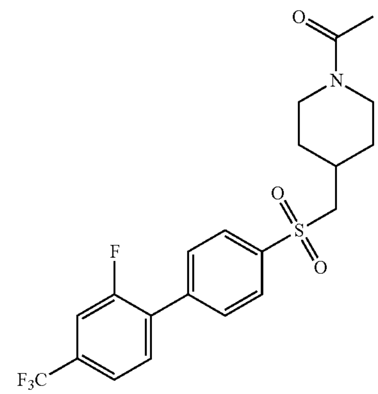 [SMILES: CC(=O)N1CCC(CS(=O)(=O)c2ccc(-c3ccc(C(F)(F)F)cc3F)cc2)CC1] |
| NASMP-08 | 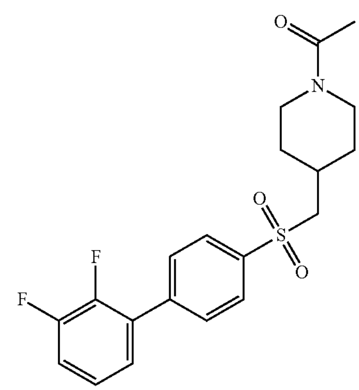 [SMILES: CC(=O)N1CCC(CS(=O)(=O)c2ccc(-c3cccc(F)c3F)cc2)CC1] |
| NASMP-09 | 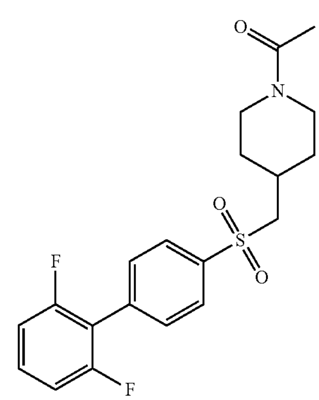 [SMILES: CC(=O)N1CCC(CS(=O)(=O)c2ccc(-c3c(F)cccc3F)cc2)CC1] |
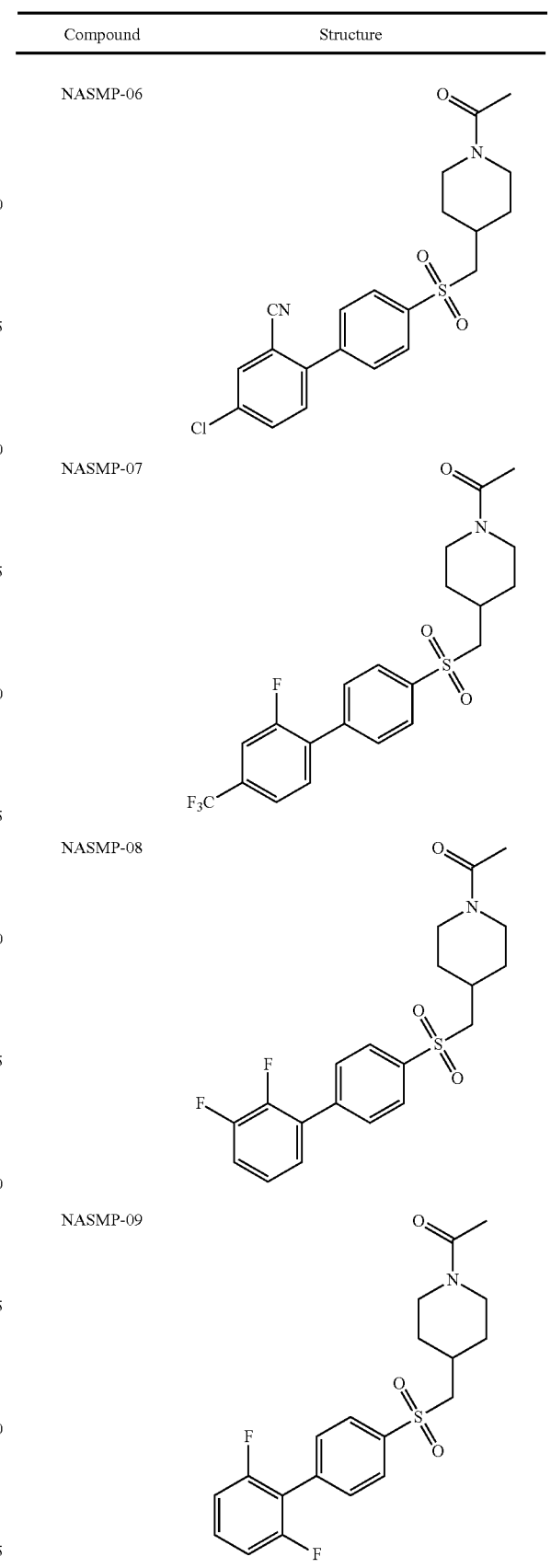

-continued
| Compound | Structure |
|---|---|
| NASMP-10 | 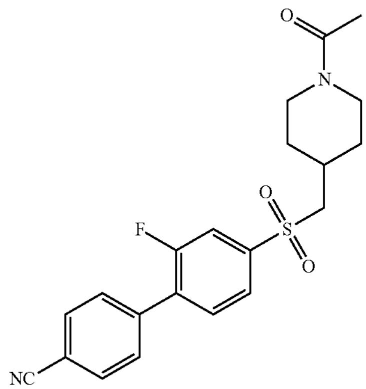 [SMILES: CC(=O)N1CCC(CS(=O)(=O)c2ccc(-c3ccc(C#N)cc3)c(F)c2)CC1] |
| NASMP-11 | 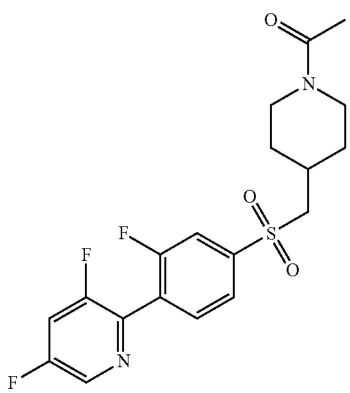 [SMILES: CC(=O)N1CCC(CS(=O)(=O)c2ccc(-c3ncc(F)cc3F)c(F)c2)CC1] |
| NASMP-12 | 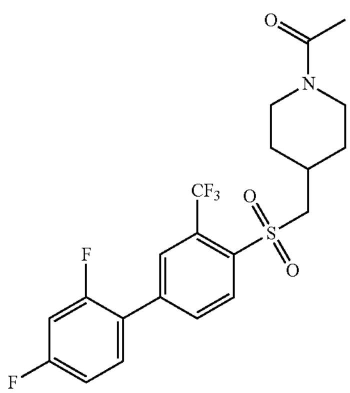 [SMILES: CC(=O)N1CCC(CS(=O)(=O)c2ccc(-c3ccc(F)cc3F)cc2C(F)(F)F)CC1] |
| NASMP-13 | 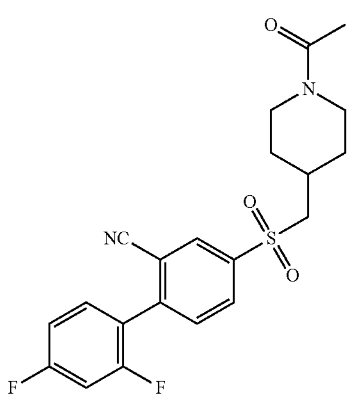 [SMILES: CC(=O)N1CCC(CS(=O)(=O)c2ccc(-c3ccc(F)cc3F)c(C#N)c2)CC1] |
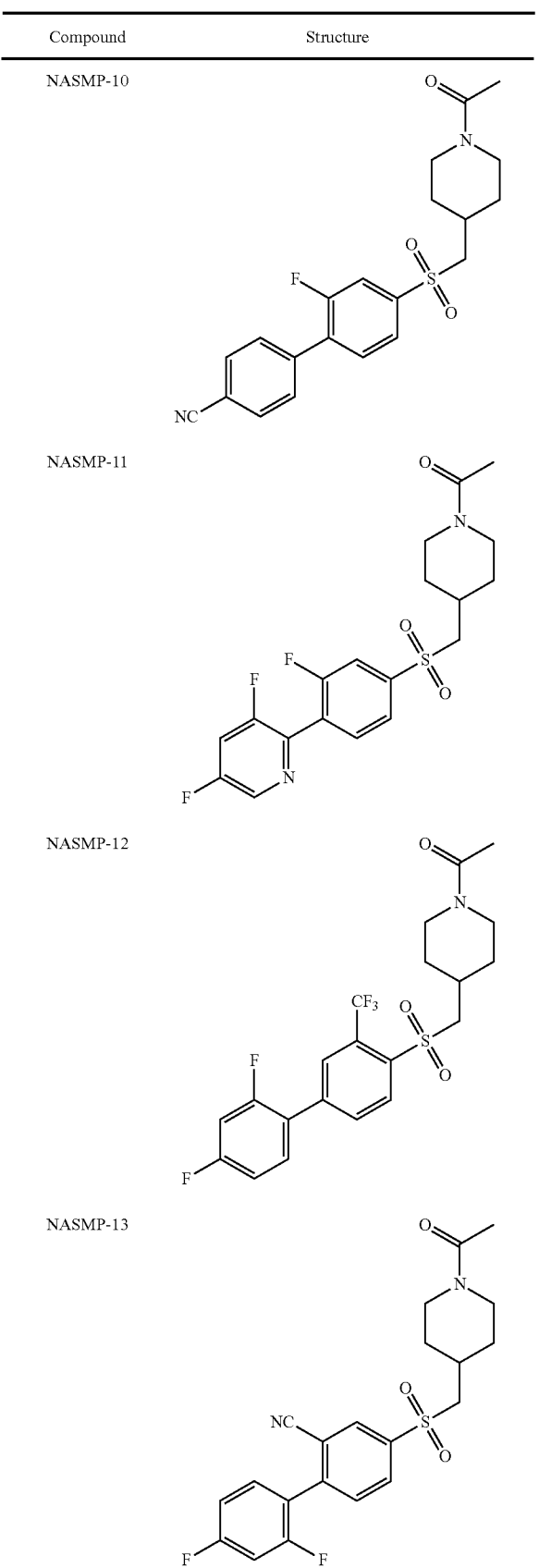
-continued
| Compound | Structure |
|---|---|
| NASMP-14 | 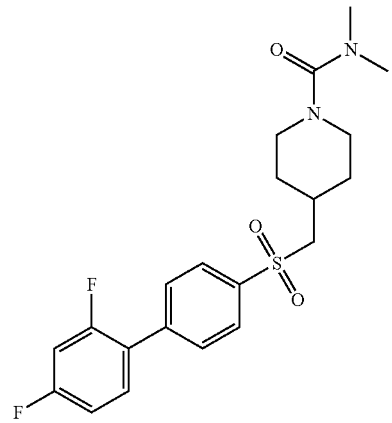 [SMILES: CN(C)C(=O)N1CCC(CS(=O)(=O)c2ccc(-c3ccc(F)cc3F)cc2)CC1] |
| NASMP-15 | 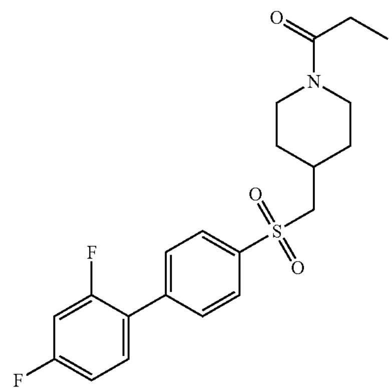 [SMILES: CCC(=O)N1CCC(CS(=O)(=O)c2ccc(-c3ccc(F)cc3F)cc2)CC1] |
| NASMP-16 | 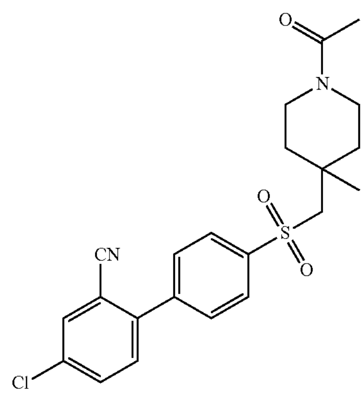 [SMILES: CC(=O)N1CCC(C)(CS(=O)(=O)c2ccc(-c3ccc(Cl)cc3C#N)cc2)CC1] |
| NASMP-17 | 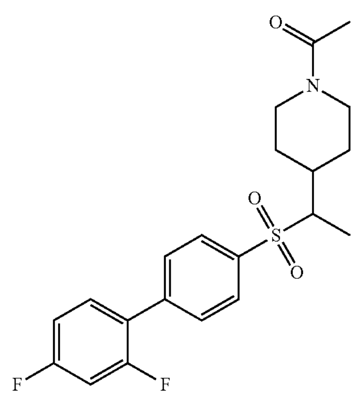 [SMILES: CC(=O)N1CCC(C(C)S(=O)(=O)c2ccc(-c3ccc(F)cc3F)cc2)CC1] |
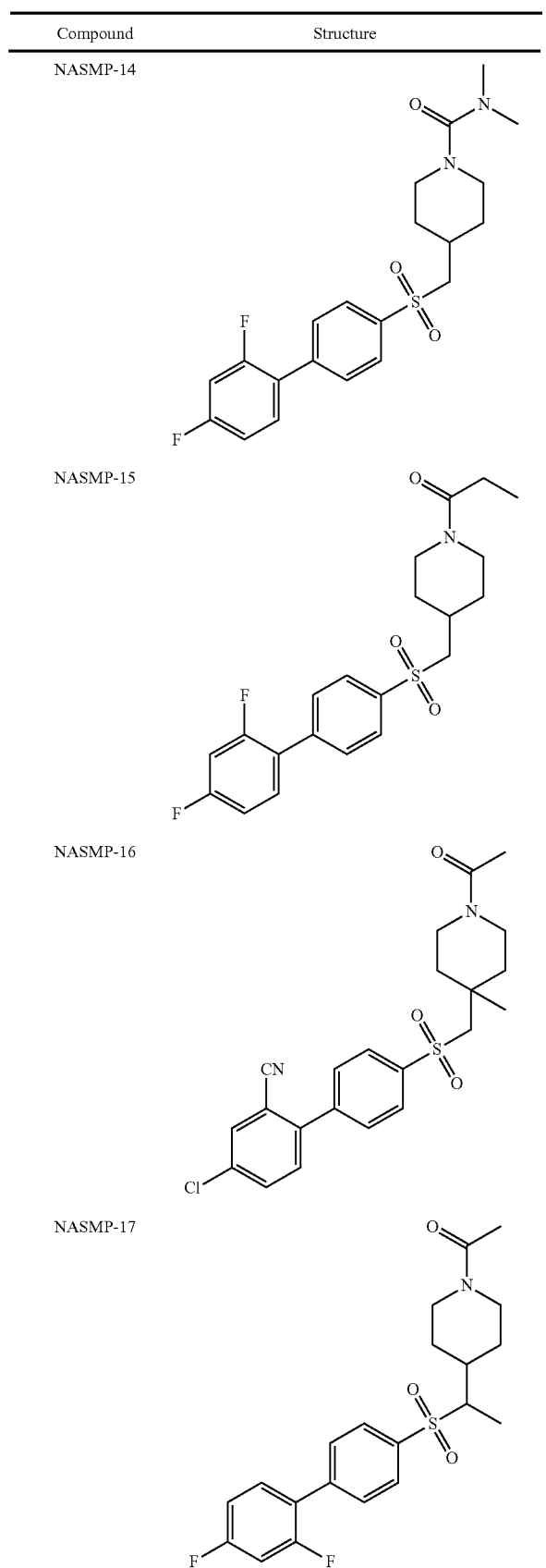

-continued

| Compound | Structure |
|---|---|
| NASMP-18 | 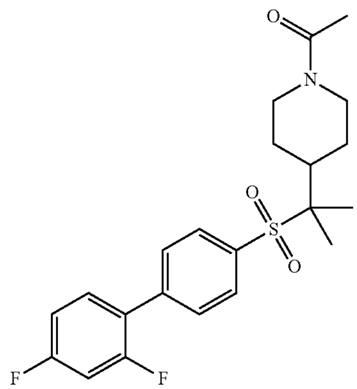 [SMILES: CC(=O)N1CCC(C(C)(C)S(=O)(=O)c2ccc(-c3ccc(F)cc3F)cc2)CC1] |
| NASMP-19 | 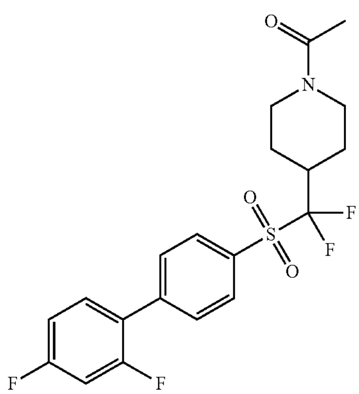 [SMILES: CC(=O)N1CCC(C(F)(F)S(=O)(=O)c2ccc(-c3ccc(F)cc3F)cc2)CC1] |
| NASMP-20 | 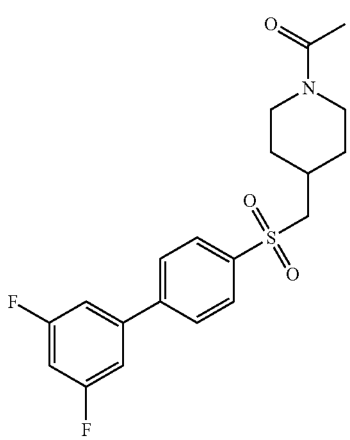 [SMILES: CC(=O)N1CCC(CS(=O)(=O)c2ccc(-c3cc(F)cc(F)c3)cc2)CC1] |

-continued

| Compound | Structure |
|---|---|
| NASMP-21 | 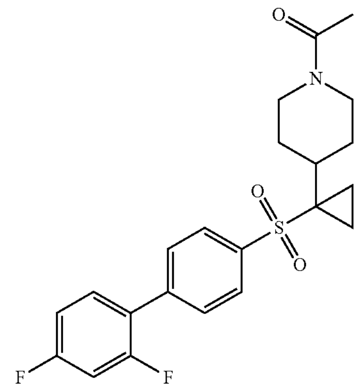 [SMILES: CC(=O)N1CCC(C2(S(=O)(=O)c3ccc(-c4ccc(F)cc4F)cc3)CC2)CC1] |

Combinations

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the chemical groups represented by the variables (e.g., $=X-$, m, $-R^A$, $-R^{AC}$, $-R^{AF}$, n, $-R^B$, $-R^{BC}$, $-R^{BF}$, $-R^{A1}$, $-R^{A1C}$, $-R^{A1F}$, $-R^{A2}$, $-R^{A2C}$, $-R^{A2F}$, $-R^{A3}$, $-R^{A3C}$, $-R^{A3F}$, $-R^{A4}$, $-R^{A4C}$, $-R^{A4F}$, $-R^{A5}$, $-R^{A5C}$, $-R^{A5F}$, $-R^{B1}$, $-R^{B1C}$, $-R^{B1F}$, $-R^{B2}$, $-R^{B2C}$, $-R^{B2F}$, $-R^1$, $-R^{1X}$, $-R^{1C}$, $-R^{1F}$, $-R^2$, $-R^{2X}$, $-R^{2C}$, $-R^{2F}$, $-R^3$, $-R^{3X}$, $-R^{3C}$, $-R^{3F}$, $-R^4$, $-R^{4C}$, $-R^{4CC}$, $-R^{4N1}$, $-R^{4N1C}$, $-R^{4N2}$, $-R^{4N2C}$ etc.) are specifically embraced by the present invention and are disclosed herein just as if each and every combination was individually and explicitly disclosed, to the extent that such combinations embrace compounds that are stable compounds (i.e., compounds that can be isolated, characterised, and tested for biological activity). In this context, the skilled person will readily appreciate that certain combinations of groups (e.g., substituents) may give rise to compounds which may not be readily synthesized and/or are chemically unstable. In addition, all sub-combinations of the chemical groups listed in the embodiments describing such variables are also specifically embraced by the present invention and are disclosed herein just as if each and every such sub-combination of chemical groups was individually and explicitly disclosed herein.

Substantially Purified Forms

One aspect of the present invention pertains to NASMP compounds, as described herein, in substantially purified form and/or in a form substantially free from contaminants.

In one embodiment, the substantially purified form is at least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless otherwise specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to an equimolar mixture of enantiomers (i.e., a racemic mixture, a racemate). In one embodiment, the substantially purified form refers to one enantiomer, e.g., optically pure enantiomer.

In one embodiment, the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the substantially purified form is at least 60% optically pure (i.e., 60% of the compound, on a molar basis, is the desired stereoisomer or enantiomer, and 40% is the undesired stereoisomer or enantiomer), e.g., at least 70% optically pure, e.g., at least 80% optically pure, e.g., at least 90% optically pure, e.g., at least 95% optically pure, e.g., at least 97% optically pure, e.g., at least 98% optically pure, e.g., at least 99% optically pure.

Isomers

Certain compounds may exist in one or more particular geometric, optical, enantiomeric, diastereoisomeric, epimeric, atropic, stereoisomeric, tautomeric, conformational, or anomeric forms, including but not limited to, cis- and trans-forms; E- and Z-forms; c-, t-, and r- forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

A reference to a class of structures may well include structurally isomeric forms falling within that class (e.g., $C_{1-3}$alkyl includes n-propyl and iso-propyl; butyl includes n-, iso-, sec-, and tert-butyl; methoxyphenyl includes ortho-, meta-, and para-methoxyphenyl). However, reference to a specific group or substitution pattern is not intended to include other structural (or constitutional isomers) which differ with respect to the connections between atoms rather than by positions in space. For example, a reference to a methoxy group, —$OCH_3$, is not to be construed as a reference to its structural isomer, a hydroxymethyl group, —$CH_2OH$.

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro. A reference herein to one tautomer is intended to encompass both tautomers.

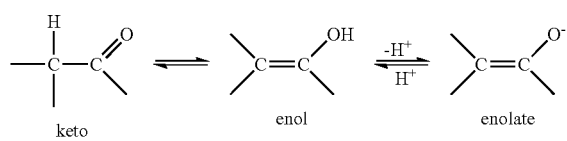

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}O$, $^{13}O$, and $^{14}O$; O may be in any isotopic form, including $^{16}O$ and $^{18}O$; and the like.

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group, which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{3+}$ as well as the ammonium ion (i.e., NH$_4^+$). Examples of suitable organic cations include, but are not limited to substituted ammonium ions (e.g., NH$_3$R$^+$, NH$_2$R$_2^+$, NHR$_3^+$, NR$_4^+$), for example, where each R is independently linear or branched saturated $C_{1-18}$alkyl, $C_{3-8}$cycloalkyl, $C_{3-8}$cycloalkyl-$C_{1-6}$alkyl, and phenyl-$C_{1-6}$alkyl, wherein the phenyl group is optionally substituted. Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group, which upon protonation may become cationic (e.g., —NH$_2$ may become —NH$_3^+$), then a salt may be formed with a suitable anion.

For example, if a parent structure contains a cationic group (e.g., —NMe$_2^+$), or has a functional group, which upon protonation may become cationic (e.g., —NH$_2$ may become —NH$_3^+$), then a salt may be formed with a suitable anion. In the case of a quaternary ammonium compound a counter-anion is generally always present in order to balance the positive charge. If, in addition to a cationic group (e.g., —NMe$_2^+$, —NH$_3^+$), the compound also contains a group capable of forming an anion (e.g., —COOH), then an inner salt (also referred to as a zwitterion) may be formed.

Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyloxybenzoic, acetic, trifluoroacetic, ascorbic, aspartic, benzoic, camphorsulfonic, cinnamic, citric, edetic, 1,2-ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Examples of suitable counter-ions which are especially suitable for quaternary ammonium compounds (e.g., those with a pendant —$NMe_3^+$ group) include 1-adamantanesulfonate, benzenesulfonate, bisulfate, bromide, chloride, iodide, methanesulfonate, methylsulfate, 1,5-napthalene-bis-sulfonate, 4-nitrobenzenesulfonate, formate, tartrate, tosylate, trifluoroacetate, trifluoromethylsulfonate, sulphate. Again, if the compound also contains a group capable of forming an anion (e.g., —COOH), then an inner salt may be formed.

Unless otherwise specified, a reference to a particular compound also includes salt forms thereof.

Solvates and Hydrates

It may be convenient or desirable to prepare, purify, and/or handle a corresponding solvate of the compound. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate and hydrate forms thereof.

Chemically Protected Forms

It may be convenient or desirable to prepare, purify, and/or handle the compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well-known chemical methods are employed to reversibly render unreactive a functional group, which otherwise would be reactive, under specified conditions. In a chemically protected form, one or more reactive functional groups are in the form of a protected or protecting group (alternatively as a masked or masking group or a blocked or blocking group). By protecting a reactive functional group, reactions involving other unprotected reactive functional groups can be performed, without affecting the protected group; the protecting group may be removed or the masking group transformed, usually in a subsequent step, without substantially affecting the remainder of the molecule. See, for example, Protective Groups in Organic Synthesis (T. Green and P. Wuts; 4th Edition; John Wiley and Sons, 2006).

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)$CH_3$, —OAc).

Prodrugs

It may be convenient or desirable to prepare, purify, and/or handle the compound in the form of a prodrug. The term "prodrug," as used herein, pertains to a compound, which yields the desired active compound in vivo. Typically, the prodrug is inactive, or less active than the desired active compound, but may provide advantageous handling, administration, or metabolic properties.

For example, some prodrugs are esters of the active compound (e.g., a physiologically acceptable metabolically labile ester). During metabolism, the ester group (—C(=O) OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Also, some prodrugs are activated enzymatically to yield the active compound, or a compound, which, upon further chemical reaction, yields the active compound (for example, as in antibody directed enzyme prodrug therapy (ADEPT), gene directed enzyme prodrug therapy (GDEPT), lipid directed enzyme prodrug therapy (LIDEPT), etc.). For example, the prodrug may be a sugar derivative or other glycoside conjugate, or may be an amino acid ester derivative.

General Chemical Synthesis

Methods for the chemical synthesis of the NASMP compounds are described herein. These and/or other well-known methods may be modified and/or adapted in known ways in order to provide additional NASMP compounds and/or alternative or improved methods of synthesis.

In one approach (as illustrated in Scheme A), a piperidine-4-methanol is N-acylated or N-carbamoylated with, for example acetic anhydride or acetyl chloride in the presence of a base such as trimethylamine. The N-acylated or N-carbamoyl derivative is subsequently converted to the mesylate with methanesulphonyl chloride (MsCl) in the presence of a base such as triethylamine. The mesylate is displaced by an aromatic thiolate anion using a base such as caesium carbonate ($Cs_2CO_3$) and the sulphide derivative so formed is oxidised to the sulphone using m-chloroperbenzoic acid (m-CPBA) or potassium permanganate ($KMnO_4$). The biaryl sulphone is formed by coupling an appropriate aromatic boronic ester or acid to the bromophenyl sulphone using transition metal catalysis such as tetrakis(triphenylphosphine)palladium(0) ($Pd(PPh_3)_4$).

Scheme A

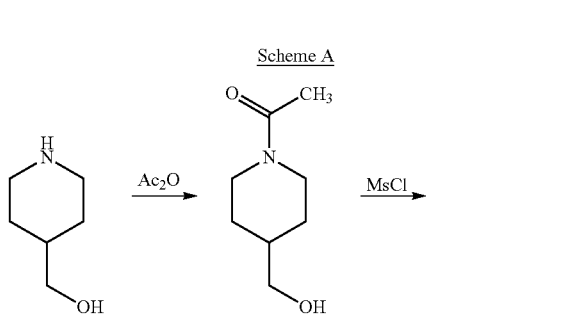

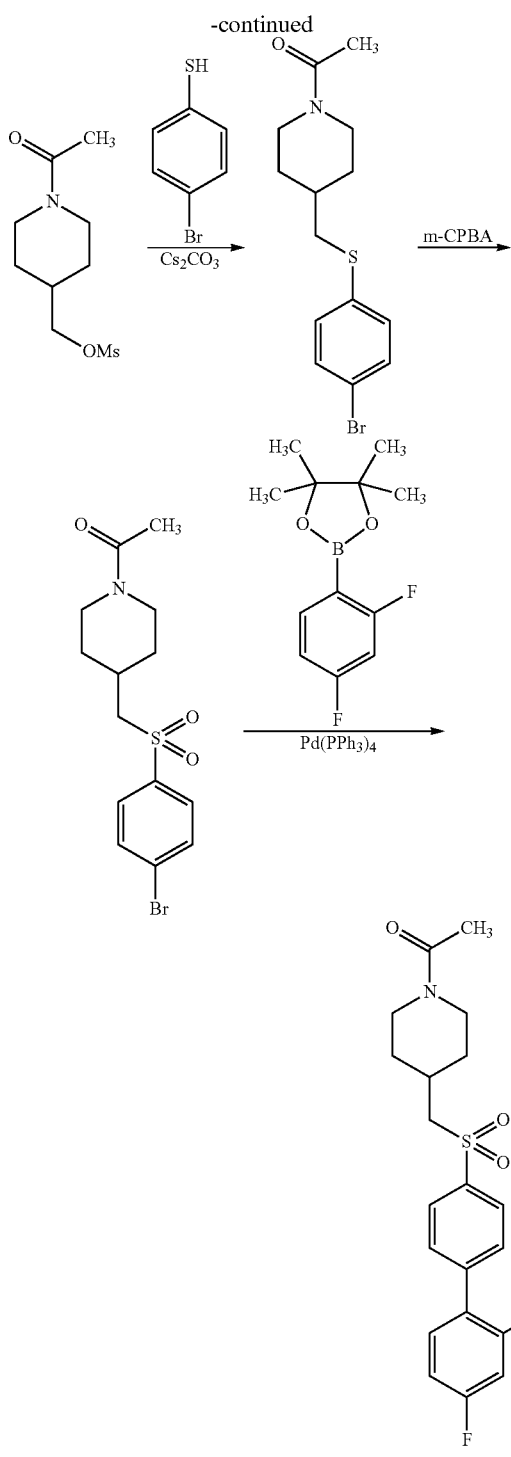

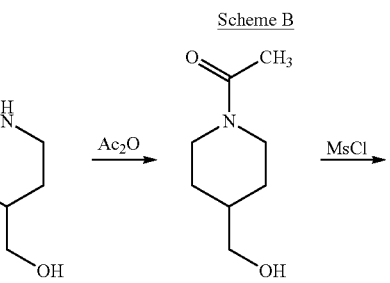

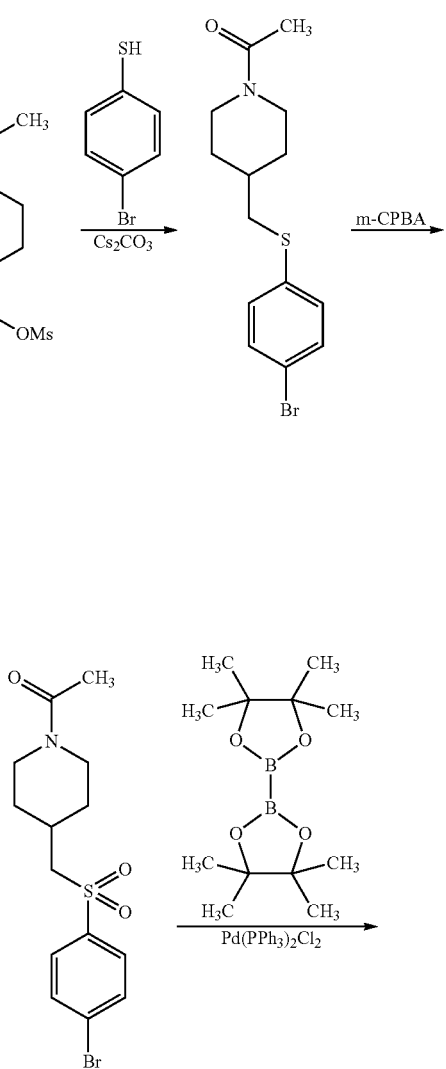

enylphosphine)palladium(0) (Pd(PPh$_3$)$_4$) or [1,1'-Bis(diphenylphosphino)ferrocene] dichloropalladium(II) (Pd(dppf)Cl$_2$).

In a second approach (as illustrated in Scheme B), the bromo(mono)phenyl sulphone formed in Scheme A is converted into a boronic ester using 4,4,5,5-tetramethyl-2-(4,4,5,5-tetramethyl-1,3,2-dioxaborolan-2-yl)-1,3,2-dioxaborolane and transition metal catalysis such as bis(triphenylphosphine) palladium (II) dichloride (Pd(PPh$_3$)$_2$Cl$_2$). The biaryl sulphone is formed by coupling the boronic ester with an appropriate aromatic bromide, iodide or triflate using transition metal catalysis such as tetrakis(triph-

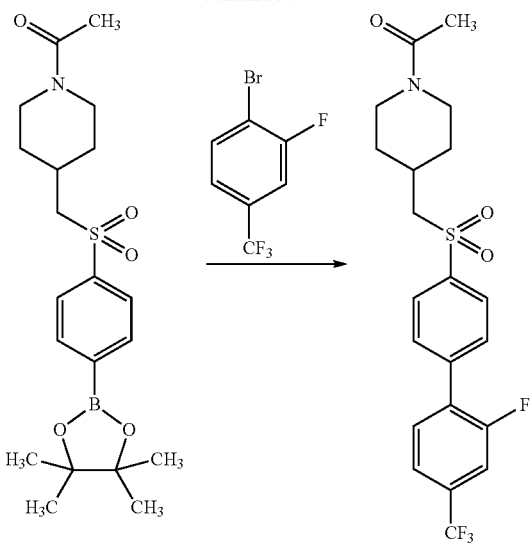

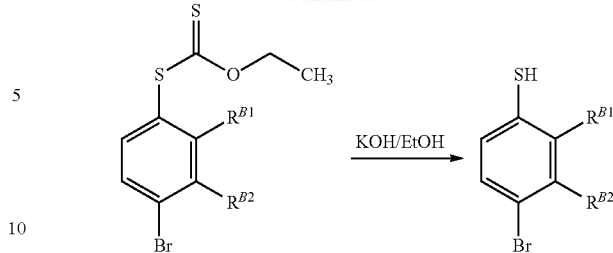

In instances in which the appropriate aromatic thiol is not readily commercially available, it may be made by reduction of the corresponding sulphonyl chloride with a reducing agent such as triphenylphosphine (PPh₃) (as illustrated in Scheme C).

Scheme C

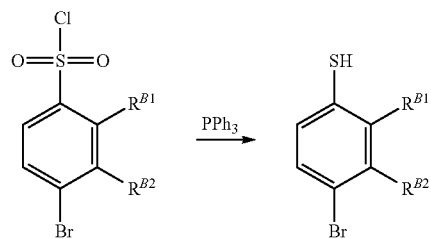

Alternatively (as illustrated in Scheme D1), an appropriately substituted aniline may be diazotised with sodium nitrite (NaNO₂) and acid such as hydrochloric acid (HCl). The diazonium salt is then reacted with potassium ethyl xanthate and subsequently hydrolysed with potassium hydroxide (KOH) to give the aromatic thiol.

Scheme D1

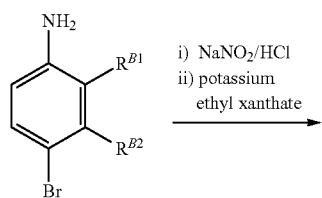

In the case in which one of the substituents is a nitrile group (as illustrated in Scheme D2), the nitrile may be hydrated to the primary amide during the potassium hydroxide hydrolysis. If this is the case, the aromatic thiol containing the primary amide substituent is coupled with the bromide as in Schemes A and B and then treated with a dehydrating agent such as trifluoroacetic anhydride (TFAA) to regenerate the nitrile from the primary amide.

Scheme D2

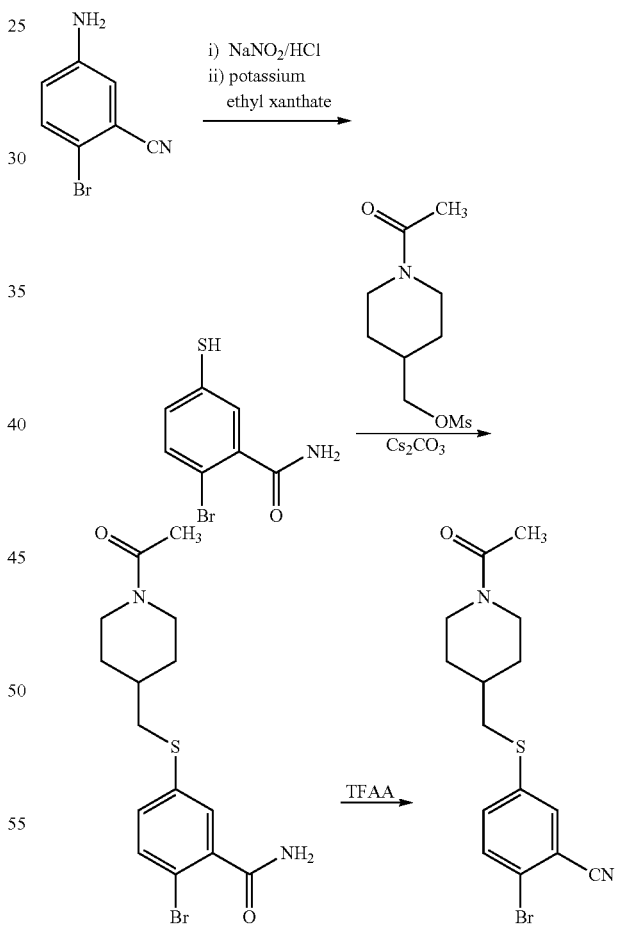

Access to biaryl thiols may be achieved as follows (as illustrated in Scheme E): An appropriate biphenyl compound is prepared from a boronic acid and a halobenzene via a Suzuki coupling. The biphenyl is sulfonylated using chlorosulfonic acid (ClSO₃H) to give the corresponding sulfonic acid. The acid is then reacted with thionyl chloride (SOCl₂) to give the corresponding aryl sulfonyl chloride. Reduction of the sulphonyl chloride with, for example triphenylphosphine (PPh₃), gives the biarylthiol derivative.

Scheme E

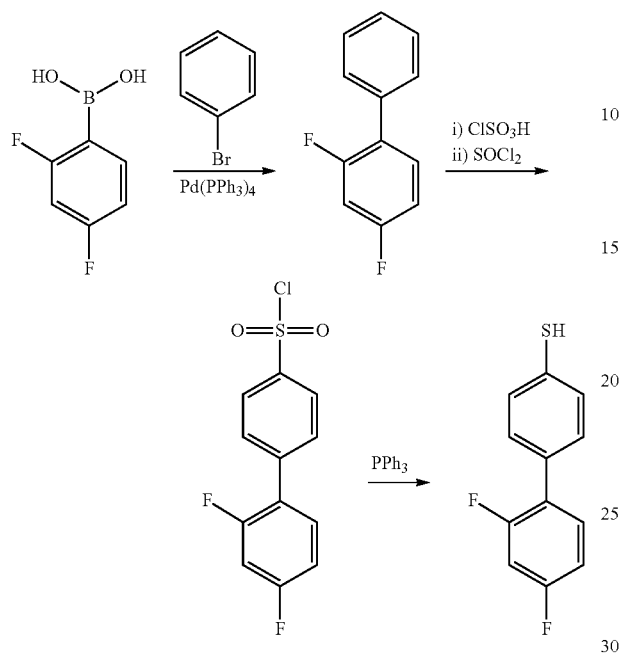

The biaryl thiols may be reacted with the N-acylated/N-carbamoylated-O-mesylated-piperidine-4-methanol derivatives, for example, as in Schemes A and B.

Alternatively (as illustrated in Scheme F), a tert-butyl 4-(bromomethyl)piperidine-1-carboxylate may be treated with trifluoroacetic acid (TFA) in the presence of triethylsilane (Et₃SiH) to remove the Boc group. The resulting product may then be N-acetylated or N-carbamoylated in the presence of a base such as pyridine. This bromomethylpiperidine may be reacted with the biaryl thiol in the presence of a base such as caesium carbonate (Cs₂CO₃) and the sulphide so formed oxidised with, for example, m-chloroperbenzoic acid (m-CPBA) or potassium permanganate (KMnO₄) to give the target compound.

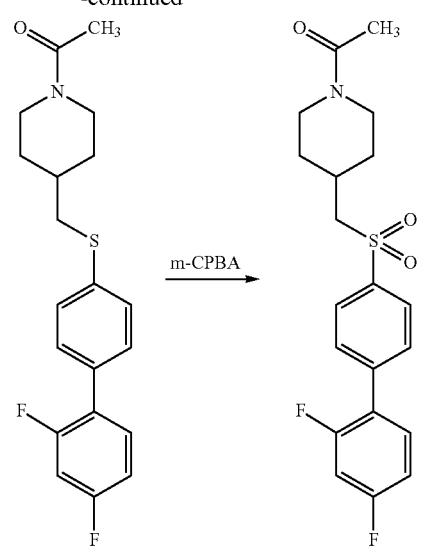

The N-acylated bromomethylpiperidine may also be used in place of the mesylate in Schemes A and B.

In an alternative approach (as illustrated in Scheme G1), a biaryl thiol may be reacted with an N-Boc-4-bromomethylpiperidine or N-Boc-4-methanesulphonyloxymethylpiperidine to give a sulphide which is oxidised with, for example m-chloroperbenzoic acid (m-CPBA) to give the biaryl sulphone (Z1).

Scheme F

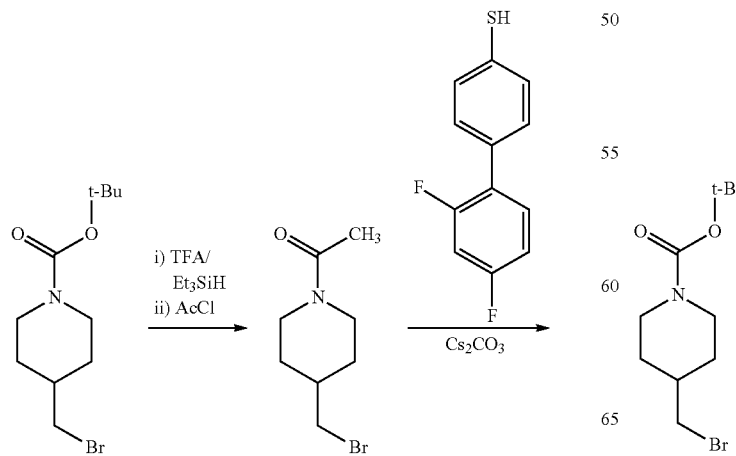

Scheme G1

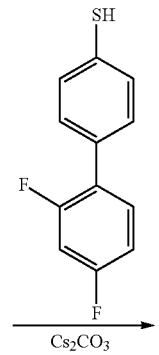

45
-continued

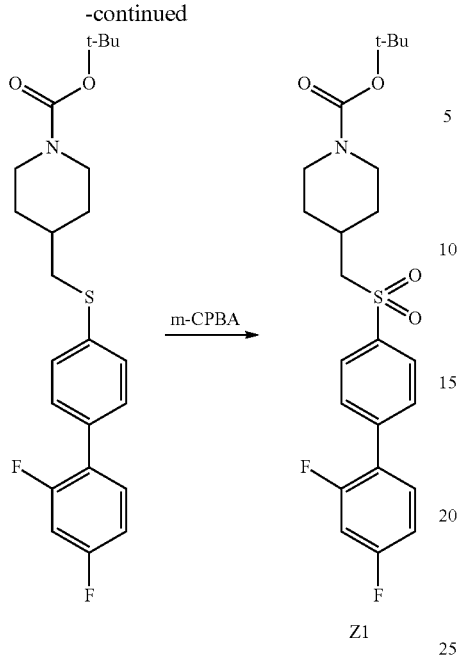

46
-continued

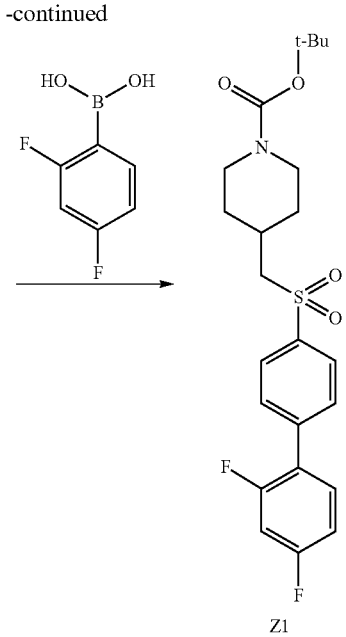

In an alternative approach (as illustrated in Scheme G2), the biaryl may be built up via reaction of an appropriate monoaryl thiol, oxidation, and coupling with an appropriate boronic acid or ester derivative as in Scheme A.

For compounds where R1=R2=H in the biaryl sulphone (Z1), the Boc group may be removed by treatment with trifluoroacetic acid and the piperidine so formed may then be N-acylated or N-carbamoylated (for example, as illustrated in Scheme H).

Scheme G2

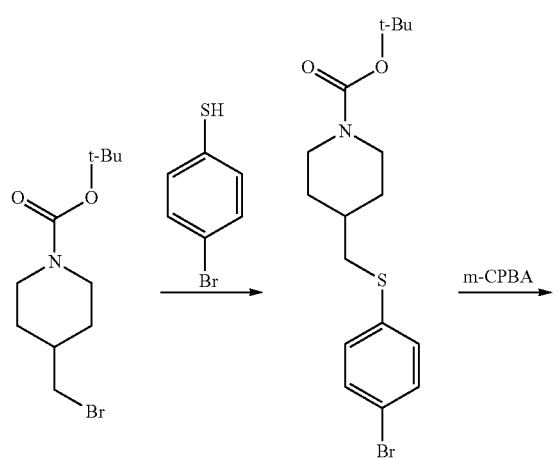

Scheme H

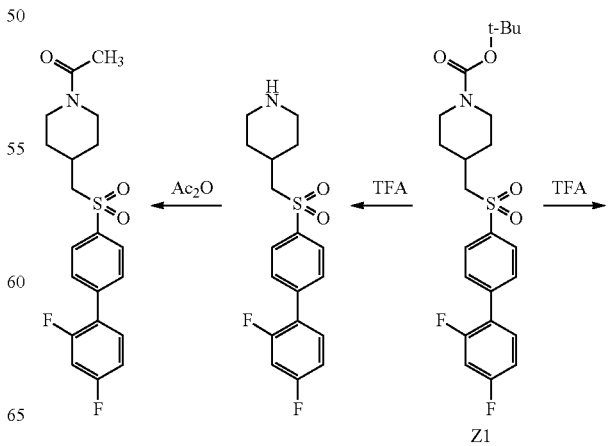

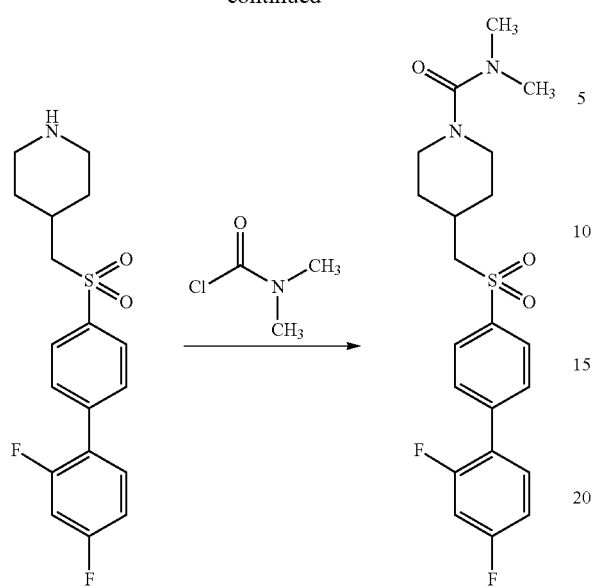

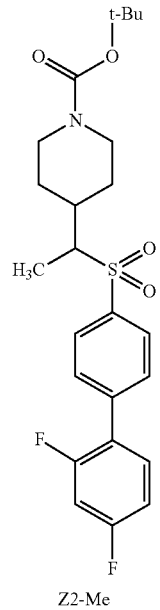

In addition (as illustrated in Scheme J1), the biaryl sulphone (Z1) may be treated with a base such as sodium hexamethyldisilazide (NaHMDS) followed by either a fluorinating agent such as N-fluorobenzenesulfonimide (NFSI) or an alkylating agent such as methyl iodide (MeI) to give the biaryl sulphone with R1=fluoro (Z2-F) or R1=methyl (Z2-Me), respectively. The Boc group may then be removed by treatment with trifluoroacetic acid and the piperidine so formed may then be N-acylated or N-carbamoylated. Isomers may be separated if desired.

In addition (as illustrated in Scheme J2), the biaryl sulphone with R1=fluoro (Z2-F) may be subsequently treated with a base such as sodium hexamethyldisilazide (NaHMDS) followed by a fluorinating agent such as N-fluorobenzenesulfonimide (NFSI) to give the compound with R1=R2=F(Z3-F2). The Boc group may then be removed by treatment with trifluoroacetic acid and the piperidine so formed may then be N-acylated or N-carbamoylated.

Scheme J2

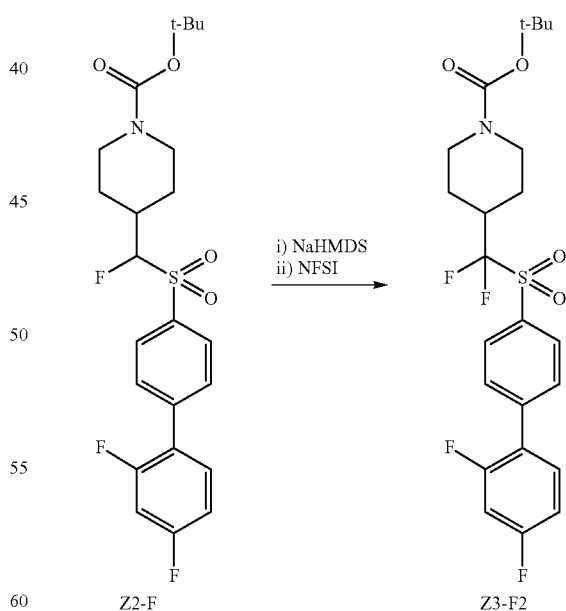

Scheme J1

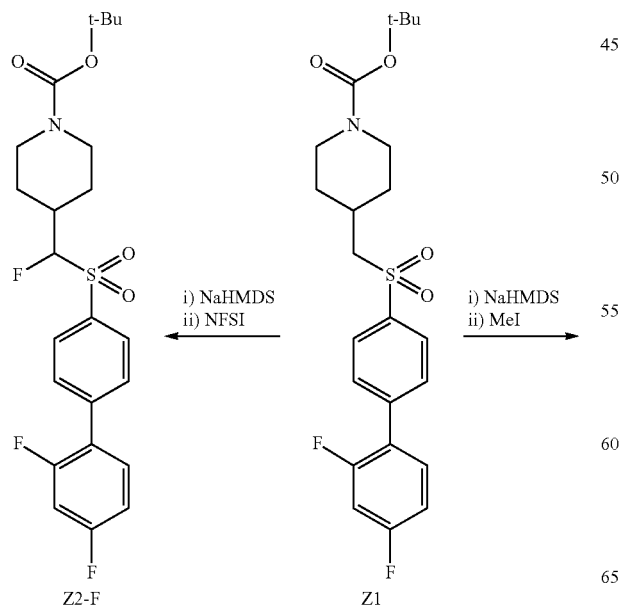

In a similar manner (as illustrated in Scheme J3), the biaryl sulphone with R1=alkyl, e.g., methyl (Z2-Me), may be treated with a similar base followed by an alkylating agent such as methyl iodide to give the compound with R1=R2=alkyl, e.g., methyl (Z3-Me2). The Boc group may then be removed by treatment with trifluoroacetic acid and the piperidine so formed may then be N-acylated or N-carbamoylated.

Scheme J3

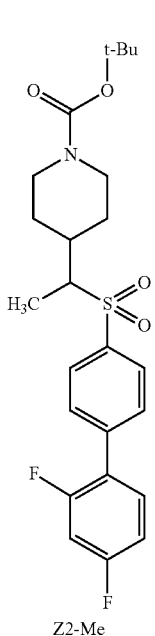

Additionally, the biaryl sulphone (e.g., Z2-F, with R1=fluoro; Z2-Me, with R1=methyl) may be treated with a base, for example, lithium diisopropylamide (LDA), followed by either a fluorinating agent, for example, N-fluorobenzenesulfonimide (NFSI), or an alkylating agent, for example, MeI, to give the biaryl sulphone with R2=fluoro or R2=alkyl (e.g., methyl). In this way, compounds where R1 and R2 are different (e.g., R1=fluoro and R2=methyl; R1=methyl and R2=ethyl; etc.), can be prepared. In the case where R1 is not the same as R2, the isomers may be separated if desired.

Alternatively (as illustrated in Scheme J4), in the cases in which R1=R2, the biaryl sulphone (Z1) maybe be treated with an excess of sodium hexamethyldisilazide (NaHMDS) and an excess of alkyl halide or N-fluorobenzenesulfonimide (NFSI) to lead directly to the disubstituted sulphone with R1=R2=alkyl or R1=R2=fluoro. The Boc group may then be removed by treatment with trifluoroacetic acid and the piperidine so formed may then be N-acylated or N-carbamoylated.

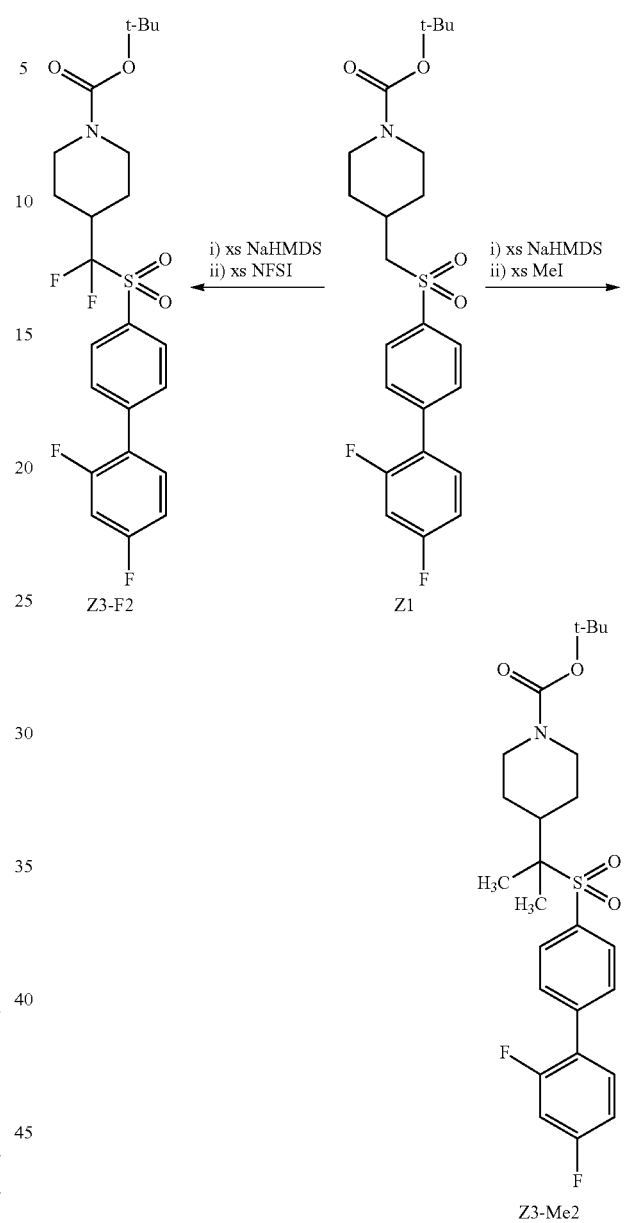

In a further approach (as illustrated in Scheme K), 4-chloromethylpyridine is reacted with an aromatic thiolate anion using a base such potassium carbonate ($K_2CO_3$) and the sulphide derivative so formed is oxidised to the sulphone using m-chloroperbenzoic acid (m-CPBA). This sulphone is reacted with an alkyl derivative that has a leaving group on each of the terminal carbon atoms, such as 1-bromo-2-chloroethane, in the presence of a base such a caesium carbonate ($Cs_2CO_3$). The resulting cycloalkyl derivative is then coupled to a suitable aryl partner, such as an aryl boronic ester using transition metal catalysis such as tetrakis (triphenylphosphine)palladium(0), the pyridine ring is reduced using hydrogen ($H_2$) with a catalyst such as platinum dioxide ($PtO_2$) and the product of the reduction is then N-acylated or N-carbamoylated as required.

Scheme K

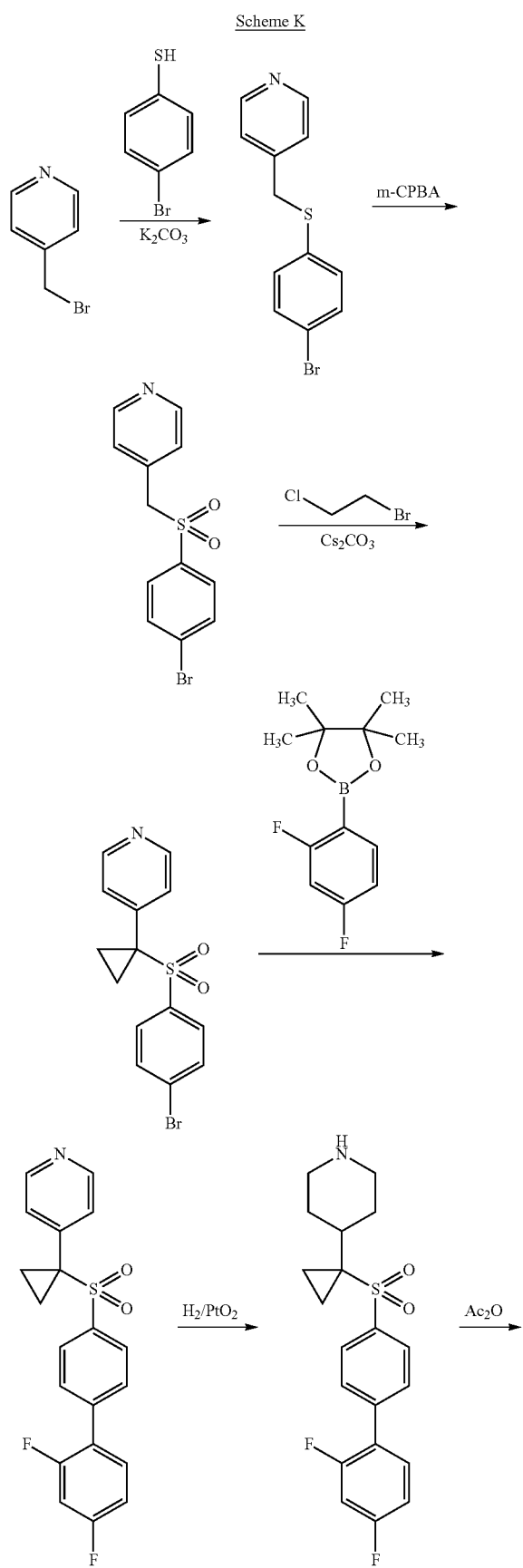

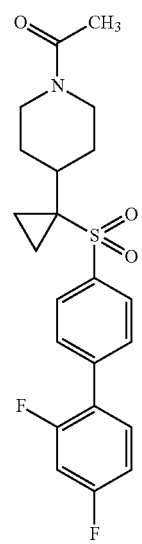

These and/or other well-known methods may be modified and/or adapted in known ways in order to facilitate the synthesis of additional compounds described herein. See, for example:

*Comprehensive Organic Transformations: A Guide to Functional Group Preparations,* 2$^{nd}$ Edition (Wiley) 2010. Ed. R. C. Larock. ISBN: 978-1-118-03758-4.

*Comprehensive Organic Synthesis,* 2nd Edition (Elsevier) 2014. Editor in Chiefs P. Knochel, G. A. Molander. eBook ISBN: 9780080977430. Hardcover ISBN: 9780080977423.

*Science of Synthesis: Cross Coupling and Heck-Type Reactions,* Workbench Edition (Thieme) 2013. Ed. G. Molander, J. P. Wolfe, Mats Larhed. ISBN 9783131734112.

*Greene's Protective Groups in Organic Synthesis,* 4$^{th}$ Edition (Wiley) 2006. P. G. M. Wuts, T. W. Greene. Print ISBN: 9780471697541. Online ISBN: 9780470053485.

*e-EROS Encyclopedia of Reagents for Organic Synthesis,* (Wiley). Online ISBN: 9780470842898. DOI: 10.1002/047084289X.

*Organic Reactions: Electrophilic Fluorination with N—F Reagents,* (Wiley) 2008. J. Baudoux, D. Cahard. DOI: 10.1002/0471264180.or069.02.

Compositions

One aspect of the present invention pertains to a composition (e.g., a pharmaceutical composition) comprising a NASMP compound, as described herein, and a carrier, diluent, or excipient (e.g., a pharmaceutically acceptable carrier, diluent, or excipient).

In one embodiment, the composition further comprises one or more (e.g., 1, 2, 3, 4) additional therapeutic agents, as described herein.

Another aspect of the present invention pertains to a method of preparing a composition (e.g., a pharmaceutical composition) comprising admixing a NASMP compound, as described herein, and a carrier, diluent, or excipient (e.g., a pharmaceutically acceptable carrier, diluent, or excipient).

Another aspect of the present invention pertains to a method of preparing a composition (e.g., a pharmaceutical composition) comprising admixing a NASMP compound, as described herein; one or more (e.g., 1, 2, 3, 4) additional therapeutic agents, as described herein; and a carrier, diluent, or excipient (e.g., a pharmaceutically acceptable carrier, diluent, or excipient).

Uses

The NASMP compounds, as described herein, are useful, for example, in the treatment of disorders (e.g., diseases) including, for example, the disorders (e.g., diseases) described herein.

Use in Methods of Therapy

Another aspect of the present invention pertains to a NASMP compound, as described herein, for use in a method of treatment of the human or animal body by therapy, for example, for use a method of treatment of a disorder (e.g., a disease) as described herein.

Another aspect of the present invention pertains to a NASMP compound, as described herein, in combination with one or more (e.g., 1, 2, 3, 4) additional therapeutic agents, as described herein, for use in a method of treatment of the human or animal body by therapy, for example, for use in a method of treatment of a disorder (e.g., a disease) as described herein.

Use in the Manufacture of Medicaments

Another aspect of the present invention pertains to use of a NASMP compound, as described herein, in the manufacture of a medicament for treatment, for example, treatment of a disorder (e.g., a disease) as described herein.

In one embodiment, the medicament comprises the NASMP compound.

Another aspect of the present invention pertains to use of a NASMP compound, as described herein, and one or more (e.g., 1, 2, 3, 4) additional therapeutic agents, as described herein, in the manufacture of a medicament for treatment, for example, treatment of a disorder (e.g., a disease) as described herein.

In one embodiment, the medicament comprises the NASMP compound and the one or more (e.g., 1, 2, 3, 4) additional therapeutic agents.

Methods of Treatment

Another aspect of the present invention pertains to a method of treatment, for example, of a disorder (e.g., a disease) as described herein, comprising administering to a patient in need of treatment a therapeutically effective amount of a NASMP compound, as described herein, preferably in the form of a pharmaceutical composition.

Another aspect of the present invention pertains to a method of treatment, for example, of a disorder (e.g., a disease) as described herein, comprising administering to a patient in need of treatment a therapeutically effective amount of a NASMP compound, as described herein, preferably in the form of a pharmaceutical composition, and one or more (e.g., 1, 2, 3, 4) additional therapeutic agents, as described herein, preferably in the form of a pharmaceutical composition.

Conditions Treated—Disorders Associated with Changes in Cellular Metabolism

In one embodiment, the treatment is treatment of: a disorder associated with changes in cellular metabolism.

In one embodiment, the treatment is treatment of: a disorder in which cellular metabolism is dysregulated.

Examples of such disorders include many of those described below, including, e.g., an autoimmune/inflammatory disorder; cancer; and a disorder mediated by osteoclasts.

In one embodiment, the treatment is treatment of multiple myeloma, diffuse large B-cell lymphoma, acute myeloid leukemia, eosinophilic leukemia, glioblastoma, melanoma, ovarian cancer, chemotherapy resistant cancer, radiation resistant cancer, inflammatory arthritis, rheumatoid arthritis, psoriatic arthritis, psoriasis, ulcerative colitis, Crohn's disease, systemic lupus erythematosus (SLE), lupus nephritis, asthma, chronic obstructive pulmonary disease (COPD).

Conditions Treated—Autoimmune/Inflammatory Disorders

In one embodiment, the treatment is treatment of: an autoimmune/inflammatory disorder.

In one embodiment, the treatment is treatment of: an autoimmune disorder.

In one embodiment, the treatment is treatment of: an inflammatory disorder.

In one embodiment, the treatment is treatment of: inflammatory arthritis (including, e.g., rheumatoid arthritis; psoriatic arthritis; ankylosing spondylitis; spondyloarthritis; reactive arthritis; infectious arthritis; systemic lupus erythematosus; scleroderma; gout; adult-onset Still's disease; juvenile idiopathic arthritis); psoriasis; systemic lupus erythematosus; lupus nephritis; systemic sclerosis; scleroderma; hepatitis; endometriosis; adenomyosis; Sjogren's syndrome; inflammatory bowel disease; ulcerative colitis; Crohn's disease; multiple sclerosis; asthma; atherosclerosis; chronic obstructive pulmonary disease (COPD); uveitis; Hidradenitis suppurativa; autoimmune hepatitis; pulmonary fibrosis; allergic disease (including, e.g., atopy, allergic rhinitis, atopic dermatitis, anaphylaxis, allergic bronchopulmonary aspergillosis, allergic gastroenteritis, hypersensitivity pneumonitis); an allergy; type I diabetes; rheumatic fever; celiac disease; encephalitis; oophoritis; primary biliary cirrhosis; insulin-resistant diabetes; autoimmune adrenal insufficiency (Addison's disease); acne; acne conglobate; acne fulminans; autoimmune oophoritis; autoimmune orchitis; autoimmune haemolytic anaemia; paroxysmal cold hemoglobinuria; Behçet's disease; autoimmune thrombocytopenia; autoimmune neutropenia; pernicious anaemia; pure red cell anaemia; autoimmune coagulopathy; myasthenia gravis; autoimmune polyneuritis; pemphigus; rheumatic carditis; Goodpasture's syndrome; postcardiotomy syndrome; polymyositis; dermatomyositis; irritable bowel syndrome; pancreatitis; gastritis, lichen planus; delayed type hypersensitivity; chronic pulmonary inflammation; pulmonary alveolitis; pulmonary granuloma; gingival inflammation; endodontic disease; periodontal disease; hypersensitivity pneumonitis; hay fever; anaphylaxis; skin allergy; hives; gout; polycystic kidney disease; cryopyrin-associated periodic syndrome (CAPS); Muckle-Wells Syndrome; Guillain-Barre syndrome; chronic inflammatory demyelinating polyneuropathy; organ or transplant rejection; chronic allograft rejection; acute or chronic graft versus-host disease; dermatitis; atopic dermatomyositis; Graves' disease; autoimmune (Hashimoto's) thyroiditis; blistering disorder; vasculitis syndrome; immune-complex mediated vasculitis; bronchitis; cystic fibrosis; pneumonia; pulmonary oedema; pulmonary embolism; sarcoidosis; hypertension; emphysema; respiratory failure; acute respiratory distress syndrome; BENTA disease; or polymyositis.

In one embodiment, the treatment is treatment of: inflammatory arthritis (including, e.g., rheumatoid arthritis; psoriatic arthritis; ankylosing spondylitis; spondyloarthritis; reactive arthritis; infectious arthritis; systemic lupus erythematosus; scleroderma; gout; adult-onset Still's disease; juvenile idiopathic arthritis); psoriasis; systemic lupus erythematosus, lupus nephritis; systemic sclerosis; scleroderma; hepatitis; endometriosis; adenomyosis; Sjogren's syndrome; inflammatory bowel disease; ulcerative colitis; Crohn's disease; Hidradenitis suppurativa; autoimmune hepatitis; multiple sclerosis; asthma, atherosclerosis; chronic obstructive pulmonary disease (COPD); uveitis; or pulmonary fibrosis.

In one embodiment, the treatment is treatment of: inflammatory arthritis (including, e.g., rheumatoid arthritis; psoriatic arthritis; ankylosing spondylitis; spondyloarthritis; reactive arthritis; infectious arthritis; systemic lupus erythematosus; scleroderma; gout; adult-onset Still's disease; juvenile idiopathic arthritis).

In one embodiment, the treatment is treatment of: psoriasis; psoriatic arthritis; systemic lupus erythematosus, lupus nephritis; systemic sclerosis; scleroderma; hepatitis; endometriosis; adenomyosis; Sjogren's syndrome; inflammatory bowel disease; ulcerative colitis; Crohn's disease; Hidradenitis suppurativa; autoimmune hepatitis; multiple sclerosis; asthma, atherosclerosis; chronic obstructive pulmonary disease (COPD); uveitis; or pulmonary fibrosis.

In one embodiment, the treatment is treatment of: inflammatory arthritis (including, e.g., rheumatoid arthritis; psoriatic arthritis; systemic lupus erythematosus; juvenile idiopathic arthritis); psoriasis; lupus nephritis; systemic sclerosis; inflammatory bowel disease; ulcerative colitis; Crohn's disease; Hidradenitis suppurativa; autoimmune hepatitis; or multiple sclerosis.

In one embodiment, the treatment is treatment of: inflammatory arthritis.

In one embodiment, the treatment is treatment of: rheumatoid arthritis.

In one embodiment, the treatment is treatment of: psoriatic arthritis.

In one embodiment, the treatment is treatment of: systemic lupus erythematosus.

In one embodiment, the treatment is treatment of: juvenile idiopathic arthritis.

In one embodiment, the treatment is treatment of: psoriasis.

In one embodiment, the treatment is treatment of: lupus nephritis.

In one embodiment, the treatment is treatment of: systemic sclerosis.

In one embodiment, the treatment is treatment of: inflammatory bowel disease.

In one embodiment, the treatment is treatment of: ulcerative colitis.

In one embodiment, the treatment is treatment of: Crohn's disease.

In one embodiment, the treatment is treatment of: Hidradenitis suppurativa.

In one embodiment, the treatment is treatment of: autoimmune hepatitis.

In one embodiment, the treatment is treatment of: multiple sclerosis.

Conditions Treated—Cancer

In one embodiment, the treatment is treatment of: cancer.

In one embodiment, the treatment is treatment of: multiple myeloma; lymphoma; leukaemia; carcinoma; or sarcoma.

Multiple Myeloma:

In one embodiment, the treatment is treatment of: multiple myeloma.

Lymphoma:

In one embodiment, the treatment is treatment of: lymphoma.

In one embodiment, the treatment is treatment of: Hodgkin's lymphoma; non-Hodgkin's lymphoma; lymphocytic lymphoma; granulocytic lymphoma; monocytic lymphoma; diffuse large B-cell lymphoma (DLBCL); mantel cell lymphoma (MCL); follicular cell lymphoma (FL); mucosa-associated lymphoid tissue (MALT) lymphoma; marginal zone lymphoma; T-cell lymphoma; marginal zone lymphoma; or Burkitt's lymphoma.

In one embodiment, the treatment is treatment of lymphocytic lymphoma; granulocytic lymphoma; monocytic lymphoma; or diffuse large B-cell lymphoma (DLBCL).

In one embodiment, the treatment is treatment of: diffuse large B-cell lymphoma (DLBCL).

Leukaemia:

In one embodiment, the treatment is treatment of: leukaemia.

In one embodiment, the treatment is treatment of: chronic lymphocytic leukemia (CLL); acute myeloid leukemia (AML); acute lymphocytic leukemia (ALL); lymphoblastic T-cell leukemia; chronic myelogenous leukemia (CML); hairy-cell leukemia; acute lymphoblastic T-cell leukemia; acute eosinophilic leukemia; immunoblastic large-cell leukemia; megakaryoblastic leukemia; acute megakaryocytic leukemia; promyelocytic leukemia; erythroleukemia; or plasmacytoma.

In one embodiment, the treatment is treatment of: chronic lymphocytic leukemia (CLL); acute myeloid leukemia (AML); acute lymphocytic leukemia (ALL); lymphoblastic T-cell leukemia; chronic myelogenous leukemia (CML); or acute eosinophilic leukemia.

In one embodiment, the treatment is treatment of: chronic lymphocytic leukemia (CLL).

In one embodiment, the treatment is treatment of: acute myeloid leukemia (AML).

In one embodiment, the treatment is treatment of: acute lymphocytic leukemia (ALL).

In one embodiment, the treatment is treatment of: lymphoblastic T-cell leukemia.

In one embodiment, the treatment is treatment of: chronic myelogenous leukemia (CML).

Carcinoma:

In one embodiment, the treatment is treatment of: carcinoma.

In one embodiment, the treatment is treatment of: colon cancer; breast cancer; ovarian cancer; lung cancer (including, e.g., small cell lung carcinoma and non-small cell lung carcinoma); prostate cancer; cancer of the oral cavity or pharynx (including, e.g., cancer of the lip, tongue, mouth, larynx, pharynx, salivary gland, buccal mucosa); esophageal cancer; stomach cancer; small intestine cancer; large intestine cancer; rectal cancer; liver passage cancer; biliary passage cancer; pancreatic cancer; bone cancer; connective tissue cancer; skin cancer; cervical cancer; uterine cancer; corpus cancer; endometrial cancer; vulval cancer; vaginal cancer; testicular cancer; bladder cancer; kidney cancer; ureter cancer; urethral cancer; urachus cancer; eye cancer; glioma; spinal cord cancer; central nervous system cancer; peripheral nervous system cancer; meningeal cancer; thyroid cancer; adrenocarcinoma; astrocytoma; acoustic neuroma; anaplastic astrocytoma; basal cell carcinoma; blastoglioma; choriocarcinoma; chordoma; craniopharyngioma; cutaneous melanoma; cystadenocarcinoma; embryonal carcinoma; ependymoma; epithelial carcinoma; gastric cancer; genitourinary tract cancer; glioblastoma multiforme; head and neck cancer; hemangioblastoma; hepatocellular carcinoma; renal cell carcinoma (RCC); hepatoma; large cell carcinoma; medullary thyroid carcinoma; medulloblastoma; meningioma mesothelioma; myeloma; neuroblastoma; oligodendroglioma; epithelial ovarian cancer; papillary carcinoma; papillary adenocarcinoma; paraganglioma; parathyroid tumour; pheochromocytoma; pinealoma; plasmacytoma; retinoblastoma; sebaceous gland carcinoma;

seminoma; melanoma; squamous cell carcinoma; sweat gland carcinoma; synovioma; thyroid cancer; uveal melanoma; or Wilm's tumour.

In one embodiment, the treatment is treatment of: colon cancer; breast cancer; ovarian cancer; lung cancer (including, e.g., small cell lung carcinoma and non-small cell lung carcinoma); prostate cancer; stomach cancer; pancreatic cancer; bone cancer; skin cancer; cervical cancer; uterine cancer; endometrial cancer; testicular cancer; bladder cancer; kidney cancer; eye cancer; liver cancer; glioma; thyroid cancer; adrenocarcinoma; astrocytoma; acoustic neuroma; anaplastic astrocytoma; cutaneous melanoma; gastric cancer; glioblastoma multiforme; head and neck cancer; hepatocellular carcinoma; renal cell carcinoma (RCC); melanoma; or squamous cell carcinoma.

In one embodiment, the treatment is treatment of: colon cancer; breast cancer; ovarian cancer; lung cancer (including, e.g., small cell lung carcinoma and non-small cell lung carcinoma); prostate cancer; pancreatic cancer; bone cancer; liver cancer; glioblastoma multiforme; head and neck cancer; or melanoma.

In one embodiment, the treatment is treatment of: melanoma.

In one embodiment, the treatment is treatment of: glioblastoma multiforme.

In one embodiment, the treatment is treatment of: breast cancer.

In one embodiment, the treatment is treatment of: prostate cancer.

In one embodiment, the treatment is treatment of: bone cancer.

In one embodiment, the treatment is treatment of: pancreatic cancer.

In one embodiment, the treatment is treatment of: head and neck cancer.

In one embodiment, the treatment is treatment of: lung cancer (including, e.g., small cell lung carcinoma and non-small cell lung carcinoma).

In one embodiment, the treatment is treatment of: ovarian cancer.

In one embodiment, the treatment is treatment of: liver cancer.

Sarcoma:

In one embodiment, the treatment is treatment of: sarcoma.

In one embodiment, the treatment is treatment of: Askin's tumour; sarcoma botryoides; chondrosarcoma; endotheliosarcoma; Ewing's sarcoma; Malignant hemagioendothelioma; malignant Schwannoma; osteosarcoma; gastrointestinal stromal tumour (GIST); myxosarcoma; alveolar soft part sarcoma; angiosarcoma; cystosarcoma phyllodes; dermatofibrosarcoma; desmoid tumour; desmoplastic small round cell tumour; extraskeletal chondrosarcoma; osteosarcoma; fibrosarcoma; hemagiopericytoma; hemangiosarcoma; Kaposi's sarcoma; leiomyosarcoma; liposarcoma; lyphangiosarcoma; lymphangioendotheliosarcoma; lymphosarcoma; malignant peripheral nerve sheath tumour; neurofibrosarcoma; plexiform fibrohistiocytic tumour; rhabdomyosarcoma; or synovial sarcoma.

Treatment of Refractory Cancer:

In one embodiment, the treatment is treatment of: treatment refractory cancer (including, e.g., chemotherapy resistant cancer and radiotherapy resistant cancer); metastatic cancer; metastases; or recurrent cancer.

In one embodiment, the treatment is treatment of: chemotherapy resistant cancer (including, e.g., chemotherapy resistant multiple myeloma, lymphoma, leukaemia, carcinoma, and sarcoma).

In one embodiment, the treatment is treatment of: radiotherapy resistant cancer (including, e.g., radiotherapy resistant multiple myeloma, lymphoma, leukaemia, carcinoma, and sarcoma).

In one embodiment, the treatment is treatment of: metastatic cancer.

In one embodiment, the treatment is treatment of: metastases.

In one embodiment, the treatment is treatment of: recurrent cancer.

In one embodiment, the treatment is use in: preventing, reducing, or overcoming resistance to radiotherapy or chemotherapy (for example, due to changes in cellular metabolism); preventing or reducing tumour invasion; preventing or reducing tumour metastasis; improving the action of anti-tumour agents; and/or augmenting the action of immunomodulators.

In one embodiment, the treatment is use in: preventing, reducing, or overcoming resistance to radiotherapy.

In one embodiment, the treatment is use: in preventing, reducing, or overcoming resistance to chemotherapy.

In one embodiment, the treatment is use in: preventing or reducing tumour invasion or tumour metastasis; improving the action of anti-tumour agents; and/or augmenting the action of immunomodulators.

In one embodiment, the treatment is use in: improving the action of anti-tumour agents; and/or augmenting the action of immunomodulators.

In one embodiment, the treatment is use in: improving the action of immunomodulators.

Conditions Treated—Disorders Mediated by Osteoclasts

In one embodiment, the treatment is treatment of: a disorder mediated by osteoclasts.

In one embodiment, the treatment is treatment of: rheumatoid arthritis; osteoporosis; Paget's disease; osteopetrosis; osteoarthritis; ectopic bone formation; bone loss associated with endometriosis; neoplasia of bones (including, e.g., as a primary tumour or as metastases and including, e.g., bone cancer; osteosarcoma; or osteoma); cancer-associated bone disease (including, e.g., metastatic bone disease associated with, e.g., breast cancer, lung cancer, prostate cancer, or multiple myeloma; changes in bone mineralisation and density associated with cancer, including, e.g., hypercalcaemia associated with cancer); bone metastases (including, e.g., osteolytic bone metastases); hypercalcaemia (including, e.g., hypercalcaemia associated with cancer; hypercalcaemia caused by conditions associated with increased bone resorption (including, e.g., hypercalcaemia caused by vitamin D intoxication, primary or tertiary hyperparathyroidism, immobilisation, or sarcoidosis); or aseptic loosening of prosthetic implants (e.g., artificial joints, e.g., knees, hips, etc.).

In one embodiment, the treatment is treatment of: rheumatoid arthritis; osteoporosis; neoplasia of bones (including, e.g., as a primary tumour or as metastases and including, e.g., bone cancer; osteosarcoma; or osteoma); cancer-associated bone disease (including, e.g., metastatic bone disease associated with, e.g., breast cancer, lung cancer, prostate cancer, or multiple myeloma; changes in bone mineralisation and density associated with cancer, including, e.g., hypercalcaemia associated with cancer); or bone metastases (including, e.g., osteolytic bone metastases).

In one embodiment, the treatment is treatment of: rheumatoid arthritis.

In one embodiment, the treatment is treatment of: osteoporosis.

In one embodiment, the treatment is treatment of: neoplasia of bones (including, e.g., as a primary tumour or as metastases and including, e.g., bone cancer; osteosarcoma; or osteoma).

In one embodiment, the treatment is treatment of: bone cancer; osteosarcoma; or osteoma.

In one embodiment, the treatment is treatment of: cancer-associated bone disease (including, e.g., metastatic bone disease associated with, e.g., breast cancer, lung cancer, prostate cancer, or multiple myeloma; changes in bone mineralisation and density associated with cancer, including, e.g., hypercalcaemia associated with cancer).

In one embodiment, the treatment is treatment of: bone metastases.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, alleviation of symptoms of the condition, amelioration of the condition, and cure of the condition. Treatment as a prophylactic measure (i.e., prophylaxis) is also included. For example, use with patients who have not yet developed the condition, but who are at risk of developing the condition, is encompassed by the term "treatment."

For example, treatment of inflammation includes the prophylaxis of inflammation, reducing the incidence of inflammation, reducing the severity of inflammation, alleviating the symptoms of inflammation, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously.

For example, the compounds described herein may also be used in combination therapies, e.g., in conjunction with other agents, for example, anti-inflammation agents, etc. Examples of treatments and therapies include chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; photodynamic therapy; gene therapy; and controlled diets.

One aspect of the present invention pertains to a compound as described herein, in combination with one or more additional therapeutic agents.

The particular combination would be at the discretion of the physician who would select dosages using his common general knowledge and dosing regimens known to a skilled practitioner.

The agents (i.e., the compound described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the compound described here, plus one or more other agents) may be formulated together in a single dosage form, or alternatively, the individual agents may be formulated separately and presented together in the form of a kit, optionally with instructions for their use.

Other Uses

The NASMP compounds described herein may also be used as part of an in vitro assay, for example, in order to determine whether a candidate host is likely to benefit from treatment with the compound in question.

The NASMP compounds described herein may also be used as a standard, for example, in an assay, in order to identify other compounds, other anti-inflammation agents, etc.

Kits

One aspect of the invention pertains to a kit comprising (a) a NASMP compound as described herein, or a composition comprising a NASMP compound as described herein, e.g., preferably provided in a suitable container and/or with suitable packaging; and (b) instructions for use, e.g., written instructions on how to administer the compound or composition.

In one embodiment, the kit further comprises one or more (e.g., 1, 2, 3, 4) additional therapeutic agents, as described herein.

The written instructions may also include a list of indications for which the active ingredient is a suitable treatment.

Routes of Administration

The NASMP compound or pharmaceutical composition comprising the NASMP compound may be administered to a subject by any convenient route of administration, whether systemically/peripherally or topically (i.e., at the site of desired action).

Routes of administration include oral (e.g., by ingestion); buccal; sublingual; transdermal (including, e.g., by a patch, plaster, etc.); transmucosal (including, e.g., by a patch, plaster, etc.); intranasal (e.g., by nasal spray, drops or from an atomiser or dry powder delivery device); ocular (e.g., by eye drops); pulmonary (e.g., by inhalation or insufflation therapy using, e.g., an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

In one preferred embodiment, the route of administration is oral (e.g., by ingestion). In one preferred embodiment, the route of administration is parenteral (e.g., by injection).

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutan, gibbon), or a human. Furthermore, the subject/patient may be any of its forms of development, for example, a foetus.

In one preferred embodiment, the subject/patient is a human.

Formulations

While it is possible for the NASMP compound to be administered alone, it is preferable to present it as a pharmaceutical formulation (e.g., composition, preparation, medicament) comprising at least one NASMP compound, as described herein, together with one or more other pharmaceutically acceptable ingredients well known to those skilled in the art, including pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined herein, and methods of making a pharmaceutical composition comprising admixing at least one NASMP compound, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences*, 18th edition, Mack Publishing Company, Easton, Pa., 1990; and *Handbook of Pharmaceutical Excipients*, 5th edition, 2005.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, lozenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or admixed with one or more other pharmaceutically acceptable ingredients. The compound may be presented in a liposome or other microparticulate which is designed to target the compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, lozenges, pastilles, as well as patches, adhesive plasters, depots, and reservoirs. Lozenges typically comprise the compound in a flavoured basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, lozenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, lozenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1, 3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprise a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichloro-tetrafluoroethane, carbon dioxide, or other suitable gases.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient.

Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/mL to about 10 µg/mL, for example, from about 10 ng/mL to about 1 µg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the NASMP compounds, and compositions comprising the NASMP compounds, can vary from patient to patient. Determining the optimal dosage will generally involve the balancing of the level of therapeutic benefit against any risk or deleterious side effects. The selected dosage level will depend on a variety of factors including the activity of the particular NASMP compound, the route of administration, the time of administration, the rate of excretion of the NASMP compound, the duration of the treatment, other drugs, compounds, and/or materials used in combination, the severity of the condition, and the species, sex, age, weight, condition, general health, and prior medical history of the patient. The amount of NASMP compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the NASMP compound is in the range of about 10 µg to about 20 mg (more typically about 100 µg to about 10 mg) per kilogram body weight of the subject per day. Where the compound is a salt, an ester, an amide, a prodrug, or the like, the amount administered is calculated on the basis of the parent compound and so the actual weight to be used is increased proportionately.

Chemical Synthesis

Acronyms and Abbreviations

AcCl: acetyl chloride
Ac$_2$O: acetic anhydride
B$_2$pin$_2$: bis(pinacolato)diboron
DCM: dichloromethane
DMAP: 4-dimethylaminopyridine
DMF: dimethylformamide
DMSO: dimethyl sulfoxide
ESI: electrospray ionization
Et$_3$N: triethylamine
EtOAc: ethyl acetate
HPLC: high-performance liquid chromatography
LCMS: liquid chromatography-mass spectrometry
m-CPBA: meta-chloroperoxybenzoic acid
MeOH: methanol
Ms: mesylate
m/z: mass-to-charge ratio
NaHMDS: sodium bis(trimethylsilyl)amide
NFSI: N-fluorobenzenesulfonimide
NMR: nuclear magnetic resonance (spectroscopy)
rt: room temperature
TBAB: tetra-n-butylammonium bromide
TES: triethylsilane
TFA: trifluoroacetic acid
TFAA: trifluoroacetic anhydride
THF: tetrahydrofuran
TLC: thin-layer chromatography Analytical HPLC (Method A)

Unless specified, the analytical HPLC characterisation of the target compounds (i.e., the "Synthesis Compounds") was conducted on the following system:
 Column: X-select CSH C18, 4.6 mm×150 mm, ID 3.5 µm
 Injection volume: 5 µL
 Flow rate: 1 mL/min
 Solvents: A: 0.1% formic acid in water:acetonitrile (95:5)
  B: acetonitrile
 Gradient (B % is increased linearly between 1 minute and 8 minutes):

| Time (min) | A % | B % |
|---|---|---|
| 0 | 95 | 5 |
| 1 | 95 | 5 |
| 8 | 0 | 100 |
| 12 | 0 | 100 |
| 14 | 95 | 5 |
| 18 | 95 | 5 |

Analytical HPLC (Method B)

The analytical HPLC characterisation of Intermediates 47, 49, 50 and 51 plus the larger scale synthesis of Synthesis Compound 1 was conducted on the following system:
 Column: Acquity BEH Phenyl, 4.6 mm×30 mm, ID 1.7 µm
 Injection volume: 5 µL
 Flow rate: 2 mL/min
 Solvents: A: 0.03% TFA in water
  B: 0.03% TFA in acetonitrile Gradient:

| Time (min) | A % | B % |
|---|---|---|
| 0 | 95 | 5 |
| 5.2 | 5 | 95 |
| 5.7 | 5 | 95 |
| 5.8 | 95 | 5 |
| 6.2 | 95 | 5 |

Thin-Layer Chromatography (TLC)

TLC analyses were carried out using pre-coated TLC sheets with silica gel 60 with fluorescent indicator UV-254 from Loba Chemie.

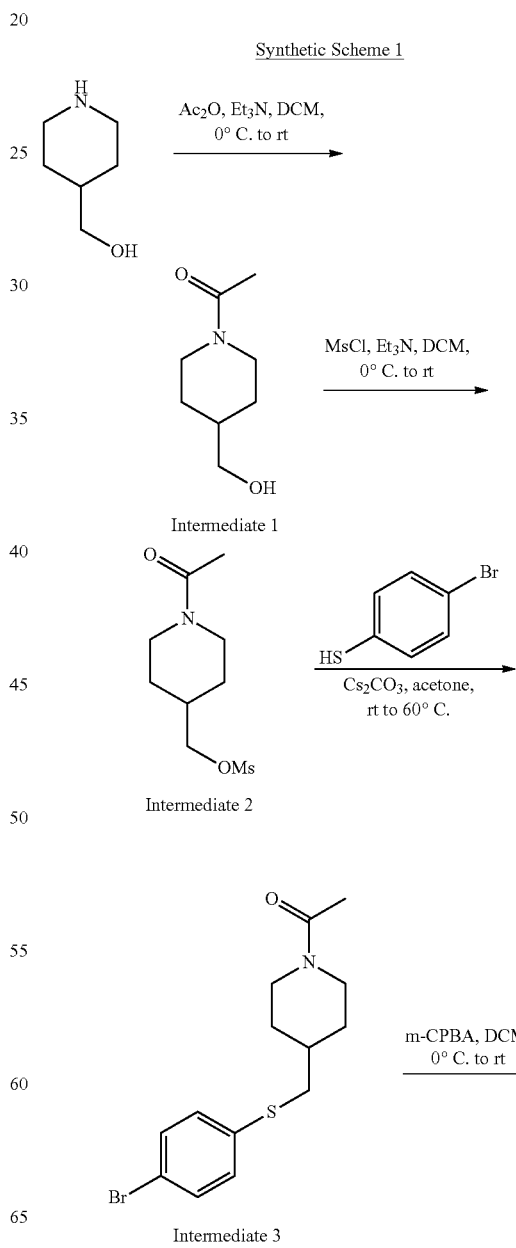

Synthetic Scheme 1

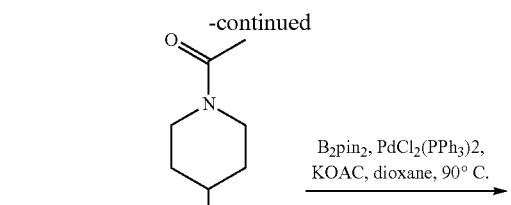

Intermediate 4

B₂pin₂, PdCl₂(PPh₃)₂, KOAC, dioxane, 90° C.

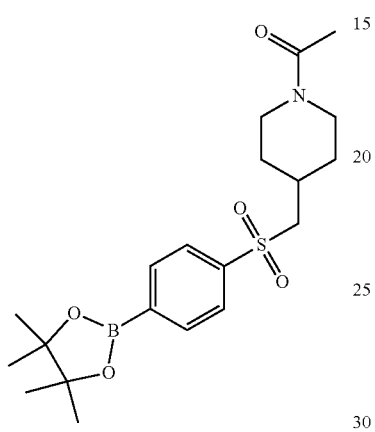

Intermediate 5

Intermediate 1

1-(4-(Hydroxymethyl)piperidin-1-yl)ethan-1-one

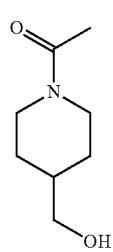

To a solution of piperidin-4-yl methanol (25.00 g, 217.05 mmol) in DCM (250 mL), triethylamine (60.50 mL, 434.10 mmol) and acetic anhydride (22.56 mL, 238.75 mmol) were added at 0° C. The reaction mixture was warmed to room temperature and stirred for 16 h. The progress of the reaction was monitored by TLC [mobile phase: 10% methanol in DCM]. After completion of the reaction, water (250 mL) was added to the reaction mixture and the layers were separated. The aqueous layer was extracted with DCM (3×250 mL). The combined organic layer was dried over anhydrous sodium sulfate, filtered and concentrated under reduced pressure to dryness to afford the title compound Intermediate 1 (20.00 g, crude) as colorless oil. This compound was carried on to the next step without further purification.

Analytical Data:
¹H NMR (400 MHz, DMSO-d₆) δ (ppm): 4.48 (t, J=5.2 Hz, 1H), 4.35 (dd, J=11.2, 2.0 Hz, 1H), 3.78 (d, J=14.0 Hz, 1H), 3.25 (t, J=5.6 Hz, 2H), 2.97 (td, J=13.2, 2.8 Hz, 1H), 2.46 (td, J=12.4, 2.4 Hz, 1H), 1.97 (s, 3H), 1.70-1.50 (m, 3H), 1.10-0.85 (m, 2H).

Intermediate 2

(1-Acetylpiperidin-4-yl)methyl methanesulfonate

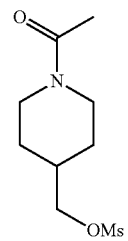

To a solution of 1-(4-(hydroxymethyl)piperidin-1-yl) ethan-1-one Intermediate 1 (20.00 g, 127.21 mmol) in DCM (200 mL), triethylamine (35.39 mL, 254.43 mmol) and methanesulfonyl chloride (10.83 mL, 139.94 mmol) were added dropwise at 0° C. The reaction mixture was then warmed to room temperature and stirred for 4 h. The progress of the reaction was monitored by TLC [mobile phase: 10% Methanol in DCM]. After completion of the reaction, the reaction mixture was quenched with water (50 mL) and extracted with DCM (3×200 mL). The combined organic layer was dried over anhydrous sodium sulfate, filtered and concentrated under reduced pressure to dryness to afford the title compound Intermediate 2 (25.00 g, crude) as yellow oil. This compound was used in the next step without further purification.

Analytical Data:
LCMS (ESI) m/z=235.95 [M+H]⁺.

Intermediate 3

1-(4-(((4-Bromophenyl)thio)methyl)piperidin-1-yl) ethan-1-one

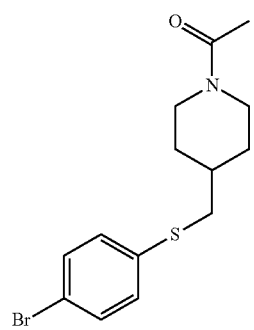

To a solution of 4-bromobenzenethiol (2.82 g, 14.95 mmol) in acetone (50 mL), caesium carbonate (8.85 g, 27.18 mmol) was added under an argon atmosphere at room temperature and the reaction mixture was stirred for 30 min. Then, (1-acetylpiperidin-4-yl)methyl methanesulfonate Intermediate 2 (3.20 g, 13.59 mmol) was added to the reaction mixture and the reaction was heated to 60° C. for 16 h under an argon atmosphere. The progress of the reaction was monitored by TLC [mobile phase: 100% ethyl acetate]. After completion of the reaction, the reaction mixture was cooled to room temperature, filtered through a pad of celite and the filtrate was concentrated under reduced pressure to dryness. The crude product was purified by column chromatography on silica gel (CombiFlash®, gradient 10-100% ethyl acetate in hexane to 5% methanol in DCM) to afford the title compound Intermediate 3 (3.95 g, 80%) as a colorless thick oil.

Analytical Data:

$^1$H NMR (400 MHz, CDCl$_3$) δ (ppm): 7.39 (d, J=8.4 Hz, 2H), 7.18 (d, J=8.4 Hz, 2H), 4.61 (d, J=13.2 Hz, 1H), 3.81 (d, J=14.0 Hz, 1H), 3.04-2.95 (m, 1H), 2.90-2.75 (m, 2H), 2.55-2.45 (m, 1H), 2.08 (s, 3H), 1.96-1.80 (m, 2H), 1.80-1.65 (m, 1H), 1.25-1.11 (m, 2H).

Intermediate 4

1-(4-(((4-Bromophenyl)sulfonyl)methyl)piperidin-1-yl)ethan-1-one

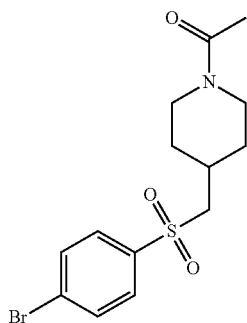 [SMILES: CC(=O)N1CCC(CS(=O)(=O)c2ccc(Br)cc2)CC1]

To a stirred solution of 1-(4-(((4-bromophenyl)thio)methyl)piperidin-1-yl)ethan-1-one Intermediate 3 (3.90 g, 11.88 mmol) in DCM (60 mL), meta-chloroperbenzoic acid (60%) (10.25 g, 35.64 mmol) was added in portions at 0° C. The reaction mixture was warmed to room temperature and stirred for 16 h. The progress of the reaction was monitored by TLC [mobile phase: 10% methanol in DCM]. After completion of the reaction, the reaction mixture was quenched with saturated aqueous sodium thiosulfate (50 mL). The layers were separated, and the organic layer was washed with saturated aqueous sodium bicarbonate (2×50 mL). The organic layer was dried over sodium sulfate, filtered and concentrated under reduced pressure to dryness to afford the title compound Intermediate 4 (4.02 g, crude) as an off-white solid. This compound was used in the next step without further purification.

Analytical Data:

LCMS (ESI): m/z=361.90 [M+H]$^+$ ($^{81}$Br).

Intermediate 5

1-(4-(((4-(4,4,5,5-Tetramethyl-1,3,2-dioxaborolan-2-yl)phenyl)sulfonyl)methyl)piperidin-1-yl)ethan-1-one

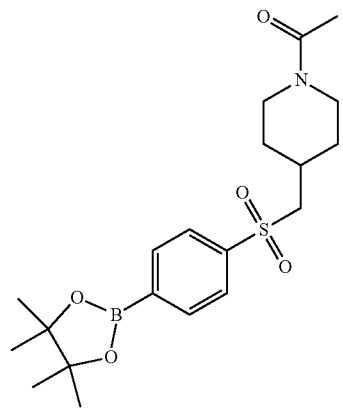 [SMILES: CC(=O)N1CCC(CS(=O)(=O)c2ccc(B3OC(C)(C)C(C)(C)O3)cc2)CC1]

To a reaction tube were added a solution of 1-(4-(((4-bromophenyl)sulfonyl)methyl)piperidin-1-yl)ethan-1-one Intermediate 4 (2.00 g, 5.55 mmol), bis(pinacolato)diborane (1.70 g, 6.66 mmol) and potassium acetate (1.63 g, 16.65 mmol) in 1,4-dioxane (30 mL). The tube was sealed and degassed by purging with nitrogen for 15 min. Bis(triphenylphosphine)palladium(II) dichloride (0.060 g, 0.083 mmol) was added to the reaction mixture under a nitrogen atmosphere and the purging with nitrogen was continued for 5 min. The reaction mixture was heated to 90° C. for 4 h. The progress of the reaction was monitored by TLC [mobile phase: 10% methanol in DCM]. After completion of the reaction, the reaction mixture was cooled to room temperature and concentrated under reduced pressure to dryness. The crude product was purified by column chromatography on silica gel (100-200 mesh, gradient 0-5% methanol in DCM) to afford the title compound Intermediate 5 (1.50 g, 66%) as a black solid.

Analytical Data:

LCMS (ESI) m/z=408.21 [M+H]$^+$ (boronic ester), 326.04 [M+H]$^+$ (corresponding boronic acid).

Synthetic Scheme 2

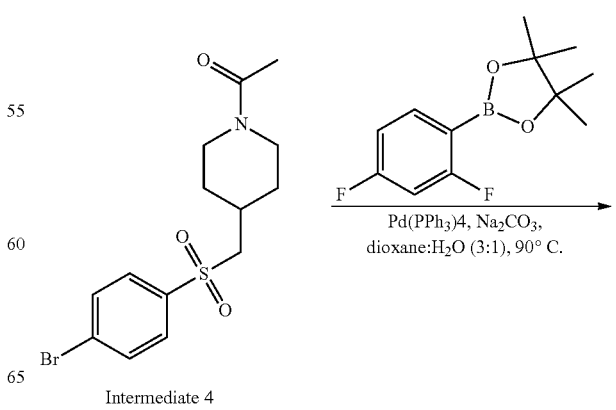

Intermediate 4

-continued

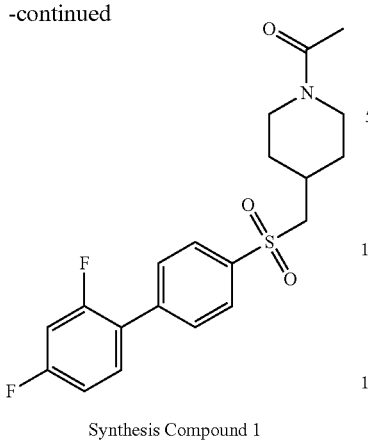

Synthesis Compound 1

Synthesis Compound 1

1-(4-(((2',4'-Difluoro-[1,1'-biphenyl]-4-yl)sulfonyl)methyl)piperidin-1-yl)ethan-1-one (NASMP-01)

To a reaction tube were added a solution of 1-(4-(((4-bromophenyl)sulfonyl)methyl)piperidin-1-yl)ethan-1-one Intermediate 4 (0.500 g, 1.39 mmol), 2-(2,4-difluorophenyl)-4,4,5,5-tetramethyl-1,3,2-dioxaborolane (0.366 g, 1.52 mmol) and sodium carbonate (0.367 g, 3.46 mmol) in a mixture of 1,4-dioxane-water (3:1, 8 mL). The tube was sealed and degassed by purging with argon for 15 min. Tetrakis(triphenylphosphine)palladium(0) (0.160 g, 0.139 mmol) was added to the reaction mixture under an argon atmosphere and the purging with argon was continued for 5 min. The reaction mixture was heated at 90° C. for 12 h. The progress of the reaction was monitored by TLC [mobile phase: 10% methanol in DCM]. After completion of the reaction, the reaction mixture was cooled to room temperature and concentrated under reduced pressure to dryness. The crude product was purified by column chromatography on silica gel (230-400 mesh, gradient 0-10% methanol in DCM). The compound was further purified by preparative HPLC (mobile phase: 0.5% formic acid in a mixture of acetonitrile/water; solid phase: C18 silica) to afford the title compound Synthesis Compound 1 (0.220 g, 40%) as an off-white solid.

Analytical Data:

LCMS (ESI) m/z=394.10 [M+H]$^+$.

HPLC (see generic method): Retention time: 8.03 min.; Purity: 99.75%.

$^1$H NMR (400 MHz, DMSO-d$_6$) δ (ppm): 7.97 (d, J=8.4 Hz, 2H), 7.78 (d, J=7.2 Hz, 2H), 7.63-7.59 (m, 1H), 7.33-7.28 (m, 1H), 7.21-7.17 (m, 1H), 4.19 (d, J=13.2 Hz, 1H), 3.71 (d, J=14.0 Hz, 1H), 3.28 (d, J=6.0 Hz, 2H), 2.98 (t, J=8.4 Hz, 1H), 2.62-2.52 (m, 1H), 2.10-2.02 (m, 1H), 1.93 (s, 3H), 1.87-1.72 (m, 2H), 1.32-1.20 (m, 1H), 1.20-1.07 (m, 1H).

Synthetic Scheme 3

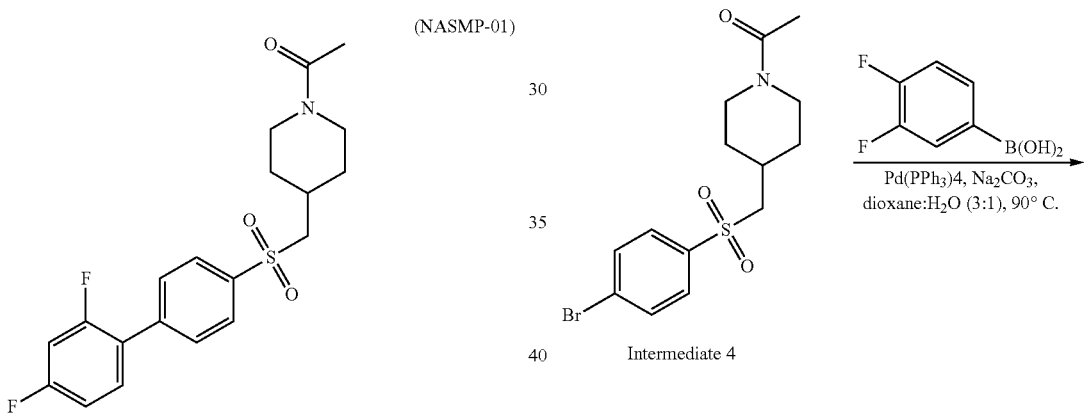

Intermediate 4

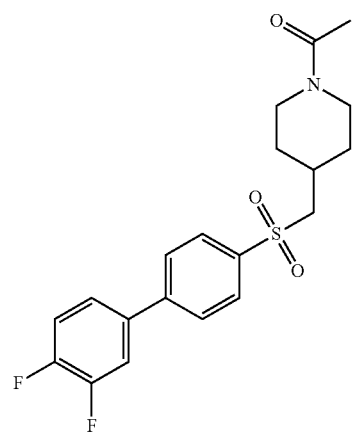

Synthesis Compound 2

Synthesis Compound 2

1-(4-(((3',4'-Difluoro-[1,1'-biphenyl]-4-yl)sulfonyl)methyl)piperidin-1-yl)ethan-1-one (NASMP-02)

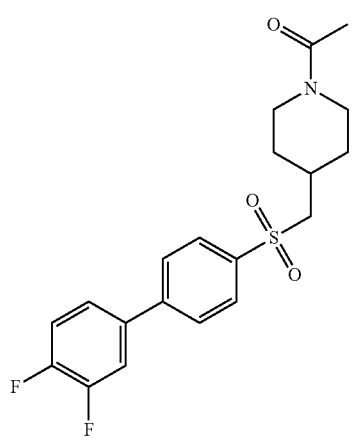

To a reaction tube were added a solution of 1-(4-(((4-bromophenyl)sulfonyl)methyl)piperidin-1-yl) ethan-1-one Intermediate 4 (0.500 g, 1.38 mmol), (3,4-difluorophenyl) boronic acid (0.263 g, 1.66 mmol) and sodium carbonate (0.367 g, 3.46 mmol) in a mixture of 1,4-dioxane: water (3:1, 13 mL). The tube was sealed and degassed by purging with nitrogen for 5 min, followed by addition of tetrakis (triphenylphosphine)palladium(0) (0.159 g, 0.138 mmol) to the reaction mixture under a nitrogen atmosphere and the purging with nitrogen was continued for another 5 min. The reaction mixture was then heated at 90° C. for 16 h under a nitrogen atmosphere. The progress of the reaction was monitored by TLC [mobile phase: 50% ethyl acetate in hexanes]. After completion of the reaction, the reaction mixture was cooled to room temperature and filtered through a pad of Celite. The Celite pad was washed with ethyl acetate (2×100 mL). The combined organic layer was concentrated under reduced pressure to dryness. The crude product was purified by column chromatography on silica gel (CombiFlash®, gradient 10-50% ethyl acetate in hexanes). The resulting compound was further purified by stirring with diethyl ether (25 mL) and n-pentane (50 mL), the solids were filtered out and dried under reduced pressure to afford the title compound (Synthesis Compound 2) (0.410 g, 76%) as an off-white solid.

Analytical Data:

LCMS (ESI) m/z=393.85 [M+H]$^+$.

HPLC (see generic method): Retention time: 8.06 min.; Purity: 99.22%.

$^1$H NMR (400 MHz, DMSO-d$_6$) δ (ppm): 7.98 (s, 4H), 7.97-7.88 (m, 1H), 7.68-7.62 (m, 1H), 7.62-7.54 (m, 1H), 4.21 (d, J=13.2 Hz, 1H), 3.72 (d, J=14.0 Hz, 1H), 3.36 (d, J=6.4 Hz, 2H), 3.00 (t, J=11.6 Hz, 1H), 2.60-2.50 (m, 1H), 2.10-2.00 (m, 1H), 1.94 (s, 3H), 1.84-1.70 (m, 2H), 1.30-1.19 (m, 1H), 1.19-1.05 (m, 1H).

Synthetic Scheme 4

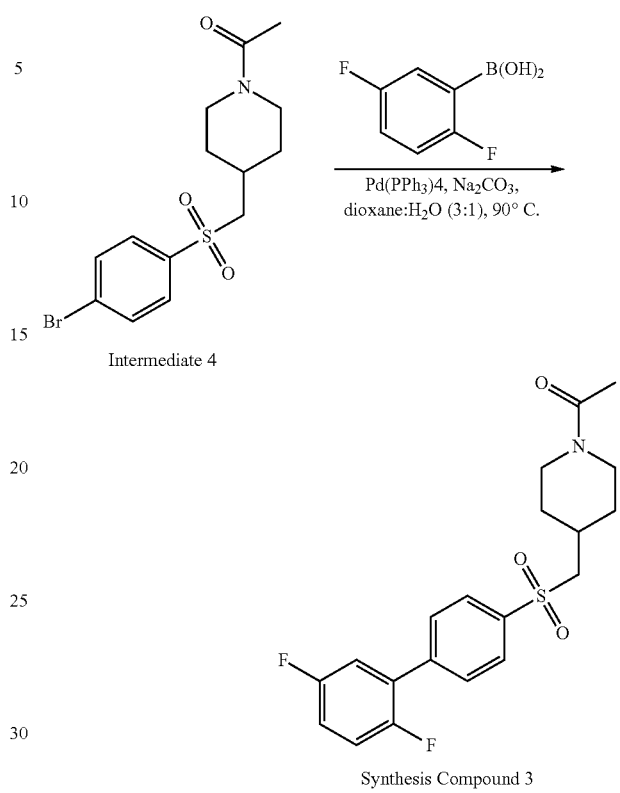

Synthesis Compound 3

Synthesis Compound 3

1-(4-(((2',5'-Difluoro-[1,1'-biphenyl]-4-yl)sulfonyl)methyl)piperidin-1-yl)ethan-1-one (NASMP-03)

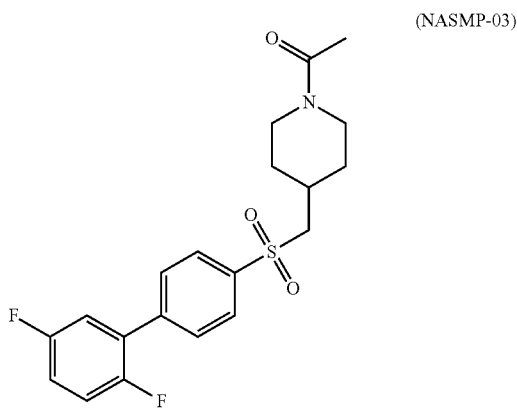 [SMILES: CC(=O)N1CCC(CS(=O)(=O)c2ccc(-c3cc(F)ccc3F)cc2)CC1]

To a reaction tube were added a solution of 1-(4-(((4-bromophenyl)sulfonyl)methyl)piperidin-1-yl)ethan-1-one Intermediate 4 (0.500 g, 1.38 mmol), (2,5-difluorophenyl) boronic acid (0.263 g, 1.66 mmol) and sodium carbonate (0.367 g, 3.46 mmol) in a mixture of 1,4-dioxane: water (3:1, 13 mL). The tube was sealed and degassed by purging with nitrogen for 10 min, followed by addition of tetrakis (triphenylphosphine)palladium(0) (0.159 g, 0.138 mmol) to the reaction mixture under a nitrogen atmosphere and the purging with nitrogen was continued for another 5 min. The reaction mixture was then heated at 90° C. for 16 h under a nitrogen atmosphere. The progress of the reaction was monitored by TLC [mobile phase: 50% ethyl acetate in hexanes]. After completion of reaction, the reaction mixture was cooled to room temperature and filtered through a pad of Celite. The Celite pad was washed with ethyl acetate (2×100 mL). The combined organic layer was concentrated under reduced pressure to dryness. The crude product was purified by column chromatography on silica gel (Combi-Flash®, gradient 10-50% ethyl acetate in hexanes). The obtained compound was further purified by stirring with diethyl ether and n-pentane (50 mL), filtered and dried under reduced pressure to afford the title compound (Synthesis Compound 3) (0.430 g, 79%) as an off-white solid.

Analytical Data:

LCMS (ESI) m/z=394.05 [M+H]⁺.

HPLC (see generic method): Retention time: 7.79 min.; Purity: 99.43%.

¹H NMR (400 MHz, DMSO-d₆) δ (ppm): 8.02 (d, J=8.0 Hz, 2H), 7.87 (d, J=7.2 Hz, 2H), 7.57-7.51 (m, 1H), 7.48-7.41 (m, 1H), 7.40-7.33 (m, 1H), 4.23 (d, J=12.4 Hz, 1H), 3.74 (d, J=13.2 Hz, 1H), 3.38 (d, J=6.0 Hz, 2H), 3.02 (t, J=11.2 Hz, 1H), 2.57 (t, J=12.4 Hz, 1H), 2.14-2.03 (m, 1H), 1.96 (s, 3H), 1.80 (dd, J=13.6 & 22.8 Hz, 2H), 1.32-1.20 (m, 1H), 1.20-1.06 (m, 1H).

Synthetic Scheme 5

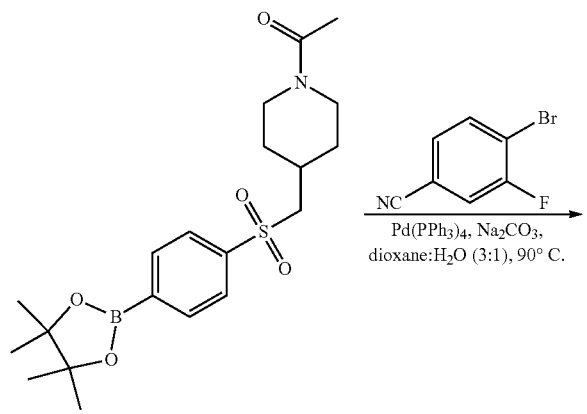

Intermediate 5

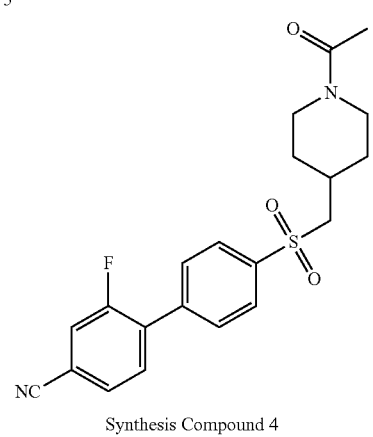

Synthesis Compound 4

Synthesis Compound 4

4'-(((1-Acetylpiperidin-4-yl)methyl)sulfonyl)-2-fluoro-[1,1'-biphenyl]-4-carbonitrile

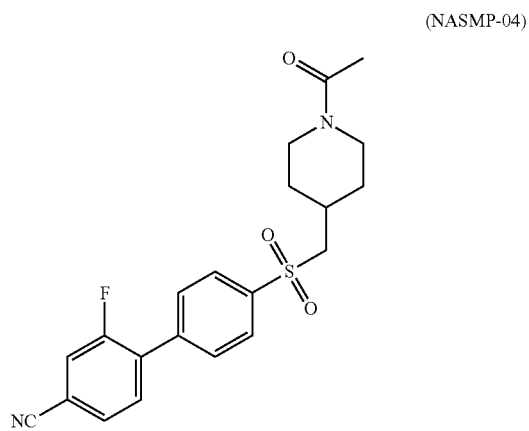 [SMILES: CC(=O)N1CCC(CS(=O)(=O)c2ccc(-c3ccc(C#N)cc3F)cc2)CC1]

(NASMP-04)

To a reaction tube were added a solution of 1-(4-(((4-(4,4,5,5-tetramethyl-1,3,2-dioxaborolan-2-yl)phenyl)sulfonyl) methyl)piperidin-1-yl)ethan-1-one Intermediate 5 (0.750 g, 1.84 mmol), 4-bromo-3-fluorobenzonitrile (0.405 g, 2.03 mmol) and sodium carbonate (0.487 g, 4.60 mmol) in a mixture of 1,4-dioxane-water (3:1, 13 mL). The tube was sealed and degassed by purging with argon for 10 min. Tetrakis(triphenylphosphine)palladium(0) (0.210 g, 0.180 mmol) was added to the reaction mixture under an argon atmosphere and the purging with argon was continued for 5 min. The reaction mixture was heated at 100° C. for 12 h. The progress of the reaction was monitored by TLC [mobile phase: 10% methanol in DCM]. After completion of the reaction, the reaction mixture was cooled to room temperature and concentrated under reduced pressure to dryness. The crude product was purified by column chromatography on silica gel (230-400 mesh, gradient 0-5% methanol in DCM) to afford the title compound (Synthesis Compound 4) (0.210 g, 29%) as a white solid.

Analytical Data:

LCMS (ESI) m/z=401.10 [M+H]⁺.

HPLC (see generic method): Retention time: 7.63 min.; Purity: 99.25%.

¹H NMR (400 MHz, DMSO-d₆) δ (ppm): 8.08-8.03 (m, 3H), 7.91-7.81 (m, 4H), 4.23 (d, J=13.2 Hz, 1H), 3.73 (d, J=13.2 Hz, 1H), 3.39 (d, J=6.0 Hz, 2H), 3.06-2.98 (m, 1H), 2.61-2.50 (m, 1H), 2.15-2.04 (br m, 1H), 1.96 (s, 3H), 1.87-1.73 (m, 2H), 1.31-1.20 (m, 1H), 1.20-1.07 (m, 1H).

Synthetic Scheme 6

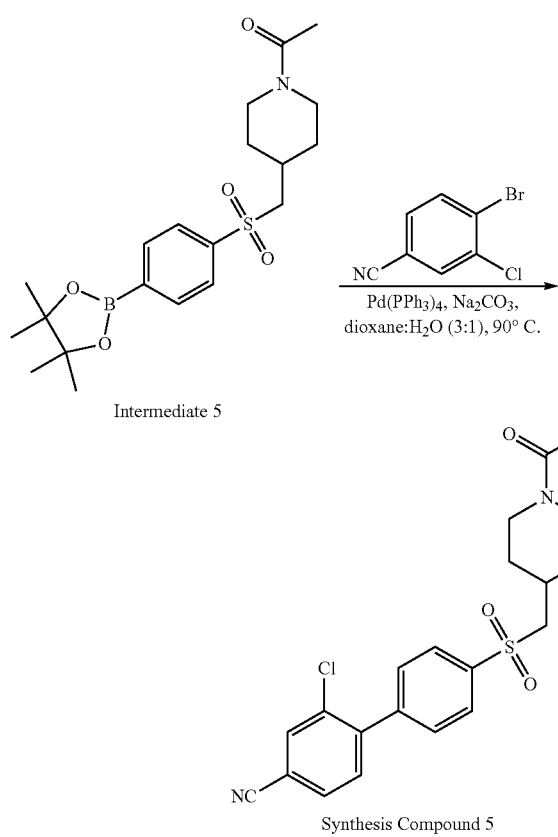

Intermediate 5

Synthesis Compound 5

Synthesis Compound 5

4'-(((1-Acetylpiperidin-4-yl)methyl)sulfonyl)-2-chloro-[1,1'-biphenyl]-4-carbonitrile (NASMP-05)

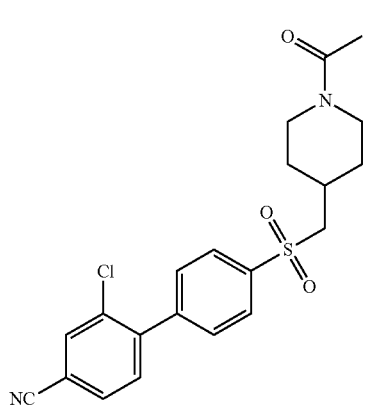

To a reaction tube were added a solution of 1-(4-(((4-(4,4,5,5-tetramethyl-1,3,2-dioxaborolan-2-yl)phenyl)sulfonyl)methyl)piperidin-1-yl)ethan-1-one Intermediate 5 (0.750 g, 1.84 mmol), 4-bromo-3-chlorobenzonitrile (0.438 g, 2.03 mmol) and sodium carbonate (0.487 g, 4.60 mmol) in a mixture of 1,4-dioxane-water (3:1, 13 mL). The tube was sealed and degassed by purging with argon for 15 min.

Tetrakis(triphenylphosphine)palladium(0) (0.213 g, 0.184 mmol) was added to the reaction mixture under an argon atmosphere and the purging with argon was continued for 10 min. The reaction mixture was heated at 90° C. for 16 h. The progress of the reaction was monitored by TLC [mobile phase: 10% methanol in DCM]. After completion of the reaction, the reaction mixture was cooled to room temperature and concentrated under reduced pressure to dryness. The crude product was purified by column chromatography on silica gel (230-400 mesh, gradient 0-5% methanol in DCM). The product was further purified by preparative HPLC (mobile phase: 0.5% formic acid in a mixture of acetonitrile/water; solid phase: 018 silica) to afford the title compound (Synthesis Compound 5) (0.250 g, 32%) as a white solid.

Analytical Data:

LCMS (ESI) m/z=417.10 [M+H]$^+$.

HPLC (see generic method): Retention time: 8.01 min.; Purity: 99.52%.

$^1$H NMR (400 MHz, DMSO-$d_6$) δ (ppm): 8.24 (s, 1H), 8.03 (d, J=8.0 Hz, 2H), 7.96 (d, J=8.0 Hz, 1H), 7.75 (d, J=8.0 Hz, 2H), 7.68 (d, J=8.0 Hz, 1H), 4.22 (d, J=13.6 Hz, 1H), 3.73 (d, J=13.2 Hz, 1H), 3.38 (d, J=6.0 Hz, 2H), 3.05-2.97 (m, 1H), 2.60-2.50 (m, 1H), 2.16-2.04 (br m, 1H), 1.95 (s, 3H), 1.86-1.70 (m, 2H), 1.32-1.20 (m, 1H), 1.20-1.05 (m, 1H).

Synthetic Scheme 7

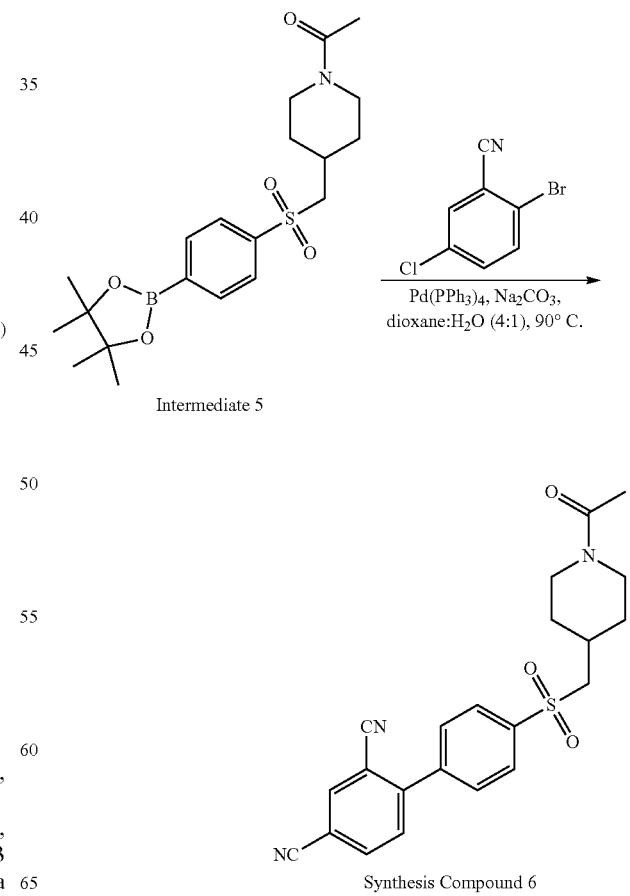

Intermediate 5

Synthesis Compound 6

Synthesis Compound 6

4'-(((1-Acetylpiperidin-4-yl)methyl)sulfonyl)-4-chloro-[1,1'-biphenyl]-2-carbonitrile

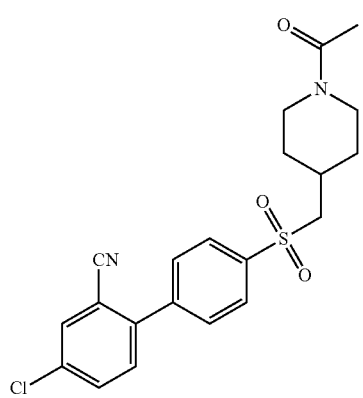

(NASMP-06)

To a reaction tube were added a solution of 2-bromo-5-chlorobenzonitrile (0.60 g, 2.77 mmol), 1-(4-(((4-(4,4,5,5-tetramethyl-1,3,2-dioxaborolan-2-yl)phenyl)sulfonyl)methyl)piperidin-1-yl)ethan-1-one Intermediate 5 (1.35 g, 3.32 mmol) and sodium carbonate (0.68 g, 6.42 mmol) in a mixture of 1,4-dioxane and water (4:1, 15 mL). The tube was sealed and degassed by purging with argon for 15 min, followed by addition of tetrakis(triphenylphosphine)palladium(0) (0.32 g, 0.27 mmol) to the reaction mixture under an argon atmosphere and then purged with argon for 5 min. The reaction was heated at 90° C. for 16 h. The progress of the reaction was monitored by TLC [mobile phase: 80% ethyl acetate in hexane]. After completion of the reaction, the mixture was cooled to room temperature, filtered through a pad of celite and the celite pad was washed with ethyl acetate (300 mL). The combined filtrates were concentrated under reduced pressure to dryness. The crude product was purified by column chromatography on silica gel (230-400 mesh, gradient 50% ethyl acetate in hexane then 60% ethyl acetate in DCM) to afford the compound which was stirred in diethyl ether (25 mL). The solids were filtered, washed with diethyl ether (50 mL), pentane (50 mL) and dried under reduced pressure to dryness to afford the title compound (Synthesis Compound 6) (0.61 g 53%) as an off-white solid.

Analytical Data:

LCMS (ESI) m/z=416.90 [M+H]$^+$.

HPLC (see generic method): Retention time: 7.99 min.; Purity: 98.11%.

$^1$H NMR (400 MHz, DMSO-d$_6$) δ (ppm): 8.23 (d, J=2.0 Hz, 1H), 8.08 (d, J=8.4 Hz, 2H), 7.93 (dd, J=8.4, 2.0 Hz, 1H), 7.88 (d, J=8.4 Hz, 2H), 7.72 (d, J=8.8 Hz, 1H), 4.22 (d, J=13.2 Hz, 1H), 3.73 (d, J=13.6 Hz, 1H), 3.41 (d, J=6.0 Hz, 2H), 3.06-2.97 (m, 1H), 2.61-2.52 (m, 1H), 2.15-2.05 (m, 1H), 1.96 (s, 3H), 1.85-1.72 (m, 2H), 1.32-1.06 (m, 2H).

Synthetic Scheme 8

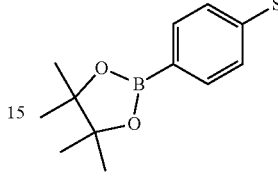 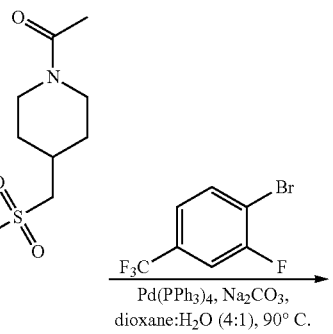

Intermediate 5

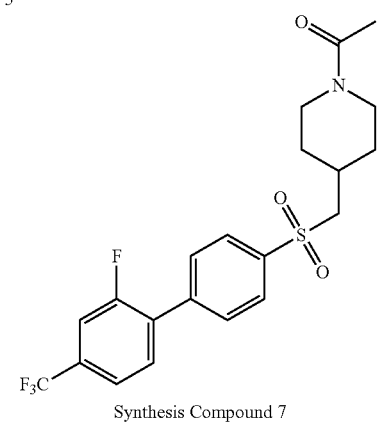

Synthesis Compound 7

Synthesis Compound 7

1-(4-(((2'-Fluoro-4'-(trifluoromethyl)-[1,1'-biphenyl]-4-yl)sulfonyl)methyl)piperidin-1-yl)ethan-1-one (NASMP-07)

To a reaction tube were added a solution of 1-bromo-2-fluoro-4-(trifluoromethyl)benzene (0.60 g, 2.47 mmol), 1-(4-(((4-(4,4,5,5-tetramethyl-1,3,2-dioxaborolan-2-yl)phenyl)sulfonyl)methyl)piperidin-1-yl)ethan-1-one Intermediate 5 (1.21 g, 2.96 mmol) and sodium carbonate (0.653 g, 6.17 mmol) in a mixture of 1,4-dioxane and water (4:1, 15 mL). The tube was sealed and degassed by purging with argon for 15 min, followed by addition of tetrakis(triphenylphosphine)palladium(0) (0.29 g, 0.25 mmol) to the reaction mixture and then purging with argon for 5 min. The reaction mixture was heated at 90° C. for 16 h. The progress of the reaction was monitored by TLC [mobile phase: 80% ethyl acetate in hexane]. After completion of the reaction, the reaction mixture was filtered through a pad of celite and the celite pad was washed with ethyl acetate (2×150 mL). The combined filtrate was concentrated under reduced pressure to dryness. The crude product was purified by column chromatography on silica gel (CombiFlash®, gradient 50% ethyl acetate in hexane, then 60% ethyl acetate in DCM) to afford the compound which was stirred in diethyl ether (20 mL) for 15 min. The solids were filtered out and dried under reduced pressure to afford the title compound (Synthesis Compound 7) (0.31 g, 28%) as an off-white solid.

Analytical Data:

LCMS (ESI) m/z=443.90 [M+H]$^+$.

HPLC (see generic method): Retention time: 8.60 min.; Purity: 99.66%.

$^1$H NMR (400 MHz, DMSO-d$_6$) δ (ppm): 8.06 (d, J=8.4 Hz, 2H), 7.92-7.83 (m, 4H), 7.75 (d, J=8.0 Hz, 1H), 4.23 (d, J=13.2 Hz, 1H), 3.74 (d, J=13.6 Hz, 1H), 3.40 (d, J=6.0 Hz, 2H), 3.06-2.98 (m, 1H), 2.61-2.52 (m, 1H), 2.15-2.04 (m, 1H), 1.96 (s, 3H), 1.88-1.73 (m, 2H), 1.32-1.20 (m, 1H), 1.20-1.06 (m, 1H).

Synthetic Scheme 9

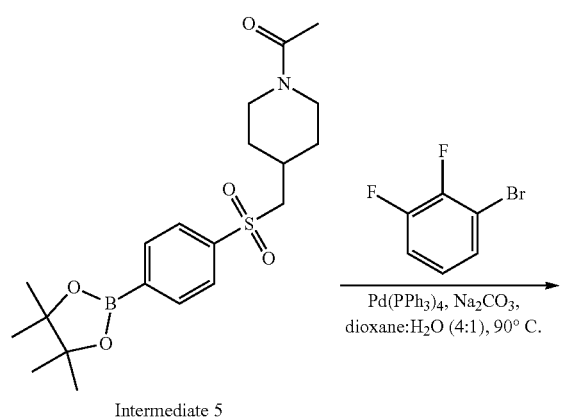

Intermediate 5

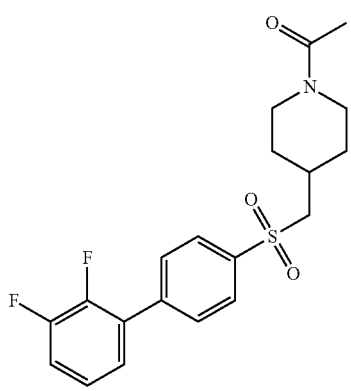

Synthesis Compound 8

Synthesis Compound 8

1-(4-(((2',3'-Difluoro-[1,1'-biphenyl]-4-yl)sulfonyl)methyl)piperidin-1-yl)ethan-1-one

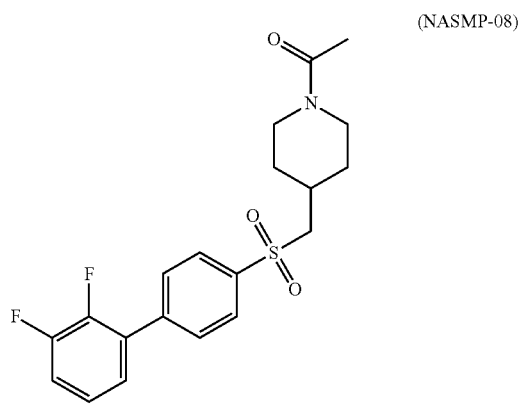 [SMILES: CC(=O)N1CCC(CS(=O)(=O)c2ccc(-c3cccc(F)c3F)cc2)CC1]

(NASMP-08)

To a reaction tube were added a solution of 1-bromo-2,3-difluorobenzene (0.60 g, 3.11 mmol), 1-(4-(((4-(4,4,5,5-tetramethyl-1,3,2-dioxaborolan-2-yl)phenyl)sulfonyl)methyl)piperidin-1-yl)ethan-1-one Intermediate 5 (1.52 g, 3.73 mmol) and sodium carbonate (0.82 g, 7.77 mmol) in a mixture of 1,4-dioxane and water (4:1, 15 mL). The tube was sealed and degassed by purging with argon for 30 min, followed by addition of tetrakis(triphenylphosphine)palladium(0) (0.36 g, 0.31 mmol) to the reaction mixture and again purging with argon for 5 min. The reaction mixture was then heated at 90° C. for 16 h. The progress of the reaction was monitored by TLC [mobile phase: 100% ethyl acetate]. After completion of the reaction, the reaction mixture was cooled to room temperature, filtered through a pad of celite, celite pad was washed with ethyl acetate (50 mL) and the combined filtrate was concentrated under reduced pressure to dryness. The crude product was purified by column chromatography on silica gel (CombiFlash®, gradient 0-100% ethyl acetate in hexane) to afford the title compound (Synthesis Compound 8) (0.30 g, 25%) as white solid.

Analytical Data:

LCMS (ESI) m/z=393.95 [M+H]$^+$.

HPLC (see generic method): Retention time: 7.98 min.; Purity: 95.43%.

$^1$H NMR (400 MHz, DMSO-d$_6$) δ (ppm): 8.01 (d, J=8.0 Hz, 2H), 7.84 (d, J=7.2 Hz, 2H), 7.55-7.47 (m, 1H), 7.43-7.38 (m, 1H), 7.36-7.30 (m, 1H), 4.20 (d, J=13.2 Hz, 1H), 3.70 (d, J=13.2 Hz, 1H), 3.35 (d, J=6.4 Hz, 2H), 3.03-2.95 (m, 1H), 2.57-2.48 (m, 1H), 2.12-2.00 (m, 1H), 1.92 (s, 3H), 1.84-1.70 (m, 2H), 1.29-1.18 (m, 1H), 1.18-1.04 (m, 1H).

Synthetic Scheme 10

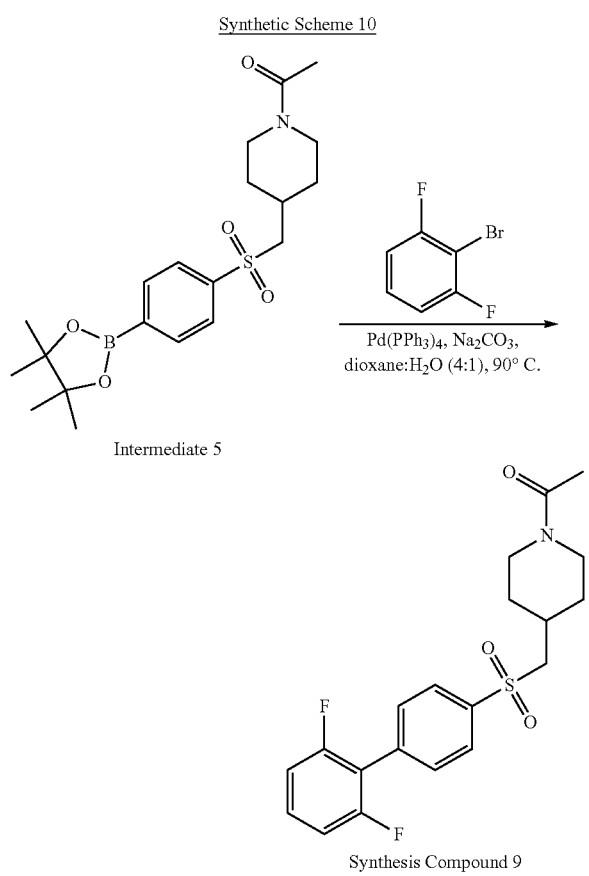

Intermediate 5

Synthesis Compound 9

1-(4-(((2',6'-Difluoro-[1,1'-biphenyl]-4-yl)sulfonyl)methyl)piperidin-1-yl)ethan-1-one (NASMP-09)

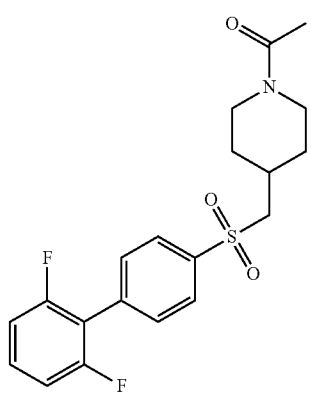

To a reaction tube were added a solution of 2-bromo-1,3-difluorobenzene (0.500 g, 2.59 mmol), 1-(4-(((4-(4,4,5,5-tetramethyl-1,3,2-dioxaborolan-2-yl)phenyl)sulfonyl)methyl)piperidin-1-yl)ethan-1-one Intermediate 5 (2.109 g, 5.18 mmol) and sodium carbonate (0.686 g, 6.47 mmol) in a mixture of 1,4-dioxane and water (4:1, 50 mL). The tube was sealed and degassed by purging with argon for 10 min, followed by addition of tetrakis(triphenylphosphine)palladium(0) (0.299 g, 0.259 mmol) to the reaction mixture under an argon atmosphere and the purging with argon was continued for another 5 min. The reaction mixture was then heated at 90° C. for 16 h under an argon atmosphere. The progress of the reaction was monitored by TLC [mobile phase: 5% methanol in DCM]. After completion of reaction, the reaction mixture was filtered through a pad of Celite and the Celite pad was washed with ethyl acetate (2×150 mL). The combined filtrate was concentrated under reduced pressure to dryness. The crude product was purified by column chromatography on silica gel (230-400 mesh, gradient 100% DCM then 20-50% ethyl acetate in DCM). The obtained compound was further purified by stirring in diethyl ether (20 mL) for 15 min followed by trituration with 10% ethyl acetate in diethyl ether (15 mL). The solids were filtered out and dried under reduced pressure to afford the title compound (Synthesis Compound 9) (0.190 g, 19%) as an off-white solid.

Analytical Data:

LCMS (ESI) m/z=394.00 [M+H]$^+$.

HPLC (see generic method): Retention time: 7.88 min.; Purity: 98.49%.

$^1$H NMR (400 MHz, DMSO-d$_6$) δ (ppm): 8.04 (d, J=8.0 Hz, 2H), 7.77 (d, J=7.6 Hz, 2H), 7.60-7.50 (m, 1H), 7.29 (t, J=8.4 Hz, 2H), 4.23 (d, J=12.4 Hz, 1H), 3.75 (d, J=13.2 Hz, 1H), 3.39 (d, J=6.4 Hz, 2H), 3.03 (t, J=11.2 Hz, 1H), 2.58 (t, J=11.6 Hz, 1H), 2.17-2.04 (m, 1H), 1.96 (s, 3H), 1.80 (dd, J=12.4 & 25.2 Hz, 2H), 1.32-1.20 (m, 1H), 1.20-1.06 (m, 1H).

Synthetic Scheme 11

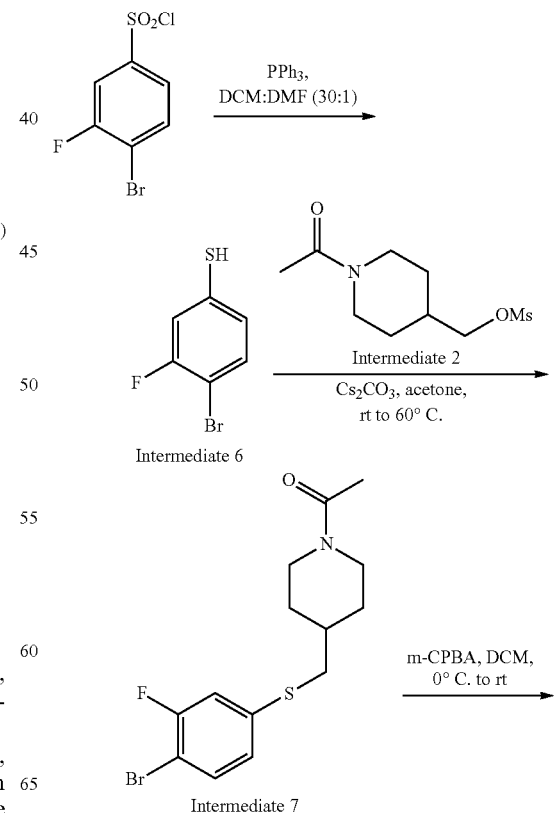

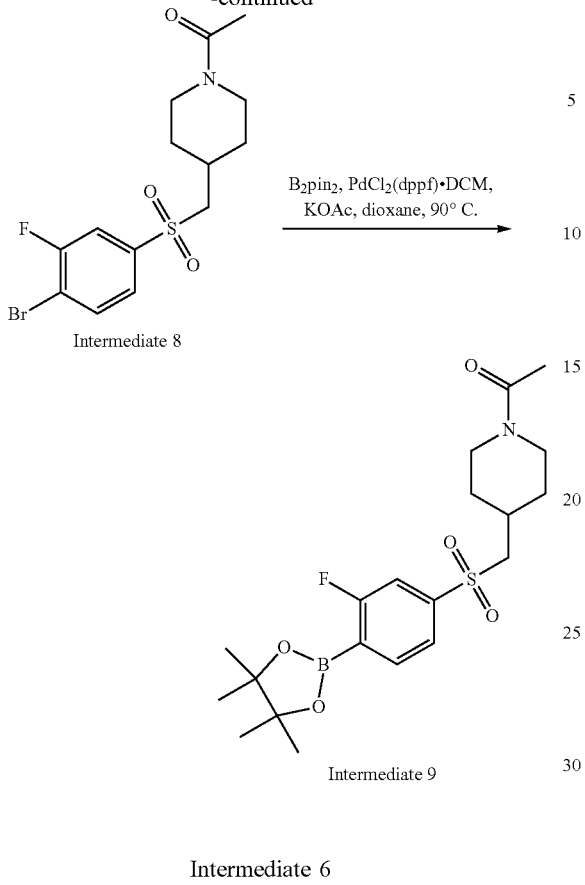

Intermediate 8

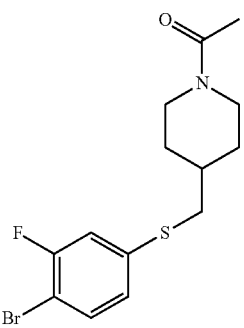 [SMILES: CC(=O)N1CCC(CSc2ccc(Br)c(F)c2)CC1]

Intermediate 9

Intermediate 6

4-Bromo-3-fluorobenzenethiol

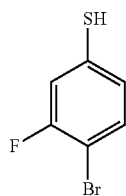

To a solution of triphenylphosphine (8.63 g, 32.91 mmol) in DCM (30 mL) and DMF (1 mL), 4-bromo-3-fluorobenzenesulfonyl chloride (3.00 g, 10.97 mmol) was added dropwise at room temperature. The reaction was stirred for 16 h at room temperature. The progress of the reaction was monitored by TLC [mobile phase: 10% ethyl acetate in hexane]. After completion of the reaction, 1 M aqueous HCl (50 mL) was added to the reaction mixture and the layers were separated. The organic layer was concentrated under reduced pressure to dryness. The residue was taken in 1 M aqueous NaOH (50 mL) and the mixture was filtered through a pad of celite. The filtrate was washed with diethyl ether (3×50 mL), neutralized with 1 M aqueous HCl (60 mL) and extracted with diethyl ether (3×50 mL). The combined organic layers were dried over anhydrous sodium sulfate, filtered and concentrated under reduced pressure to dryness to afford the title compound Intermediate 6 (1.41 g, crude) as colorless oil. This compound was used in the next step without further purification.

Intermediate 7

1-(4-(((4-Bromo-3-fluorophenyl)thio)methyl)piperidin-1-yl)ethan-1-one

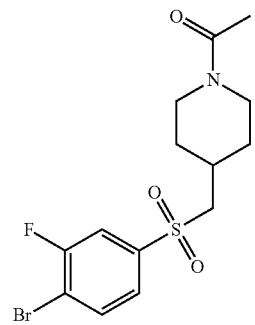 [SMILES: CC(=O)N1CCC(CS(=O)(=O)c2ccc(Br)c(F)c2)CC1]

To a solution of 4-bromo-3-fluorobenzenethiol Intermediate 6 (1.30 g, 6.31 mmol) in acetone (40 mL), caesium carbonate (3.73 g, 11.46 mmol) was added under an argon atmosphere at room temperature and the reaction mixture was stirred for 30 min. To the resulting reaction mixture, (1-acetylpiperidin-4-yl)methyl methanesulfonate Intermediate 2 (1.35 g, 5.73 mmol) was added at room temperature. The reaction mixture was then heated at 60° C. for 16 h. The progress of the reaction was monitored by TLC [mobile phase: 50% ethyl acetate in hexane]. After completion of the reaction, the reaction mixture was cooled to room temperature, filtered through a pad of celite and the filtrate was concentrated under reduced pressure to dryness. The crude product was purified by column chromatography on silica gel (CombiFlash®, gradient 10-50% ethyl acetate in hexane) to afford the title compound Intermediate 7 (1.63 g, 82%) as pale yellow thick oil.

Analytical Data:

LCMS (ESI) m/z=348.05 [M+H]$^+$ ($^{81}$Br).

Intermediate 8

1-(4-(((4-Bromo-3-fluorophenyl)sulfonyl)methyl)piperidin-1-yl)ethan-1-one

To a solution of 1-(4-(((4-bromo-3-fluorophenyl)thio)methyl)piperidin-1-yl)ethan-1-one Intermediate 7 (1.60 g, 4.62 mmol) in DCM (40 mL), meta-chloroperbenzoic acid (60%) (3.98 g, 13.86 mmol) was added in portions at 0° C. The reaction mixture was warmed to room temperature and stirred for 16 h. The progress of the reaction was monitored by TLC [mobile phase: 5% Methanol in DCM]. After completion of the reaction, the reaction mixture was quenched with saturated aqueous sodium thiosulfate (25 mL), the layers were separated, and the organic layer was washed with saturated aqueous sodium bicarbonate (2×25 mL). The combined organic layers were dried over anhydrous sodium sulfate, filtered and concentrated under reduced pressure to dryness to afford the title compound Intermediate 8 (1.63 g, crude) as an off-white solid. This compound was used in the next step without further purification.

Analytical Data:

LCMS (ESI) m/z=377.80 [M+H]$^+$ ($^{79}$Br).

Intermediate 9

1-(4-(((3-Fluoro-4-(4,4,5,5-tetramethyl-1,3,2-dioxaborolan-2-yl)phenyl)sulfonyl)methyl)piperidin-1-yl)ethan-1-one

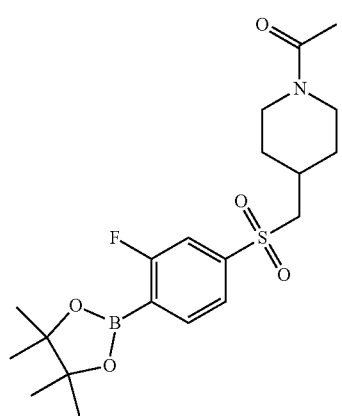 [SMILES: CC(=O)N1CCC(CS(=O)(=O)c2ccc(B3OC(C)(C)C(C)(C)O3)c(F)c2)CC1]

A reaction tube was charged with a solution of 1-(4-(((4-bromo-3-fluorophenyl) sulfonyl)methyl)piperidin-1-yl) ethan-1-one Intermediate 8 (1.60 g, 4.23 mmol), bis(pinacolato)diborane (1.29 g, 5.07 mmol) and potassium acetate (1.25 g, 12.69 mmol) in 1,4-dioxane (25 mL). The tube was sealed and degassed by purging with nitrogen gas for 15 min followed by addition of 1,1'-bis(diphenylphosphino)ferrocene-palladium (II) dichloride, DCM complex (0.104 g, 0.126 mmol) to the reaction mixture under a nitrogen atmosphere and the purging with nitrogen was continued for another 5 min. The reaction mixture was then heated to 90° C. for 16 h. The progress of the reaction was monitored by TLC [mobile phase: 5% methanol in DCM]. After completion of the reaction, the reaction mixture was cooled to room temperature, filtered through a celite pad and washed with ethyl acetate (75 mL). The combined filtrates were concentrated under reduced pressure to dryness. The residue obtained was stirred in pentane (2×25 mL), the solvents were decanted and the solids were dried under reduced pressure to afford the title compound Intermediate 9 (3.01 g, crude) as dark brown solid. This compound was used in the next step without further purification.

Analytical Data:

LCMS (ESI) m/z=343.90 [M+H]$^+$ (corresponding boronic acid).

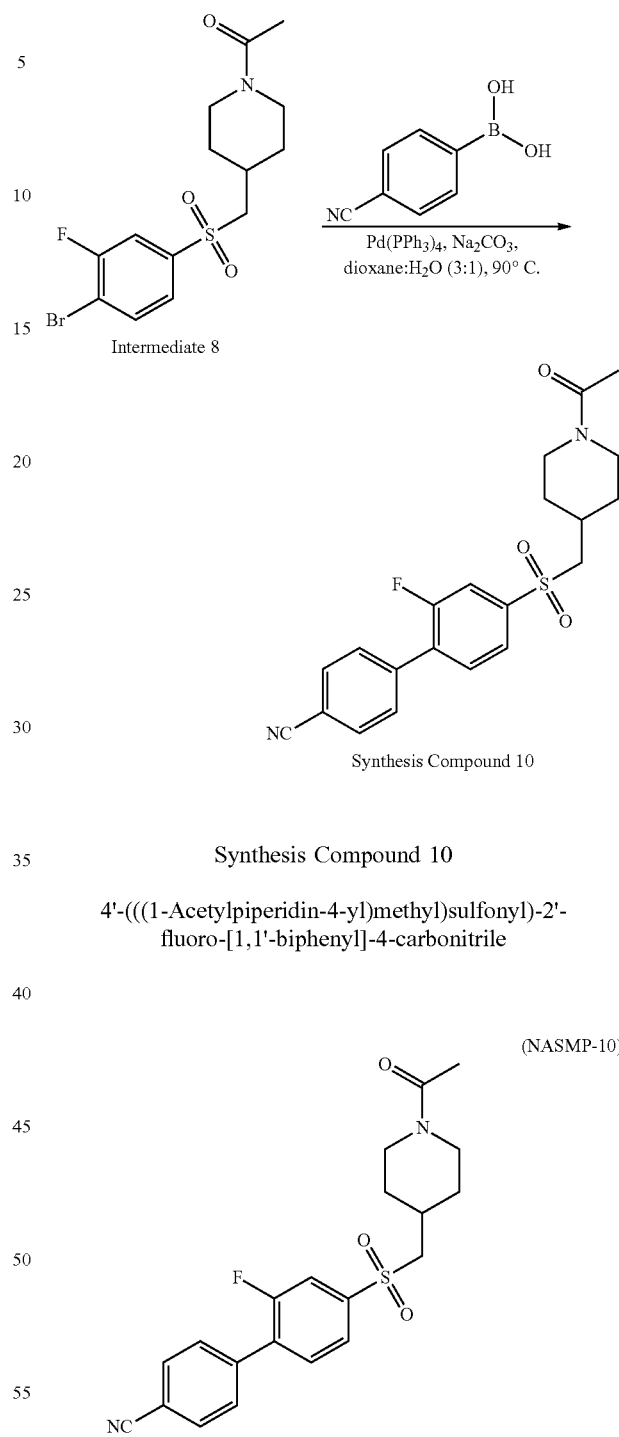

Synthesis Compound 10

4'-(((1-Acetylpiperidin-4-yl)methyl)sulfonyl)-2'-fluoro-[1,1'-biphenyl]-4-carbonitrile To a reaction tube were added a solution of 1-(4-(((4-bromo-3-fluorophenyl) sulfonyl)methyl)piperidin-1-yl) ethan-1-one Intermediate 8 (1.00 g, 2.64 mmol), (4-cyanophenyl)boronic acid (0.427 g, 2.91 mmol) and sodium carbonate (0.700 g, 6.61 mmol) in a mixture of 1,4-dioxane-water (3:1, 13 mL). The tube was sealed and degassed by purging with argon for 10 min. Tetrakis(triphenylphosphine)palladium(0) (0.306 g, 0.264 mmol) was added to the reaction mixture under an argon atmosphere and the purging with argon was continued for 10 min. The reaction mixture was heated at 90° C. for 12 h. The progress of the reaction was monitored by TLC [mobile phase: 10% methanol in DCM]. After completion of the reaction, the reaction mixture was cooled to room temperature and concentrated under reduced pressure to dryness. The crude product was purified by column chromatography on silica gel (230-400 mesh, gradient 0-10% methanol in DCM) to afford the title compound (Synthesis Compound 10) (0.450 g, 43%) as a white solid.

Analytical Data:

LCMS (ESI) m/z=401.05 [M+H]$^+$.

HPLC (see generic method): Retention time: 7.86 min.; Purity: 98.37%.

$^1$H NMR (400 MHz, DMSO-d$_6$) δ (ppm): 8.01 (d, J=8.4 Hz, 2H), 7.96-7.86 (m, 3H), 7.84 (d, J=7.2 Hz, 2H), 4.23 (d, J=12.8 Hz, 1H), 3.74 (d, J=13.6 Hz, 1H), 3.45 (d, J=6.4 Hz, 2H), 3.07-2.98 (m, 1H), 2.62-2.52 (m, 1H), 2.15-2.04 (br m, 1H), 1.96 (s, 3H), 1.88-1.73 (m, 2H), 1.32-1.20 (m, 1H), 1.20-1.08 (m, 1H).

Synthetic Scheme 13

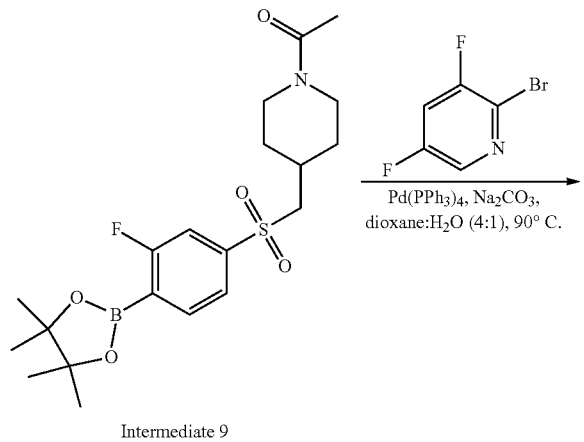

Intermediate 9

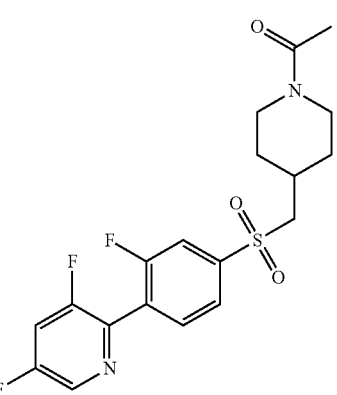

Synthesis Compound 11

Synthesis Compound 11

1-(4-(((4-(3,5-Difluoropyridin-2-yl)-3-fluorophenyl)sulfonyl)methyl)piperidin-1-yl)ethan-1-one (NASMP-11)

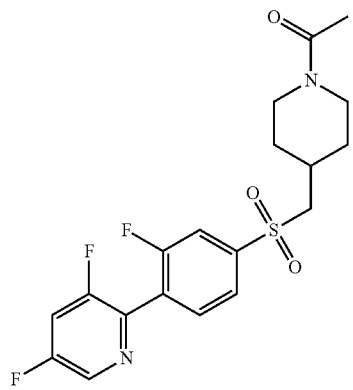

To a reaction tube were added a solution of 2-bromo-3,5-difluoropyridine (0.60 g, 3.09 mmol), 1-(4-(((3-fluoro-4-(4,4,5,5-tetramethyl-1,3,2-dioxaborolan-2-yl)phenyl)sulfonyl)methyl)piperidin-1-yl)ethan-1-one Intermediate 9 (1.45 g, 3.40 mmol) and sodium carbonate (0.76 g, 7.17 mmol) in a mixture of 1,4-dioxane-water (4:1, 15 mL). The tube was sealed and degassed by purging with argon gas for 15 min followed by addition of tetrakis(triphenylphosphine)palladium(0) (0.36 g, 0.30 mmol) to the reaction mixture under an argon atmosphere and the purging with argon was continued for another 5 min. The reaction mixture was heated at 90° C. for 16 h. The progress of the reaction was monitored by TLC [mobile phase: 70% ethyl acetate in hexane]. After completion of the reaction, the reaction mixture was cooled to room temperature, filtered through a pad of celite and the celite pad was washed with ethyl acetate (2×150 mL). The combined organic layers were concentrated under reduced pressure to dryness. The crude product was purified by column chromatography on silica gel (CombiFlash®, gradient 50-100% ethyl acetate in hexane). The compound was triturated with diethyl ether (25 mL), the solids were filtered out and dried. The compound was further purified by preparative HPLC (mobile phase: 0.5% formic acid in a mixture of acetonitrile/water; solid phase: C18 silica). The product obtained was dissolved with saturated aqueous sodium bicarbonate (25 mL) and extracted with DCM (3×50 mL). The combined organic layers were dried over anhydrous sodium sulfate, filtered and concentrated under reduced pressure to dryness to afford the title compound (Synthesis Compound 11) (0.39 g, 31%) as an off-white solid.

Analytical Data:

LCMS (ESI) m/z=412.90 [M+H]$^+$.

HPLC (see generic method): Retention time: 7.43 min.; Purity: 97.73%.

$^1$H NMR (400 MHz, DMSO-d$_6$) δ (ppm): 8.71 (d, J=2.0 Hz, 1H), 8.19-8.14 (m, 1H), 7.95-7.86 (m, 3H), 4.20 (d, J=13.2 Hz, 1H), 3.71 (d, J=13.6 Hz, 1H), 3.44 (d, J=6.4 Hz, 2H), 3.04-2.92 (m, 1H), 2.60-2.50 (m, 1H), 2.21-2.02 (m, 1H), 1.93 (s, 3H), 1.83-1.70 (m, 2H), 1.30-1.05 (m, 2H).

Synthetic Scheme 14

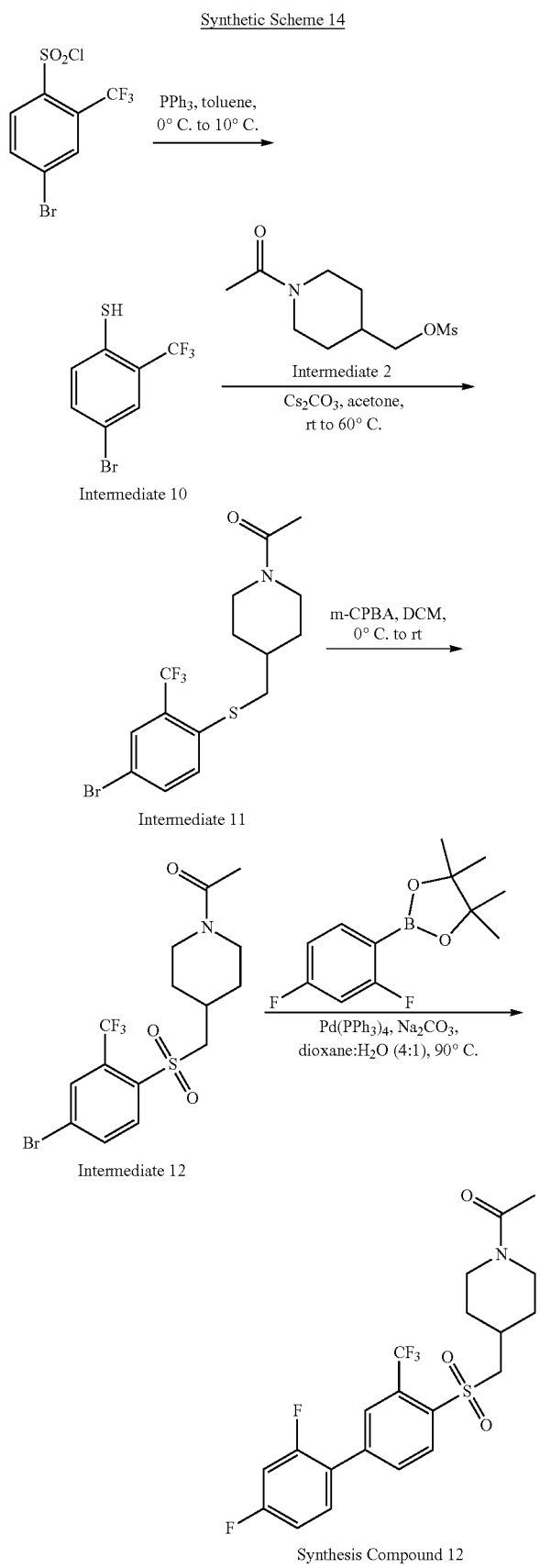

Intermediate 10

4-Bromo-2-(trifluoromethyl)benzenethiol

To a stirred solution of 4-bromo-2-(trifluoromethyl)benzenesulfonyl chloride (4.00 g, 12.36 mmol) in toluene (20 mL), a solution of triphenylphosphine (9.72 g, 37.09 mmol) in toluene (8 mL) was added dropwise at 0° C. The reaction mixture was stirred at 5° C. to 10° C. for 45 min. The progress of the reaction was monitored by TLC [mobile phase, 25% ethyl acetate in hexane]. After completion of the reaction, the reaction mixture was quenched with water (8 mL), the precipitate obtained was filtered and the filtrate was taken into a separating funnel. Then, 1N aqueous KOH (20 mL) was added to the filtrate, three layers were observed, and the upper layer was discarded. The remaining layers were extracted with toluene (2×50 mL) and the toluene layer discarded. The aqueous layer was acidified to pH ~3 with citric acid and extracted with ethyl acetate (3×50 mL). The combined organic layer was washed with brine (50 mL), dried over anhydrous sodium sulfate, filtered and concentrated under reduced pressure to dryness to afford the title compound Intermediate 10 (3.00 g, crude) as brown liquid. This compound was used in the next step without further purification.

Intermediate 11

1-(4-(((4-Bromo-2-(trifluoromethyl)phenyl)thio) methyl)piperidin-1-yl)ethan-1-one To a stirred solution of 4-bromo-2-(trifluoromethyl)benzenethiol Intermediate 10 (3.00 g, 11.68 mmol) in acetone (20 mL), caesium carbonate (6.92 g, 21.24 mmol) and a solution of (1-acetylpiperidin-4-yl)methyl methanesulfonate Intermediate 2 (2.50 g, 10.62 mmol) in acetone (5 mL) were added at room temperature. The reaction mixture was then heated at 60° C. for 16 h. The progress of the reaction was monitored by TLC [mobile phase: 70% ethyl acetate in hexane]. After completion of the reaction, the reaction mixture was cooled to room temperature, filtered through a pad of celite and the filtrate was concentrated under reduced pressure to dryness. The crude product was purified by column chromatography on silica gel (100-200, gradient 0-70% ethyl acetate in hexane) to afford the title compound Intermediate 11 (3.50 g 83%) as yellow oil.

Analytical data:
LCMS (ESI): m/z=398.15 [M+H]$^+$ ($^{81}$Br).

Intermediate 12

1-(4-(((4-Bromo-2-(trifluoromethyl)phenyl)sulfonyl)methyl)piperidin-1-yl)ethan-1-one

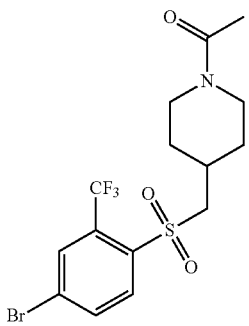 [SMILES: CC(=O)N1CCC(CS(=O)(=O)c2ccc(Br)cc2C(F)(F)F)CC1]

To a stirred solution of 1-(4-(((4-bromo-2-(trifluoromethyl)phenyl)thio)methyl)piperidin-1-yl)ethan-1-one Intermediate 11 (3.50 g, 8.83 mmol) in DCM (35 mL), meta-chloroperbenzoic acid (60%) (4.57 g, 26.49 mmol) was added in portions at 0° C. The reaction mixture was warmed to room temperature and stirred for 16 h. The progress of the reaction was monitored by TLC [mobile phase: 80% ethyl acetate in hexane]. After completion of the reaction, the reaction mixture was quenched with saturated aqueous sodium thiosulfate and the layers were separated. The organic layer was washed with saturated aqueous sodium bicarbonate (2×50 mL) and brine (50 mL). The combined organic layer was dried over anhydrous sodium sulfate, filtered and concentrated under reduced pressure to dryness to afford the title compound Intermediate 12 (3.00 g) as yellow oil. This compound was used in the next step without further purification.

Analytical Data:
LCMS (ESI): m/z=429.85 [M+H]$^+$ ($^{81}$Br).

Synthesis Compound 12

1-(4-(((2',4'-Difluoro-3-(trifluoromethyl)-[1,1'-biphenyl]-4-yl)sulfonyl)methyl)piperidin-1-yl)ethan-1-one (NASMP-12)

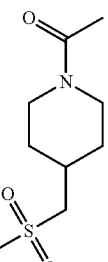

To a reaction tube were added a solution of 1-(4-(((4-bromo-2-(trifluoromethyl)phenyl) sulfonyl)methyl)piperidin-1-yl)ethan-1-one Intermediate 12 (1.00 g, 2.33 mmol), 2-(2,4-difluorophenyl)-4,4,5,5-tetramethyl-1,3,2-dioxaborolane (0.67 g, 2.80 mmol) and sodium carbonate (0.61 g, 5.83 mmol) in a mixture of 1,4-dioxane and water (4:1, 15 mL). The tube was sealed and degassed by purging with argon for 15 min, followed by addition of tetrakis(triphenylphosphine)palladium(0) (0.27 g, 0.23 mmol) to the reaction mixture and again purging with argon for 5 min. The reaction mixture was then heated at 90° C. for 16 h. The progress of the reaction was monitored by TLC [mobile phase: 70% ethyl acetate in hexane]. After completion of reaction, the reaction mixture was cooled to room temperature and filtered through a pad of celite and the pad of celite was washed with ethyl acetate (50 mL). The combined filtrate was concentrated under reduced pressure to dryness. The crude product was purified by column chromatography on silica gel (230-400 mesh, gradient 0-100% ethyl acetate in hexane) to afford the title compound (Synthesis Compound 12) (0.24 g, 22%) as white sticky solid.

Analytical Data:
LCMS (ESI) m/z=461.90 [M+H]$^+$.
HPLC (see generic method): Retention time: 8.65 min.; Purity: 98.14%.
$^1$H NMR (400 MHz, DMSO-d$_6$) δ (ppm): 8.31 (d, J=8.8 Hz, 1H), 8.15 (s, 2H), 7.83-7.75 (m, 1H), 7.53-7.46 (m, 1H), 7.33-7.27 (m, 1H), 4.26 (d, J=13.2 Hz, 1H), 3.75 (d, J=13.2 Hz, 1H), 3.40 (d, J=6.4 Hz, 2H), 3.10-3.00 (m, 1H), 2.62-2.52 (m, 1H), 2.30-2.20 (m, 1H), 1.96 (s, 3H), 1.90-1.75 (m, 2H), 1.35-1.10 (m, 2H).

Synthetic Scheme 15

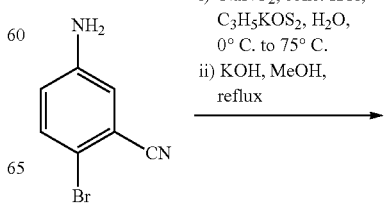

i) NaNO$_2$, conc. HCl, C$_3$H$_5$KOS$_2$, H$_2$O, 0° C. to 75° C.
ii) KOH, MeOH, reflux

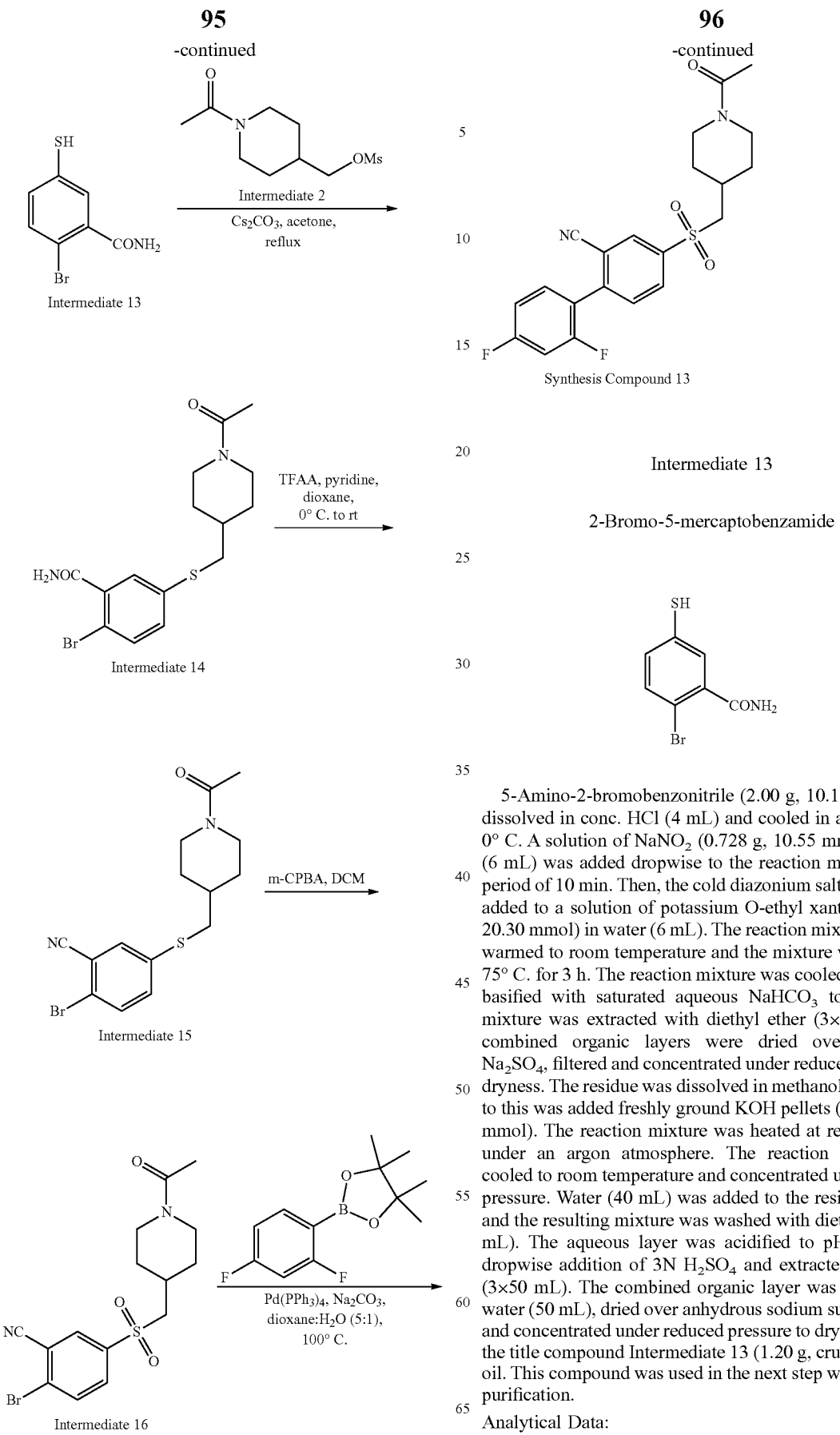

Intermediate 13

2-Bromo-5-mercaptobenzamide

5-Amino-2-bromobenzonitrile (2.00 g, 10.15 mmol) was dissolved in conc. HCl (4 mL) and cooled in an ice-bath to 0° C. A solution of $NaNO_2$ (0.728 g, 10.55 mmol) in water (6 mL) was added dropwise to the reaction mixture over a period of 10 min. Then, the cold diazonium salt solution was added to a solution of potassium O-ethyl xanthate (3.31 g, 20.30 mmol) in water (6 mL). The reaction mixture was then warmed to room temperature and the mixture was heated at 75° C. for 3 h. The reaction mixture was cooled to 0° C. and basified with saturated aqueous $NaHCO_3$ to pH 8. The mixture was extracted with diethyl ether (3×50 mL). The combined organic layers were dried over anhydrous $Na_2SO_4$, filtered and concentrated under reduced pressure to dryness. The residue was dissolved in methanol (70 mL) and to this was added freshly ground KOH pellets (2.84 g, 50.75 mmol). The reaction mixture was heated at reflux for 17 h under an argon atmosphere. The reaction mixture was cooled to room temperature and concentrated under reduced pressure. Water (40 mL) was added to the residue obtained and the resulting mixture was washed with diethyl ether (50 mL). The aqueous layer was acidified to pH 1-2 by the dropwise addition of 3N $H_2SO_4$ and extracted with DCM (3×50 mL). The combined organic layer was washed with water (50 mL), dried over anhydrous sodium sulfate, filtered and concentrated under reduced pressure to dryness to afford the title compound Intermediate 13 (1.20 g, crude) as yellow oil. This compound was used in the next step without further purification.

Analytical Data:

LCMS (ESI) m/z=233.85 $[M+H]^+$ ($^{81}Br$).

Intermediate 14

5-(((1-Acetylpiperidin-4-yl)methyl)thio)-2-bromobenzamide

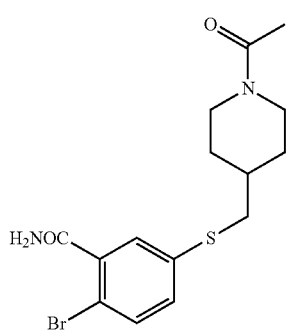 [SMILES: CC(=O)N1CCC(CSc2ccc(Br)c(C(N)=O)c2)CC1]

To a stirred solution of 2-bromo-5-mercaptobenzamide Intermediate 13 (1.10 g, 4.74 mmol) and (1-acetylpiperidin-4-yl)methyl methanesulfonate Intermediate 2 (1.12 g, 4.74 mmol) in acetone (30 mL), caesium carbonate (1.85 g, 5.69 mmol) was added at room temperature. The reaction mixture was heated at reflux for 16 h. The progress of the reaction was monitored by TLC [mobile phase: 60% ethyl acetate in hexane]. After completion of the reaction, the reaction mixture was cooled to room temperature and concentrated under reduced pressure. The residue was dissolved in water (60 mL) and extracted with ethyl acetate (3×50 mL). The combined organic layer was dried over anhydrous sodium sulphate, filtered and concentrated under reduced pressure. The crude product was purified by column chromatography on silica gel (100-200 mesh, gradient 10-50% ethyl acetate in hexane) to afford the title compound Intermediate 14 (1.55 g, 88%) as brown solid.

Analytical Data:
LCMS (ESI) m/z=370.95 [M+H]$^+$ ($^{79}$Br).

Intermediate 15

5-(((1-Acetylpiperidin-4-yl)methyl)thio)-2-bromobenzonitrile

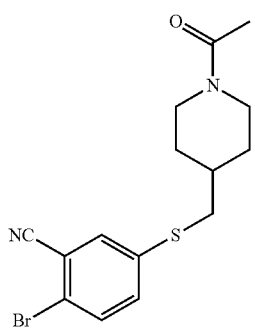 [SMILES: CC(=O)N1CCC(CSc2ccc(Br)c(C#N)c2)CC1]

To a stirred solution of 5-(((1-acetylpiperidin-4-yl)methyl)thio)-2-bromobenzamide Intermediate 14 (1.50 g, 4.04 mmol) and pyridine (0.652 mL, 8.08 mmol) in 1,4-dioxane (30 mL), TFAA (0.626 mL, 4.44 mmol) was added dropwise at 0° C. The reaction mixture was warmed to room temperature and stirred for 1.5 h. The progress of the reaction was monitored by TLC [mobile phase: 50% ethyl acetate in hexane]. After completion of the reaction, the reaction mixture was quenched with water (60 mL) and extracted with ethyl acetate (3×50 mL). The combined organic layer was dried over anhydrous sodium sulphate, filtered and concentrated under reduced pressure. The crude product was purified by column chromatography on silica gel (100-200 mesh, gradient 0-50% ethyl acetate in hexane) to afford the title compound Intermediate 15 (1.35 g, 95%) as pale yellow thick oil.

Analytical Data:
LCMS (ESI) m/z=352.95 [M+H]$^+$ ($^{79}$Br).

Intermediate 16

5-(((1-Acetylpiperidin-4-yl)methyl)sulfonyl)-2-bromobenzonitrile

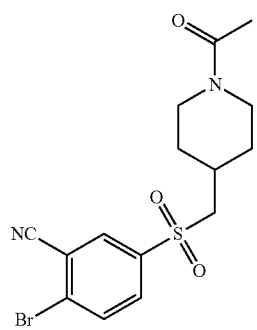 [SMILES: CC(=O)N1CCC(CS(=O)(=O)c2ccc(Br)c(C#N)c2)CC1]

To a stirred solution of 5-(((1-acetylpiperidin-4-yl)methyl)thio)-2-bromobenzonitrile Intermediate 15 (1.30 g, 3.69 mmol) in DCM (30 mL), meta-chloroperbenzoic acid (55%) (3.47 g, 11.07 mmol) was added in portions at room temperature. The reaction mixture was stirred at room temperature for 16 h. The progress of the reaction was monitored by TLC [mobile phase: 60% ethyl acetate in hexane]. After completion of the reaction, the reaction mixture was diluted with DCM (70 mL), washed with saturated aqueous sodium bicarbonate (2×50 mL) and brine (50 mL). The organic layer was dried over anhydrous sodium sulfate, filtered and concentrated under reduced pressure to dryness. The crude product was purified by column chromatography on silica gel (100-200 mesh, gradient 10-60% ethyl acetate in hexane) to afford the title compound Intermediate 16 (1.20 g, 84%) as brown thick oil.

Analytical Data:
$^1$H NMR (400 MHz, DMSO-d$_6$) δ (ppm): 8.44 (d, J=2.0 Hz, 1H), 8.15 (d, J=8.0 Hz, 1H), 8.07 (dd, J=8.8, 2.4 Hz, 1H), 4.19 (d, J=13.2 Hz, 1H), 3.69 (d, J=13.6 Hz, 1H), 3.41 (d, J=6.8 Hz, 2H), 3.03-2.94 (m, 1H), 2.58-2.48 (m, 1H), 2.08-1.95 (m, 1H), 1.92 (s, 3H), 1.79-1.67 (m, 2H), 1.25-1.01 (m, 2H).

Synthesis Compound 13

4-(((1-Acetylpiperidin-4-yl)methyl)sulfonyl)-2',4'-difluoro-[1,1'-biphenyl]-2-carbonitrile

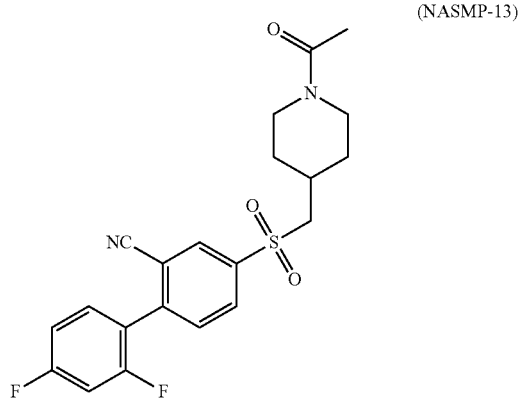 [SMILES: CC(=O)N1CCC(CS(=O)(=O)c2ccc(-c3ccc(F)cc3F)c(C#N)c2)CC1]

(NASMP-13)

To a reaction tube were added a solution of 5-(((1-acetylpiperidin-4-yl)methyl)sulfonyl)-2-bromobenzonitrile Intermediate 16 (1.20 g, 3.11 mmol), 2-(2,4-difluorophenyl)-4,4,5,5-tetramethyl-1,3,2-dioxaborolane (0.897 g, 3.73 mmol) and sodium carbonate (0.825 g, 7.78 mmol) in a mixture of 1,4-dioxane: water (5:1, 24 mL). The tube was sealed and degassed by purging with nitrogen for 15 min followed by addition of tetrakis(triphenylphosphine)palladium(0) (0.36 g, 0.30 mmol) under a nitrogen atmosphere and the purging with nitrogen was continued for 5 min. The reaction mixture was heated at 100° C. for 16 h. The progress of the reaction was monitored by TLC [mobile phase: 60% ethyl acetate in hexane]. After completion of the reaction, the reaction mixture was cooled to room temperature and concentrated under reduced pressure to dryness. The crude product was purified by column chromatography on silica gel (100-200 mesh, gradient 10-60% ethyl acetate in hexane) to afford the title compound (Synthesis Compound 13) (0.40 g, 31%) as a white solid.

Analytical Data:

LCMS (ESI): m/z=419.04 [M+H]$^+$.

HPLC (see generic method): Retention time: 7.87 min.; Purity: 98.52%.

$^1$H NMR (400 MHz, DMSO-d$_6$) δ (ppm): 8.51 (d, J=1.6 Hz, 1H), 8.26 (dd, J=8.4, 1.6 Hz, 1H), 7.88 (d, J=8.0 Hz, 1H), 7.70-7.62 (m, 1H), 7.56-7.48 (m, 1H), 7.34-7.28 (m, 1H), 4.20 (d, J=14.0 Hz, 1H), 3.71 (d, J=13.6 Hz, 1H), 3.47 (d, J=6.8 Hz, 2H), 3.06-2.96 (m, 1H), 2.64-2.52 (m, 1H), 2.16-2.05 (m, 1H), 1.93 (s, 3H), 1.85-1.70 (m, 2H), 1.30-1.19 (m, 1H), 1.17-1.05 (m, 1H).

Synthetic Scheme 16

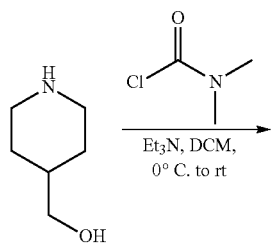

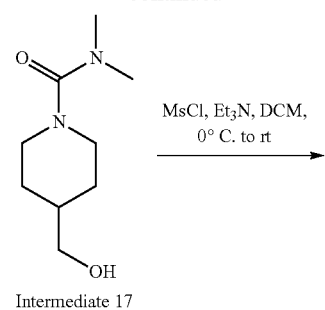

Intermediate 17

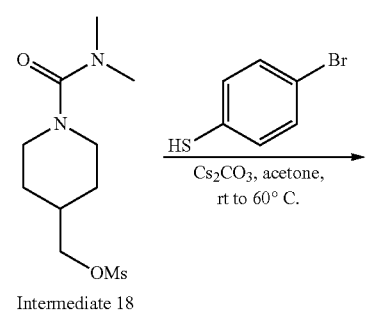

Intermediate 18

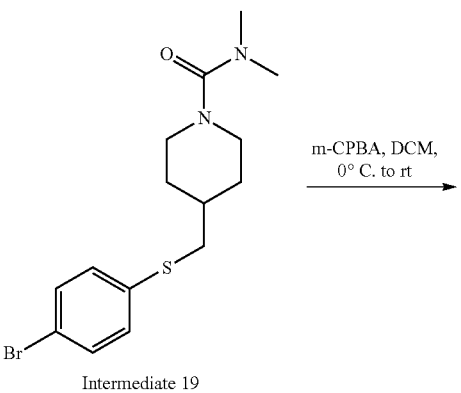

Intermediate 19

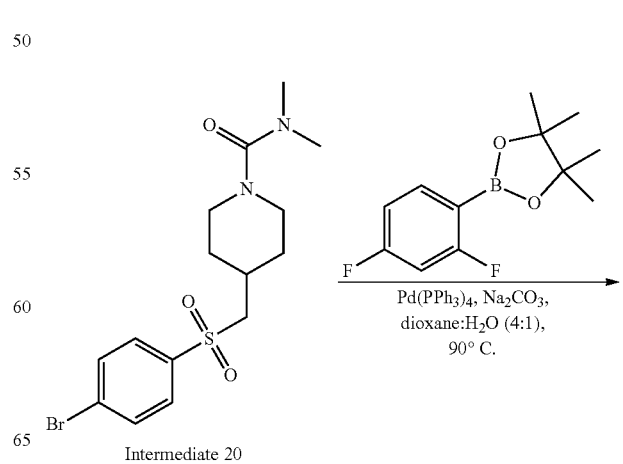

Intermediate 20

101
-continued

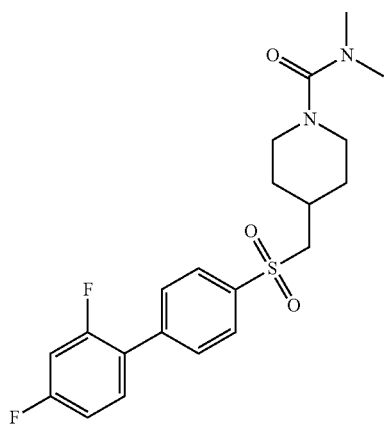

Synthesis Compound 14

Intermediate 17

4-(Hydroxymethyl)-N,N-dimethylpiperidine-1-carboxamide

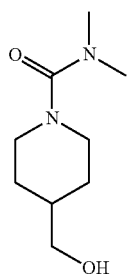

To a stirred solution of piperidin-4-ylmethanol (5.00 g, 43.41 mmol) in DCM (50 mL), triethylamine (12.70 mL, 91.16 mmol) was added and the reaction mixture was stirred for 15 min. To the reaction mixture, dimethylcarbamoyl chloride (4.19 mL, 45.50 mmol) was added dropwise at 0° C. The reaction mixture was warmed to room temperature and stirred for 3 h. The progress of the reaction was monitored by TLC [mobile phase: 5% methanol in DCM]. After completion of the reaction, the reaction mixture was quenched with the addition of ice-water (50 mL) and extracted with DCM (2×150 mL). The combined organic layer was dried over anhydrous sodium sulfate, filtered and concentrated under reduced pressure to dryness to afford the title compound Intermediate 17 (5.05 g, crude) as colorless thick oil. This compound was used in the next step without further purification.

Analytical Data:
LCMS (ESI) m/z=186.95 [M+H]$^+$.

Intermediate 18

(1-(Dimethylcarbamoyl)piperidin-4-yl)methyl methanesulfonate

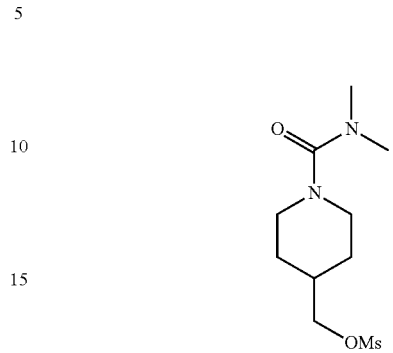

To a stirred solution of 4-(hydroxymethyl)-N,N-dimethylpiperidine-1-carboxamide Intermediate 17 (5.00 g, 26.84 mmol) in DCM (50 mL) cooled at 0° C. was added triethylamine (7.48 mL, 53.68 mmol) followed by the addition of methanesulfonyl chloride (2.28 mL, 29.52 mmol). The reaction mixture was then warmed to room temperature and stirred for 16 h. The progress of the reaction was monitored by TLC [mobile phase: 5% methanol in DCM]. After completion of the reaction, the reaction mixture was quenched with water (50 mL), the layers were separated and the organic layer was washed with water (50 mL) and brine (50 mL). The organic layer was dried over anhydrous sodium sulfate, filtered and concentrated under reduced pressure to dryness to afford the title compound Intermediate 18 (4.54 g, crude) as colorless thick oil. This compound was used in the next step without further purification.

Analytical Data:
LCMS (ESI) m/z=265.20 [M+H]$^+$.

Intermediate 19

4-(((4-Bromophenyl)thio)methyl)-N,N-dimethylpiperidine-1-carboxamide

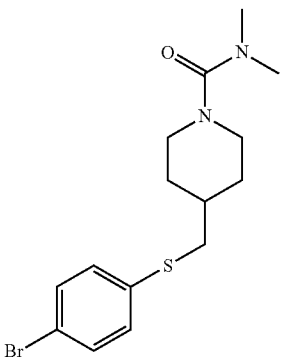 [SMILES: CN(C)C(=O)N1CCC(CSc2ccc(Br)cc2)CC1]

To a stirred solution of 4-bromobenzenethiol (3.14 g, 16.64 mmol) in acetone (70 mL) was added caesium carbonate (9.85 g, 30.26 mmol) under an argon atmosphere and the reaction mixture was stirred at room temperature for 30 min. To the resulting mixture, (1-(dimethylcarbamoyl)piperidin-4-yl)methyl methanesulfonate Intermediate 18 (4.00 g, 15.13 mmol) was added and the reaction mixture was heated to 60° C. for 16 h. The progress of the reaction was monitored by TLC [mobile phase: 50% ethyl acetate in hexane]. After completion of the reaction, the reaction mixture was filtered through a pad of celite and the filtrate was concentrated under reduced pressure to dryness. The crude product was purified by column chromatography on silica gel (CombiFlash®, gradient 50-100% Ethyl acetate in hexane) to afford the title compound Intermediate 19 (3.20 g, 59%) as white solid.

Analytical Data:
LCMS (ESI) m/z=359.05 [M+H]+ ($^{81}$Br).

Intermediate 20

4-(((4-Bromophenyl)sulfonyl)methyl)-N,N-dimethylpiperidine-1-carboxamide

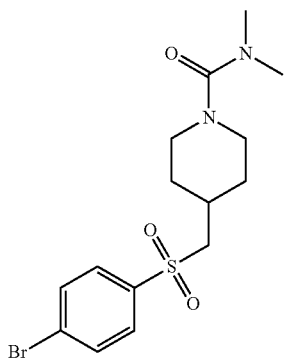 [SMILES: CN(C)C(=O)N1CCC(CS(=O)(=O)c2ccc(Br)cc2)CC1]

To a stirred solution of 4-(((4-bromophenyl)thio)methyl)-N,N-dimethylpiperidine-1-carboxamide Intermediate 19 (3.10 g, 8.67 mmol) in DCM (50 mL) was added meta-chloroperbenzoic acid (60%) (7.48 g, 26.02 mmol) at 0° C. The reaction mixture was then warmed to room temperature and stirred for 16 h. The progress of the reaction was monitored by TLC [mobile phase: 5% methanol in DCM]. After completion of the reaction, the reaction mixture was quenched with saturated aqueous sodium thiosulfate (50 mL), the layers were separated, and the organic layer was washed with saturated aqueous sodium bicarbonate (2×50 mL). The combined organic layer was dried over anhydrous sodium sulfate, filtered and concentrated under reduced pressure to dryness to afford the title compound Intermediate 20 (3.00 g, crude) as an off-white solid. This compound was used in the next step without further purification.

Analytical Data:
LCMS (ESI) m/z=388.90 [M+H]+ ($^{79}$Br).

Synthesis Compound 14

4-(((2',4'-Difluoro-[1,1'-biphenyl]-4-yl)sulfonyl)methyl)-N,N-dimethylpiperidine-1-carboxamide (NASMP-14)

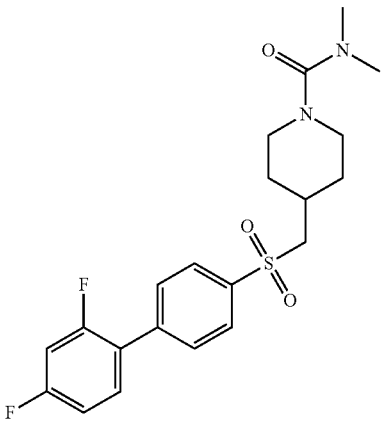

To a reaction tube were added a solution of 4-(((4-bromophenyl)sulfonyl)methyl)-N,N-dimethylpiperidine-1-carboxamide Intermediate 20 (1.00 g, 2.56 mmol), 2-(2,4-difluorophenyl)-4,4,5,5-tetramethyl-1,3,2-dioxaborolane (0.678 g, 2.82 mmol) and sodium carbonate (0.629 g, 5.93 mmol) in a mixture of 1,4-dioxane and water (4:1, 15 mL). The tube was sealed and degassed with argon for 15 min, followed by addition of tetrakis(triphenylphosphine)palladium(0) (0.296 g, 0.25 mmol) under an argon atmosphere and the purging with argon was continued for 5 min. The reaction mixture was then heated at 90° C. for 16 h. The progress of the reaction was monitored by TLC [mobile phase: 60% ethyl acetate in hexane]. After completion of the reaction, the reaction mixture was filtered through a pad of celite and the celite pad was washed with ethyl acetate (2×150 mL). The combined filtrate was concentrated under reduced pressure to dryness. The crude product was purified by column chromatography on silica gel (CombiFlash®, gradient 50-100% ethyl acetate in hexanes) to afford the compound which was stirred in diethyl ether (25 mL) for 15 min. The solids were filtered, washed with diethyl ether (15 mL) and pentane (15 mL), and dried under reduced pressure to afford the title compound (Synthesis Compound 14) (0.69 g, 64%) as an off-white solid.

Analytical Data:
LCMS (ESI) m/z=422.95 [M+H]+.
HPLC (see generic method): Retention time: 8.33 min.; Purity: 99.26%.
$^1$H NMR (400 MHz, DMSO-d$_6$) δ (ppm): 8.01 (d, J=8.0 Hz, 2H), 7.82 (d, J=7.2 Hz, 2H), 7.72-7.58 (m, 1H), 7.48-7.41 (m, 1H), 7.29-7.23 (m, 1H), 3.46 (d, J=13.2 Hz, 2H), 3.36 (d, J=6.4 Hz, 2H), 2.69 (s, 6H), 2.72-2.62 (m, 2H), 2.08-1.94 (m, 1H), 1.77 (d, J=12.0 Hz, 2H), 1.32-1.20 (m, 2H).

Synthetic Scheme 17

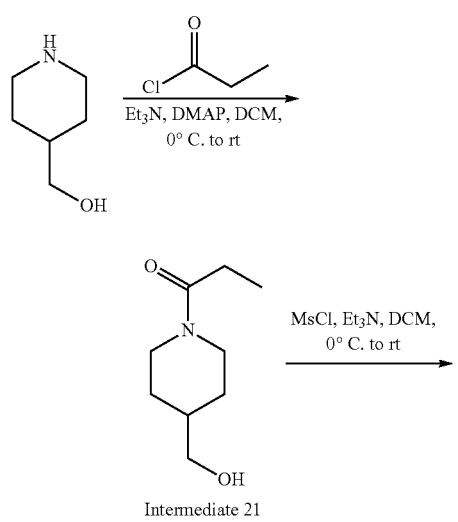

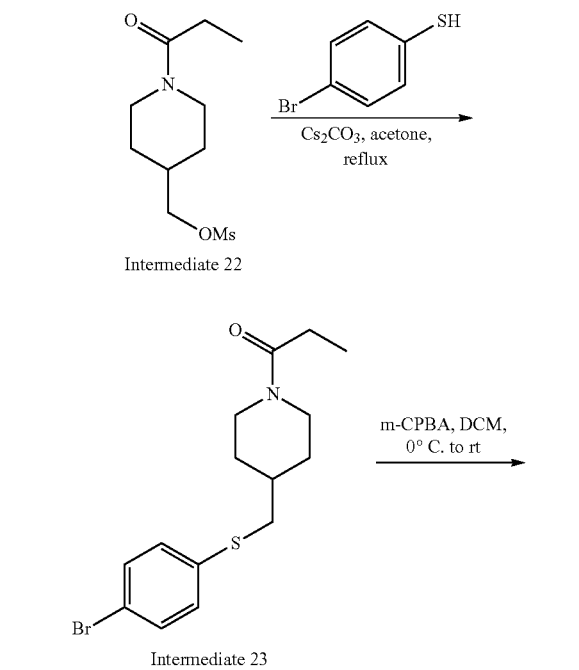

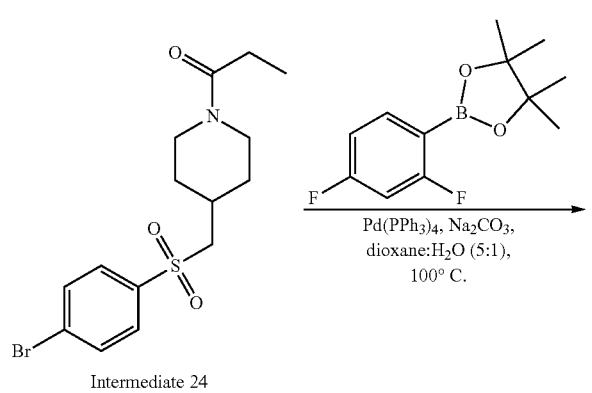

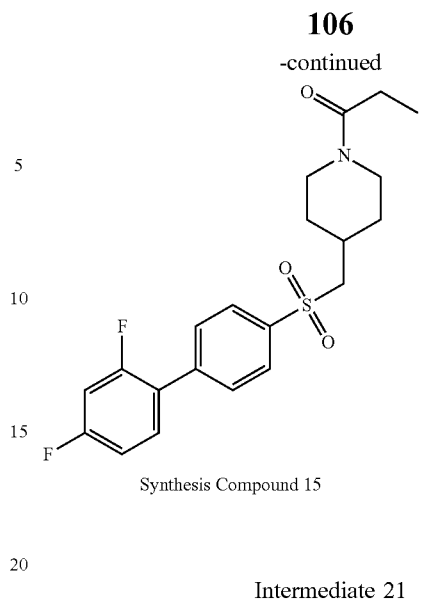

Synthesis Compound 15

Intermediate 21

1-(4-(Hydroxymethyl)piperidin-1-yl)propan-1-one

To a stirred solution of piperidin-4-ylmethanol (5.00 g, 43.41 mmol) in DCM (60 mL), triethylamine (7.87 mL, 56.43 mmol) and DMAP (1.06 g, 8.68 mmol) were added and the reaction mixture was cooled in an ice-bath to 0° C. To the reaction mixture was then added propionyl chloride (4.17 mL, 47.75 mmol) at 0° C. The reaction mixture was warmed to room temperature and stirred for 3 h. The progress of the reaction was monitored by TLC [mobile phase: 10% methanol in DCM]. After completion of the reaction, the reaction mixture was diluted with water (100 mL) and extracted with DCM (3×50 mL). The combined organic layer was dried over anhydrous sodium sulfate, filtered and concentrated under reduced pressure to dryness to afford the title compound Intermediate 21 (4.25 g, crude) as colourless oil. This compound was used in the next step without further purification.

Analytical Data:
LCMS (ESI) m/z=172.00 [M+H]$^+$.

Intermediate 22

(1-Propionylpiperidin-4-yl)methyl methanesulfonate

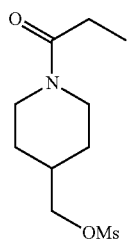 [SMILES: CCC(=O)N1CCC(COS(C)(=O)=O)CC1]

To a stirred solution of 1-(4-(hydroxymethyl)piperidin-1-yl)propan-1-one Intermediate 21 (4.20 g, 24.53 mmol) in DCM (50 mL), triethylamine (4.44 mL, 31.88 mmol) followed by methanesulfonyl chloride (2.28 mL, 29.43 mmol) were added at 0° C. The reaction mixture was warmed to room temperature and stirred for 1 h. The progress of the reaction was monitored by TLC [mobile phase: 5% methanol in DCM]. After completion of the reaction, the reaction mixture was diluted with water (70 mL) and extracted with DCM (2×60 mL). The combined organic layers were dried over anhydrous sodium sulfate, filtered and concentrated under reduced pressure to dryness to afford the title compound Intermediate 22 (4.41 g, crude) as brown oil. This compound was used in the next step without further purification.

Analytical Data:
LCMS (ESI) m/z=250.10 $[M+H]^+$.

Intermediate 23

1-(4-(((4-Bromophenyl)thio)methyl)piperidin-1-yl)propan-1-one

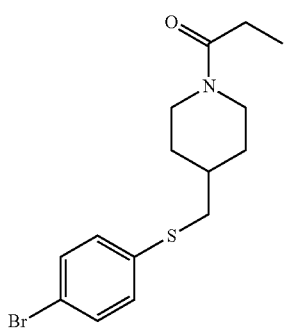 [SMILES: CCC(=O)N1CCC(CSc2ccc(Br)cc2)CC1]

To a stirred solution of (1-propionylpiperidin-4-yl)methyl methanesulfonate Intermediate 22 (4.30 g, 17.25 mmol) and 4-bromobenzenethiol (3.59 g, 18.97 mmol) in acetone (60 mL), caesium carbonate (6.74 g, 20.70 mmol) was added at room temperature. The reaction mixture was heated at reflux for 16 h. The progress of the reaction was monitored by TLC [mobile phase: 60% ethyl acetate in hexanes]. After completion of the reaction, the reaction mixture was cooled to room temperature and concentrated under reduced pressure to dryness. Water (80 mL) was added to the residue obtained and the resulting mixture was extracted with ethyl acetate (3×60 mL). The combined organic layers were washed with brine (30 mL), dried over anhydrous sodium sulfate, filtered and concentrated under reduced pressure to dryness. The crude product was purified by column chromatography on silica gel (100-200 mesh, gradient 10-60% ethyl acetate in hexanes) to afford the title compound Intermediate 23 (4.85 g, 82%) as sticky yellow oil.

Analytical Data:
LCMS (ESI) m/z=344.15 $[M+H]^+$ ($^{81}Br$).

Intermediate 24

1-(4-(((4-Bromophenyl)sulfonyl)methyl)piperidin-1-yl)propan-1-one

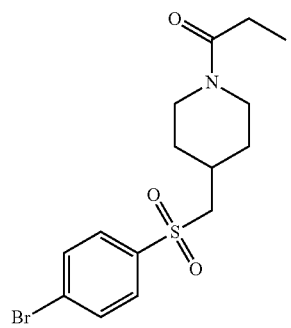 [SMILES: CCC(=O)N1CCC(CS(=O)(=O)c2ccc(Br)cc2)CC1]

To a stirred solution of 1-(4-(((4-bromophenyl)thio)methyl)piperidin-1-yl)propan-1-one Intermediate 23 (4.80 g, 14.02 mmol) in DCM (60 mL), meta-chloroperbenzoic acid (55%) (13.24 g, 42.21 mmol) was added in portions at 0° C. The reaction mixture was warmed to room temperature and stirred for 16 h. The progress of the reaction was monitored by TLC [mobile phase: 80% ethyl acetate in hexane]. After completion of the reaction, the reaction mixture was diluted with DCM (100 mL), washed with saturated aqueous sodium bicarbonate (100 mL) and brine (50 mL). The organic layer was dried over anhydrous sodium sulfate, filtered and concentrated under reduced pressure to dryness. The crude product was purified by column chromatography on silica gel (100-200 mesh, gradient 10-80% ethyl acetate in hexanes) to afford the title compound Intermediate 24 (4.30 g, 82%) as yellow thick oil.

Analytical Data:
LCMS (ESI) m/z=374.10 $[M+H]^+$ ($^{79}Br$).

Synthesis Compound 15

1-(4-(((2',4'-Difluoro-[1,1'-biphenyl]-4-yl)sulfonyl)methyl)piperidin-1-yl)propan-1-one (NASMP-15)

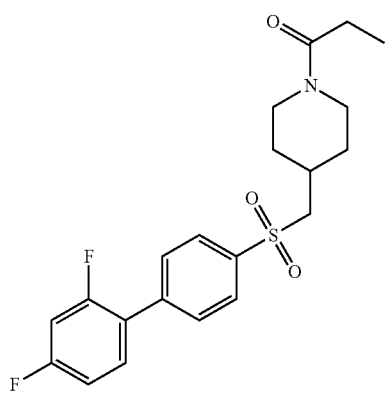

Synthetic Scheme 18

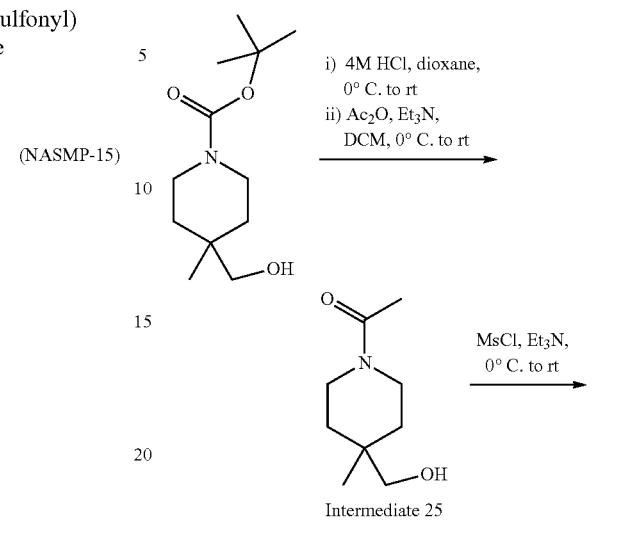

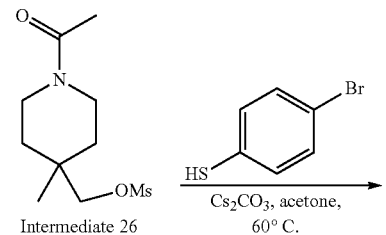

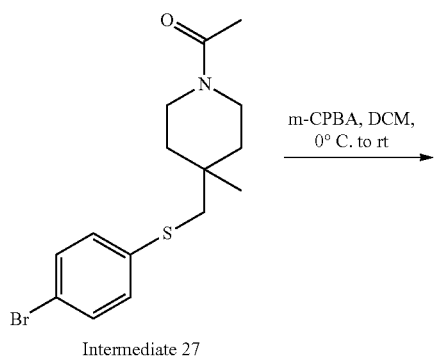

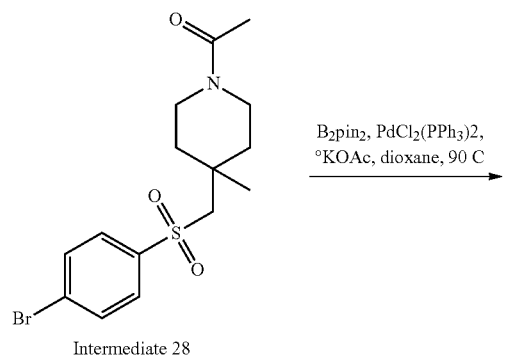

To a reaction tube were added a solution of 1-(4-(((4-bromophenyl)sulfonyl)methyl)piperidin-1-yl)propan-1-one Intermediate 24 (1.60 g, 4.27 mmol), 2-(2,4-difluorophenyl)-4,4,5,5-tetramethyl-1,3,2-dioxaborolane (1.23 g, 5.13 mmol) and sodium carbonate (1.13 g, 10.72 mmol) in a mixture of 1,4-dioxane-water (5:1, 30 mL). The tube was sealed and degassed by purging with argon for 15 min. Tetrakis(triphenylphosphine)palladium(0) (0.495 g, 0.427 mmol) was added to the reaction mixture under an argon atmosphere and then purging with argon for 5 min. The reaction mixture was heated at 100° C. for 16 h. The progress of the reaction was monitored by TLC [mobile phase: 60% ethyl acetate]. After completion of the reaction, the reaction mixture was cooled to room temperature and concentrated under reduced pressure to dryness. The crude product was purified by column chromatography on silica gel (100-200 mesh, gradient 10-70% ethyl acetate in hexanes) to afford the title compound (Synthesis Compound 15) (0.73 g, 42%) as white solid.

Analytical data:

LCMS (ESI): m/z=408.10 [M+H]$^+$.

HPLC (see generic method): Retention time: 8.40 min.; Purity: 99.03%.

$^1$H NMR (400 MHz, DMSO-d$_6$) δ (ppm): 8.01 (d, J=8.4 Hz, 2H), 7.82 (dd, J=7.6, 0.8 Hz, 2H), 7.72-7.65 (m, 1H), 7.48-7.46 (m, 1H), 7.29-7.23 (m, 1H), 4.25 (d, J=12.4 Hz, 1H), 3.78 (d, J=14.0 Hz, 1H), 3.36 (d, J=6.4 Hz, 2H), 2.99 (t, J=11.6 Hz, 1H), 2.58 (t, J=13.2 Hz, 1H), 2.27 (q, J=7.6 Hz, 2H), 2.14-2.02 (m, 1H), 1.87-1.73 (m, 2H), 1.30-1.06 (m, 2H), 0.96 (t, J=7.2 Hz, 3H).

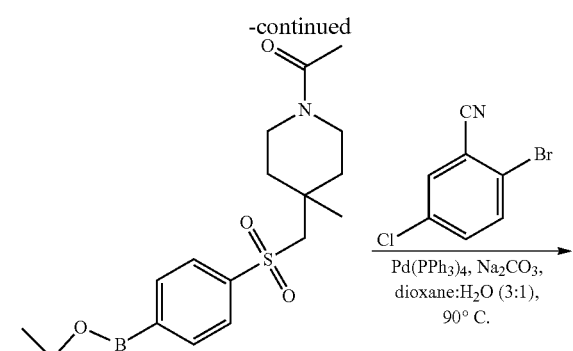

Intermediate 29

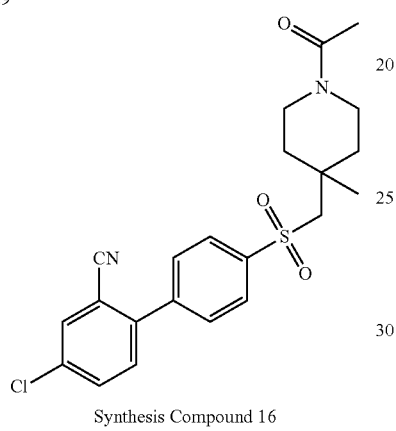

Synthesis Compound 16

Intermediate 25

1-(4-(Hydroxymethyl)-4-methylpiperidin-1-yl)ethan-1-one

To a stirred solution of tert-butyl 4-(hydroxymethyl)-4-methylpiperidine-1-carboxylate (2.50 g, 10.90 mmol) in 1,4-dioxane (25 mL), 4 M HCl in 1,4-dioxane (15 mL) was added at 0° C. The reaction mixture was warmed to room temperature and stirred for 4 h. The progress of the reaction was monitored by TLC [mobile phase: 5% methanol in DCM]. After completion of the reaction, the reaction mixture was concentrated under reduced pressure to dryness to afford a white solid (1.90 g, crude). To a stirred solution of the crude compound in DCM (40 mL), triethylamine (6.40 mL, 45.84 mmol) followed by acetic anhydride (1.20 mL, 12.61 mmol) were added at 0° C. The reaction mixture was warmed to room temperature and stirred for 5 h. The progress of the reaction was monitored by TLC [mobile phase: 5% methanol in DCM]. After completion of the reaction, the reaction mixture was diluted with water (25 mL) and extracted with DCM (3×25 mL). The combined organic layers were washed with brine (50 mL), dried over anhydrous sodium sulphate, filtered and concentrated under reduced pressure to dryness to afford the title compound Intermediate 25 (1.59 g, crude) as yellow oil. This compound was used in the next step without further purification.
Analytical Data:
LCMS (ESI) m/z=171.90 [M+H]$^+$.

Intermediate 26

(1-Acetyl-4-methylpiperidin-4-yl)methyl methanesulfonate

To a stirred solution of 1-(4-(hydroxymethyl)-4-methylpiperidin-1-yl)ethan-1-one Intermediate 25 (1.59 g, 9.28 mmol) in DCM (15 mL) was added triethylamine (2.58 mL, 18.57 mmol) followed by methanesulfonyl chloride (0.79 mL, 10.21 mmol) at 0° C. The reaction mixture was warmed to room temperature and stirred for 16 h. The progress of the reaction was monitored by TLC [mobile phase: 5% methanol in DCM]. After completion of the reaction, the reaction mixture was diluted with DCM (50 mL), washed with water (50 mL) and brine (25 mL). The organic layer was dried over anhydrous sodium sulphate, filtered and concentrated under reduced pressure to dryness to afford the title compound Intermediate 26 (1.88 g, crude) as a yellow oil. This compound was used in the next step without further purification.
Analytical Data:
LCMS (ESI) m/z=250.00 [M+H]$^+$.

Intermediate 27

1-(4-(((4-Bromophenyl)thio)methyl)-4-methylpiperidin-1-yl)ethan-1-one

To a stirred solution of (1-acetyl-4-methylpiperidin-4-yl)methyl methanesulfonate Intermediate 26 (1.88 g, 7.54 mmol) and 4-bromobenzenethiol (1.56 g, 8.29 mmol) in acetone (35 mL), caesium carbonate (4.91 g, 15.08 mmol)

was added at room temperature. The reaction mixture was then heated at 60° C. for 16 h. The progress of the reaction was monitored by TLC [mobile phase: 70% ethyl acetate in hexane]. After completion of the reaction, the reaction mixture was cooled to room temperature and filtered. The filtrate was concentrated under reduced pressure to dryness. The crude product was purified by column chromatography on silica gel (100-200 mesh, gradient 0-70% ethyl acetate in hexanes) to afford the title compound Intermediate 27 (1.00 g, 39%) as yellow oil.

Analytical Data:
LCMS (ESI) m/z=343.90 [M+H]$^+$ ($^{81}$Br).

Intermediate 28

1-(4-(((4-Bromophenyl)sulfonyl)methyl)-4-methylpiperidin-1-yl)ethan-1-one

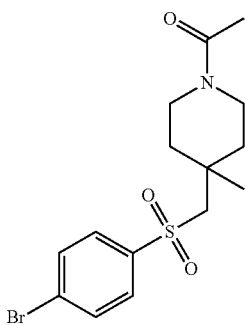 [SMILES: CC(=O)N1CCC(C)(CS(=O)(=O)c2ccc(Br)cc2)CC1]

To a stirred solution of 1-(4-(((4-bromophenyl)thio)methyl)-4-methylpiperidin-1-yl)ethan-1-one Intermediate 27 (1.00 g, 2.92 mmol) in DCM (10 mL), meta-chloroperbenzoic acid (60%) (2.52 g, 8.76 mmol) was added in portions at 0° C. The reaction mixture was then warmed to room temperature and stirred for 6 h. The progress of the reaction was monitored by TLC [mobile phase: 70% ethyl acetate in hexanes]. After completion of the reaction, the reaction was quenched with saturated aqueous sodium thiosulfate (10 mL) and stirred until all the solid dissolved. The organic layer was separated, washed with saturated aqueous sodium bicarbonate (2×25 mL) and brine (25 mL). The organic layer was dried over anhydrous sodium sulfate, filtered and concentrated under reduced pressure to dryness to afford the title compound Intermediate 28 (1.00 g, crude) as a yellow oil. This compound was used in the next step without further purification.

Analytical Data:
LCMS (ESI) m/z=376.05 [M+H]$^+$ ($^{81}$Br).

Intermediate 29

1-(4-Methyl-4-(((4-(4,4,5,5-tetramethyl-1,3,2-dioxaborolan-2-yl)phenyl)sulfonyl)methyl)piperidin-1-yl)ethan-1-one

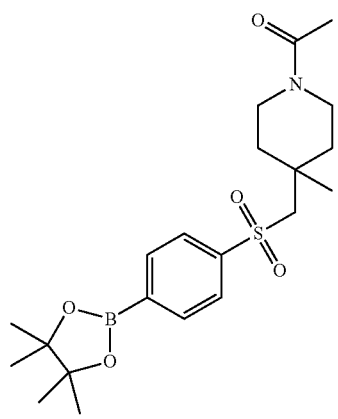

To a reaction tube were added a solution of 1-(4-(((4-bromophenyl)sulfonyl)methyl)-4-methylpiperidin-1-yl)ethan-1-one Intermediate 28 (1.00 g, 2.67 mmol), bis(pinacolato)diborane (0.814 g, 3.20 mmol) and potassium acetate (0.786 g, 8.01 mmol) in 1,4-dioxane (10 mL). The tube was sealed and degassed by purging with nitrogen for 15 min followed by addition of bis(triphenylphosphine)palladium (II) dichloride (0.038 g, 0.053 mmol) to the reaction mixture under a nitrogen atmosphere and then again purging with nitrogen for 5 min. The reaction mixture was heated at 90° C. for 16 h. The progress of the reaction was monitored by TLC [mobile phase: 100% ethyl acetate]. After completion of the reaction, the reaction mixture was cooled to room temperature, filtered through a pad of celite and the celite pad was washed with ethyl acetate (50 mL). The combined filtrate was concentrated under reduced pressure to dryness. The residue was triturated with pentane (2×25 mL), the solids were filtered out and dried under reduced pressure to afford the title compound Intermediate 29 (0.93 g, crude) as brown solid. This compound was used in the next step without further purification.

Analytical Data:
LCMS (ESI) m/z=340.05 [M+H]$^+$ (corresponding boronic acid).

Synthesis Compound 16

4'-(((1-Acetyl-4-methylpiperidin-4-yl)methyl)sulfonyl)-4-chloro-[1,1'-biphenyl]-2-carbonitrile (NASMP-16)

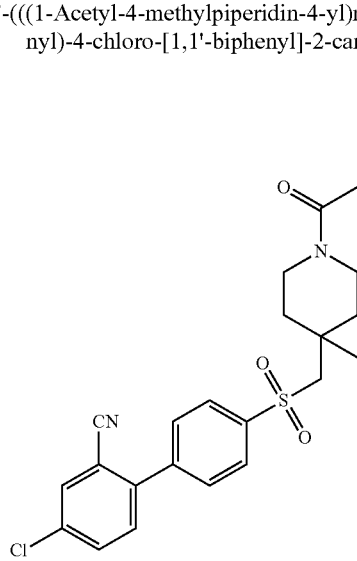

To a reaction tube were added a solution of 2-bromo-5-chlorobenzonitrile (0.400 g, 1.85 mmol), 1-(4-methyl-4-(((4-(4,4,5,5-tetramethyl-1,3,2-dioxaborolan-2-yl)phenyl)sulfonyl)methyl)piperidin-1-yl)ethan-1-one Intermediate 29 (0.934 g, 2.22 mmol) and sodium carbonate (0.490 g, 4.63 mmol) in a mixture of 1,4-dioxane: water (3:1, 13 mL). The tube was sealed and degassed by purging with argon for 15 min, followed by addition of tetrakis(triphenylphosphine)palladium(0) (0.213 g, 0.184 mmol) to the reaction mixture under an argon atmosphere and then again purging with argon for 5 min. The reaction mixture was heated at 90° C. for 16 h. The progress of the reaction was monitored by TLC [mobile phase: 100% ethyl acetate]. After completion of the reaction, the reaction mixture was cooled to room temperature, filtered through a pad of celite and the celite pad was washed with ethyl acetate (50 mL). The combined filtrate was concentrated under reduced pressure to dryness. The crude product was purified by column chromatography on silica gel (100-200 mesh, gradient 0-100% ethyl acetate in hexane) to afford the title compound (Synthesis Compound 16) (0.50 g, 63%) as a white solid.

Analytical Data:
LCMS (ESI): m/z=431.05 [M+H]$^+$.
HPLC (see generic method): Retention time: 8.26 min.; Purity: 98.56%.
$^1$H NMR (400 MHz, DMSO-d$_6$) δ (ppm): 8.23 (d, J=2.4 Hz, 1H), 8.09 (d, J=8.4 Hz, 2H), 7.93 (dd, J=8.8, 2.4 Hz, 1H), 7.86 (d, J=8.0 Hz, 2H), 7.71 (d, J=8.4 Hz, 1H), 3.58-3.42 (m, 2H), 3.50 (d, J=4.0 Hz, 2H), 3.38-3.28 (m, 2H), 1.96 (s, 3H), 1.78-1.70 (m, 1H), 1.66-1.58 (m, 1H), 1.52-1.44 (m, 1H), 1.40-1.32 (m, 1H), 1.26 (s, 3H).

Synthetic Scheme 19

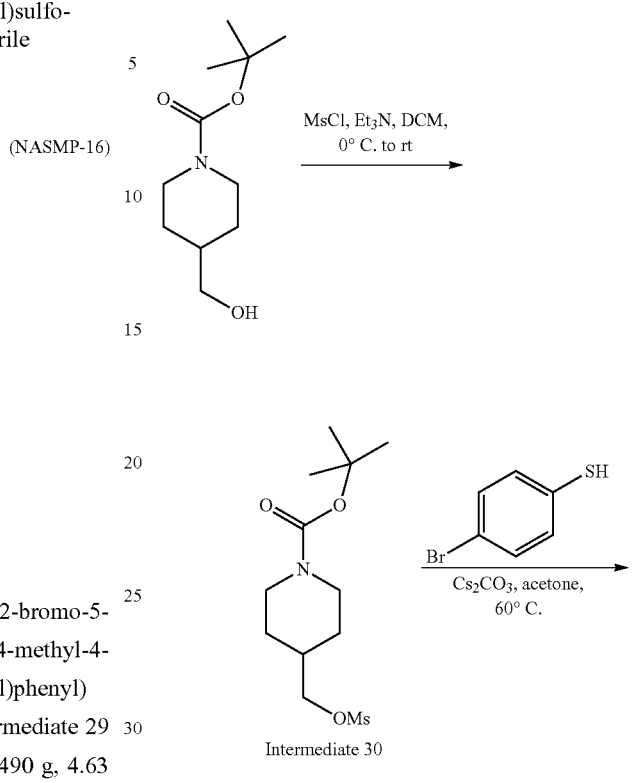

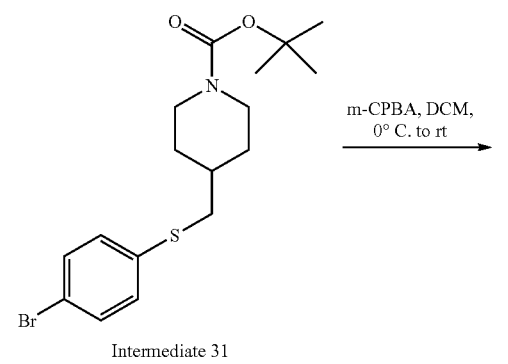

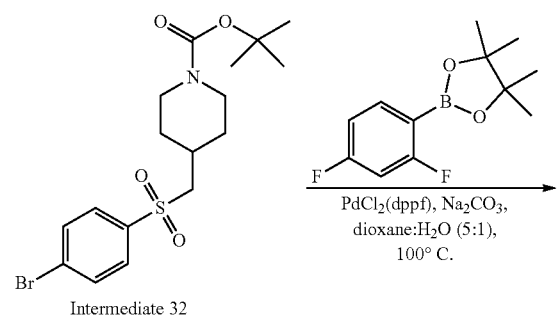

Intermediate 30 tert-Butyl 4-(((methylsulfonyl)oxy)methyl)piperidine-1-carboxylate

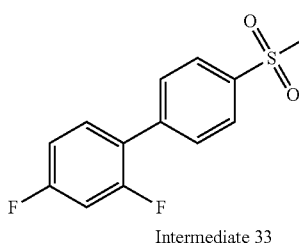

To a stirred solution of tert-butyl 4-(hydroxymethyl)piperidine-1-carboxylate (15.0 g, 69.67 mmol) in DCM (80 mL), triethylamine (19.42 mL, 139.34 mmol) was added at 0° C. and stirred for 10 min at the same temperature. Then, methanesulfonyl chloride (5.93 mL, 76.64 mmol) was added dropwise to the reaction at 0° C. The reaction was warmed to room temperature and stirred for 24 h. The progress of the reaction was monitored by TLC [mobile phase: 30% ethyl acetate in hexanes]. After completion of the reaction, it was quenched with water (100 mL) and extracted with DCM (3×60 mL). The combined organic layer was dried over anhydrous sodium sulfate, filtered and concentrated under reduced pressure to dryness to afford the title compound Intermediate 30 (21.0 g, crude) as yellowish viscous oil. This compound was used in the next step without further purification.

Analytical Data:

$^1$H NMR (400 MHz, DMSO-$d_6$) δ (ppm): 4.06 (d, J=6.4 Hz, 2H), 3.95 (br d, J=11.2 Hz, 2H), 3.17 (s, 3H), 2.70 (br s, 2H), 1.92-1.78 (m, 1H), 1.65 (d, J=12.8 Hz, 2H), 1.39 (s, 9H), 1.14-1.02 (m, 2H).

Intermediate 31 tert-Butyl 4-(((4-bromophenyl)thio)methyl)piperidine-1-carboxylate

To a stirred solution of tert-butyl 4-(((methylsulfonyl)oxy)methyl)piperidine-1-carboxylate Intermediate 30 (21.0 g, 71.57 mmol) in acetone (150 mL), 4-bromobenzenethiol (14.88 g, 78.73 mmol) and caesium carbonate (46.64 g, 143.15 mmol) were added under nitrogen atmosphere at room temperature. The reaction mixture was heated at 60° C. for 16 h. The progress of the reaction was monitored by TLC [mobile phase: 50% ethyl acetate in hexanes]. After completion of the reaction, the reaction mixture was cooled to room temperature and concentrated under reduced pressure. Water (100 mL) was added to the residue obtained and the resulting mixture was extracted with ethyl acetate (3×70 mL). The combined organic layer was dried over anhydrous sodium sulfate, filtered and concentrated under reduced pressure to dryness to afford the title compound Intermediate 31 (18.0 g, crude) as brown solid. This compound was used in the next step without further purification.

Analytical data:

LCMS (ESI) m/z=332.00 [M–$^t$Bu+H]$^+$ ($^{81}$Br).

$^1$H NMR (400 MHz, CDCl$_3$) δ (ppm): 7.43-7.39 (m, 2H), 7.21-7.17 (m, 2H), 4.11 (br s, 2H), 2.83 (d, J=6.8 Hz, 2H), 2.67 (m, 2H), 1.71-1.60 (m, 1H), 1.83 (d, J=13.2 Hz, 2H), 1.47 (s, 9H), 1.24-1.12 (m, 2H).

Intermediate 32 tert-Butyl 4-(((4-bromophenyl)sulfonyl)methyl)piperidine-1-carboxylate

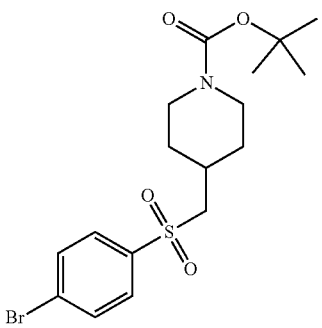 [SMILES: CC(C)(C)OC(=O)N1CCC(CS(=O)(=O)c2ccc(Br)cc2)CC1]

To a stirred solution of tert-butyl 4-(((4-bromophenyl) thio)methyl)piperidine-1-carboxylate Intermediate 31 (18.0 g, 46.58 mmol) in DCM (200 mL), meta-chloroperbenzoic acid (60%) (40.2 g, 139.76 mmol) was added in portions over a period of 20 min at 0° C. The reaction mixture was warmed to room temperature and stirred for 16 h. The progress of the reaction was monitored by TLC [mobile phase: 40% ethyl acetate in hexanes]. After completion of the reaction, the reaction mixture was diluted with DCM (100 mL) and washed with saturated aqueous sodium thiosulfate (100 mL) and saturated aqueous sodium bicarbonate (100 mL). The organic layer was dried over anhydrous sodium sulfate, filtered and concentrated under reduced pressure to dryness. The crude product was purified by column chromatography on silica gel (100-200 mesh, gradient 0-40% ethyl acetate in hexanes) to afford the title compound Intermediate 32 (9.50 g, 49%) as a white solid.

Analytical data:

$^1$H NMR (400 MHz, CDCl$_3$) δ (ppm): 7.82-7.71 (m, 4H), 4.07 (br s, 2H), 3.01 (d, J=6.4 Hz, 2H), 2.75 (t, J=12.4 Hz, 2H), 2.24-2.12 (m, 1H), 1.88 (d, J=11.6 Hz, 2H), 1.46 (s, 9H), 1.33-1.20 (m, 2H).

Intermediate 33 tert-Butyl 4-(((2',4'-difluoro-[1,1'-biphenyl]-4-yl) sulfonyl)methyl)piperidine-1-carboxylate

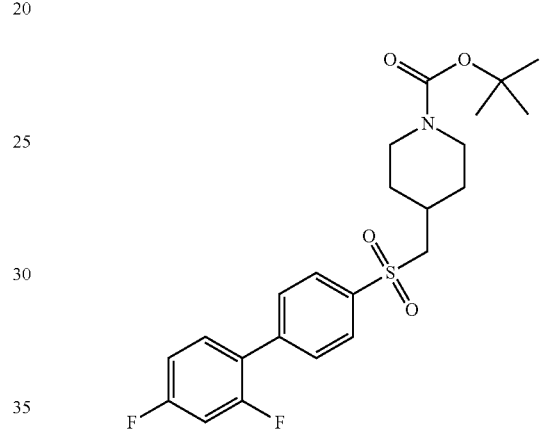

To a reaction tube were added a solution of tert-butyl 4-(((4-bromophenyl)sulfonyl)methyl) piperidine-1-carboxylate Intermediate 32 (2.00 g, 4.78 mmol), 2-(2,4-difluorophenyl)-4,4,5,5-tetramethyl-1,3,2-dioxaborolane (1.37 g, 5.73 mmol) and sodium carbonate (1.51 g, 14.34 mmol) in a mixture of 1,4-dioxane: water (5:1, 12 mL). The tube was sealed and degassed by purging with nitrogen for 10 min followed by addition of [1,1'-bis(diphenylphosphino) ferrocene]palladium(II) dichloride (0.349 g, 0.478 mmol) under a nitrogen atmosphere and the purging with nitrogen was continued for 10 min. The reaction mixture was heated at 100° C. for 16 h under a nitrogen atmosphere. The progress of the reaction was monitored by TLC [mobile phase: 40% ethyl acetate in hexanes]. After completion of the reaction, the reaction mixture was cooled to room temperature and concentrated under reduced pressure to dryness. The crude product was purified by column chromatography on silica gel (100-200 mesh, gradient 10-70% ethyl acetate in hexanes) to afford the title compound Intermediate 33 (1.80 g, 84%) as a brown solid.

Analytical Data:

LCMS (ESI) m/z=352.05 [M–Boc+H]$^+$.

Intermediate 34 and Intermediate 35 tert-butyl 4-(1-((2',4'-difluoro-[1,1'-biphenyl]-4-yl)sulfonyl)ethyl)piperidine-1-carboxylate (Intermediate 34) and tert-Butyl 4-(2-((2',4'-difluoro-[1,1'-biphenyl]-4-yl)sulfonyl)propan-2-yl)piperidine-1-carboxylate (Intermediate 35)

Analytical Data:

Intermediate 34:

LCMS (ESI) m/z=488.15 [M+Na]$^+$.

Intermediate 35:

LCMS (ESI) m/z=502.60 [M+Na]$^+$.

$^1$H NMR (400 MHz, DMSO-d$_6$) δ (ppm): 7.91 (d, J=8.0 Hz, 2H), 7.83 (d, J=8.0 Hz, 2H), 7.75-7.67 (m, 1H), 7.49-7.41 (m, 1H), 7.30-7.23 (m, 1H), 4.00 (d, J=10.8 Hz, 2H), 2.76-2.55 (m, 2H), 2.00-1.88 (m, 3H), 1.39 (s, 9H), 1.30-1.18 (m, 2H), 1.18 (s, 6H).

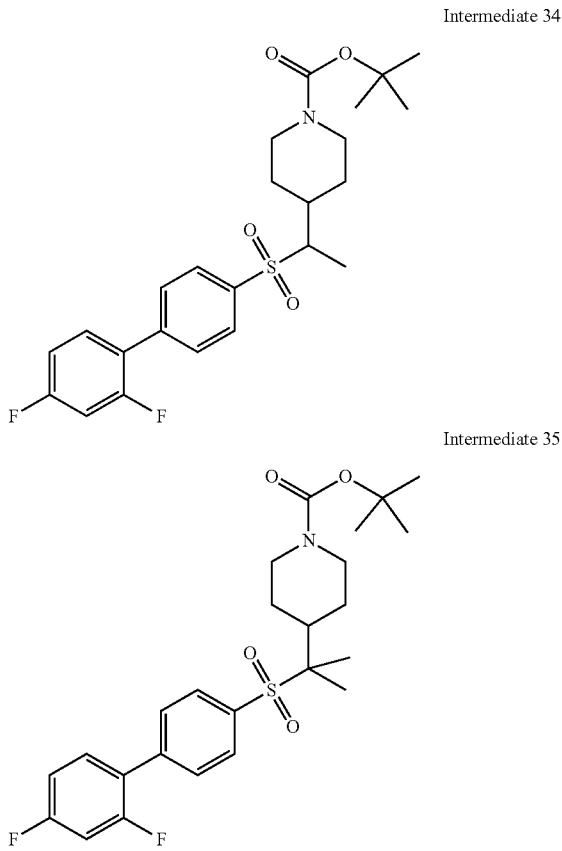

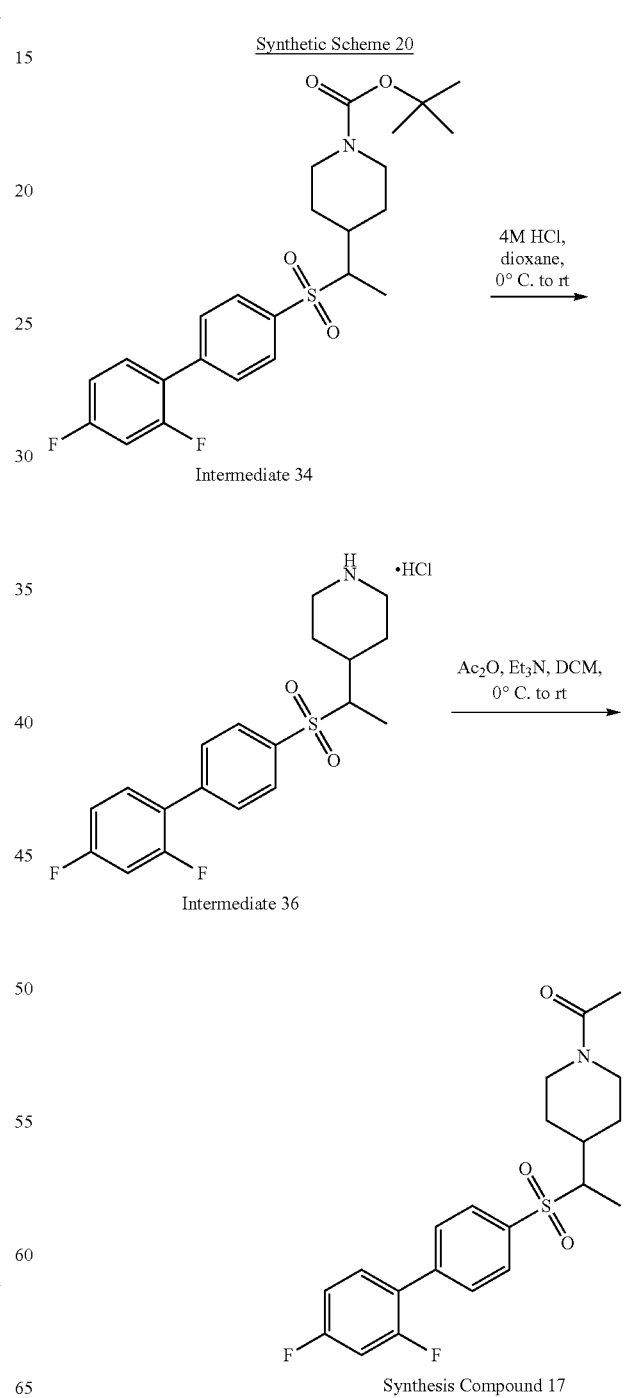

Synthetic Scheme 20

To as stirred solution of tert-butyl 4-(((2',4'-difluoro-[1,1'-biphenyl]-4-yl)sulfonyl)methyl)piperidine-1-carboxylate Intermediate 33 (1.00 g, 2.21 mmol) in THF (100 mL), a solution of NaHMDS (17.72 mL, 17.72 mmol, 1 M in THF) was added dropwise at −78° C. and stirred for 30 min at the same temperature. Then, methyl iodide (1.10 mL, 17.72 mmol) was added dropwise to the reaction mixture at the same temperature. The reaction was allowed to warm to room temperature and stirred for 16 h. The progress of the reaction was monitored by TLC [mobile phase: 40% ethyl acetate in hexanes]. After completion of the reaction, the reaction was quenched with saturated aqueous ammonium chloride (30 mL) and extracted with ethyl acetate (3×30 mL). The combined organic layer was dried over anhydrous sodium sulfate, filtered and concentrated under reduced pressure to dryness. The crude product was purified by column chromatography on silica gel (100-200 mesh, gradient 0-40% ethyl acetate in hexanes) to afford Intermediate 35 (0.350 g, 33%) as a white solid along with mono methylated compound Intermediate 34 (0.055 g, 5%) as a white solid.

Intermediate 36

4-(1-((2',4'-Difluoro-[1,1'-biphenyl]-4-yl)sulfonyl)ethyl)piperidine hydrochloride

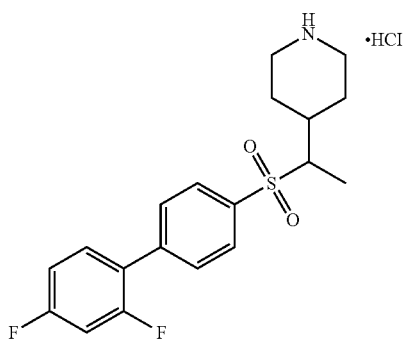

To a stirred solution of tert-butyl 4-(1-((2',4'-difluoro-[1,1'-biphenyl]-4-yl)sulfonyl)ethyl)piperidine-1-carboxylate Intermediate 34 (0.055 g, 0.118 mmol) in 1,4-dioxane (2 mL), a 4 M solution of HCl in 1,4-dioxane (2 mL) was added at 0° C. The reaction was warmed to room temperature and stirred for 2 h. The progress of the reaction was monitored by TLC [mobile phase: 60% ethyl acetate in hexanes]. After completion of the reaction, the reaction mixture was concentrated under reduced pressure to dryness to afford the title compound Intermediate 36 (0.045 g, crude) as a brown solid in the form of hydrochloride salt. This compound was used in the next step without further purification.

Analytical Data:

LCMS (ESI) m/z=366.10 [M+H]+ (free base).

Synthesis Compound 17

1-(4-(1-((2',4'-Difluoro-[1,1'-biphenyl]-4-yl)sulfonyl)ethyl)piperidin-1-yl)ethan-1-one (NASMP-17)

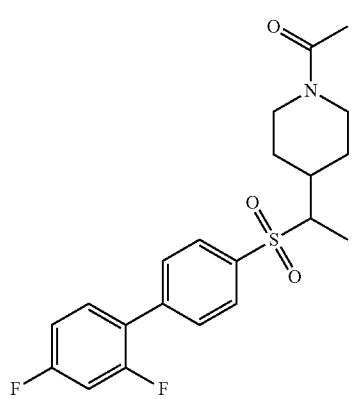

To a stirred solution of 4-(1-((2',4'-difluoro-[1,1'-biphenyl]-4-yl)sulfonyl)ethyl)piperidine hydrochloride Intermediate 36 (0.045 g, 0.112 mmol) in DCM (4 mL), triethylamine (0.039 mL, 0.280 mmol) was added at 0° C. and stirred for 10 min. Acetic anhydride (0.011 mL, 0.112 mmol) was then added to the reaction at the same temperature. The reaction was warmed to room temperature and stirred for 2 h. The progress of the reaction was monitored by TLC [mobile phase: 60% ethyl acetate in hexanes]. After completion of the reaction, the reaction mixture was concentrated under reduced pressure to dryness. The crude product was purified by column chromatography on silica gel (100-200 mesh, gradient 10-50% ethyl acetate in hexanes) to afford the title compound (Synthesis Compound 17) (0.012 g, 26%) as a white solid.

Analytical Data:

LCMS (ESI) m/z=408.05 [M+H]+.

HPLC (see generic method): Retention time: 8.26 min.; Purity: 96.98%.

$^1$H NMR (400 MHz, DMSO-d$_6$) δ (ppm): 7.97 (d, J=8.0 Hz, 2H), 7.82 (d, J=7.6 Hz, 2H), 7.73-7.66 (m, 1H), 7.48-7.42 (m, 1H), 7.26 (dt, J=2.0 & 8.4 Hz, 1H), 4.42 (d, J=12.8 Hz, 1H), 3.83 (d, J=13.6 Hz, 1H), 3.44-3.35 (m, 1H), 3.06-2.92 (m, 1H), 2.60-2.40 (m, 1H; merged with solvent peak), 2.35-2.25 (m, 1H), 1.97 (d, J=1.2 Hz, 3H), 1.81 (t, J=11.6 Hz, 1H), 1.67-1.55 (m, 1H), 1.45-1.30 (m, 1H), 1.30-1.15 (m, 1H), 1.10 (d, J=6.8 Hz, 3H).

Synthetic Scheme 21

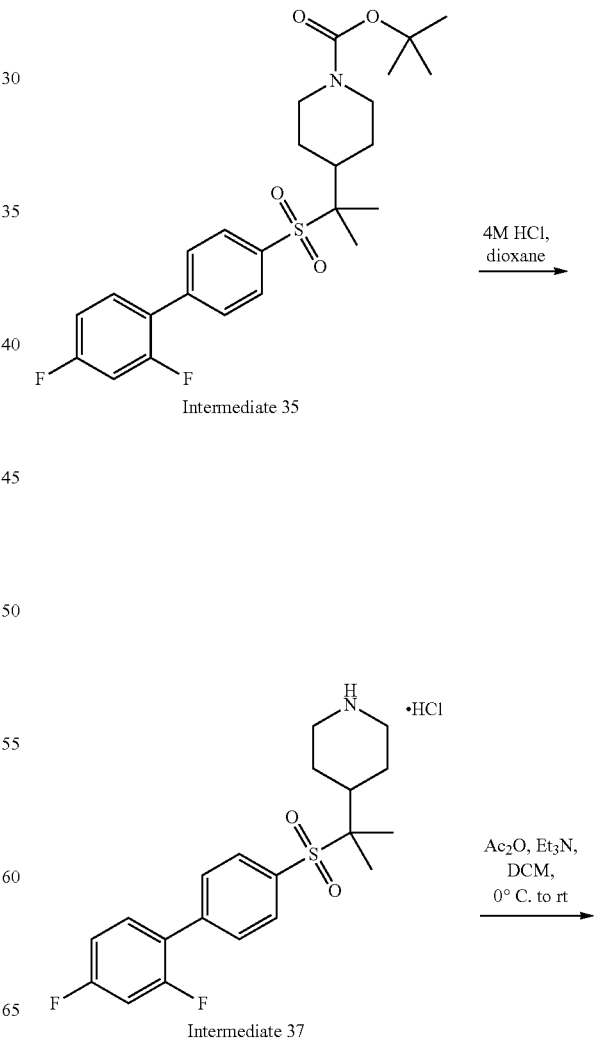

-continued

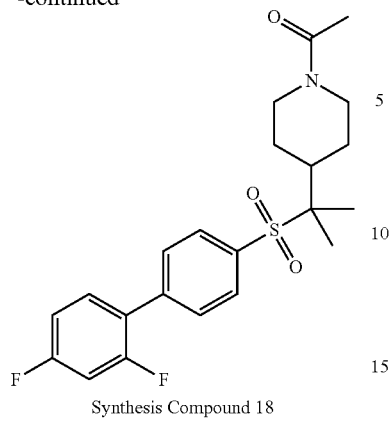

Synthesis Compound 18

Intermediate 37

4-(2-((2',4'-Difluoro-[1,1'-biphenyl]-4-yl)sulfonyl)propan-2-yl)piperidine hydrochloride

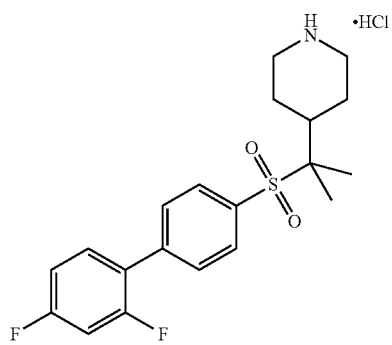 [SMILES: Cl ; CC(C)(C1CCNCC1)S(=O)(=O)c1ccc(-c2ccc(F)cc2F)cc1]

To a stirred solution of tert-butyl 4-(2-((2',4'-difluoro-[1,1'-biphenyl]-4-yl)sulfonyl)propan-2-yl)piperidine-1-carboxylate Intermediate 35 (0.350 g, 0.729 mmol) in 1,4-dioxane (2 mL) was added 4 M HCl in 1,4-dioxane (2 mL) at room temperature and stirred for 3 h. The progress of the reaction was monitored by TLC [mobile phase: 40% ethyl acetate in hexanes]. After completion of the reaction, the reaction mixture was concentrated under reduced pressure to dryness to afford the title compound Intermediate 37 (0.22 g, crude) as a brown solid in the form of hydrochloride salt. This compound was used in the next step without further purification.

Analytical Data:

LCMS (ESI) m/z=380.40 [M+H]$^+$ (free base).

Synthesis Compound 18

1-(4-(2-((2',4'-Difluoro-[1,1'-biphenyl]-4-yl)sulfonyl)propan-2-yl)piperidin-1-yl)ethan-1-one

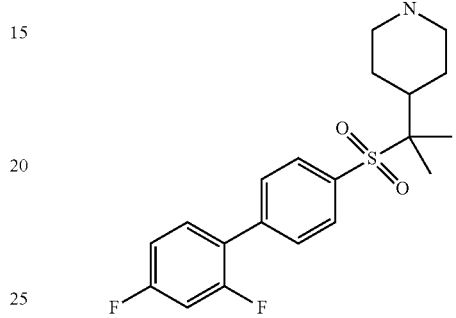

(NASMP-18)

To a stirred solution of 4-(2-((2',4'-difluoro-[1,1'-biphenyl]-4-yl)sulfonyl)propan-2-yl)piperidine hydrochloride Intermediate 37 (0.220 g, 0.529 mmol) in DCM (5 mL), triethylamine (0.184 mL, 1.32 mmol) was added at 0° C. and stirred for 10 min. Then, acetic anhydride (0.050 mL, 0.529 mmol) was added to the reaction mixture at the same temperature. The reaction was warmed to room temperature and stirred for 1 h. The progress of the reaction was monitored by TLC [mobile phase: 60% ethyl acetate in hexanes]. After completion of the reaction, the reaction mixture was concentrated under reduced pressure to dryness. The crude product was purified by column chromatography on silica gel (100-200 mesh, gradient 10-60% ethyl acetate in hexanes) to afford the title compound (Synthesis Compound 18) (0.208 g, 93%) as a white solid.

Analytical Data:

LCMS (ESI) m/z=422.05 [M+H]$^+$.

HPLC (see generic method): Retention time: 8.48 min.; Purity: 99.53%.

$^1$H NMR (400 MHz, DMSO-d$_6$) δ (ppm): 7.92 (d, J=8.4 Hz, 2H), 7.83 (d, J=8.0 Hz, 2H), 7.75-7.67 (m, 1H), 7.49-7.42 (m, 1H), 7.30-7.24 (m, 1H), 4.45 (d, J=12.8 Hz, 1H), 3.87 (d, J=13.2 Hz, 1H), 2.97 (t, J=12.4 Hz, 1H), 2.43 (t, J=12.4 Hz, 1H), 2.08-1.88 (m, 3H), 1.98 (s, 3H), 1.41-1.30 (m, 1H), 1.25-1.12 (m, 1H), 1.18 (s, 6H).

127

Synthetic Scheme 22

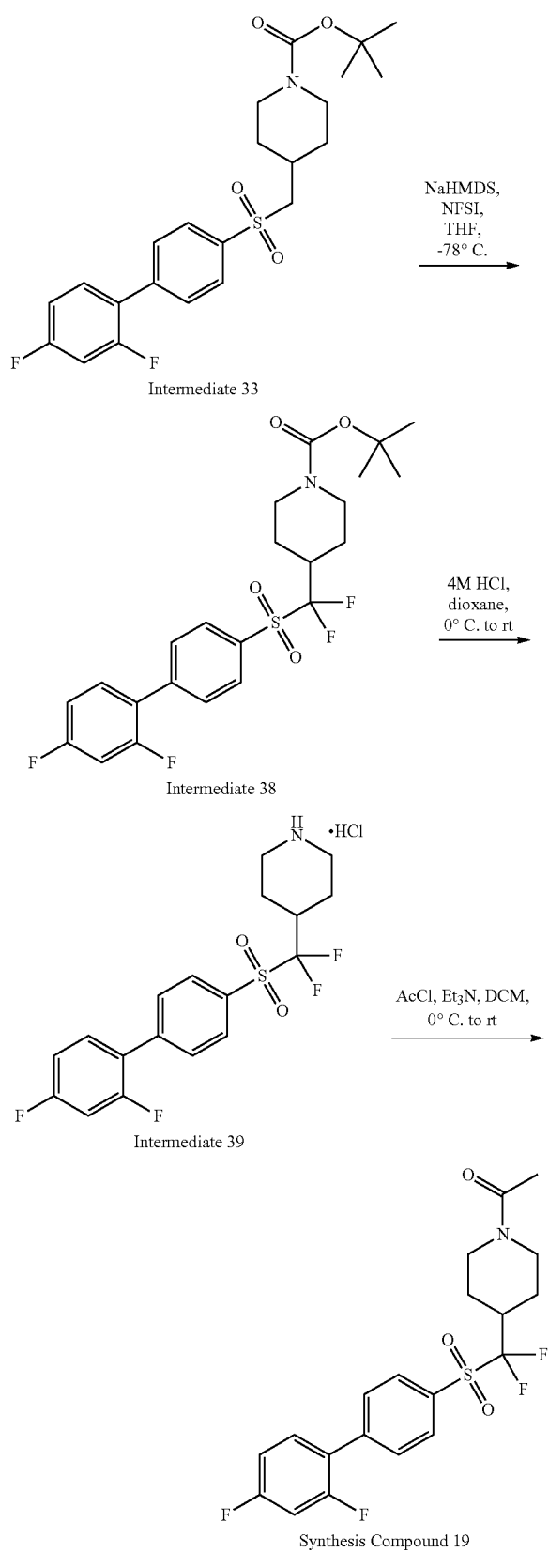

128

Intermediate 38 tert-Butyl 4-(((2',4'-difluoro-[1,1'-biphenyl]-4-yl)sulfonyl)difluoromethyl)piperidine-1-carboxylate

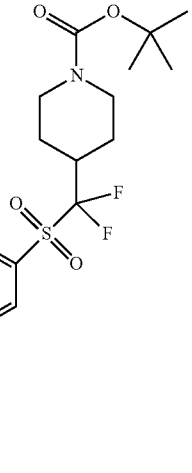

A stirred solution of tert-butyl 4-(((2',4'-difluoro-[1,1'-biphenyl]-4-yl)sulfonyl)methyl)piperidine-1-carboxylate Intermediate 33 (0.800 g, 1.77 mmol) in dry THF (20 mL) was cooled to −78° C. Then, a solution of N-fluorobenzenesulfonimide (NFSI) (2.79 g, 8.85 mmol) in dry THF (5 mL) was added, followed by a solution of NaHMDS (7.08 mL, 14.17 mmol, 2 M in THF) at −78° C. The reaction mixture was stirred at the same temperature for 1 h. The progress of reaction was monitored by TLC [mobile phase: 30% ethyl acetate in hexanes]. After completion of the reaction, the reaction was warmed to room temperature and quenched with saturated aqueous ammonium chloride (10 mL). The mixture was diluted with water (50 mL) and extracted with ethyl acetate (3×30 mL). The combined organic layer was dried over anhydrous sodium sulfate, filtered and concentrated under reduced pressure. The crude product was purified by column chromatography on silica gel (100-200 mesh, gradient 0-25% ethyl acetate in hexanes) to afford the title compound Intermediate 38 (0.665 g, 77%) as a white solid.

Analytical Data:

LCMS (ESI) m/z=432.30 [M−$^t$Bu+H]$^+$.

$^1$H NMR (400 MHz, CDCl$_3$) δ (ppm): 8.04 (d, J=8.4 Hz, 2H), 7.76 (d, J=7.6 Hz, 2H), 7.50-7.43 (m, 1H), 7.06-6.95 (m, 2H), 4.26 (br s, 2H), 2.85-2.65 (m, 3H), 2.12 (d, J=12.8 Hz, 2H), 1.70-1.55 (m, 2H), 1.48 (s, 9H).

Intermediate 39

4-(((2',4'-Difluoro-[1,1'-biphenyl]-4-yl)sulfonyl)difluoromethyl)piperidine hydrochloride

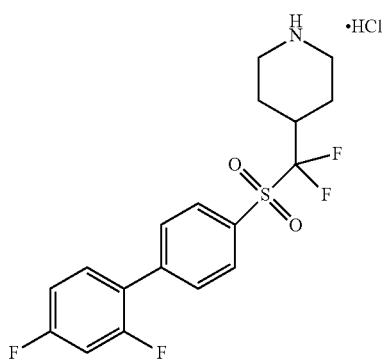 [SMILES: Cl ; O=S(=O)(c1ccc(-c2ccc(F)cc2F)cc1)C(F)(F)C1CCNCC1]

To a stirred solution of tert-butyl 4-(((2',4'-difluoro-[1,1'-biphenyl]-4-yl)sulfonyl)difluoromethyl)piperidine-1-carboxylate Intermediate 38 (0.660 g, 1.35 mmol) in 1,4-dioxane (20 mL) was added a 4 M solution of HCl in 1,4-dioxane (20 mL) at 0° C. The reaction was warmed to room temperature and stirred for overnight. The progress of the reaction was monitored by TLC [mobile phase: 70% ethyl acetate in hexanes]. After completion of the reaction, the reaction mixture was concentrated under reduced pressure to dryness to afford the title compound Intermediate 39 (0.500 g, crude) as a yellowish gum in the form of hydrochloride salt. This compound was used in the next step without further purification.

Analytical Data:

LCMS (ESI) m/z=388.30 [M+H]$^+$ (free base).

Synthesis Compound 19

1-(4-(((2',4'-Difluoro-[1,1'-biphenyl]-4-yl)sulfonyl)difluoromethyl)piperidin-1-yl)ethan-1-one (NASMP-19)

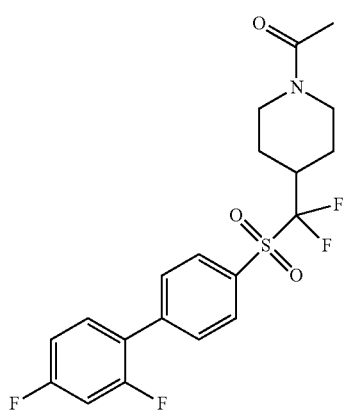

To a stirred solution of 4-(((2',4'-difluoro-[1,1'-biphenyl]-4-yl)sulfonyl)difluoromethyl)piperidine hydrochloride Intermediate 39 (0.400 g, 0.943 mmol) in DCM (10 mL) was added triethylamine (0.329 mL, 2.359 mmol) at 0° C. and stirred at the same temperature for 10 min. Then, acetyl chloride (0.081 mL, 1.132 mmol) was added to the reaction at 0° C. The reaction mixture was warmed to room temperature and stirred for 1 h. The progress of reaction was monitored by TLC [mobile phase: 60% ethyl acetate in hexanes]. After completion of reaction, the reaction was quenched with water (30 mL) and extracted with DCM (3×20 mL). The combined organic layer was dried over anhydrous sodium sulfate, filtered and concentrated under reduced pressure to dryness. The crude product was purified by column chromatography on silica gel (100-200 mesh, gradient 0-50% ethyl acetate in hexanes) to afford (Synthesis Compound 19) (0.205 g, 51%) as a white solid.

Analytical Data:

LCMS (ESI) m/z=430.05 [M+H]$^+$.

HPLC [Method: Column: X-Select CSH C18 (4.6*150) mm, 5µ; Mobile Phase: A—0.1% TFA in water; B-Acetonitrile; Inj. Vol.: 5.0 µL; Flow Rate: 1.2 mL/min.; Gradient program: Time (min)/B conc.: 0.01/5, 1.0/5, 8.0/100, 12.0/100, 14.0/5, 18.0/5; Retention time: 8.37 min.; Purity: 95.96%.

$^1$H NMR (400 MHz, CDCl$_3$) δ (ppm): 8.04 (d, J=8.4 Hz, 2H), 7.76 (d, J=7.6 Hz, 2H), 7.50-7.43 (m, 1H), 7.06-6.95 (m, 2H), 4.80 (d, J=13.2 Hz, 1H), 3.96 (d, J=13.2 Hz, 1H), 3.16 (t, J=13.6 Hz, 1H), 2.92-2.75 (m, 1H), 2.62 (t, J=12.0 Hz, 1H), 2.25 (d, J=13.6 Hz, 1H), 2.17-2.10 (m, 1H), 2.14 (s, 3H), 1.74-1.55 (m, 2H).

Synthetic Scheme 23

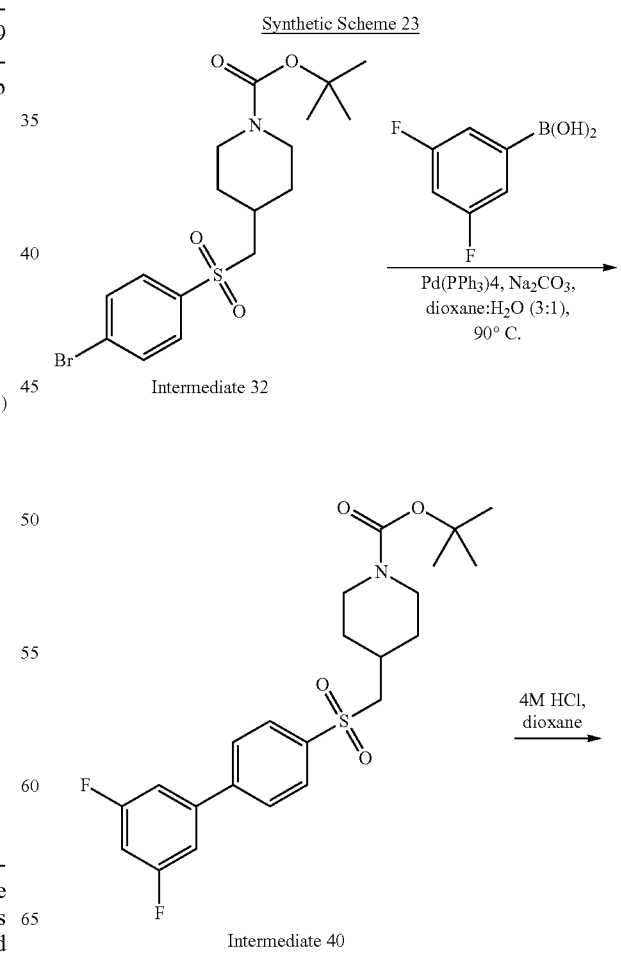

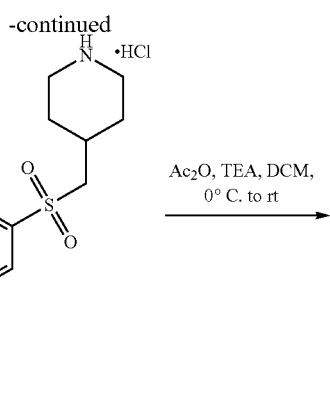

Intermediate 41

Ac₂O, TEA, DCM,
0° C. to rt
→

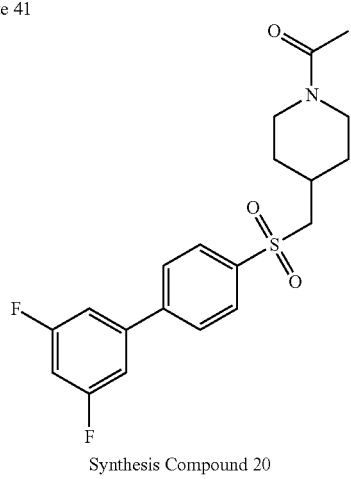

Synthesis Compound 20

Intermediate 40 tert-Butyl 4-(((3',5'-difluoro-[1,1'-biphenyl]-4-yl)sulfonyl)methyl)piperidine-1-carboxylate

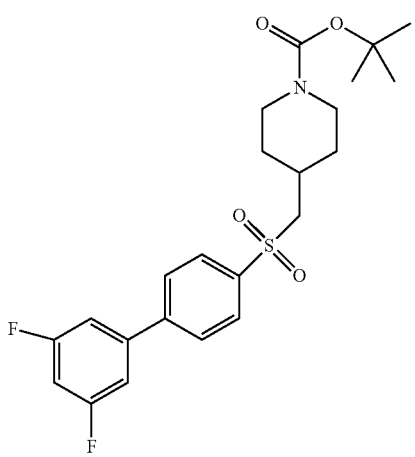 [SMILES: CC(C)(C)OC(=O)N1CCC(CS(=O)(=O)c2ccc(-c3cc(F)cc(F)c3)cc2)CC1]

To a reaction tube were added a solution of tert-butyl 4-(((4-bromophenyl)sulfonyl)methyl)piperidine-1-carboxylate Intermediate 32 (1.00 g, 2.39 mmol), (3,5-difluorophenyl)boronic acid (0.566 g, 3.585 mmol) and sodium carbonate (0.633 g, 5.975 mmol) in a mixture of 1,4-dioxane: water (3:1, 21 mL). The tube was sealed and degassed by purging with argon for 10 min, followed by addition of tetrakis(triphenylphosphine)palladium(0) (0.276 g, 0.239 mmol) to the reaction mixture under an argon atmosphere and the purging with argon was continued for 5 min. The reaction mixture was then heated at 90° C. for 16 h under an argon atmosphere. The progress of the reaction was monitored by TLC [mobile phase: 80% ethyl acetate in hexanes]. After completion of the reaction, the reaction mixture was cooled to room temperature and filtered through a pad of Celite. The Celite pad was washed with ethyl acetate (2×50 mL). The combined organic layer was concentrated under reduced pressure to dryness. The crude product was purified by column chromatography on silica gel (CombiFlash®, gradient 0-80% ethyl acetate in hexanes) to afford the title compound Intermediate 40 (0.650 g, 60%) as a yellow oil.

Analytical Data:

LCMS (ESI) m/z=351.95 [M−Boc+H]+.

¹H NMR (400 MHz, CDCl₃) δ (ppm): 8.01 (d, J=8.4 Hz, 2H), 7.75 (d, J=8.0 Hz, 2H), 7.18-7.10 (m, 2H), 6.92-6.85 (m, 1H), 4.16-4.02 (m, 2H), 3.06 (d, J=6.4 Hz, 2H), 2.76 (t, J=10.8 Hz, 2H), 2.30-2.18 (m, 1H), 1.91 (br d, J=11.2 Hz, 2H), 1.46 (s, 9H), 1.35-1.22 (m, 2H).

Intermediate 41

4-(((3',5'-Difluoro-[1,1'-biphenyl]-4-yl)sulfonyl)methyl)piperidine hydrochloride

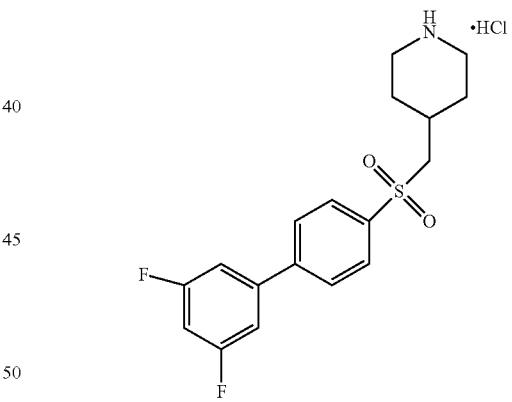

To a stirred solution of tert-butyl 4-(((3',5'-difluoro-[1,1'-biphenyl]-4-yl)sulfonyl)methyl)piperidine-1-carboxylate Intermediate 40 (0.650 g, 1.439 mmol) in 1,4-dioxane (1 mL), a 4 M solution of HCl in 1,4-dioxane (10 mL) was added at room temperature and stirred for 4 h. The progress of the reaction was monitored by TLC [mobile phase: 80% ethyl acetate in hexanes]. After completion of the reaction, the reaction mixture was concentrated under reduced pressure to dryness to afford the title compound Intermediate 41 (0.460 g, crude) as a white solid in the form of hydrochloride salt. This compound was used in the next step without further purification.

Analytical Data:

LCMS (ESI) m/z=352.00 [M+H]⁺ (free base).

133

Synthesis Compound 20

1-(4-(((3',5'-Difluoro-[1,1'-biphenyl]-4-yl)sulfonyl)methyl)piperidin-1-yl)ethan-1-one (NASMP-20)

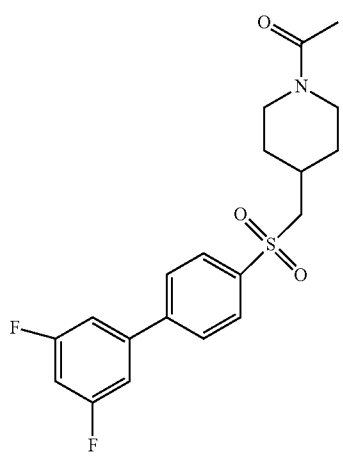

To a stirred solution of 4-(((3',5'-difluoro-[1,1'-biphenyl]-4-yl)sulfonyl)methyl)piperidine hydrochloride Intermediate 41 (0.460 g, 1.185 mmol) in DCM (10 mL), triethylamine (0.495 mL, 3.555 mmol) followed by acetic anhydride (0.144 mL, 1.422 mmol) were added at 0° C. The reaction was then warmed to room temperature and stirred for 16 h. The progress of the reaction was monitored by TLC [mobile phase: 5% methanol in DCM]. After completion of the reaction, the reaction mixture was diluted with DCM (50 mL), washed with water (2×25 mL) and brine (2×25 mL). The organic layer was dried over anhydrous sodium sulfate, filtered and concentrated under reduced pressure to dryness. The crude product was purified by triturating with diethyl ether (2×25 mL), the solids were filtered out and dried under reduced pressure to afford the title compound (Synthesis Compound 20) (0.310 g, 67%) as an off white solid.

Analytical Data:

LCMS (ESI) m/z=394.00 [M+H]⁺.

HPLC (see generic method): Retention time: 8.12 min.; Purity: 99.24%.

¹H NMR (400 MHz, DMSO-d₆) δ (ppm): 8.06-7.98 (m, 4H), 7.58 (d, J=6.8 Hz, 2H), 7.38-7.31 (m, 1H), 4.23 (d, J=13.2 Hz, 1H), 3.73 (d, J=13.2 Hz, 1H), 3.38 (d, J=6.4 Hz, 2H), 3.04-2.96 (m, 1H), 2.60-2.50 (m, 1H), 2.10-2.00 (m, 1H), 1.95 (s, 3H), 1.85-1.71 (m, 2H), 1.30-1.19 (m, 1H), 1.19-1.05 (m, 1H).

Synhtetic Scheme 24

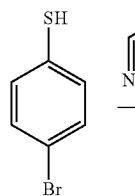 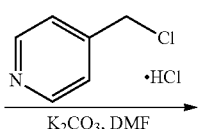

K₂CO₃, DMF

134

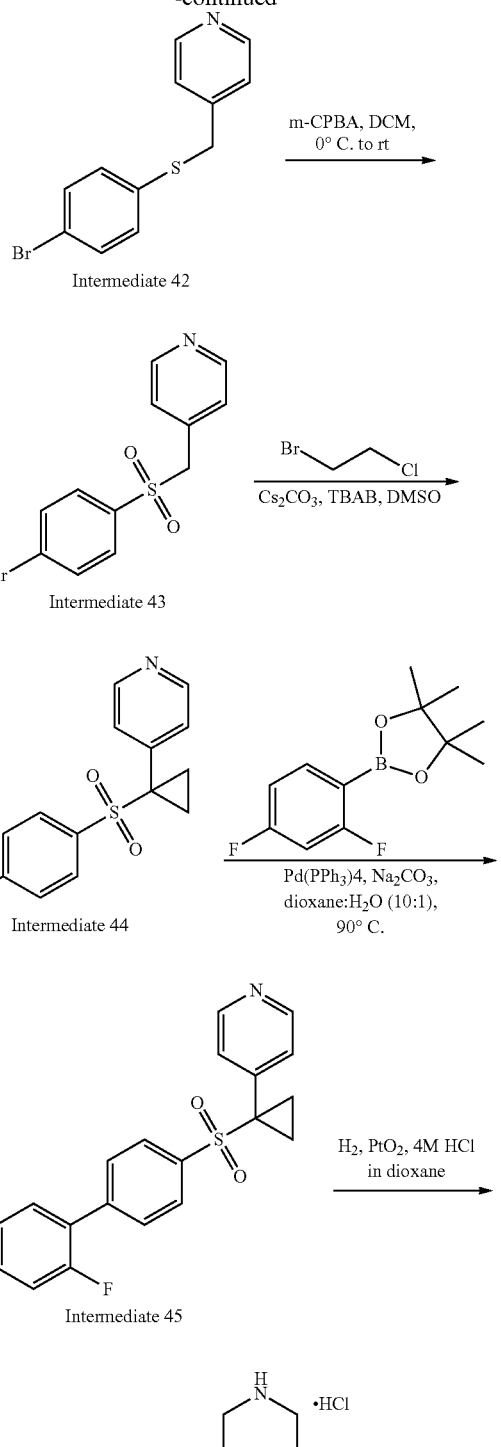

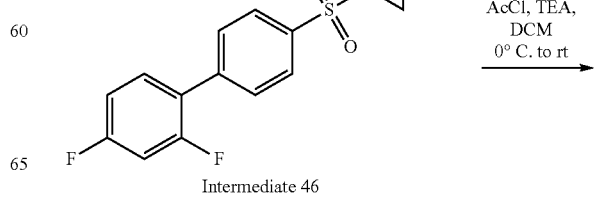

-continued

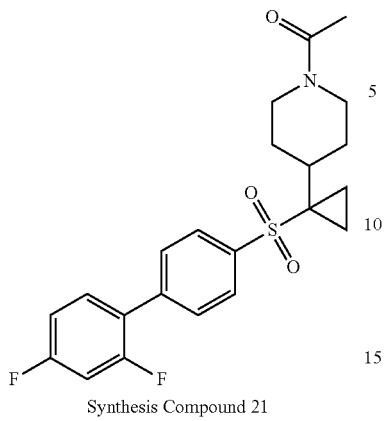

Synthesis Compound 21

Intermediate 42

4-(((4-Bromophenyl)thio)methyl)pyridine

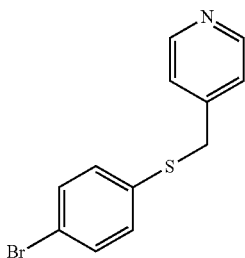 [SMILES: Brc1ccc(SCc2ccncc2)cc1]

To a stirred solution of 4-bromobenzenethiol (5.00 g, 26.44 mmol) in DMF (50 mL), 4-(chloromethyl)pyridine hydrochloride (4.33 g, 26.44 mmol) and potassium carbonate (12.79 g, 92.55 mmol) were added at room temperature and the reaction was stirred for 16 h. Progress of the reaction was monitored by TLC [mobile phase: 30% ethyl acetate in hexanes]. After completion of the reaction, the reaction mixture was quenched with water (200 mL) and extracted with ethyl acetate (4×60 mL). The combined organic layer was washed with brine (50 mL), dried over anhydrous sodium sulfate, filtered and concentrated under reduced pressure to dryness to afford the title compound Intermediate 42 (6.00 g, crude) as brown solid. This compound was used in the next step without further purification.

Analytical Data:
LCMS (ESI) m/z=281.75 [M+H]+ ([81]Br).

Intermediate 43

4-(((4-Bromophenyl)sulfonyl)methyl)pyridine

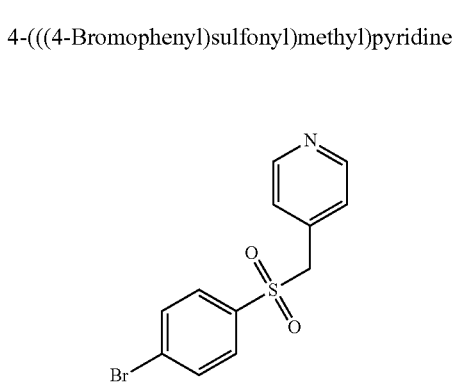

To a stirred solution of 4-(((4-bromophenyl)thio)methyl)pyridine Intermediate 42 (6.00 g, 21.41 mmol) in DCM (100 mL), cooled at 0° C., was added in portions meta-chloroperbenzoic acid (60%) (13.55 g, 47.11 mmol) over a period of 20 min. The reaction mixture was then warmed to room temperature and stirred for 3 h. The progress of reaction was monitored by TLC [mobile phase: 50% ethyl acetate in hexanes]. After completion of reaction, the reaction mixture was diluted with DCM (100 mL) and washed with saturated aqueous sodium thiosulfate (50 mL) and saturated aqueous sodium bicarbonate (50 mL). The organic layer was dried over anhydrous sodium sulfate, filtered and concentrated under reduced pressure to dryness. The crude product was purified by column chromatography on silica gel (100-200 mesh, gradient 0-40% ethyl acetate in hexanes) to afford the title compound Intermediate 43 (3.30 g, 49%) as a white solid.

Analytical data:
LCMS (ESI) m/z=313.85 [M+H]+ ([81]Br).

Intermediate 44

4-(1-((4-Bromophenyl)sulfonyl)cyclopropyl)pyridine

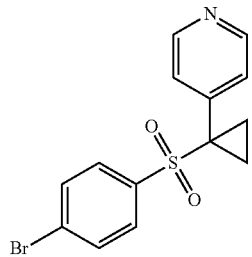 [SMILES: O=S(=O)(c1ccc(Br)cc1)C1(c2ccncc2)CC1]

To a stirred solution of 4-(((4-bromophenyl)sulfonyl)methyl)pyridine Intermediate 43 (2.00 g, 6.41 mmol) in DMSO (10 mL), 1-bromo-2-chloroethane (2.76 g, 19.22 mmol), caesium carbonate (6.26 g, 19.22 mmol) and tetra-n-butylammonium bromide (0.413 g, 1.28 mmol) were added at room temperature and the reaction was stirred for 3 h. The progress of reaction was monitored by TLC [mobile phase: 50% ethyl acetate in hexanes]. After completion of reaction, the reaction was quenched with water (100 mL) and extracted with ethyl acetate (3×40 mL). The combined organic layer was washed with water (2×40 mL), dried over anhydrous sodium sulfate, filtered and concentrated under reduced pressure to dryness. The crude product was purified by column chromatography on silica gel (100-200 mesh, gradient 0-25% ethyl acetate in hexanes) to afford the title compound Intermediate 44 (1.50 g, 69%) as a white solid.

Analytical data:

LCMS (ESI) m/z=339.75 [M+H]$^+$ ($^{81}$Br).

$^1$H NMR (400 MHz, DMSO-d$_6$) δ (ppm): 8.48 (d, J=6.0 Hz, 2H), 7.78 (d, J=8.8 Hz, 2H), 7.45 (d, J=8.4 Hz, 2H), 7.12 (d, J=6.0 Hz, 2H), 1.90-1.84 (m, 2H), 1.47-1.40 (m, 2H).

Intermediate 45

4-(1-((2',4'-Difluoro-[1,1'-biphenyl]-4-yl)sulfonyl)cyclopropyl)pyridine

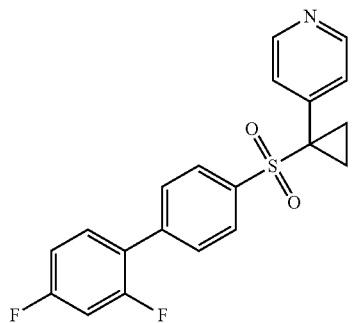 [SMILES: O=S(=O)(c1ccc(-c2ccc(F)cc2F)cc1)C1(c2ccncc2)CC1]

To a reaction tube were added a solution of 4-(1-((4-bromophenyl)sulfonyl)cyclopropyl)pyridine Intermediate 44 (1.00 g, 2.96 mmol), 2-(2,4-difluorophenyl)-4,4,5,5-tetramethyl-1,3,2-dioxaborolane (0.851 g, 3.55 mmol) and sodium carbonate (0.783 g, 7.39 mmol) in a mixture of 1,4-dioxane:water (10:1, 11 mL). The tube was sealed and degassed by purging with nitrogen for 10 min, followed by addition of tetrakis(triphenylphosphine)palladium(0) (0.341 g, 0.296 mmol) to the reaction mixture under a nitrogen atmosphere and the purging with nitrogen was continued for 5 min. The reaction mixture was then heated at 90° C. for 16 h under a nitrogen atmosphere. The progress of reaction was monitored by TLC [mobile phase: 60% ethyl acetate in hexanes]. After completion of reaction, the reaction mixture was cooled to room temperature and concentrated under reduced pressure to dryness. The crude product was purified by column chromatography on silica gel (100-200 mesh, gradient 0-40% ethyl acetate in hexanes) to afford the title compound Intermediate 45 (0.800 g, 73%) as a brown solid.

Analytical data:

LCMS (ESI) m/z=372.00 [M+H]$^+$.

$^1$H NMR (400 MHz, DMSO-d$_6$) δ (ppm): 8.47 (d, J=4.8 Hz, 2H), 7.72 (d, J=8.0 Hz, 2H), 7.68 (m, 1H), 7.62 (d, J=8.4 Hz, 2H), 7.48-7.40 (m, 1H), 7.29-7.22 (m, 1H), 7.14 (d, J=5.2 Hz, 2H), 1.93-1.86 (m, 2H), 1.49-1.42 (m, 2H).

Intermediate 46

4-(1-((2',4'-Difluoro-[1,1'-biphenyl]-4-yl)sulfonyl)cyclopropyl)piperidine hydrochloride

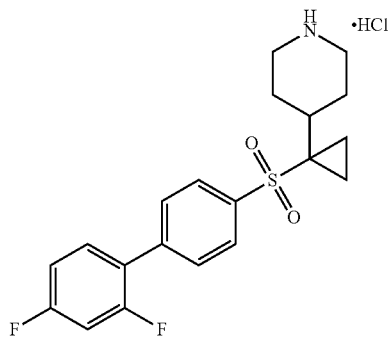 [SMILES: Cl ; O=S(=O)(c1ccc(-c2ccc(F)cc2F)cc1)C1(C2CCNCC2)CC1]

To a Parr reactor was added a solution of 4-(1-((2',4'-difluoro-[1,1'-biphenyl]-4-yl) sulfonyl)cyclopropyl)pyridine Intermediate 45 (0.500 g, 1.35 mmol) in a 4 M solution of HCl in 1,4-dioxane (10 mL). The Parr reactor was evacuated and backfilled with nitrogen.

To the reaction mixture was added platinum dioxide (50 mg, 10% w/w) under a nitrogen atmosphere. The Parr reactor was evacuated and backfilled with hydrogen. The reaction was then stirred at room temperature for 16 h under a hydrogen atmosphere at 100 psi. The progress of the reaction was monitored by TLC [mobile phase: 70% ethyl acetate in hexanes]. The reaction mixture was filtered through a pad of Celite and the Celite pad was washed with methanol (100 mL) and water (50 mL). The combined filtrate was concentrated under reduced pressure to dryness to afford the title compound Intermediate 46 (0.410 g, crude, 35% pure by LCMS) as a viscous liquid as a hydrochloride salt. This compound was used in the next step without further purification.

Analytical data:

LCMS (ESI) m/z=378.00 [M+H]$^+$ (free base).

Synthesis Compound 21

1-(4-(1-((2',4'-Difluoro-[1,1'-biphenyl]-4-yl)sulfonyl)cyclopropyl)piperidin-1-yl)ethan-1-one

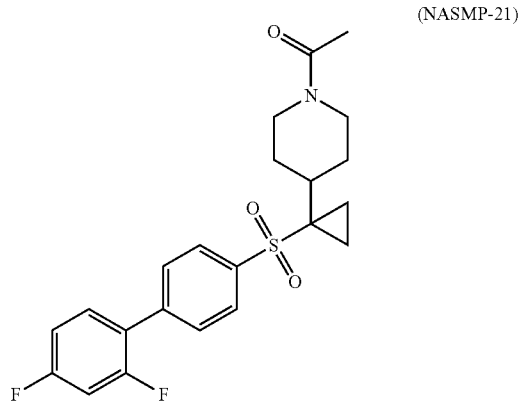 [SMILES: CC(=O)N1CCC(C2(S(=O)(=O)c3ccc(-c4ccc(F)cc4F)cc3)CC2)CC1]

To a stirred solution of 4-(1-((2',4'-difluoro-[1,1'-biphenyl]-4-yl)sulfonyl)cyclopropyl)piperidine hydrochloride Intermediate 46 [0.410 g (35% pure), 0.346 mmol] in DCM (5 mL) at 0° C. was added triethylamine (0.097 mL, 0.691 mmol) and stirred for 10 min followed by addition of acetyl chloride (0.030 mL, 0.415 mmol) to the reaction. The reaction was then warmed to room temperature and stirred for 1 h. The progress of reaction was monitored by TLC [mobile phase: 80% ethyl acetate in hexanes]. After completion of the reaction, the mixture was concentrated under reduced pressure to dryness. The crude product was purified by column chromatography on silica gel (230-400 mesh, gradient 0-60% ethyl acetate in hexanes). The product was further triturated with diethyl ether (2×5 mL) at 0° C. for 15 min. The solids were filtered out and dried under reduced pressure to afford (Synthesis Compound 21) (0.073 g, 50%) as a white solid.

Analytical Data:

LCMS (ESI) m/z=420.10 [M+H]$^+$.

HPLC (see generic method): Retention time: 8.32 min.; Purity: 95.11%.

$^1$H NMR (400 MHz, DMSO-d$_6$) δ (ppm): 8.00 (d, J=8.4 Hz, 2H), 7.82 (d, J=7.6 Hz, 2H), 7.75-7.67 (m, 1H), 7.48-7.41 (m, 1H), 7.29-7.23 (m, 1H), 4.32 (d, J=12.8 Hz, 1H), 3.72 (d, J=14.0 Hz, 1H), 2.88 (t, J=12.0 Hz, 1H), 2.33 (t, J=10.4 Hz, 1H), 2.13-2.02 (m, 1H), 1.91 (s, 3H), 1.54-1.40 (m, 2H), 1.40 (br s, 2H), 1.08 (br s, 2H), 1.10-0.97 (m, 1H), 0.92-0.80 (m, 1H).

Synthetic Scheme 25

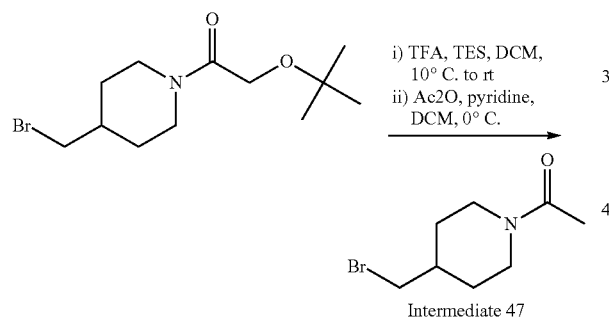

Intermediate 47

Intermediate 47

1-[4-(Bromomethyl)piperidin-1-yl]ethanone

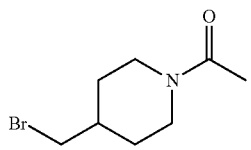

To a 2 L flange flask under N$_2$ was charged 1-[4-(bromomethyl)piperidin-1-yl]-2-(tert-butoxy)ethanone (45 g, 0.153 mol), DCM (900 mL) and triethylsilane (21.6 mL, 0.255 mol) at room temperature. The reaction was then cooled to 10° C. and TFA (107.1 mL, 0.631 mol) was charged dropwise over 15 minutes at 10-15° C. The reaction was warmed to room temperature and stirred for 1 h, where HPLC indicated no starting material remained. The reaction mixture was then concentrated in vacuo to give a crude oil. The oil was taken up in DCM (450 mL) and cooled to 0° C. Pyridine (39.1 mL, 0.483 mol) was then charged dropwise at 0-5° C. over 15 minutes followed by the addition of Ac$_2$O (46.1 mL, 0.488 mol) at 0-5° C. over 15 minutes. The reaction was stirred for 30 minutes at 0-5 QC where HPLC indicated 2.0% intermediate and 93.8% product. The reaction mixture was washed with 1 M HCl (225 mL) and the aqueous back extracted with DCM (225 mL). The organics were combined and washed with water (225 mL×2) and 10% brine (225 mL×2). The organics were separated and dried over magnesium sulfate before being concentrated to give 50.4 g of crude in a purity of 94.31% by HPLC. The crude was then purified on silica (2.25 kg) loaded in 1% MeOH/DCM and eluted using 1-3% MeOH/DCM. The clean fractions by TLC were concentrated in vacuo to provide Intermediate 47 (29.7 g, 88%) in a purity of 98.9% by HPLC and >95% by NMR.

Analytical Data:

$^1$H NMR (400 MHz, Chloroform-d) δ (ppm): 4.67-4.61 (m, 1H), 3.87-3.82 (m, 1H), 3.30 (dq, J=8.0, 12.0 Hz, 2H), 3.05 (td, J=4.0, 12.0 Hz, 1H), 2.53 (td, J=4.0, 12.0 Hz, 1H), 2.10 (s, 3H), 1.97-1.80 (m, 3H), 1.28-1.13 (m, 2H).

Synthetic Scheme 26

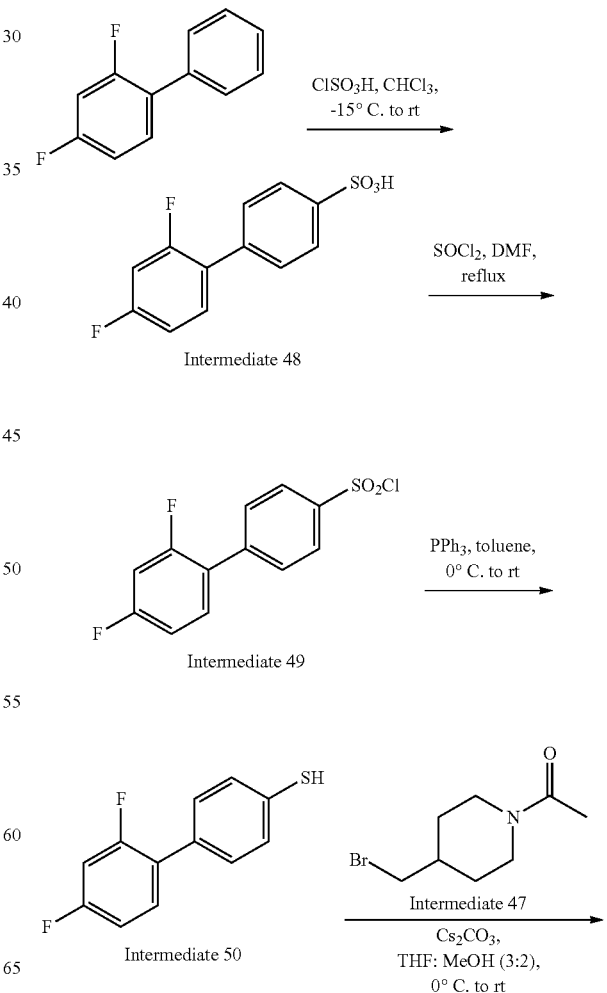

-continued

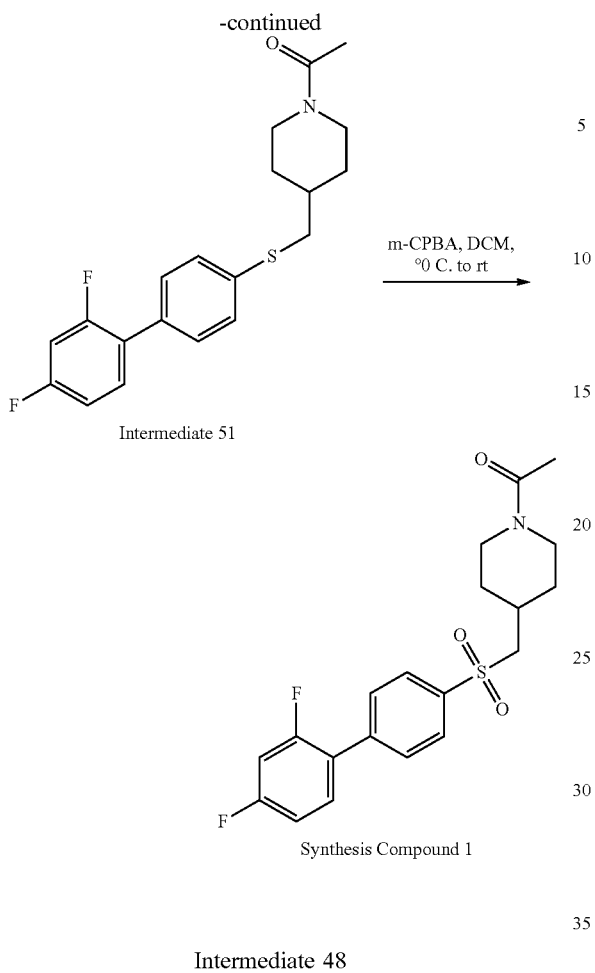

Intermediate 51 m-CPBA, DCM,
°0 C. to rt
→

Synthesis Compound 1

Intermediate 48

2',4'-Difluoro-[1,1'-biphenyl]-4-sulfonic acid

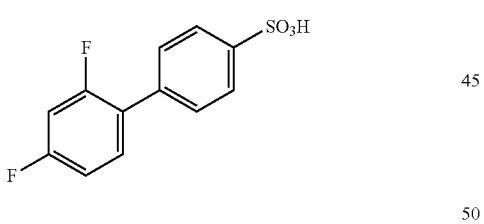

To a 1 L flange flask under $N_2$ was charged 2,4-difluoro-biphenyl (90 g, 0.473 mol) and chloroform (509 mL). Chlorosulfonic acid (53.1 mL, 0.799 mol) was then charged dropwise at −15° C. over 5 minutes. The reaction mixture was then stirred at room temperature for 1 h where HPLC indicated 0.9% starting material and 95.4% product. N2 was then bubbled through the reaction mixture for 15 minutes before concentrated in vacuo to provide a white solid. The solid was then taken up in EtOAc (422 mL) and quenched with water (333 mL). The aqueous was then separated (poor separation) and saturated brine (422 mL) was charged dropwise to the organics over 15 minutes to provide a thick white suspension. The solids were isolated and washed with EtOAc (90 mL×2) before drying overnight at 50° C. This provided Intermediate 48 (98.8 g, crude) in a purity of >95% by NMR.

Analytical Data:
$^1$H NMR (400 MHz, DMSO-$d_6$) δ (ppm): 7.69-7.66 (m, 2H), 7.55 (dt, J=6.7, 8.9 Hz, 1H), 7.47-7.43 (m, 2H), 7.37-7.30 (m, 1H), 7.19-7.14 (m, 1H), 4.05 (br s, 1H).

Intermediate 49

2',4'-Difluoro-[1,1'-biphenyl]-4-sulfonyl chloride

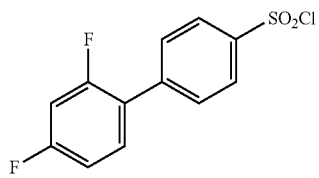 [SMILES: O=S(=O)(Cl)c1ccc(-c2ccc(F)cc2F)cc1]

To a 2 L flange flask under $N_2$ was charged 2',4'-difluoro-[1,1'-biphenyl]-4-sulfonic acid Intermediate 48 (98.8 g, 0.366 mol), thionyl chloride (766 mL, 10.50 mol) and DMF (1 mL, 12.9 mmol). The reaction mixture was then heated to reflux (79° C.) for 8 h where HPLC analysis showed 3.4% starting material remained and 95.0% product. The reaction was cooled to room temperature before being concentrated in vacuo and then azeotroped from toluene (350 mL×2). The residue was then taken up in EtOAc and washed with water (500 mL) then 10% brine (500 mL). The organics were separated and dried over magnesium sulfate before being concentrated in vacuo. This provided Intermediate 49 (95.6 g, crude) in a purity of 93.8% by HPLC and >90% by NMR.

Analytical Data:
$^1$H NMR (400 MHz, Chloroform-d) δ (ppm): 8.11 (d, J=8.0 Hz, 2H), 7.76 (dd, J=4.0, 12.0 Hz, 2H), 7.48 (dt, J=4.0, 8.0 Hz, 1H), 7.08-6.95 (m, 2H).

Intermediate 50

2',4'-Difluoro-[1,1'-biphenyl]-4-thiol

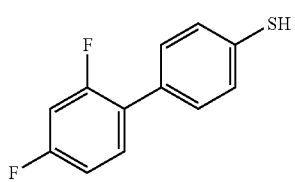 [SMILES: Fc1ccc(-c2ccc(S)cc2)c(F)c1]

To a 2 L flange flask under $N_2$ was charged 2',4'-difluoro-[1,1'-biphenyl]-4-sulfonyl chloride Intermediate 49 (90.0 g, 0.312 mol) and toluene (900 mL). The reaction mixture was then cooled to 0° C. and a solution of triphenylphosphine (245.5 g, 0.936 mol) in toluene (450 mL) was charged dropwise at 0-5° C. over 30 minutes. The reaction mixture was then stirred at room temperature for 1 h where HPLC indicated no starting material remained. The reaction mixture was quenched with 1 M HCl (225 mL) then concentrated in vacuo to remove the toluene. The remaining aqueous layer was then adjusted to pH 10-11 using 2 M potassium hydroxide (450 mL) to provide a suspension. The solids were removed by filtration and washed with water (900 mL×2). The filtrate was then washed with ether (900 mL×4). The aqueous was then pH adjusted to pH 3-4 using 1 M HCl (1 L) before being extracted with ethyl acetate (900

143 mL+450 mL). The organics were then separated and dried over magnesium sulfate and concentrated in vacuo. This provided Intermediate 50 (82.0 g, crude) in a purity of 93.8% by HPLC and 75% by NMR.

Analytical Data:

$^1$H NMR (400 MHz, Chloroform-d) δ (ppm): 7.73-7.66 (m, 2H), 7.58-7.52 (m, 1H), 7.50-7.43 (m, 2H), 6.97-6.87 (m, 2H), 3.53 (s, 1H).

Intermediate 51

1-[4-({2',4'-Difluoro-[1,1'-biphenyl]-4-yl}sulfanyl) piperidin-1-yl]ethanone

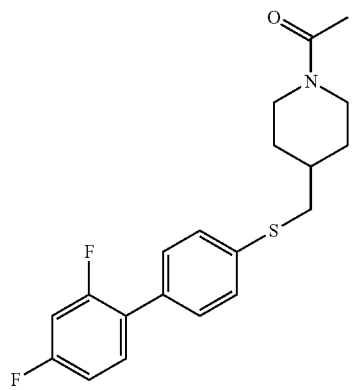 [SMILES: CC(=O)N1CCC(CSc2ccc(-c3ccc(F)cc3F)cc2)CC1]

To a 500 mL 3-neck flask under N$_2$ was charged 2',4'-difluoro-[1,1'-biphenyl]-4-thiol Intermediate 50 (47.7 g, 0.215 mol), THF (180 mL) and MeOH (120 mL). The reaction mixture was then cooled to 0° C. and caesium carbonate (87.7 g, 0.269 mol) was then charged in portions at 0-5° C. over 15 minutes. 1-[4-(Bromomethyl)piperidin-1-yl]ethanone Intermediate 47 (29.5 g, 0.134 mol) in THF (60 mL) was then charged dropwise at 5-10° C. over 10 minutes. The reaction mixture was heated to 60° C. for 45 minutes where HPLC indicated no 1-[4-(Bromomethyl) piperidin-1-yl]ethanone Intermediate 47 remained. The reaction mixture was cooled to room temperature and filtered; the solids were washed with THF (150 mL). The filtrate was concentrated in vacuo and the residue partitioned between EtOAc (600 mL) and water (450 mL). The layers were separated and the aqueous back extracted with EtOAc (300 mL). The organics were combined and dried over magnesium sulfate before being concentrated in vacuo. This provided 63.6 g of crude. The crude was purified on silica (3 kg) eluting with 1% MeOH/DCM. The clean fractions were concentrated in vacuo to provide Intermediate 51 (33.9 g, 70%) in a purity of 97.9% by HPLC and >95% by NMR.

Analytical Data:

$^1$H NMR (400 MHz, Chloroform-d) δ (ppm): 7.44-7.33 (m, 5H), 6.97-6.86 (m, 2H), 4.66-4.59 (m, 1H), 3.85-3.78 (m, 1H), 3.05-2.96 (m, 1H), 2.95-2.81 (m, 2H), 2.57-2.47 (m, 1H), 2.08 (s, 3H), 2.01-1.86 (m, 2H), 1.85-1.74 (m, 1H), 1.27-1.13 (m, 2H).

Synthesis Compound 1

1-(4-(((2',4'-Difluoro-[1,1'-biphenyl]-4-yl)sulfonyl) methyl)piperidin-1-yl)ethan-1-one To a 1 L flange flask under N$_2$ was charged 1-[4-({2',4'-difluoro-[1,1'-biphenyl]-4-yl}sulfanyl)piperidin-1-yl]ethanone Intermediate 51 (33.5 g, 0.093 mol) and DCM (400 mL). The reaction mixture was cooled to 0° C. and m-CPBA (77%) (45.7 g, 0.278 mol) was charged in portions at 0-5° C. over 45 minutes. The reaction mixture was then warmed to room temperature and stirred for 1 h. HPLC indicated no starting material remained. The reaction mixture was filtered, and the liquors were charged back to the flask. The liquors were then cooled to 0° C. and quenched with saturated sodium bicarbonate (340 mL). The layers were separated, and the organics washed with saturated sodium thiosulfate (340 mL). The organics were then separated and washed with sodium bicarbonate (340 mL×2+170 mL) and sodium thiosulfate (340 mL×2+170 mL). HPLC showed no m-CPBA/chlorobenzoic acid remained. The organics were then separated, dried over magnesium sulfate and concentrated in vacuo. This provided (Synthesis Compound 1) (31.0 g, 84%) in a purity of 95.8% by HPLC and >95% by NMR.

Analytical Data:

$^1$H NMR (400 MHz, DMSO-d$_6$) δ (ppm): 8.02 (d, J=8.0 Hz, 2H), 7.82 (d, J=8.0 Hz, 2H), 7.69 (td, J=8.0, 12.0 Hz, 1H), 7.48-7.40 (m, 1H), 7.29-7.21 (m, 1H), 4.28-4.20 (m, 1H), 3.78-3.70 (m, 1H), 3.40-3.35 (m, 2H), 3.06-2.96 (m, 1H), 2.57 (td, J=4.0, 12.0 Hz, 1H), 2.15-2.03 (m, 1H), 1.95 (s, 3H), 1.88-1.74 (m, 2H), 1.26 (ddd, J=4.0, 12.0 Hz, 1H), 1.13 (ddd, J=4.0, 12.0 Hz, 1H).

Biological Studies

Biological Study 1

Monocyte ATP Production Assay

In vitro potency of test compounds was determined by incubation with Thp1 human monocytic cells and subsequent determination of Adenosine TriPhosphate (ATP) levels using firefly luciferase.

ATP is present in all metabolically active cells. When cells lose integrity, their ability to synthesise ATP is rapidly lost. ATP concentration is hence reduced when cells undergo necrosis or apoptosis and its concentrations are commonly used as a marker of cell viability or of cellular proliferation.

See, e.g., Kang et al., 2015; Jiang et al., 2013. Levels of ATP can be monitored using a system based on firefly (Photinus pyralis) luciferase (see, e.g., Auld et al., 2009) using commercially available kits. A system known as ATPlite™ was using to measure effects of the test compounds on cellular viability in vitro. This one-step assay system is an adenosine triphosphate (ATP) monitoring system based on the production of light caused by the reaction of ATP from the cells with added luciferase and D-luciferin, as illustrated in the reaction scheme below:

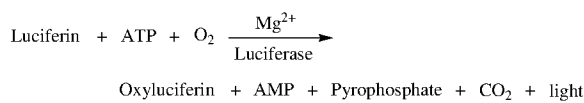

The emitted light is proportional to the ATP concentration.

Thp1 cells were plated at 112500 cells per well in 125 µL RPMI-1640 (no glucose) with 1% FBS in 96-well plates. Test compounds were prepared as 100 mM solutions in DMSO. These stock solutions were diluted in DMSO and then diluted 1000× in culture medium (RPMI) before being added directly to the wells so as to give the desired final compound concentration. After a 24 hour incubation at 37° C./5% $CO_2$, ATPLite™ (Perkin Elmer) was added to each well (1:10 v/v, 10 µL). The plate was then incubated at room temperature for 5 minutes and the emitted light was quantified on Viewlux with a measurement time of 0.3 seconds and binning 4×4.

The average results for each test compound were expressed as a percent (%) of the average control value reflecting cell viability. The average values across the concentrations tested were then plotted and the $IC_{50}$ for was calculated by fitting the data to a 4-parameter $IC_{50}$ equation using software from Graf it (Erithacus Software). Each experiment was repeated twice and the data are presented as the mean $IC_{50}$ from both experiments.

The results are summarised in the following table.

TABLE 1

Thp1 Monocyte ATP Assay

| Compound | $IC_{50}$ (µM) [1] |
|---|---|
| HMC-C-01-A | 0.63 |
| ABD899 | 0.2 |
| ABD900 | 1.1 |
| NASMP-01 | 1.0 |
| NASMP-02 | 7.9 |
| NASMP-03 | 3.0 |
| NASMP-04 | 1.7 |
| NASMP-05 | 1.1 |
| NASMP-06 | 0.9 |
| NASMP-07 | 0.8 |
| NASMP-08 | 3.8 |
| NASMP-09 | 1.4 |
| NASMP-10 | 3.5 |
| NASMP-11 | 1.6 |
| NASMP-12 | 0.1 |
| NASMP-13 | 1.7 |
| NASMP-14 | 1.4 |
| NASMP-15 | 0.6 |
| NASMP-16 | 1.5 |
| NASMP-17 | 4.6 |
| NASMP-18 | 28.5 [2] |
| NASMP-19 | 2.8 |

TABLE 1-continued

Thp1 Monocyte ATP Assay

| Compound | $IC_{50}$ (µM) [1] |
|---|---|
| NASMP-20 | 18.1 [2] |
| NASMP-21 | 6.1 |

[1] Obtained using a 9-point concentration range from 10 µM to 10 nM with n =2 replicates per concentration. Data are the mean from 2 independent experiments.
[2] Obtained using an 8-point concentration range from 100 µM to 100 nM with n = 2 replicates per concentration. Data are the mean from 2 independent experiments.

The data demonstrate that many of the NASMP compounds described herein, and particularly compounds NASMP-Cl, NASMP-07, NASMP-12, and NASMP-15 show excellent potency in the Thp1 monocytic ATP assay, as well as no loss of potency, as compared to the reference compounds.

Biological Study 2

Human Hepatocyte Study

Metabolic stability of test compounds was measured by determination of the rate of disappearance of the compound when incubated in the presence of human hepatocytes, a primary source of the most important enzymes (cytochrome P450s) involved in drug metabolism. Study of drug stability in the presence of primary hepatocytes is accepted as a valuable model permitting rapid prediction of in vivo drug stability.

Human hepatocytes were obtained from a commercial source and viability was assessed using a trypan blue solution prior to use. Test compounds (final concentration 1 µM, 0.1 DMSO, 0.9% acetonitrile) or a marker (diclofenac or diltiazem, final assay concentration 1 µM, 0.1% DMSO, 0.9% acetonitrile) were incubated with pooled hepatocytes for a 60 minute period and samples removed at up to 6 time points and analysed by LC-MS/MS for the presence/amount of test compounds.

Each compound was incubated for 0, 5, 15, 30, 45, or 60 minutes. The reactions were stopped by the addition of methanol containing an internal standard (1 µM Tolbutamide) at the appropriate time points, mixed and placed at −20° C. for 1 hour to quench and allow protein to precipitate. All samples were centrifuged (2500× g, 20 minutes, 4° C.). The aliquots were analysed using LC-MS/MS. Reactions were performed in duplicate at 37° C.

Data were processed, and the results plotted as In(concentration) vs. time. The elimination rate constant (slope of the regression line, k) was calculated using the following formula, where C(t) is the concentration at time t and C(0) is the starting concentration:

$$k = \frac{\ln C(0) - \ln C(t)}{t}$$

The half-life ($t_{1/2}$) was calculated using the following formula:

$$t_{1/2} = \frac{\ln 2}{k}$$

The intrinsic clearance ($Cl_{int}$) was calculated using the following formula, where [cell] is the hepatocyte concentration in the assay:

$$Cl_{int} = \frac{k}{[\text{cell}]}$$

The data are summarised in the following table.

TABLE 2

| Human Hepatocyte Stability | | |
|---|---|---|
| Compound | Human $t_{1/2}$ (min) | Human $Cl_{int}$ (uL/min/million cells) |
| HMC-C-01-A | 154 | 7.6 |
| ABD899 | 149 | 9 |
| ABD900 | 220 | 6.3 |
| NASMP-01 | >460.0 | <3.0 |
| NASMP-02 | >460.0 | <3.0 |
| NASMP-03 | >460.0 | <3.0 |
| NASMP-05 | NC | NC |
| NASMP-06 | >60.0 | NC |
| NASMP-07 | >60.0 | 1.1 |
| NASMP-09 | >412.5 | <3.4 |
| NASMP-11 | >60.0 | 3.3 |
| NASMP-12 | NC | NC |
| NASMP-14 | 58.2 | 28.2 |
| NASMP-15 | >60.0 | NC |
| NASMP-16 | >60.0 | NC |
| NASMP-18 | 352.2 | 3.8 |
| NASMP-19 | 114.9 | 11.7 |
| NASMP-20 | >460.0 | <3.0 |
| NASMP-21 | 104.2 | 13.4 |

(NC = Not calculated due to high stability)

The data demonstrate that many of the NASMP compounds described herein show metabolic stability greater than that of the reference compounds, with NASMP-Cl, NASMP-02, NASMP-03, NASMP-05, NASMP-06, NASMP-09, NASMP-12, NASMP-15, NASMP-16, NASMP-18 and NASMP-20 showing exceptionally good stability.

Biological Study 3

Aqueous Solubility

Aqueous solubility was measured by equilibration of compounds with fasted state simulated intestinal fluid (FaSSIF) and quantified spectrophotometrically.

FaSSIF was prepared as described below:

Preparation of blank FaSSIF: 0.21 g of sodium hydroxide (NaOH) pellets, 1.97 g of dihydrogen sodium phosphate ($NaH_2PO_4 \cdot 2H_2O$) and 3.09 g of sodium chloride (NaCl) were dissolved in 400 mL of deionised water. The pH was adjusted to 6.5 using 1 M hydrochloric acid and further deionised water added to a final volume of 500 mL.

Preparation of FaSSIF: 0.056 g of SIF Powder (containing sodium taurocholate and lecithin) (Pharses A G) was dissolved in 25 mL of blank FaSSIF and stirred until the powder was completely dissolved. The solution was allowed to stand for 2 hours during which it became opalescent; it was used within 24 hours. The final solution composition was characterised as follows:

Sodium taurocholate: 3 mM
Lecithin: 0.75 mM
Osmolarity: 270±10 mOsmol
pH: 6.5

Aqueous solubility was determined by spiking a known concentration of test compound (dissolved in DMSO) into FaSSIF followed by incubation for 16 hours. The optical density was measured at the end of the incubation period for test compounds and a reference used to determine solubility. In brief, two samples were prepared for each determination: a reference sample consisting of a stock solution of test compound in DMSO diluted in system solution (a phosphate free, low absorption buffer) and propanol; and a test sample (prepared in triplicate) consisting of 0.5 mL FaSSIF spiked with test compound at 0.2 mM. Each sample was incubated at room temperature for 16 hours with constant shaking at 250 rpm. At the end of the incubation period, 0.3 mL of each sample was filtered through a pION filter plate (PION, Woburn MA), diluted 1:1 with propanol and scanned using UV spectrophotometry at λmax (190-400 nM) using a Spectra Max Plus—Version 2.1000 (Molecular Devices, Sunnyvale, CA), with pSOL Explorer solubility determination software (pION, Woburn, MA).

FaSSIF solubility was calculated using the following formula:

$$\text{FaSSIF Solubility} \frac{\text{mg}}{\text{mL}} = \frac{\left[\frac{150}{75}\right] * \left[\frac{OD \text{ of sample}}{OD \text{ of reference}}\right] * Cr * \text{molecular weight}}{10^6}$$

wherein:
"OD" is the optical density;
"Cr" is the concentration of the reference (33.4 μM); and
"molecular weight" is for the test compound (e.g., 381.44 for ABD735).

The data are summarised in the following table.

TABLE 3

| FaSSIF Solubility | | |
|---|---|---|
| Compound | Solubility (mg/mL) [1] | Solubility (mg/mL) [2] |
| HMC-C-01-A | 0.06 [3] | |
| ABD899 | 0.06 [3] | 0.13 |
| ABD900 | | 0.12 |
| NASMP-01 | 0.075 | |
| NASMP-02 | 0.032 | |
| NASMP-03 | 0.042 | |
| NASMP-05 | 0.062 | |
| NASMP-06 | 0.083 | |
| NASMP-07 | 0.089 | |
| NASMP-09 | 0.028 | |
| NASMP-12 | 0.068 | |
| NASMP-15 | 0.073 | |
| NASMP-17 | 0.077 | |
| NASMP-18 | 0.039 | |
| NASMP-19 | 0.027 | |
| NASMP-20 | 0.037 | |
| NASMP-21 | 0.071 | |

[1] Two replicates were run per study at pH 6.5.
[2] Two replicates were run per study at pH 6.8.
[3] Three replicates were run for compounds HMC-C-01-A and ABD899.

The data demonstrate that the NASMP compounds described herein show solubility equivalent to that of the reference compounds with compounds NASMP-05, NASMP-06, NASMP-07, NASMP-12, NASMP-15, NASMP-17, and NASMP-21 showing particularly good solubility.

Biological Study 4

Metabolite Identification

The formation of metabolites in humans, rats and dogs was assessed to determine the propensity of the compounds to form a biaryl metabolite.

The related sulfonamide compounds (for example, reference compound HMC-C-01-A) give rise to a biaryl sulphonamide metabolite (MET-001) which is persistent and has a long half-life. In addition, the metabolite acts as an inducer of metabolism in rats, which may complicate the assessment of toxicity in rodents. Therefore, the lower the propensity to form a biaryl metabolite, the greater the suitability of the compound for development for human use.

TABLE 4

Reference Compound HMC-C-01-A and Biaryl Sulfonamide Metabolite (MET-001)

HMC-C-01-A

MET-001

TABLE 5

Compound NASMP-01, Postulated Biaryl Metabolite (MET-002), and Biaryl Sulphonamide version of MET-002 (CMPD-003)
(MET-002 and CMPD-003 are not predicted, and were not detected)

NASMP-01

MET-002

CMPD-003

In vitro studies on the metabolism of drugs are usually performed using liver preparations such as isolated perfused livers, liver slices, liver homogenates, isolated cryopreserved hepatocytes, subcellular liver fractions (S9, cytosol, and microsomes), or recombinant metabolizing enzymes overexpressed on non-expressing cell systems, particularly CYP enzymes. Cryopreserved hepatocytes contain all the enzymes and co-factors needed for phase I and phase II drug metabolism, making them an excellent in vitro model for assessment of drug metabolic stability and metabolite profiling.

Cryopreserved human, rat (Sprague Dawley) and dog (Beagle) hepatocytes were revived from liquid nitrogen and plated at a seeding density of $2 \times 10^6$ cells/mL (>95% viability). Following a 15 minute incubation at 37° C. a sample was removed for a zero (0) minute time point assessment. Test compound was then added at a final concentration of 10 µM and the reaction initiated by the addition of 250 µL Krebs Henseleit Buffer (KHB, pH 7.4). Samples were incubated for 5, 15, 30 and 60 minutes at 37° C./5% $CO_2$.

All samples were processed for analysis by protein precipitation using 500 µL ice-cold acetonitrile and analysed with a fit-for-purpose LC-MS/MS method.

At the completion of the study, the results were expressed as detection of the biaryl metabolite at the final time point.

The following table shows the presence or absence of the biaryl metabolite in primary hepatocyte incubations for the reference compound HMC-C-01-A and NASMP-01.

TABLE 6

| Biaryl Metabolite Detection | |
|---|---|
| Compound | Biaryl metabolite detected? |
| HMC-C-01-A | Yes (MET-001) |
| NASMP-01 | No |

The data demonstrate that the NASMP compounds described herein show greatly increased suitability for development for human use, as compared to the reference compound (HMC-C-01-A).

Whereas the reference compound HMC-C-01-A gave rise to the biaryl sulphonamide metabolite (MET-001) in large quantities, compound NASMP-01 did not produce either biaryl sulphonamide metabolite, CMPD-03, or biaryl sulphonic acid metabolite, MET-002.

Biological Study 5 hERG Ion Channel Assay

Inhibition of the human Ether-á-go-go-Related Gene (hERG) ion channel mediates the repolarizing IKr current in the cardiac action potential, thereby indicating that it contributes to the electrical activity that coordinates the beating of the heart. When the ability of hERG to conduct electrical current across the cell membrane is inhibited or compromised it can result in a potentially fatal disorder called long QT syndrome. This association between hERG and long QT syndrome has made hERG inhibition an important anti-target that must be avoided during drug development.

The activity of the compounds against the hERG ion channel was tested using a binding assay in stably transfected Human Embryonic Kidney cells (hERG-HEK293). hERG-HEK293 cells were cultured in MEM medium (Invitrogen)+10% FBS, glutamine and non-essential amino acids at 37° C. To prepare membranes, cells were homogenised on ice, centrifuged at 650×g for 10 minutes at +4° C., and the resulting supernatant centrifuged at 48000×g for 10 minutes at +4° C. The pellet was resuspended in ice-cold 50 mM Tris-HCl buffer, 5 mM KCl (pH 8.5) and stored frozen in aliquots until use.

For binding assays, membranes were thawed, re-suspended in assay buffer (10 mM HEPES pH 7.4, 0.1% BSA, 5 mM potassium chloride, 0.8 mM magnesium chloride, 130 mM sodium chloride, 1 mM sodium-EGTA, 10 mM glucose) and incubated with $^3H$ astemizole (1.5 nM), and with or without test compound at 25° C. for 60 minutes. Binding was determined following filtration of the membranes and washing in Tris-HCl buffer by scintillation counting of $^3H$ astemizole.

The degree of binding of compounds to the hERG ion channel (%) was obtained by measuring the binding of $^3H$ astemizole and its displacement by test compound. A value of 0% indicates no binding and a value of 100% indicates complete displacement of the radiolabelled ligand.

The results are summarised in the following table.

TABLE 7 hERG Ion Channel Assay Data

| Compound | % inhibition at 30 μM |
|---|---|
| HMC-C-01-A | 18 [1] |
| NASMP-01 | 14 |
| NASMP-02 | 30 |
| NASMP-03 | 20 |
| NASMP-05 | 23 |
| NASMP-06 | 35 |
| NASMP-07 | 79 |
| NASMP-09 | 7 |
| NASMP-12 | 35 |
| NASMP-15 | 45 |
| NASMP-17 | 14 |
| NASMP-18 | 14 |
| NASMP-19 | 21 |
| NASMP-20 | 39 |
| NASMP-21 | 1 |

[1] Tested at 25 μM.

The data demonstrate that the NASMP compounds described herein have cardiac safety properties required for an orally active drug, and have safety advantages as compared to the reference compounds, such as HMC-C-01-A, with NASMP-Cl, NASMP-09, NASMP-17, NASMP-18 and NASMP-21 showing a particularly positive profile.

Biological Study 6

Human Cytochrome P450 Inhibition Assay

Inhibition of cytochrome P450 (CYP450) enzymes is one of the major reasons for drug-drug interactions in clinical use, and can complicate, or stop the development of a new drug.

The ability of test compounds to inhibit five of the most relevant cytochrome P450 enzymes was measured by determination of the activity of cytochrome P450 enzymes in recombinant cytochrome preparations, called Bactosomes (Cypex Ltd, Dundee, Scotland UK DD2 1 NH), in the presence of a specific probe substrate. Bactosomes are a highly efficient and cost-effective source of recombinant CYP450s which have a higher specific activity of enzyme compared to other sources, such as liver microsomes. If a compound inhibits enzyme activity, the rate of disappearance of the probe substrate is reduced. The following CYP450 isoforms were assayed: CYP1A2, CYP2C9, CYP2C19, CYP2D6 and CYP3A4. The study of CYP450 inhibition potential in Bactosomes is accepted as a valuable model permitting rapid prediction of potential drug-drug interactions in vivo (see, e.g., Weaver et al., 2003).

Bactosomes were obtained from a commercial source (Cypex, Scotland, UK). Test compounds were incubated with Bactosomes at 6 concentrations. Samples were incubated for 10 minutes, after which the reaction was stopped and the samples analysed by LC-MS/MS Multiple Reaction Monitoring (MRM) for the presence/amount of substrate probe.

CYP450 enzymes (final protein 75 pmol/mL for CYP1A2; 12.5 pmol/mL for CYP2C19; and 25 pmol/mL for CYP2C9, 2D6 and 3A4), 0.1 M phosphate buffer pH 7.4, probe and test compound (final concentration 50, 15.8, 5, 1.58, 0.5 and 0.158 μM; diluted from 10 mM stock solution to give a final DMSO concentration of 1%) were preincubated at 37° C. for 5 minutes. The reaction was initiated by the addition of 20 μL of 10 mM NADPH in phosphate buffer. The final incubation volume was 200 μL. The following control inhibitors were used for each CYP450 inhibition assay: CYP1A2: α-naphthoflavone; CYP2C9: sulfaphenazole; CYP2C19: tranylcypromine; CYP2D6: quinidine; CYP3A4: ketoconazole.

Each compound was incubated for 10 minutes at 37° C. The reactions were stopped by the addition of methanol (final composition 1:1, aqueous: methanol). The incubation plates were shaken, chilled at 20° C. for 2 hours, and centrifuged at 3500 rpm for 15 minutes at 4° C. to precipitate the protein. The supernatant was then transferred to vials for analysis using MS/MRM, with the conditions shown in the following table.

TABLE 8

| MS Conditions | |
|---|---|
| HPLC: | Waters Alliance 2790 |
| MS/MS: | Triple Quadrupole Quattro Ultima (Micromass, Manchester) |
| Software: | Analyst 1.5 |
| Ionisation mode: | ESI+ |
| Scan mode: | Multiple reaction monitoring (MRM) |
| Column: | Devosil C30 |
| Column Temperature (° C.): | 40 |
| Phase A: | 0.1% formic acid in water |
| Phase B: | 0.1% formic acid in methanol |
| Gradient | 97% A (0-0.3 min), 5% A (0.55-1.55 min), 97% A (1.6 min) |
| Stop time | 2.5 min |
| Injection volume (μL): | 30 |
| Flow Rate (mL/min): | 1.2 |

$IC_{50}$ values were determined by linear transformation within Microsoft Excel.

The data are summarised in the following table.

TABLE 9

Human CYP450 inhibition

| | $IC_{50}$ (μM) | | | | |
|---|---|---|---|---|---|
| Compound | CYP1A2 | CYP2C9 | CYP2C19 | CYP2D6 | CYP3A4 |
| ABD899 | >25 | 3.9 | 7.3 | 45.3 | 21.6 |
| HMC-C-01-A | 25 | 21 | >25 | 16.6 | >25 |
| HMC-C-08-A | 27 | 6.7 | 30 | 19 | 29 |
| HMC-C-09-A | 23 | 34 | >50 | >50 | 33 |
| HMC-C-10-B | >16 | 2.4 | 8.5 | >16 | 9.2 |
| HMC-C-11-A | 11 | 2.7 | 5.1 | 9.3 | 12 |
| HMC-N-05-A | 36 | 27 | >50 | >50 | >50 |
| NASMP-01 | >50 | >50 | >50 | >50 | >50 |
| NASMP-05 | >50 | >50 | >50 | >50 | >50 |
| NASMP-06 | >50 | 42.7 | >50 | >50 | >50 |
| NASMP-07 | >50 | 19.6 | 36.4 | >50 | >50 |
| NASMP-09 | >50 | >50 | 17.8 | >50 | 44.5 |
| NASMP-12 | >50 | 15.4 | >50 | 45.4 | >50 |
| NASMP-15 | >50 | 21.5 | >50 | >50 | >50 |

The data demonstrate that the NASMP compounds described herein show reduced drug-drug interaction liability as compared with the reference compounds, with compounds NASMP-01 and NASMP-05 showing a particularly good profile.

Biological Study 7

Rodent Pharmacokinetics Studies

Absorption and metabolic stability were studied using an in vivo pharmacokinetics assay.

Male Han Wistar rats, 196-329 g, were dosed with test compounds administered either orally or intravenously (dose level of 0.25 mg/kg body weight intravenous or 1.25 mg/kg body weight orally). Test compounds were formulated in 0.5% carboxymethylcellulose (CMC)/0.1% Tween-80 for administration via the oral route, or in 5% DMSO/10% solutol in saline for administration via the intravenous route. For compound HMC-C-01-A the oral administration was formulated in 2% dimethylacetamide/20% hydroxypropyl-β-cyclodextrin in water. Animals were given free access to food throughout the study except for fasting overnight and until 2 hours post dose on the day of dosing.

Blood samples were taken from the retro-orbital plexus at the following time points and placed in microtubes containing 20% $K_2EDTA$ solution:

Oral Dosing: predose; 0.25, 0.5, 1, 2, 4, 6, 8, 12 and 24 hours post dose.

Intravenous Dosing: predose; 0.033, 0.1, 0.167, 0.25, 0.5, 1, 2, 4, 6, 8, 12 and 24 hours post dose.

Blood samples were centrifuged to obtain plasma, which was transferred to a separate container and frozen at −20° C.

For analysis, samples were thawed at room temperature and prepared by protein precipitation with acetonitrile spiked with internal standard (500 ng/mL glipizide) in the ratio 1:4 with plasma. The concentration of test compound in rat plasma samples was determined using LC-MS/MS, with the conditions shown in the following table.

The pharmacokinetic parameters for the test compounds were calculated by Phoenix WinNonlin version 8.0 (Certara, CA) using standard non-compartmental methods. Peak plasma concentrations ($C_{max}$) and time of the peak plasma concentration ($T_{max}$) were the observed values. The area under the plasma concentration-time curve (AUC) was determined by use of the linear trapezoidal rule up to the last measurable concentration ($AUC_{last}$) and thereafter by extrapolation of the terminal elimination phase to infinity ($AUC_{inf}$). The elimination phase half-life ($t_{1/2}$) was calculated as $0.693/k_{el}$. The tentative oral bioavailability (F) was calculated by dividing the AUC (0-24 hours) after oral administration by the adjusted AUC (0-8 hours) after intravenous administration (i.e., F=AUC(p.o.)×Dose (i.v.)/AUC (i.v.)×Dose (p.o.)) and reported as a percentage (%).

The pharmacokinetic data are summarised in the following table.

TABLE 11

Pharmacokinetic data

| Compound | Bioavail, F (%) | i.v. AUC (ng/mL/min) | p.o. AUC (ng/mL/min) | $T_{1/2}$ (h) |
| --- | --- | --- | --- | --- |
| ABD899 | 50 | 2133 | 10740 [4] | 10.8 |
| REF001 | 50 | 963 | 4766 [4] | 7.2 |
| HMC-C-07-B [1] [2] | 100 | 24072 | 146299 [5] | 9.7 |
| HMC-C-07-B [3] | 86 | 11627 | 39463 | 9.0 |
| HMC-N-05-A [1] | 88 | 891 | 3937 | 0.8 |
| NASMP-01-A | 56 | 816 | 2299 | 6.6 |
| NASMP-06-A | 24 | 349 | 3030 | 3.3 |
| NASMP-12-A | >69 | 581 | 3160 | 5.1 |
| NASMP-15-A | >62 | 282 | 1750 | 4.9 |

[1] Compound was dosed in 5% DMSO/10% solutol in saline for administration via both the oral and intravenous routes.
[2] Samples were collected at: pre-dose, 0.08, 0.25, 0.5, 1, 2, 4, 8, 23, and 24 hours post intravenous dosing, and at pre-dose, 0.25, 0.5, 1, 2, 4, 6, 8, 23, and 24 hours post oral dosing.
[3] Samples were collected at: pre-dose, 0.03, 0.1, 0.167, 0.25, 0.5, 1, 2, 4, 6, 8, and 24 hours post intravenous dosing.
[4] Dosed at 5 mg/kg orally.
[5] Dosed at 10 mg/kg orally.

TABLE 10

LC-MS/MS Conditions

| Compound | References | NASMP-01 | NASMP-06, -12, -15 |
| --- | --- | --- | --- |
| HPLC/UHPLC: | Schimadzu Agilent | Vanquish Flex | Vanquish |
| MS/MS: | API 4000 | Q-Exactive | TSQ Quantiva |
| Ionisation mode: | Turbo spray, negative mode | Positive | Positive |
| Scan mode: | Multiple reaction monitoring (MRM) | | |
| Column | Waters, Xterra, MS-C18 (2) 5 μm 50 × 3.0 mm; Discovery Grace Smart RP183p, 150 x 2.1, 3 μM; Waters Symmetry Shelf C18 75 × 4.6, 3.5 μM; Agilent Zorbax XDB, 150 × 4.6, 5 μM | Luna Omega Polar C18, 50 × 2.1 mm, 1.6 μm. | Phenomenex Luna Omega 1.6 μm, C18 100Å, 50 × 2.1 mm |
| Column Temperature (° C.): | 40 | 65 | 65 |
| Phase A: | Acetonitrile + 0.1% formic acid | MilliQ water + 0.1% formic acid | MilliQ water + 0.1% formic acid |
| Phase B: | 0.1% formic acid | Methanol + 0.1% formic acid | Methanol + 0.1% formic acid |
| Flow Rate (mL/min): | 0.8-1.2 | 0.8 | 0.8 |

These data demonstrate that the NASMP compounds described herein have excellent oral pharmacokinetic properties comparable to those of the reference compounds. This indicates that these compounds are likely to be suitable for use as oral drugs.

Biological Study 8

Mouse Collagen-Induced Arthritis

Seven- to eight-week-old male DBA/1j mice were used for all procedures. Animals were housed in groups of 10, and were maintained at 21° C.±2° C. on a 12-hour light/dark cycle with food and water ad libitum. Complete Freund's adjuvant (CFA) was prepared by emulsifying bovine type II collagen at 4 mg/mL with a 4 mg/mL suspension of *Mycobacterium tuberculosis* $H_{37}Ra$ in Incomplete Freund's Adjuvant (IFA) (0.85 mL paraffin oil and 0.15 mL mannide monooleate) in a 1:1 (v/v) ratio. All mice were immunised subcutaneously with 200 μg of bovine type II collagen in CFA. 21 days later, all mice were immunised subcutaneously with 100 μg of bovine type II collagen in IFA. The mice started to develop signs and symptoms of arthritis following the 'booster' immunisation.

For macroscopic assessment of arthritis, the following signs were monitored in each paw of each mouse three times per week and summed to generate the Arthritic Index (AI) (the maximum AI for one animal is 16):

0=no visible effects of arthritis.
1=oedema and/or erythema of 1 digit.
2=oedema and/or erythema of 2 digits.
3=oedema and/or erythema of more than 2 digits.
4=severe arthritis of entire paw and digits.

Animals were sorted into treatment groups with a mean arthritic index of 2.5 and then dosed once daily for 14 days with compound: by oral gavage for test compounds, or by subcutaneous injection at a dose of 10 mg/kg for the positive control, etanercept. After completion of the experiment, the mice were sacrificed.

The data were analysed by generating an average of the arthritic index across each treatment group. The mean arthritic index was then compared to the arthritic index of control (untreated) animals using the following formula to generate a percentage inhibition of disease.

$$\% \text{ inhibition of disease} = 100 - \left[\frac{\text{average arthritic index:treated animals}}{\text{average arthritic index:untreated animals}}\right] * 100$$

The data are summarised in the following table.

TABLE 12

Inhibition of Arthritis

| Compound | Dose (mg/kg/day) | % inhibition of disease |
| --- | --- | --- |
| ABD899 | 10 | 77 |
| HMC-C-01-A | 10 | 40 |
| HMC-N-01-A | 10 | 45 |
| HMC-C-01-B | 10 | 26 |
| HMC-N-01-B | 10→1 (*) | 38 |
| CHMSA-01-A | 10 | 63 |
| CHMSA-03-A | 10 | 62 |
| NASMP-01-A | 10 | 64 |

These data indicate that the NASMP compounds described herein show excellent oral in vivo activity in preventing the progression of established, severe arthritis.

The foregoing has described the principles, preferred embodiments, and modes of operation of the present invention. However, the invention should not be construed as limited to the particular embodiments discussed. Instead, the above-described embodiments should be regarded as illustrative rather than restrictive. It should be appreciated that variations may be made in those embodiments by workers skilled in the art without departing from the scope of the present invention.

REFERENCES

A number of publications are cited herein in order to more fully describe and disclose the invention and the state of the art to which the invention pertains. Full citations for these publications are provided below.

Each of these publications is incorporated herein by reference in its entirety into the present disclosure, to the same extent as if each individual publication was specifically and individually indicated to be incorporated by reference.

Astry et al., 2011, "A cytokine-centric view of the pathogenesis and treatment of autoimmune arthritis", *J Interferon Cytokine Res.*, Vol. 31, pp. 927-940.

Auld et al., 2009, "A basis for reduced chemical library inhibition of firefly luciferase obtained from directed evolution", J. Med. Chem., Vol. 52, No. 5, pp. 1450-1458.

Baud et al., 2009, "Is NFκB a good target for cancer therapy? Hopes and pitfalls", *Nat. Rev. Drug Disc.*, Vol. 8, pp. 33-40.

Billiau, 2010, "Etanercept improves linear growth and bone mass acquisition in MTX-resistant polyarticular-course juvenile idiopathic arthritis", Rheumatology (Oxford), Vol. 49, pp. 1550-1558.

Bilotta et al., 2014, "Antiviral compounds", international patent application publication number WO 2014/135495 A1, published 12 Sep. 2014.

Bradley et al., 2007, "GPCR Agonists", international patent application publication number WO 2007/003962 A2, published 11 Jan. 2007.

Bridges et al., 2014, "Effects of metformin and other biguanides on oxidative phosphorylation in mitochondria", *Biochem. J.*, Vol. 462, No. 3, pp. 475-487.

Chakravarty et al., 2009, "Substituted aryl sulfone derivatives as calcium channel blockers", international patent application publication number WO 2009/045382 A1, published 9 Apr. 2009.

Chimenti et al., 2015, "The interplay between inflammation and metabolism in rheumatoid arthritis", *Cell Death and Disease*, Vol. 17, No. 6, e1887.

Dallas et al., 2011, "Osteoimmunology at the nexus of arthritis, osteoporosis, cancer, and infection", *J. Clin. Invest.*, Vol. 121, pp. 2534-2542.

Duan et al., 2003, "Barbituric acid derivatives as inhibitors of TNF-alpha converting enzyme (TACE) and/or matrix metalloproteinases", international patent application publication number WO 03/053941 A2, published 3 Jul. 2003.

Ellinghaus et al., 2013, "BAY 87-2243, a highly potent and selective inhibitor of hypoxia-induced gene activation has antitumor activities by inhibition of mitochondrial complex I", *Cancer Med.*, Vol. 2, No. 5, pp. 611-624.

Evans et al., 2005, "Metformin and reduced risk of cancer in diabetic patients", *BMJ*, Vol. 330, pp. 1304-1305.

Fang et al., 2008, "Chemical compounds and uses", international patent application publication number WO 2008/070692 A2, published 12 Jun. 2008.

Fearon et al., 2016 "Hypoxia, mitochondrial dysfunction and synovial invasiveness in rheumatoid arthritis", *Nat. Rev. Rheumatol.*, Vol. 12, pp. 385-397.

Fiorillo et al., 2016, "Repurposing atovaquone: targeting mitochondrial complex III and OXPHOS to eradicate cancer stem cells", Oncotarget, Vol. 7, pp. 34084-34099.

Firestein, 2005 "Immunologic mechanisms in the pathogenesis of rheumatoid arthritis", J. Clin. Rheumatol., Vol. 11. pp. S39-S44.

Ganeshan et al., 2014, "Metabolic Regulation of Immune Responses", Ann. Rev. Immunol., Vol. 32, pp. 609-634.

Garcia-Carbonnel et al., 2016, "Critical Role of Glucose Metabolism in Rheumatoid Arthritis Fibroblast-like Synoviocytes", Arthritis Rheumatol., Vol. 68, No. 7, pp. 1614-1626.

Greig et al., 2010a, "Aryl-phenyl-sulfonamido-cycloalkyl compounds and their use", international patent publication number WO 2010/032009 A1 published 25 Mar. 2010.

Greig et al., 2010b, "Aryl-phenyl-sulfonamido-phenylene compounds and their use", international patent publication number WO 2010/032010 A1 published 25 Mar. 2010.

Hayashi et al., 2007, "MMP-13 selective inhibitor", international patent application publication number WO 2007/102392 A1, published 13 Sep. 2007.

Horiuchi et al., 2009, "Adamantylurea derivative", international patent application publication number WO 2009/020140 A1, published 12 Feb. 2009.

Jiang et al., 2013, "Letm1, the mitochondrial Ca2+/H+ antiporter, is essential for normal glucose metabolism and alters brain function in Wolf-Hirschhorn syndrome", PNAS, E2249-E2254.

Jung et al., 2014, "Cytokine-mediated bone destruction in rheumatoid arthritis", J. Immunol. Res., Vol. 2014, p. 263625.

Kang et al., 2015, "Combinations of kinase inhibitors protecting myoblasts against hypoxia", PLOS, PLoS ONE 10(6): e0126718.

Karsenty et al., 2002, "Reaching a genetic and molecular understanding of skeletal development", Dev. Cell., Vol. 2, pp. 389-406.

Klareskog et al., 2006, "Mechanisms of disease: Genetic susceptibility and environmental triggers in the development of rheumatoid arthritis," Nat. Clin. Pract. Rheumatol., Vol. 2, pp. 425-433.

Kleyer et al., 2014, "Arthritis and bone loss: a hen and egg story", Curr. Opin. Rheumatol., Vol. 26, No. 1, pp. 80-84.

Koppenol et al., 2011, "Otto Warburg's contributions to current concepts of cancer metabolism", Nat. Rev. Cancer, Vol. 11, No. 5, pp. 325-337.

Lack et al., 2011, "Targeting the binding function 3 (BF3) site of the human androgen receptor through virtual screening", Journal of Medicinal Chemistry, Vol. 54, No. 24, pp. 8563-8573.

LeBleu et al., 2014, "PGC-1α mediates mitochondrial biogenesis and oxidative phosphorylation in cancer cells to promote metastasis", Nat. Cell Biol., Vol. 16, pp. 992-1003.

Lee et al., 2003, "Piperidine derivatives for GPR119 agonist", international patent application publication number WO 2013/187646 A1, published 19 Dec. 2013.

Li et al., 2006, "Inhibitors of 11-beta hydroxysteroid dehydrogenase type I", international patent application publication number WO 2006/113261 A2, published 26 Oct. 2006.

Long, 2012, "Osteoimmunology: the expanding role of immunoreceptors in osteoclasts and bone remodeling", Bone Key Rep., Vol. 1, p. 59.

Malemud et al., 2010, "Myeloid-related protein activity in Rheumatoid Arthritis", International Journal of Interferon, Cytokine and Mediator Research, Vol. 2, pp. 97-111.

Mantovani, 2009, "Inflaming metastasis", Nature, Vol. 457, pp. 36-37. McInnes et al., 2011, "The pathogenesis of rheumatoid arthritis", N. Engl. J. Med., Vol. 365, No. 23, 2205-2219.

Moore et al., 2008, "N-Substituted piperidinyl 4-arylsulfonamides as modulators of the secreted frizzled related protein-1", international patent application publication number WO 2008/061016 A1, published 22 May 2008.

Nutsch et al. 2011, "When T cells run out of breath: the HIF-1α story", Cell, Vol. 146, No. 5 pp. 673-674.

Ogata et al., 2012, "Safety and Efficacy of Tocilizumab for the Treatment of Rheumatoid Arthritis", Clin Med Insights Arthritis Musculoskelet Disord., Vol. 5, pp. 27-42.

Oslob et al., 2016, "4-Methylsulfonyl-substituted piperidine urea compounds for the treatment of dilated cardiomyopathy (DCM)", international patent publication number WO 2016/118774 A1 published 28 Jul. 2016.

Patel et al., 2014, "N-(4-hydroxy-4-methyl-cyclohexyl)-4-phenyl-benzenesulfonamide and N-(4-hydroxy-4-methyl-cyclohexyl)-4-(2-pyridyl)benzenesulfonamide compounds and their therapeutic use", international patent publication number WO 2014/207445 A1 published 31 Dec. 2014.

Patel et al., 2016, "N-(4-hydroxy-4-methyl-cyclohexyl)-4-phenyl-benzenesulfonamide and N-(4-hydroxy-4-methyl-cyclohexyl)-4-(2-pyridyl)benzenesulfonamide compounds and their therapeutic use", international patent publication number WO 2016/097001 A1 published 23 Jun. 2016.

Perl, 2017, "Metabolic Control of Immune System Activation in Rheumatic Diseases", Arthritis & Rheumatology, Vol. 69, No. 12, pp. 2259-2270.

Philchenkov et al., 2004, "Caspases and cancer: mechanisms of inactivation and new treatment modalities", Exp. Oncol., Vol 26, pp 82-97.

Pollak, 2014, "Overcoming drug development bottlenecks with repurposing: repurposing biguanides to target energy metabolism for cancer treatment", Nat. Med., Vol. 20, No. 6, pp. 591-593.

Procaccini et al., 2012, "Intracellular metabolic pathways control immune tolerance", Trends Immunol., Vol. 33, No. 1, pp. 1-7.

Riemer et al., 1996, "Benzyl piperidine derivatives as pharmaceutical agents", international patent application publication number WO 96/35666 A1, published 14 Nov. 1996.

Roodman, 2006, "Regulation of osteoclast differentiation", Ann. N. Y. Acad. Sci; Vol. 1068, pp. 100-109.

Scott et al., 2010, "Rheumatoid Arthritis", Lancet, Vol. 376, pp. 1094-1108.

Smolen et al., 2015, "Rheumatoid arthritis therapy reappraisal: strategies, opportunities and challenges", Nat. Rev. Rheumatol., Vol. 11, pp. 276-289.

Spies et al., 2012, "Energy metabolism and rheumatic diseases: from cell to organism", Arthritis Research & Therapy, Vol. 14, p. 216.

Steger et al., 2011, "Denosumab for the treatment of bone metastases in breast cancer: evidence and opinion", Ther. Adv. Med. Oncol., Vol. 3, pp. 233-243.

Straub et al., 2010, "Energy regulation and neuroendocrine-immune control in chronic inflammatory diseases", J. Intern. Med., Vol. 267, No. 6, pp. 543-560.

Sun, 2010, "Mechanical loading, cartilage degradation and arthritis", *Annals of the New York Academy of Sciences*, Vol. 1211, pp. 37-50.

Takayanagi, 2009, "Osteoimmunology and the effects of the immune system on bone", *Nature Reviews Rheumatology*, Vol. 5, pp. 667-676.

Tanaka et al., 2003, "Signal transduction pathways regulating osteoclast differentiation and function", *J. Bone Miner. Metab.*, Vol. 21, pp. 123-133.

Weaver, et al., 2003, "Cytochrome p450 inhibition using recombinant proteins and mass spectrometry/multiple reaction monitoring technology in a cassette incubation", *Drug Metabolism and Disposition*, Vol. 31, No. 7, pp. 955-966.

Weinberg et al., 2010, "Mitochondrial metabolism and ROS generation are essential for Kras-mediated tumorigenicity", *Proc. Natl. Acad. Sci. USA*, Vol. 107, No. 19, pp. 8788-8793.

Weyand et al., 2017a, "Immunometabolism in early and late stages of rheumatoid arthritis", *Nature Reviews Rheumatology*, Vol. 13, pp. 291-301.

Weyand et al., 2017b, "Metabolic Signatures of T-cells and Macrophages in Rheumatoid Arthritis", *Curr. Opin. Immunol.*, Vol. 46, pp. 112-120.

Wheaton et al., 2014, "Metformin inhibits mitochondrial complex I of cancer cells to reduce tumorigenesis", *eLife*, Vol. 3, e02242.

Yang et al., 2013, "Phosphofructokinase deficiency impairs ATP generation, autophagy, and redox balance in rheumatoid arthritis T cells", *J. Exp. Med.*, Vol. 210, pp. 2119-2134.

The invention claimed is:

1. A compound of the following formula:

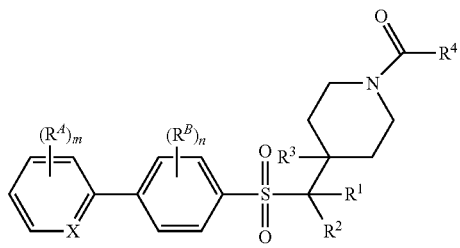

or a pharmaceutically acceptable salt thereof;
wherein:
—X= is independently —CH= or —N=;
"m" is independently 0, 1, 2, or 3;
each —$R^A$ is independently —F, —Cl, —$R^{AC}$, —$R^{AF}$, or —CN;
—$R^{AC}$ is independently saturated linear or branched $C_{1-3}$alkyl;
—$R^{AF}$ is independently saturated linear or branched $C_{1-3}$fluoroalkyl;
"n" is independently 0, 1, or 2;
each —$R^B$ is independently —F, —Cl, —$R^{BC}$, —$R^{BF}$, or —CN;
—$R^{BC}$ is independently saturated linear or branched $C_{1-3}$alkyl;
—$R^{BF}$ is independently saturated linear or branched $C_{1-3}$fluoroalkyl;
—$R^1$ is independently —H or —$R^{1X}$;
—$R^{1X}$ is independently —F, —$R^{1C}$, or —$R^{1F}$;
—$R^{1C}$ is independently saturated linear or branched $C_{1-3}$alkyl;
—$R^{1F}$ is independently saturated linear or branched $C_{1-3}$fluoroalkyl;
—$R^2$ is independently —H or —$R^{2X}$;
—$R^{2X}$ is independently —F, —$R^{2C}$, or —$R^{2F}$;
—$R^{2C}$ is independently saturated linear or branched $C_{1-3}$alkyl;
—$R^{2F}$ is independently saturated linear or branched $C_{1-3}$fluoroalkyl;
or —$R^1$ and —$R^2$, taken together with the carbon atom to which they are attached, form saturated C3-6cycloalkyl;
—$R^3$ is independently —H or —$R^{3X}$;
—$R^{3X}$ is independently —$R^{3C}$ or —$R^{3F}$;
—$R^{3C}$ is independently saturated linear or branched $C_{1-3}$alkyl;
—$R^{3F}$ is independently saturated linear or branched $C_{1-3}$fluoroalkyl;
—$R^4$ is independently —$R^{4C}$, —$R^{4CC}$, or —N($R^{4N1}$)($R^{4N2}$);
—$R^{4C}$ is independently saturated linear or branched $C_{1-6}$alkyl;
—$R^{4CC}$ is independently saturated $C_{3-6}$cycloalkyl;
—$R^{4N1}$ is independently —H or —$R^{4N1C}$;
—$R^{4N1C}$ is independently saturated linear or branched $C_{1-4}$alkyl;
—$R^{4N2}$ is independently —H or —$R^{4N2C}$; and
—$R^{4N2C}$ is independently saturated linear or branched $C_{1-4}$alkyl,
or —N($R^{4N1}$)($R^{4N2}$) is independently azetidinyl, pyrrolidinyl, piperidinyl, piperazinyl,
or morpholinyl, and is optionally substituted with one or more saturated linear or branched $C_{1-4}$alkyl groups.

2. The compound according to claim 1, wherein —X= is —CH=.

3. The compound according to claim 1, wherein "m" is 1 or 2.

4. The compound according to claim 3, wherein each —$R^A$ is independently —F, —Cl, or —CN.

5. The compound according to claim 4, wherein "n" is independently 1 or 2.

6. The compound according to claim 5, wherein each —$R^B$ is independently —F, —Cl, or —CN.

7. The compound according to claim 4, wherein "n" is 0.

8. The compound according to claim 1, wherein the group:

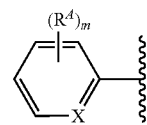

is independently selected from:

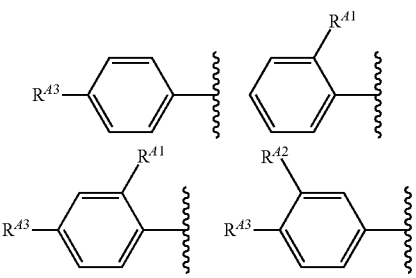

-continued

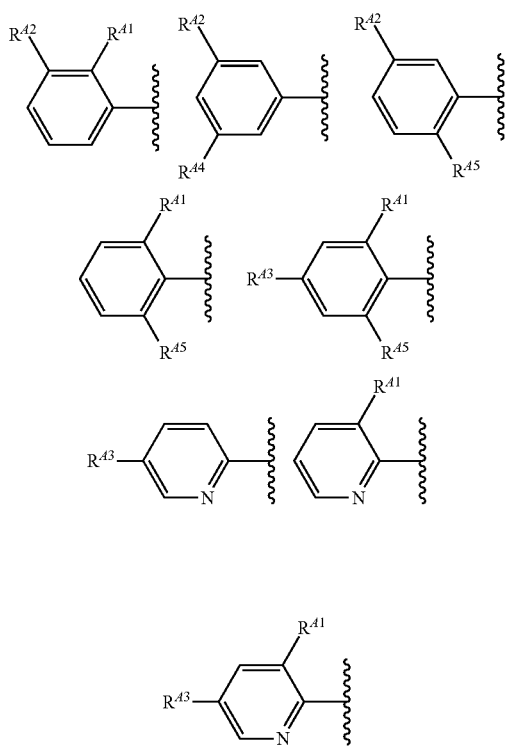

wherein each of —R$^{A1}$, —R$^{A2}$, —R$^{A3}$, —R$^{A4}$, and —R$^{A5}$ is independently —F, —Cl, or —CN.

9. The compound according to claim 1, wherein the group:

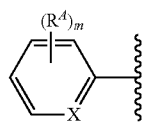

is:

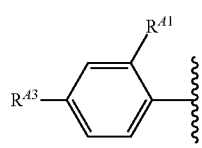

wherein each of —R$^{A1}$ and —R$^{A3}$ is independently —F, —Cl, or —CN.

10. The compound according to claim 9, wherein the group:

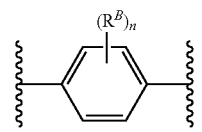

is:

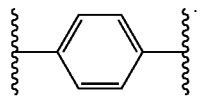 [SMILES: *c1ccc(*)cc1]

11. The compound according to claim 9, wherein the group:

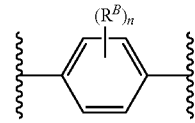

is independently selected from:

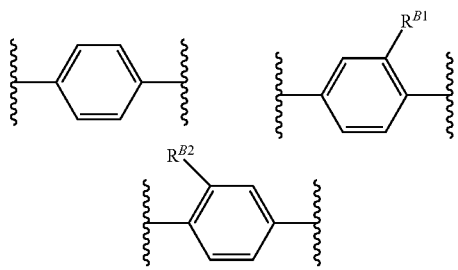

wherein each of —R$^{B1}$ and —R$^{B2}$ is independently —F, —Cl, or —CN.

12. The compound according to claim 11, wherein —R$^{1}$ is —H.

13. The compound according to claim 12, wherein —R$^{2}$ is —H.

14. The compound according to claim 13, wherein —R$^{3}$ is —H.

15. The compound according to claim 14, wherein —R$^{4}$ is —R$^{4C}$.

16. The compound according to claim 15, wherein —R$^{4C}$ is saturated linear or branched C$_{1-4}$alkyl.

17. The compound according to claim 15, wherein —R$^{4C}$ is —CH$_3$ or —CH$_2$CH$_3$.

18. A composition comprising a compound according to claim 1, and a carrier, diluent, or excipient.

19. A method of preparing a composition comprising the step of mixing a compound according to claim 1 and a carrier or diluent.

20. A method of treatment of a disorder comprising administering to a patient in need of treatment a therapeutically effective amount of a compound according to claim 1, wherein the treatment is treatment of:
an autoimmune/inflammatory disorder;
cancer; or
a disorder mediated by osteoclasts.

21. The method according to claim 20, wherein the treatment is treatment of:
inflammatory arthritis; rheumatoid arthritis; psoriatic arthritis; ankylosing spondylitis; spondyloarthritis; reactive arthritis; infectious arthritis; systemic lupus erythematosus; scleroderma; gout; adult-onset Still's disease; juvenile idiopathic arthritis; psoriasis; systemic lupus erythematosus; lupus nephritis; systemic sclerosis; scleroderma; hepatitis; endometriosis; adenomyosis; Sjogren's syndrome; inflammatory bowel disease; ulcerative colitis; Crohn's disease; multiple sclerosis; asthma; atherosclerosis; chronic obstructive pulmonary disease (COPD); uveitis; Hidradenitis suppurativa; autoimmune hepatitis; pulmonary fibrosis; allergic disease; atopy; allergic rhinitis; atopic dermatitis; anaphylaxis; allergic bronchopulmonary aspergillosis; allergic gastroenteritis; hypersensitivity pneumonitis; an allergy; type I diabetes; rheumatic fever; celiac disease; encephalitis; oophoritis; primary biliary cirrhosis; insulin-resistant diabetes; autoimmune adrenal insufficiency (Addison's disease); acne; acne conglobate; acne fulminans; autoimmune oophoritis; autoimmune orchitis; autoimmune haemolytic anaemia; paroxysmal cold hemoglobinuria; Behçet's disease; autoimmune thrombocytopenia; autoimmune neutropenia; pernicious anaemia; pure red cell anaemia; autoimmune coagulopathy; myasthenia gravis; autoimmune polyneuritis; pemphigus; rheumatic carditis; Goodpasture's syndrome; postcardiotomy syndrome; polymyositis; dermatomyositis; irritable bowel syndrome; pancreatitis; gastritis, lichen planus; delayed type hypersensitivity; chronic pulmonary inflammation; pulmonary alveolitis; pulmonary granuloma; gingival inflammation; endodontic disease; periodontal disease; hypersensitivity pneumonitis; hay fever; anaphylaxis; skin allergy; hives; gout; polycystic kidney disease; cryopyrin-associated periodic syndrome (CAPS); Muckle-Wells Syndrome; Guillain-Barre syndrome; chronic inflammatory demyelinating polyneuropathy; organ or transplant rejection; chronic allograft rejection; acute or chronic graft versus-host disease; dermatitis; atopic dermatomyositis; Graves' disease; autoimmune (Hashimoto's) thyroiditis; blistering disorder; vasculitis syndrome; immune-complex mediated vasculitis; bronchitis; cystic fibrosis; pneumonia; pulmonary oedema; pulmonary embolism; sarcoidosis; hypertension; emphysema; respiratory failure; acute respiratory distress syndrome; BENTA disease; or polymyositis.

22. The method according to claim 20, wherein the treatment is treatment of:
  inflammatory arthritis; rheumatoid arthritis; psoriatic arthritis; systemic lupus erythematosus; juvenile idiopathic arthritis; psoriasis; lupus nephritis; systemic sclerosis; inflammatory bowel disease; ulcerative colitis; Crohn's disease; Hidradenitis suppurativa; or multiple sclerosis.

23. The method according to claim 20, wherein the treatment is treatment of:
  multiple myeloma; lymphoma; leukaemia; carcinoma; sarcoma;
  Hodgkin's lymphoma; non-Hodgkin's lymphoma; lymphocytic lymphoma; granulocytic lymphoma; monocytic lymphoma; diffuse large B-cell lymphoma (DLBCL); mantel cell lymphoma (MCL); follicular cell lymphoma (FL); mucosa-associated lymphoid tissue (MALT) lymphoma; marginal zone lymphoma; T-cell lymphoma; marginal zone lymphoma; Burkitt's lymphoma;
  chronic lymphocytic leukemia (CLL); acute myeloid leukemia (AML); acute lymphocytic leukemia (ALL); lymphoblastic T-cell leukemia; chronic myelogenous leukemia (CML); hairy-cell leukemia; acute lymphoblastic T-cell leukemia; acute eosinophilic leukemia; immunoblastic large-cell leukemia; megakaryoblastic leukemia; acute megakaryocytic leukemia; promyelocytic leukemia; erythroleukemia; plasmacytoma;
  colon cancer; breast cancer; ovarian cancer; lung cancer; small cell lung carcinoma; non-small cell lung carcinoma; prostate cancer; cancer of the oral cavity or pharynx; cancer of the lip, tongue, mouth, larynx, pharynx, salivary gland, or buccal mucosa; esophageal cancer; stomach cancer; small intestine cancer; large intestine cancer; rectal cancer; liver passage cancer; biliary passage cancer; pancreatic cancer; bone cancer; connective tissue cancer; skin cancer; cervical cancer; uterine cancer; corpus cancer; endometrial cancer; vulval cancer; vaginal cancer; testicular cancer; bladder cancer; kidney cancer; ureter cancer; urethral cancer; urachus cancer; eye cancer; glioma; spinal cord cancer; central nervous system cancer; peripheral nervous system cancer; meningeal cancer; thyroid cancer; adrenocarcinoma; astrocytoma; acoustic neuroma; anaplastic astrocytoma; basal cell carcinoma; blastoglioma; choriocarcinoma; chordoma; craniopharyngioma; cutaneous melanoma; cystadenocarcinoma; embryonal carcinoma; ependymoma; epithelial carcinoma; gastric cancer; genitourinary tract cancer; glioblastoma multiforme; head and neck cancer; hemangioblastoma; hepatocellular carcinoma; renal cell carcinoma (RCC); hepatoma; large cell carcinoma; medullary thyroid carcinoma; medulloblastoma; meningioma mesothelioma; myeloma; neuroblastoma; oligodendroglioma; epithelial ovarian cancer; papillary carcinoma; papillary adenocarcinoma; paraganglioma; parathyroid tumour; pheochromocytoma; pinealoma; plasmacytoma; retinoblastoma; sebaceous gland carcinoma; seminoma; melanoma; squamous cell carcinoma; sweat gland carcinoma; synovioma; thyroid cancer; uveal melanoma; Wilm's tumour;
  Askin's tumour; sarcoma botryoides; chondrosarcoma; endotheliosarcoma; Ewing's sarcoma; Malignant hemagioendothelioma; malignant Schwannoma; osteosarcoma; gastrointestinal stromal tumour (GIST); myxosarcoma; alveolar soft part sarcoma; angiosarcoma; cystosarcoma phyllodes; dermatofibrosarcoma; desmoid tumour; desmoplastic small round cell tumour; extraskeletal chondrosarcoma; osteosarcoma; fibrosarcoma; hemagiopericytoma; hemangiosarcoma; Kaposi's sarcoma; leiomyosarcoma; liposarcoma; lyphangiosarcoma; lymphangioendotheliosarcoma; lymphosarcoma; malignant peripheral nerve sheath tumour; neurofibrosarcoma; plexiform fibrohistiocytic tumour; rhabdomyosarcoma; or synovial sarcoma.

24. A compound of one of following formulae, or a pharmaceutically acceptable salt thereof:

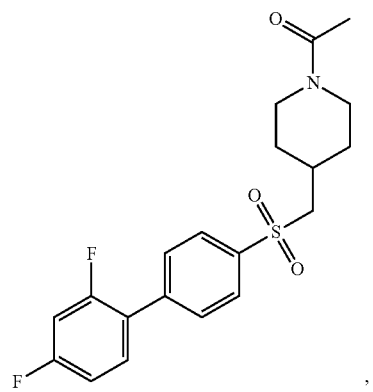

165
-continued
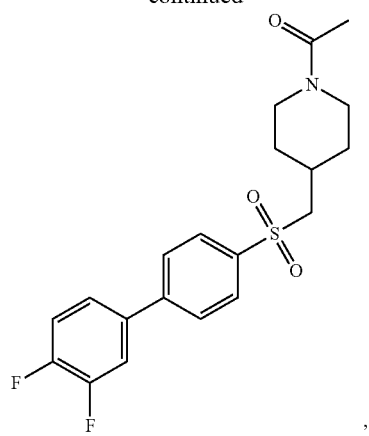
166
-continued
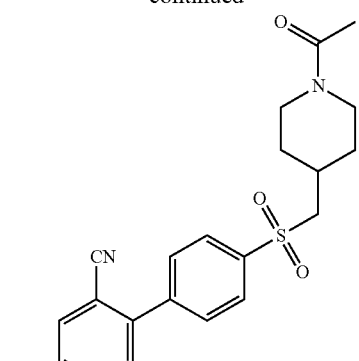
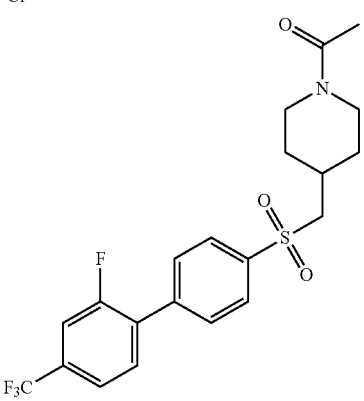
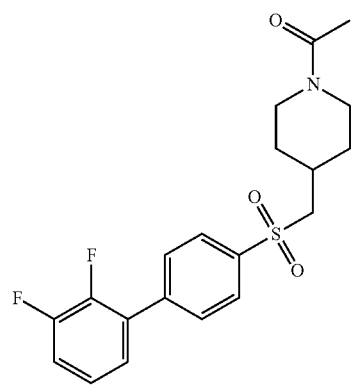
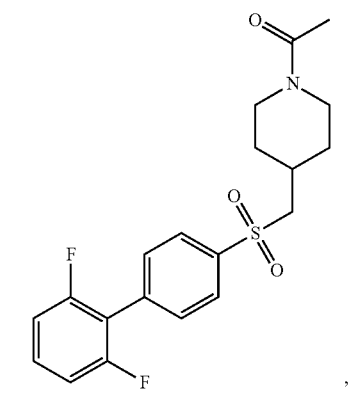

167
-continued
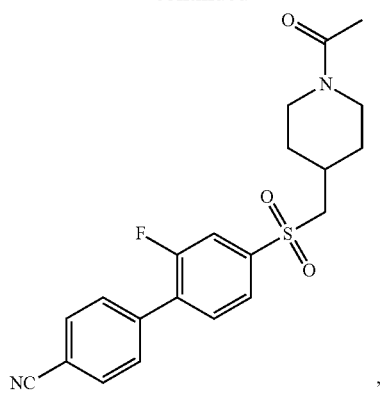
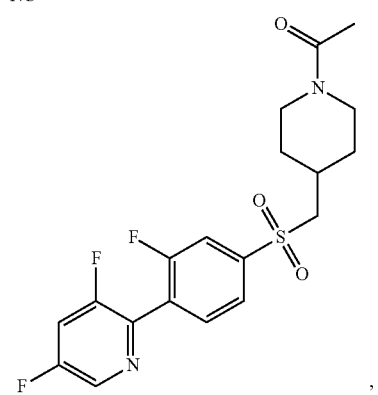
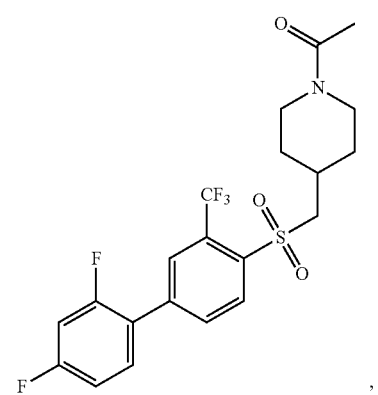
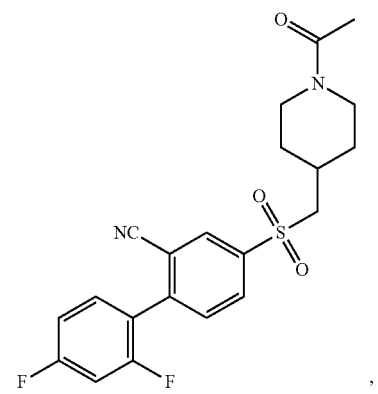
168
-continued
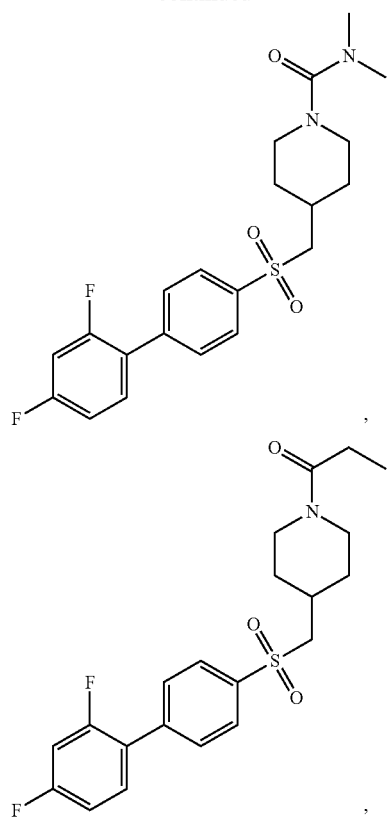
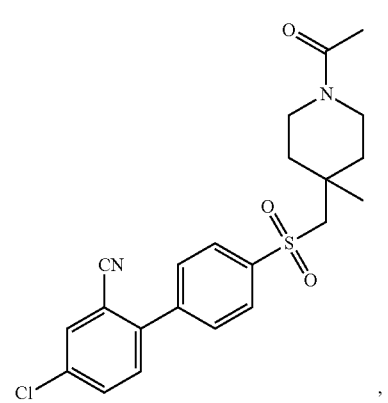
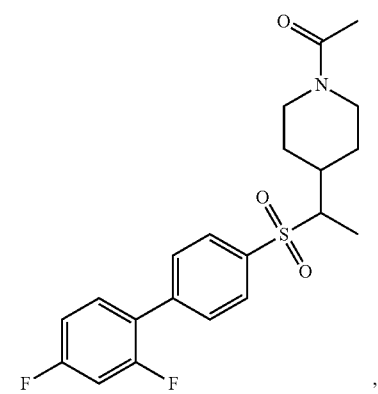

169
-continued
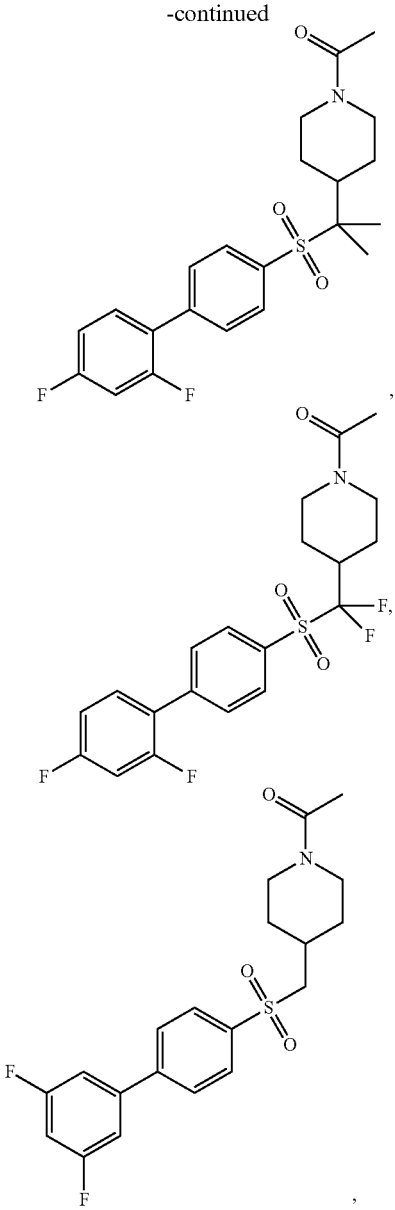
, and
170
-continued
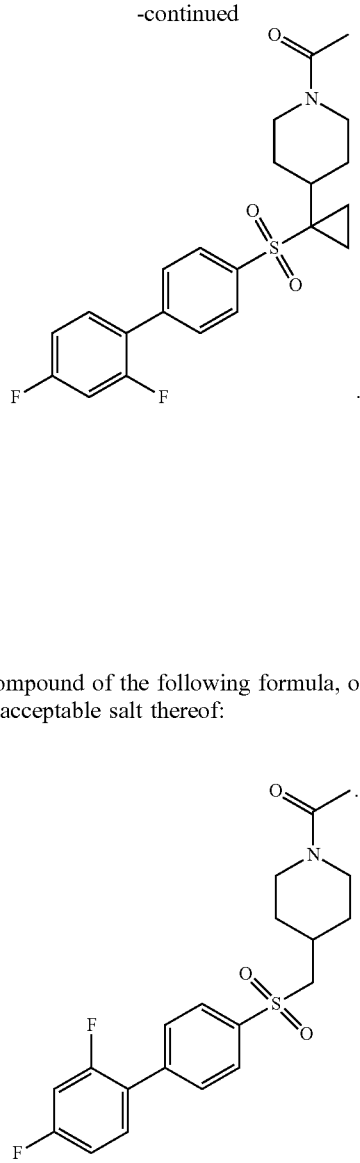
25. A compound of the following formula, or a pharmaceutically acceptable salt thereof:
* * * * *

UNITED STATES PATENT AND TRADEMARK OFFICE
CERTIFICATE OF CORRECTION

| | |
|---|---|
| PATENT NO. | : 12,162,836 B2 |
| APPLICATION NO. | : 17/602408 |
| DATED | : December 10, 2024 |
| INVENTOR(S) | : Patel et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 659 days.

Signed and Sealed this
Tenth Day of June, 2025

Coke Morgan Stewart
*Acting Director of the United States Patent and Trademark Office*